(12) United States Patent
Thiery et al.

(10) Patent No.: US 9,953,129 B2
(45) Date of Patent: Apr. 24, 2018

(54) PATIENT STRATIFICATION AND DETERMINING CLINICAL OUTCOME FOR CANCER PATIENTS

(71) Applicants: Agency for Science, Technology and Research, Singapore (SG); National University of Singapore, Singapore (SG)

(72) Inventors: Jean Paul Thiery, Proteos (SG); Yun-Ju Ruby Huang, Singapore (SG); Kian Ngiap Chua, Singapore (SG); Wen Jing Sim, Proteos (SG); Seiichi Mori, Singapore (SG)

(73) Assignees: Agency for Science, Technology and Research, Singapore (SG); National University of Singapore, Singapore (SG)

( * ) Notice: Subject to any disclaimer, the term of this patent is extended or adjusted under 35 U.S.C. 154(b) by 853 days.

(21) Appl. No.: 14/346,693

(22) PCT Filed: Sep. 24, 2012

(86) PCT No.: PCT/SG2012/000354
§ 371 (c)(1),
(2) Date: Mar. 21, 2014

(87) PCT Pub. No.: WO2013/043132
PCT Pub. Date: Mar. 28, 2013

(65) Prior Publication Data
US 2014/0236495 A1    Aug. 21, 2014

Related U.S. Application Data

(60) Provisional application No. 61/538,487, filed on Sep. 23, 2011.

(51) Int. Cl.
*G01N 33/48* (2006.01)
*G06F 19/18* (2011.01)
*C12Q 1/68* (2018.01)

(52) U.S. Cl.
CPC .......... *G06F 19/18* (2013.01); *C12Q 1/6886* (2013.01); *C12Q 2600/112* (2013.01); *C12Q 2600/158* (2013.01)

(58) Field of Classification Search
CPC ....................................................... G06F 19/18
USPC ........................................................ 702/19
See application file for complete search history.

(56) References Cited

U.S. PATENT DOCUMENTS

| | | |
|---|---|---|
| 2006/0078941 A1 | 4/2006 | Santin |
| 2007/0231822 A1 | 10/2007 | Mitas |
| 2009/0092596 A1 | 4/2009 | Haley et al. |
| 2009/0226396 A1 | 9/2009 | Haley et al. |

FOREIGN PATENT DOCUMENTS

| | | |
|---|---|---|
| WO | WO-2005/083128 A2 | 9/2005 |
| WO | WO-2008/079269 A2 | 7/2008 |
| WO | WO-2010/011642 A2 | 1/2010 |
| WO | WO-2010/125117 A2 | 11/2010 |
| WO | WO-2011/044513 A1 | 4/2011 |
| WO | WO-2012/061515 A2 | 5/2012 |
| WO | WO-2013/043132 A1 | 3/2013 |

OTHER PUBLICATIONS

"Singaporean Application Serial No. 11201400919R, Search Report dated Sep. 16, 2015", 6 pgs.
"Singaporean Application Serial No. 11201400919R, Written Opinion dated Sep. 17, 2015", 12 pgs.
Beyers, L., et al., "An epithelial to mesenchymal transition (EMT) gene expression signature identifies Axl as an EMT marker in non-small cell lung cancer (NSCLC) and head and neck cancer (HNC) lines and predicts response to erlotinib", *European Journal of Cancer, Supplement*, vol. 8, No. 7, (2010), p. 21.
Choi, R. J., et al., "P78. In vitro epithelial mesenchymal transition status predicts geftinib sensitivity in pancreatic adenocarcinoma cell lines", *Journal of Surgical Research*, 137(2), (2007), p. 268.
Sabbah, M., et al., "Molecular signature and therapeutic perspective of the epithelial-to-mesenchymal transitions in epithelial cancers", *Drug Resistance Updates*, 11(4-5), (2008), 123-151.
Voulgari, Angeliki, et al., "Epithelial-mesenchymal transition in cancer metastasis: Mechanisms, markers and strategies to overcome drug resistance in the clinic", *Biochimica et Biophysica Acta*, 1796, (2009), 75-90.
Cancer Genome Atlas Research Network, "Integrated genomic analyses of ovarian carcinoma", *Nature*, 474(7353), (2011), 609-615.
Ahmed, N., et al., "Epithelial-mesenchymal interconversions in normal ovarian surface epithelium and ovarian carcinomas: an exception to the norm", *J Cell Physiol.*, 213(3), (Dec. 2007), 581-588.
Ahmed, N., et al., "Neuronal transcription factor Brn-3a(l) is over expressed in high-grade ovarian carcinomas and tumor cells from ascites of patients with advanced-stage ovarian cancer.", *J. Ovarian Res.*, 3, (2010), 12 pgs.
Alizadeh, A. A, et al., "Distinct types of diffuse large B-cell lymphoma identified by gene expression profiling", *Nature*, 403(6769), (Feb. 3, 2000), 503-511.
Barbie, D. A, et al., "Systematic RNA interference reveals that oncogenic *KRAS*-driven cancers require TBK1", *Nature*, 462(7269), (Nov. 5, 2009), 108-112.

(Continued)

Primary Examiner — Jerry Lin
(74) Attorney, Agent, or Firm — Schwegman Lundberg & Woessner, P.A.

(57) ABSTRACT

In a first aspect the present invention is directed to a method of generating a scheme allowing classification of a cancer of an individual patient for estimating a clinical outcome for said patient. It also refers to a method of estimating a clinical outcome of a patient suffering from epithelial ovarian cancer (EOC). The present invention also refers to a method of determining whether the epithelial mesenchymal score of a patient suffering from a cancer can be changed by administering an EMT reversal agent to increase patients susceptibility for an anti-cancer treatment.

6 Claims, 48 Drawing Sheets

(56) References Cited

OTHER PUBLICATIONS

Bast, R. C, et al., "The biology of ovarian cancer: new opportunities for translation", *Nat Rev Cancer*, 9(6), (Jun. 2009), 415-428.

Bild, A. H., et al., "Oncogenic pathway signatures in human cancers as a guide to targeted therapies", *Nature*, 439(7074), (Jan. 19, 2006), 353-357.

Blyth, K., et al., "The RUNX genes: gain or loss of function in cancer", *Nat Rev Cancer*, 5(5), (May 2005), 376-387.

Brabletz, T., et al., "Variable beta-catenin expression in colorectal cancers indicates tumor progression driven by the tumor environment", *Proc Natl Acad Sci USA*, 98(18), (2001), 10356-10361.

Bryan, E. J, et al., "Mutation analysis of *EP300* in colon, breast and ovarian carcinomas", *Int J Cancer*, 102(2), (Nov. 10, 2002), 137-141.

Chin, L., et al., "Making sense of cancer genomic data", *Genes Dev.*, 25(6), (Mar. 15, 2011), 534-555.

Chou, C. H, et al., "Up-regulation of interleukin-6 in human ovarian cancer cell via a Gi/PI3K-Akt/NF-κB pathway by lysophosphatidic acid, an ovarian cancer-activating factor", *Carcinogenesis*, 26(1), (Jan. 2005), 45-52.

Chua, Kian-Ngiap, et al., "Target cell movement in tumor and cardiovascular diseases based on the epithelial-mesenchymal transition concept", *Adv Drug Deliv Rev.*, 63(8), (2011), 558-567.

Ewens, W. J, et al., *Statistical Methods in Bioinformatics: An Introduction*, (2001), 476 pgs.

Fodde, R., "The Stem of Cancer", *Cancer Cell.*, 15(2), (Feb. 3, 2009), 87-89.

Futreal, P. A, et al., "A census of human cancer genes", *Nat Rev Cancer*, 4(3), (Mar. 2004), 177-183.

Gilks, C. B, et al., "Ovarian carcinoma pathology and genetics: recent advances", *Hum Pathol.*, 40(9), (Sep. 2009), 1213-1223.

Gorringe, K. L, et al., "Copy number analysis identifies novel interactions between genomic loci in ovarian cancer", *PLoS One*, 5(9), e11408. (Sep. 10, 2010), 1-13.

Gupta, P. B, et al., "Cancer stem cells: mirage or reality?", *Nat Med.*, 15(9), (Sep. 2009), 1010-2.

Hahn, W. C, et al., "Integrative genomic approaches to understanding cancer", *Biochim. Biophys. Acta.*, 1790(6), (Jun. 2009), 478-84.

Helland, A., et al., "Deregulation of *MYCN*, *LIN28* and *LET7* in a molecular subtype of aggressive high-grade serous ovarian cancers", *PLoS One*, 6(4), e18064, (Apr. 13, 2011).

Helleman, J., et al., "Pathway analysis of gene lists associated with platinum-based chemotherapy resistance in ovarian cancer: the big picture", *Gynecol Oncol.*, 117(2), (May 2010), 170-176.

Hu, L., et al., "Paracrine VEGF/VE-Cadherin Action on Ovarian Cancer Permeability", *Exp Biol Med (Maywood)*, 231(10), (Nov. 2006), 1646-1652.

Huang, R. Y, et al., "Lysophosphatidic acid induces ovarian cancer cell dispersal by activating Fyn kinase associated with p120-catenin", *Int J Cancer*, 123(4), (Aug. 15, 2008), 801-809.

Jochumsen, K. M., et al., "Gene expression profiles as prognostic markers in women with ovarian cancer", *Int J Gynecol Cancer*, 19(7), (Oct. 2009), 1205-1213.

Jung, A., et al., "The Invasion Front of Human Colorectal Adenocarcinomas Shows Co-Localization of Nuclear β-Catenin, Cyclin $D_1$, and p16$^{INK4A}$ and is a Region of Low Proliferation.", *Am J Pathol.*, 159(5), (Nov. 2001), 1613-1617.

King, E. R., et al., "The Anterior Gradient Homolog 3 (*AGR3*) Gene is Associated With Differentiation and Survival in Ovarian Cancer", *Am J Surg Pathol.* 35(6), (Jun. 2011), 904-912.

Konstantinopoulos, P. A, et al., "Gene Expression Profile of *BRCA*-ness That Correlates With Responsiveness to Chemotherapy and With Outcome in Patients With Epithelial Ovarian Cancer", *J Clin Oncol.*, 28(22), (Aug. 1, 2010), 3555-3561.

Kudo-Saito, C., et al., "Cancer metastasis is accelerated through immunosuppression during Snail-induced EMT of cancer cells", *Cancer Cell*, 15(3), (Mar. 3, 2009), 195-206.

Kurman, R. J, et al., "Pathogenesis of ovarian cancer: lessons from morphology and molecular biology and their clinical implications", *Int J Gynecol Pathol.*, 27(2), (Apr. 2008), 151-160.

Kurrey, N. K, et al., "Snail and Slug are major determinants of ovarian cancer invasiveness at the transcription level", *Gynecol Oncol.*, 97(1), (Apr. 2005), 155-165.

Kurrey, N. K, et al., "Snail and slug mediate radioresistance and chemoresistance by antagonizing p53-mediated apoptosis and acquiring a stem-like phenotype in ovarian cancer cells", *Stem Cells*, 27(9), (Sep. 2009), 2059-2068.

Lenz, G., et al., "Molecular subtypes of diffuse large B-cell lymphoma arise by distinct genetic pathways", *Proc. Natl. Acad. Sci. USA.*, 105(36), (Sep. 9, 2008), 13520-13525.

Liu, H., et al., "Cysteine-rich protein 61 and connective tissue growth factor induce deadhesion and anoikis of retinal pericytes", *Endocrinology*, 149(4), (Apr. 2008), 1666-1677.

Luo, B., et al., "Highly parallel identification of essential genes in cancer cells", *Proc. Natl. Acad.. Sci. USA*, 105(51), (Dec. 23, 2008), 20380-20385.

Maas, H. A, et al., "The influence of age and co-morbidity on treatment and prognosis of ovarian cancer: a population-based study", *Gynecol Oncol.*, 97(1), (Apr. 2005), 104-109.

Mani, S. A, et al., "The epithelial-mesenchymal transition generates cells with properties of stem cells", *Cell*, 133(4), (May 16, 2008), 704-715.

Maruyama, K., et al., "Cytoplasmic Beta-Catenin Accumulation as a Predictor of Hematogenous Metastasis in Human Colorectal Cancer", *Oncology*, 59(4), (Nov. 2000), 302-309.

Meyniel, Jean-Philippe, et al., "A genomic and transcriptomic approach for a differential diagnosis between primary and secondary ovarian carcinomas in patients with a previous history of breast cancer", *BMC Cancer*,10: 222, (2010), 10 pgs.

Modesitt, S. C, et al., "Recurrent epithelial ovarian cancer: pharmacotherapy and novel therapeutics", *Expert Opin Pharmacother.*, 8(14), (Oct. 2007), 2293-2305.

Mori, S., et al., "Anchorage-independent cell growth signature identifies tumors with metastatic potential", *Oncogene*, 28(31), (Aug. 6, 2009), 2796-2805.

Neve, R. M, et al., "A collection of breast cancer cell lines for the study of functionally distinct cancer subtypes", *Cancer Cell.*, 10(6), (Dec. 2006), 515-527.

Perou, C. M, et al., "Molecular portraits of human breast tumours", *Nature*, 406(6797), (Aug. 17, 2000), 747-52.

Pollack, J. R, et al., "Genome-wide analysis of DNA copy-number changes using cDNA microarrays", *Nat Genet.*, 23(1), (Sep. 1999), 41-46.

Prat, A., et al., "Phenotypic and molecular characterization of the claudin-low intrinsic subtype of breast cancer", *Breast Cancer Res.*, 12(5), (2010), 18 pgs.

Quintás-Cardama, A., et al., "Imatinib and beyond—exploring the full potential of targeted therapy for CML", *Nat Rev Clin Oncol.*, 6(9), (Sep. 2009), 535-543.

Ramakrishna, M., et al., "Identification of candidate growth promoting genes in ovarian cancer through integrated copy number and expression analysis", *PLoS One*, 5(4), e9983, (Apr. 8, 2010), 1-12.

Rosell, R., et al., "Epidermal growth factor receptor tyrosine kinase inhibitors as first-line treatment in advanced nonsmall-cell lung cancer", *Curr. Opin. Oncol.*, 22(2), (Mar. 2010), 112-120.

Sarrio, D., et al., "'Epithelial-mesenchymal transition in breast cancer relates to the basal-like phenotype", *Cancer Res.*, 68(4), (Feb. 15, 2008), 989-997.

Schmalhofer, O., et al., "E-cadherin, β-catenin, and ZEB1 in malignant progression of cancer", *Cancer Metastasis Rev.*, 28(1-2), (Jun. 2009), 151-166.

Scholl, C., et al., "Synthetic Lethal Interaction Between Oncogenic *KRAS* Dependency and *STK33* Suppression in Human Cancer Cells", *Cell*, 137(5), (May 29, 2009), 821-834.

Shoemaker, R. H, "The NCI60 human tumour cell line anticancer drug screen", *Nat Rev Cancer.*, 6(10), (Oct. 2006), 813-823.

Sordella, R., et al., "Gefitinib-sensitizing EGFR mutations in lung cancer activate anti-apoptotic pathways", *Science*, 305(5687), (Aug. 20, 2004), 1163-1167.

(56) References Cited

OTHER PUBLICATIONS

Sorlie, T., et al., "Repeated observation of breast tumor subtypes in independent gene expression data sets", *Proc. Natl. Acad. Sci. USA*, 100(14), (Jul. 8, 2003), 8418-8423.

Staudt, L. M, et al., "The biology of human lymphoid malignancies revealed by gene expression profiling", *Adv Immunol.*, 87, (2005), 163-208.

Taube, J. H, et al., "Core epithelial-to-mesenchymal transition interactome gene-expression signature is associated with claudin-low and metaplastic breast cancer subtypes", *Proc. Natl. Acad. Sci. USA*, 107(35), (Aug. 31, 2010), 15449-15454.

Therneau, T. M, et al., *Modeling Survival Data: Extending the Cox Model*, Springer-Verlag; New York, MY, (2000), 350 pgs.

Thiery, J. P, "Epithelial-mesenchymal transitions in tumour progression", *Nat Rev Cancer*, 2(6), (Jun. 2002), 442-54.

Thiery, Jean Paul, et al., "Epithelial-mesenchymal transitions in development and disease", *Cell*, 139(5), (Nov. 25, 2009), 871-890.

Wang, Z., et al., "Pancreatic cancer: understanding and overcoming chemoresistance", *Nat Rev Gastroenterol Hepatol.*, 8(1), (Jan. 2011), 27-33.

Wiedemeyer, R., et al., "Feedback Circuit Among INK4 Tumor Suppressors Constrains Human Glioblastoma Development.", *Cancer Cell.*, 13(4), (Apr. 2008), 355-64.

Yaziji, H., et al., "HER-2 testing in breast cancer using parallel tissue-based methods", *JAMA*, 291(16), (Apr. 28, 2004), 1972-7.

Yin, J. J, et al., "TGF-β signaling blockade inhibits PTHrP secretion by breast cancer cells and bone metastases development.", *J Clin Invest.*, 103(2), (Jan. 1999), 197-206.

"International Application No. PCT/SG2012/000354, Written Opinion dated Dec. 18, 2012", 11 pgs.

"International Application No. PCT/SG2012/000354, International Preliminary Report on Patentability dated Mar. 25, 2014", 12 pgs.

Anglesio, M., et al., "Mutation of ERBB2 Provides a Novel Alternative Mechanism for the Ubiquitous Activation of RAS-MAPK in Ovarian Serous Low Malignant Potential Tumors", *Mol. Cancer Res.*, 6(11), (2008), 1678-1690.

Bild, A. H., et al., "Linking oncogenic pathways with therapeutic opportunities", *Nat. Rev. Cancer*, 6(9), (2006), 735-741.

Bowen, N. J., et al., "Gene expression profiling supports the hypothesis that human ovarian surface epithelia are multipotent and capable of serving as ovarian cancer initiating cells", BMC *Med. Genomics*, 2:71, (2009), 14 pgs.

Dabney, A. R., "ClaNC: point-and-click software for classifying microarrays to nearest centroids", *Bioinformatics*, 22(1), (2006), 122-123.

Denkert, C., et al., "A prognostic gene expression index in ovarian cancer—validation across different independent data sets", *J. Pathol.*, 218(2), (2009), 273-280.

Gatza, M. L., et al., "A pathway-based classification of human breast cancer", *Proc. Natl. Acad. Sci. USA*, 107(15), (2010), 6994-6999.

Guan, Y., et al., "Amplification of *PVT1* Contributes to the Pathophysiology of Ovarian and Breast Cancer", *Clin. Cancer Res.*, 13(19), (2007), 5745-5755.

Hanahan, D., et al., "Hallmarks of Cancer: The Next Generation", *Cell*, 144(5), (2011), 646-674.

Hendrix, N. D., et al., "Fibroblast Growth Factor 9 Has Oncogenic Activity and Is a Downstream Target of Wnt Signaling in Ovarian Endometrioid Adenocarcinomas", *Cancer Res.*, 66(3), (2006), 1354-1362.

Høgdall, E. V., et al,, "Distribution of HER-2 Overexpression in Ovarian Carcinoma Tissue and Its Prognostic Value in Patients with Ovarian Carcinoma: *From the Danish MALOVA Ovarian Cancer Study*", *Cancer*, 98(1), (2003), 66-73.

Hsu, D. S., et al., "Pharmacogenomic Strategies Provide a Rational Approach to the Treatment of Cisplatin-Resistant Patients With Advanced Cancer", *J. Clin. Oncol.*, 25(28), (2007), 4350-4357.

Iorio, E., et al., "Activation of Phosphatidylcholine Cycle Enzymes in Human Epithelial Ovarian Cancer Cells", *Cancer Res.*, 70(5), (2010), 2126-2135.

Irizarry, R. A., "Exploration, normalization, and summaries of high density oligonucleotide array probe level data", *Biostatistics*, 4(2), (2003), 249-264.

Jochumsen, K. M., et al., "Gene expression in epithelial ovarian cancer: a study of intratumor heterogeneity", *Int. J. Gynecol. Cancer*, 17(5), (2007), 979-985.

Johnson, W. E., et al., "Adjusting batch effects in microarray expression data using empirical Bayes methods", *Biostatistics*, 8(1), (2007), 118-127.

Matsumura, N., et al., "Epigenetic suppression of the TGF-beta pathway revealed by transcriptome profiling in ovarian cancer", *Genome Res.*, 21(1), (2011), 74-82.

Mok, S. C., et al., "A Gene Signature Predictive for Outcome in Advanced Ovarian Cancer Identifies a Survival Factor: Microfibril-Associated Glycoprotein 2.", *Cancer Cell*, 16(6), (2009), 521-532.

Monti, S., et al., "Consensus Clustering: A Resampling-Based Method for Class Discovery and Visualization of Gene Expression Microarray Data", *Machine Learning*, 52, (2003), 91-118.

Monti, S., et al., "Molecular profiling of diffuse large B-cell lymphoma identifies robust subtypes including one characterized by host inflammatory response", *Blood*, 105(5), (2005), 1851-1861.

Mori, S., et al., "Utilization of Pathway Signatures to Reveal Distinct Types of B Lymphoma in the Eμ-myc Model and Human Diffuse Large B-Cell Lymphoma", *Cancer Res.*, 68(20), (2008), 8525-8534.

Pejovic, T., et al., "Expression Profiling of the Ovarian Surface Kinome Reveals Candidate Genes for Early Neoplastic Changes", *Transl. Oncol.*, 2(4), (2009), 341-349.

Reich, M., et al., "GenePattern 2.0", *Nat. Genet.*, 38(5), (2006), 500-501.

Rousseeuw, P. J., "Silhouettes: a graphical aid to the interpretation and validation of cluster analysis", *Journal of Computation and Applied Mathematics*, 20, (1987), 53-65.

Subramanian, J., et al., "An evaluation of resampling methods for assessment of survival risk prediction in high-dimensional settings", *Stat. Med.*, 30(6), (2011), 642-652.

Tone, A. A., et al., "Gene Expression Profiles of Luteal Phase Fallopian Tube Epithelium from BRCA Mutation Carriers Resemble High-Grade Serous Carcinoma", *Clin. Cancer Res.*, 14(13), (2008), 4067-4078.

Tothill, R. W., et al., "Novel Molecular Subtypes of Serous and Endometrioid Ovarian Cancer Linked to Clinical Outcome", *Clin. Cancer Res.*, 14(16), (2008), 5198-5208.

Tung, C. S., et al., "*PAX2* expression in low malignant potential ovarian tumors and low-grade ovarian serous carcinomas", *Mod. Pathol.*, 22(9), (2009), 1243-1250.

Tusher, V. G., et al., "Significance Analysis of Microarrays Applied to the Ionizing Radiation Response", *Proc. Natl. Acad. Sci.*, 98(9), (2001), 5116-5121.

Verhaak, R. G. W., et al., "Integrated Genomic Analysis Identifies Clinically Relevant Subtypes of Glioblastoma Characterized by Abnormalities in PDGFRA, IDH1, EGFR, and NF1", *Cancer Cell*, 17(1), (2010), 98-110.

"International Application No. PCT/SG2012/000354, International Search Report dated Dec. 18, 2012", (Dec. 18, 2012), 7 pgs.

Generation of Epithelial Signature by Using 4 Markers

| | DDR1 | CDH1 | ERBB3 | ZEB1 |
|---|---|---|---|---|
| Hi | Caov3 | Caov3 | A1847 | OV7 |
| | OVCAR3 | OVCA432 | JHOS4 | TykNu |
| | C13 | OVCA420 | OVCA420 | SKOV3 |
| | A2008 | OAW42 | PEO1 | Hey |
| | OV2008 | OVCA433 | OVCA429 | COLO720E |
| | OVCA420 | C13 | OVCAR8 | BG1 |
| Low | SKOV3 | Hey | TykNu | OVCAR3 |
| | HeyC2 | TykNu | HeyC2 | OV2008 |
| | Hey | OVCAR10 | OV7 | A2008 |
| | BG1 | A2780 | OV56 | C13 |
| | HeyA8 | BG1 | HeyA8 | OVCAR8 |
| | TykNu | HeyA8 | SKOV3 | JHOS4 |

B (continued)

B (continued)

B (continued)

PATIENT STRATIFICATION AND DETERMINING CLINICAL OUTCOME FOR CANCER PATIENTS

CROSS-REFERENCE TO RELATED APPLICATIONS

This application is a national stage application under 35 U.S.C. § 371 of PCT/SG2012/000354, filed Sep. 24, 2012, and published as WO 2013/043132 on Mar. 28, 2013, which claims the benefit of priority of U.S. provisional application No. 61/538,487, filed Sep. 23, 2011, which applications and publication are incorporated by reference as if reproduced herein and made a part hereof in their entirety, and the benefit of priority of each of which is claimed herein.

FIELD OF THE INVENTION

The present invention refers to the field of bioinformatics and biochemistry of cancer.

BACKGROUND OF THE INVENTION

The hallmark of human cancer is heterogeneity. The heterogeneity of human cancer can be demonstrated in at least three aspects: diverse histopathological characteristics, different genetic traits, and complex molecular events and signaling mechanisms. These factors reflect the complexity of the underlying molecular mechanisms governing carcinogenesis and carcinoma progression. Therefore, these factors contributing to heterogeneity also impose great challenges in designing effective therapeutic strategies to benefit cancer patients.

To tackle this challenge, it is critical to take innovative approaches to identify patient subgroups that share common molecular characteristics. This approach would further provide frameworks to assist in developing rational cancer diagnostics and therapeutic strategies. One of the best examples is the development of trastuzumab in treating Her2 positive breast cancers. Her2 is a growth promoting oncogene over-expressed in approximately 18% of breast cancer patients. A substantial body of work, including those using genome-scale gene expression measures, has demonstrated that Her2 positive breast cancer is a distinct disease entity which is distinctive in phenotypic behaviours such as the tendency for distant metastasis. Trastuzumab, a monoclonal antibody against Her2, has been shown to be an effective treatment only for breast cancer patients that show Her2 amplification. Another example is the discovery of the positive correlation between EGFR mutation and the response to EGFR inhibitor Iressa in treating non-small cell lung cancer patients.

Innovations like these have not been rapidly and successfully translated to other cancer types. For example, the therapeutic innovation for epithelial ovarian cancer (EOC) is slow. One major reason for this slow innovation for novel therapeutics in EOC is the lack of strong evidence supporting the applicability of patient stratification by using robust molecular diagnostics in the prediction of survival or therapeutic response. The heterogeneity of EOC might be even more complex which can be evident in at least four aspects.

Firstly, EOC represents a broad and heterogeneous entity which includes different invasive behavior (low malignant potential and invasive) as well as four major distinct histopathological subtypes, serous, mucinous, endometrioid, and clear cell carcinomas.

Secondly, EOC can occur in women harboring germline mutations of genes such as BRCA1/2 and mismatch repair genes as the hereditary trait, and in women without germline mutations as the sporadic trait.

Thirdly, the carcinogenesis process of EOC does not follow the step-wise model as in the colorectal cancer but rather has been proposed to follow two pathways: Type I and Type II. Type I diseases consist mainly of low-grade tumors with frequent KRAS or BRAF mutations and identifiable pre-malignant lesions (borderline malignancy). Type II diseases consist of high-grade tumors with predominant p53 mutations and potential precursor lesions harboring the same p53 mutations.

Finally, multiple signaling pathways contribute to growth promotion, insensitivity to antigrowth signals, inhibition of apoptosis and immune surveillance, enhanced angiogenesis, and promotion of invasion and metastasis in EOC. However, most EOC patients receive the same taxene/platinum-based chemotherapy regardless of the existing heterogeneity. For EOC, targeted therapies against VEGF (angiogenesis), EGFR (survival), or c-Kit (stem cell) pathways have not provided encouraging results from clinical trials. Therefore, the therapeutic modalities for EOC have remained at the primitive ground and have not provided additional benefits to the patients.

Genome-scale expression data has been utilized to characterize the complex biological diversity in human cancer. The substantial number of data points provides the robustness to detect not only common properties but also subtle biological differences across the whole variety of cancer samples. Several studies on breast cancer, glioblastoma multiforme (GBM), and diffuse large B-cell lymphoma have demonstrated this application on identifying patient subtypes.

Subtypes identified through expression microarray analyses are well linked with multiple important clinical parameters such as age, expression patterns of molecular markers, and patient survival prognosis. These efforts have helped advancing the understanding of cancer heterogeneity and designing potential diagnostic and therapeutic schemes which have made personalized medicine possible. For cancers that have not benefited from these advances, such as EOC, several microarray studies have been conducted to correlate the expression pattern with clinical features such as histological types, aggressiveness, and patient outcomes. These studies have shed light that molecular subtyping might be able to provide hope of innovations in therapies for complex diseases such as EOC.

There have been accumulative evidences suggesting that epithelial-mesenchymal transition (EMT), a fundamental mechanism in embryonic development, plays a crucial role in promoting carcinoma progression. EMT describes the process driving epithelial cells to form cells exhibiting a fibroblastic-like morphology (mesenchymal). This mechanism involves multiple steps including the loss of an apico-basolateral polarity. The loss of epithelial cell polarity is induced by the dissolution of junctional complexes (desmosomes and adherens junctions) and tight junctions, and the concomitant remodeling of the actin cytoskeleton. Epithelial cells also delocalize polarity gene products and modulate their integrin adhesome to favor cell substrate adhesions to eventually acquire a mesenchymal phenotype. This critical transdifferentiation program leads to cells with low intercellular adhesion and equipped with rear-front polarity favoring cell locomotion and invasion.

In cancer progression, EMT explains how carcinoma cells invade and metastasize by transforming the epithelial state via an intermediate potentially metastable state to the mesenchymal state. The EMT program could also contribute to the dissemination of carcinoma cells from solid tumors and to the formation of micrometastatic foci which subsequently develop into clinically detectable metastases. EMT is also involved in the acquisition of chemoresistance maintaining cancer stemness and causing immune escape. The proof of concept that EMT indeed is involved in human cancers arises from several recent genome-scale expression analyses. EMT signatures have been found in the claudin-low (Basal B) subtypes of breast cancers, a subgroup of GBM, and the C1 and C5 clusters of EOC. In EOC, the progression and dissemination have been suggested to involve a vicious EMT-MET cycle.

Unique features of ovarian carcinoma are the ability to spread by shedding from the primary tumour to the surrounding peritoneal cavity and to generate large amount of ascites. The shedding of ovarian carcinoma cells requires the loss of cell-cell and cell-matrix adhesions. The production of ascites is mainly due to increased vascular permeability and extravasation of the intravascular fluid to the peritoneal cavity resulting from the presence of angiogenic factors such as VEGF. Some of the shed cells escape from apoptosis and survive as aggregates and form floating spheroids in the ascitic fluids. Cytokines and growth factors (ex. IL-6, IL-8, HB-EGF, TGF-α, VEGF, b-FGF, LPA, etc.) secreted from the cancer spheroids, reactive immune cells, and peritoneal mesothelial cells provide an autocrine and paracrine milieu for the survival of spheroids. These spheroids then adhere to and invade the peritoneum resulting in extensive dissemination of the disease. Transcriptional repressors such as SNAI1 and SNAI2 have been shown to govern the EMT process in ovarian cancer cells. Recent data have also demonstrated that pathway related to EMT is associated with platinum-based chemotherapy resistance (Helleman, Smid et al. 2010). Also, EMT is also related to a "migratory cancer stem cell-like" phenotype in recurrent ovarian cancers. In GBM, a mesenchyme like subtype was found by unsupervised clustering but not extensively. In breast cancer, several molecular subtypes are exhibiting a mesenchymal like phenotype. They include a newly described subtype named claudin-low. The basal subtype is also a mesenchymal-like phenotype; it includes sporadic tumors, BRCA1 tumors and sarcomatoid carcinoma.

EMT is best demonstrated at the tumor invasive fronts of colorectal cancers where in-transit mesenchymal-like cells can be identified. The invasive fronts indicate the interface between the main tumor mass and the microenvironment milieu. This frontline can be regarded as the starting point of the pressure gradient generated by the microenvironment. Signals of EMT thus follow a gradient from the invasive front toward the inner tumor mass. Also, within the inner tumor mass, pressures coming from hypoxia and nutrient depletion create another gradient for EMT. Therefore, EMT contributes to tumor heterogeneity. In fact, the different degree of EMT involvement provides a novel aspect to understand tumor heterogeneity that each individual tumor can be regarded as a mixture of different populations with or without undergoing EMT. The heterogeneity of each individual tumor is summarized in FIG. 1 and represented as an EMT Status (or EMT Score).

EMT can be triggered by different signal transduction pathways, including a large number of cell surface receptors like receptor tyrosine kinases, integrins, TGF-β receptors, as well as several intracellular kinases such as ILK and SRC. Most of the known inhibitors of these signaling pathways (e.g. Erlotinib, Dasatinib, Vatalanib, Sunitinib, etc.) were not originally identified based on their involvement on EMT regulation, but often as anti-proliferative agents. Anti-proliferation or growth inhibition has long been adopted as the standard endpoint for anti-cancer drug screen. Therefore, the current paradigm in cancer treatment still focuses on the discovery and development of cytotoxic therapeutic agents that alter the 5 hallmark mechanisms of cancer proposed by Hanahan and Weinberg (Hanahan and Weinberg, 2011, Cell, vol. 144, no. 5, pp. 646).

Experimental systems, whether in vitro cancer cell lines or tumor xenografts, have been established to fulfill that purpose. The development of the US National Cancer Institute (NCI) 60 human tumour cell line (NCI60) which includes nine distinct tumour types: leukaemia, CNS, renal, melanoma, ovarian, breast and prostate, has served as a great asset for cancer researchers to provide an in vitro model for drug discovery by identifying compounds with growth-inhibitory effects.

However, experiences from treatment failure of cytotoxic drugs suggested that incorporating other biological mechanisms which regulate tumour invasiveness and dissemination as additional endpoints might help design novel therapeutics to overcome resistance. In fact, an increasing number of studies that have demonstrated failure of established drugs in arresting cancer progression at its invasive phase have indirectly highlighted the importance of EMT control. One study identified potential cytotoxic agents against breast cancer cells that have undergone EMT. To our knowledge, there has been no drug-screen platform reported to solely inhibit EMT and achieve phenotype reversion without altering cell proliferation.

An important aspect of the development of a scheme targeting EMT phenotype is to establish a framework of facilitating the use of experimental systems, whether in vitro cell lines or xenografts, to incorporate into the subtype identification of in vivo cancers to model the reality in human. Cancer cell line collections such as breast cancer have been shown to retain their subtype characteristics corresponding to those of the in vivo counterparts and these cell lines have been demonstrated as powerful tools to model heterogeneity in cancer in vitro.

It has been shown that the gene expression profiles and genomic signatures of NCI60 have been further utilised to identify phenotype-specific drugs. The gene expression signature of NCI60 incorporated with the drug sensitivity results from over 40,000 compound screens have effectively identified targets not only with selectivity to the RAS and PI3K pathways but also with disease specificity to breast cancer subtypes (basal vs. luminal). This shows that oncogenomic data derived from a mixed assembly of cancer cell lines can be robust to provide valid therapeutic leads which are disease or phenotype specific, which further supports the possibility to establish a diagnostic-therapeutic framework incorporating both genome-scale data for cancer subtype identification and experimental models for therapeutic target discovery.

It is an object of the present invention to facilitate the development of better prognostic and therapeutic strategies which will benefit cancer patients with novel treatment options and to improve the overall survival.

SUMMARY OF THE INVENTION

In a first aspect the present invention is directed to a method of generating a scheme allowing classification of a cancer of an individual patient for estimating a clinical outcome for said patient, wherein the method comprises:

a) identifying subtype clusters of a cancer type based on comparison of a set of gene expression data derived from clinical cancer samples of multiple test subjects suffering from said cancer type; wherein clinical samples are divided into subtype clusters of said cancer type based on the similarity of their gene expression data;

b) correlating the subtype clusters identified under a) to a specific clinical outcome of cancer;

c) determining an epithelial-mesenchymal transition (EMT) score, comprising:
   i) determining the quantitative expression of at least two markers wherein each of these markers is either characteristic for a mesenchymal cell phenotype or for a epithelial cell phenotype, for determining said epithelial-mesenchymal transition (EMT) signature;
   ii) determining the quantitative expression of the at least two markers in said patient sample and comparing it with the epithelial-mesenchymal transition (EMT) signature to assign an epithelial-mesenchymal transition (EMT) score for said patient sample;

d) estimating an outcome of a patient suffering from said cancer by assigning the set of gene expression data of said patient sample to any one of the subtype clusters according to a) and b), and by determining the patients epithelial-mesenchymal transition (EMT) score.

In a second aspect, the present invention refers to a method of estimating a clinical outcome of a patient suffering from epithelial ovarian cancer (EOC) wherein the method comprises:

a) providing a set of expression data in a patient sample obtained from a patient suffering from epithelial ovarian cancer (EOC);

b) assigning the set of expression data derived from said patient sample to one of five subtype clusters for epithelial ovarian cancer (EOC), wherein the first of the five subtype clusters of epithelial ovarian cancer (EOC) is characterized by the genes referred to in Gene List 2-Epi A;

wherein the second of the five subtype clusters of epithelial ovarian cancer (EOC) is characterized by the genes referred to in Gene List 2-EpiB;

wherein the third of the five subtype clusters of epithelial ovarian cancer (EOC) is characterized by the genes referred to in Gene List 2-Mes;

wherein the fourth of the five subtype clusters of epithelial ovarian cancer (EOC) is characterized by the genes referred to in Gene List 2-StemA;

wherein the fifth of the five subtype clusters of epithelial ovarian cancer (EOC) is characterized by the genes referred to in Gene List 2-StemB;

c) determining an EMT score for the patient sample; and d) estimating the clinical outcome depending on any one of the five subtype clusters and the EMT score to which the patient sample is assigned.

In a third aspect, the present invention refers to a method of determining whether the epithelial mesenchymal score of a patient suffering from a cancer can be changed by administering an EMT reversal agent to increase patients susceptibility for an anti-cancer treatment, wherein the method comprises classifying a tumor sample of said patient using a method of the present invention to determine the cancer subtype and EMT score; after determining the cancer subtype and EMT score determining whether a treatment with an EMT reversal agent is necessary to sensitize said patient to anti-cancer treatment.

In a fourth aspect the present invention refers to a cluster characterized in that it comprises at least one subtype cluster selected from the group consisting of subtype clusters shown in Gene List 2-Epi A, subtype cluster shown in Gene List 2 Epi-B, subtype cluster shown in Gene List 2-Mes, subtype cluster shown in Gene List 2-Stem A and subtype cluster shown in Gene List 2-Stem B.

In a fifth aspect, the present invention refers to a computer readable medium having stored therein a computer program comprising a set of executable instructions, when executed by a computer processor, controls the processor to perform the method of the present invention.

In a sixth aspect, the present invention refers to a computer program comprising a set of executable instructions, when executed by a computer processor, controls the processor to perform the method of the present invention.

BRIEF DESCRIPTION OF THE DRAWINGS

The invention will be better understood with reference to the detailed description when considered in conjunction with the non-limiting examples and the accompanying drawings, in which.

DETAILED DESCRIPTION OF THE PRESENT INVENTION

Figure 1:
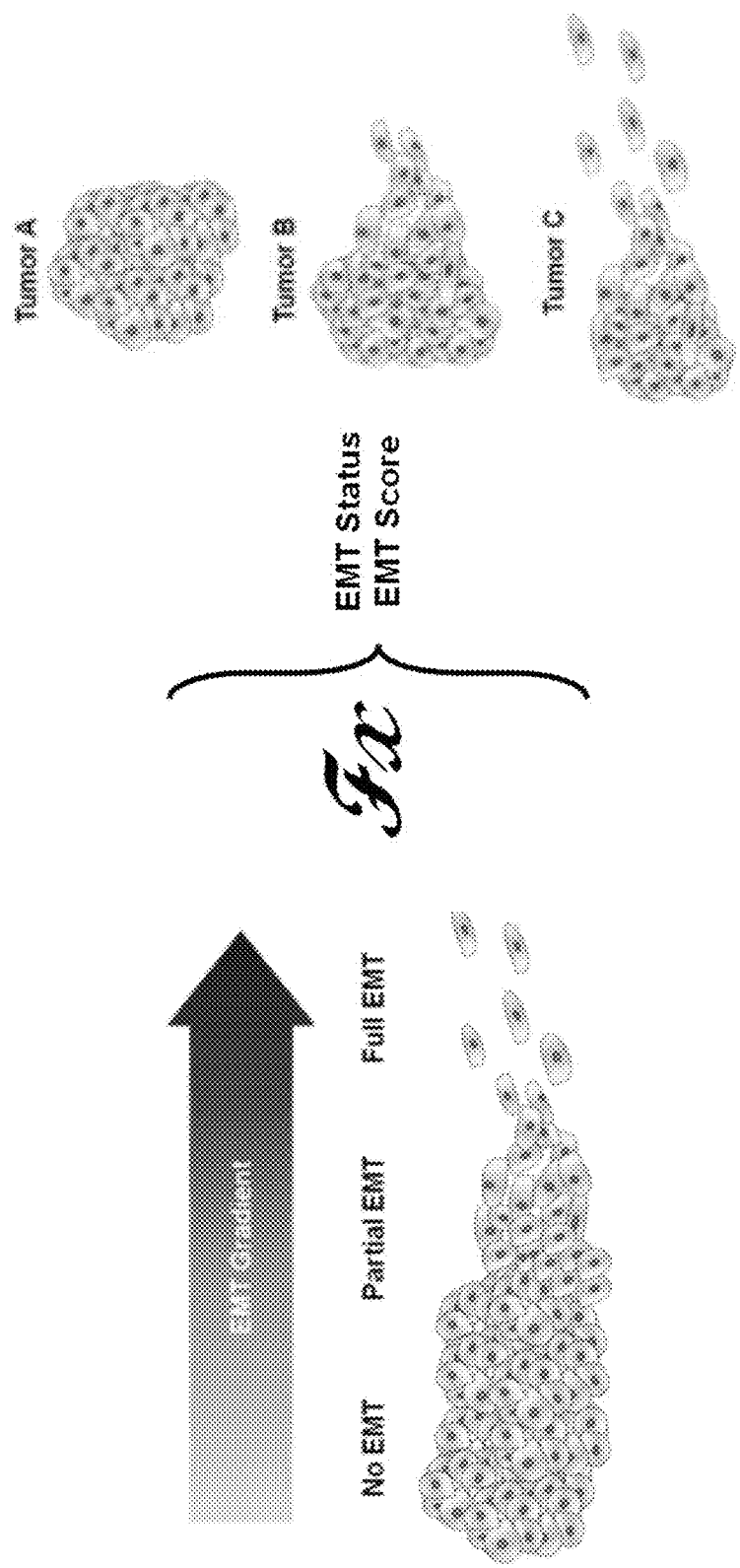
FIG. 1 shows that epithelial-mesenchymal expression (EMT) gradient contributes to tumor heterogeneity. The entire tumor can be regarded as a function (Fx) of the EMT process which encompasses different proportion of cancer cells that have not undergone EMT (No EMT), those have undergone partial EMT, and those have undergone full EMT. The EMT Status or EMT Score can thus represent different tumors (Tumor A, Tumor B, and Tumor C).

To be able to provide a method which allows assisting determination or classification of the possible outcome of cancer of a patient suffering or suspected to suffer from cancer, it is necessary at first to establish a general classification scheme established on the basis of data from patients who are confirmed to suffer from said cancer.

Therefore, in a first aspect the present invention is directed to a method of generating a scheme for classifying a cancer of an individual patient. The classification scheme allows estimating the clinical outcome for said patient suffering from cancer or suspected to suffer from cancer. In one example, the method comprises:
a) identifying subtype clusters of a cancer type based on comparison of a set of gene expression data derived from clinical cancer samples (such as tissue samples or single cells) of multiple test subjects suffering from said cancer type; wherein clinical samples are divided into subtype clusters of said cancer type based on the similarity of their gene expression data;
b) correlating the subtype clusters identified under a) to a specific clinical outcome of cancer by comparing the single samples assigned to any one of the subtype clusters with the clinical development of the test subject from which the respective set of gene expression data is obtained;
c) determining an epithelial-mesenchymal transition (EMT) score, comprising:
  i) determining the quantitative expression of at least two markers wherein each of these markers is either characteristic for a mesenchymal cell phenotype or for a epithelial cell phenotype, for determining said epithelial-mesenchymal transition (EMT) signature;
  ii) determining the quantitative expression of the at least two markers in said patient sample and comparing it with the epithelial-mesenchymal transition (EMT) signature to assign an epithelial-mesenchymal transition (EMT) score for said patient sample;
d) estimating an outcome of a patient suffering from said cancer by assigning the set of gene expression data of said patient sample to any one of the subtype clusters according to a) and b), and by determining the patients epithelial-mesenchymal transition (EMT) score.

For identifying subtype clusters expression data sets of genes, such as microarray expression data sets, from patients suffering from the type of cancer for which the classification scheme is to be established are obtained. In one example the microarray technology used in these studies was for example from Affymetrix. However, any microarray technology known in the art can be used herein. Following hybridization with complementary cDNA of each tumor sample RNA a first data file is generated by scanning each microarray. The scanning results are provided as a table comprised of the fluorescence measurement and feature identity for each pixel of a scan. A microarray feature is an area on the array occupied by a population of oligonucleotide probes with the same sequence. A feature is comprised of many pixels. The expression data in the first file can be processed to generate the values found in a second file comprising a single value for each feature. Each value in the second file is a statistical "summary" of the fluorescence from a single feature. The second file contains the information for viewing the images that result from scanning the hybridized arrays.

In a next step the data can be normalized and standardized to allow comparison of expression data in case they were obtained from different sources. Methods to normalize and standardize data from different sources are known in the art. For example robust multichip average (RMA) normalization can be performed on each different dataset from a different source. Such a method comprises adjusting background and/or quantile normalization and/or log transformation of probe values. RMA is an algorithm used to create an expression matrix from expression data, such as Affymetrix data. The raw intensity values are background corrected, log 2 transformed and then quantile normalized. Next a linear model is fit to the normalized data to obtain an expression measure for each probe set on each array (Irizarry, R. A., 2003, Biostatistics, vol. 4, no. 2, pp. 249).

For example, for quantile normalization it is assumed that the distribution of gene abundances is nearly the same in all samples. For convenience the pooled distribution of probes on all chips is taken. Then to normalize each chip, for each value, the quantile of that value in the distribution of probe intensities is computed; the original value is then transformed to that quantile's value on the reference chip. In a formula, the transform is $x_{norm}=F_2-1(F_1(x))$, where $F_1$ is the distribution function of the actual chip, and $F_2$ is the distribution function of the reference chip.

As already mentioned normalization can be another step necessary when datasets come from different sources. Standardization is used to eliminate batch effects. The normalized data can be first visualized by principal component analysis (PCA) which reports the value of each patient gene expression reduced to 3 dimensions. In reality each patient should be represented by a 22000 dimension vector. Since such a vector is impossible to calculate the projected vector is only in 3 dimensions; a 3D representation offers more than 30% of the total information contained in such a vector and allows visualizing the relative position of each patient in a cohort. For example, in an exemplary study described herein it was found that patients in different datasets were scattered and did not overlap (data not shown). In one example ComBat was used to remove batch effects.

ComBat is based on parametric and nonparametric empirical Bayes frameworks for adjusting data for batch effects that is robust to outliers in small sample sizes and performs comparable to existing methods for large samples (Johnson, W. E., Li, C., Biostatistics, 2007, vol. 8, no. 1, pp. 118).

In one example identifying subtype clusters comprises:
a') selecting a subset of genes which are most variably expressed across all set of gene expression data;
b') subjecting the most variably expressed genes determined under a) to consensus clustering to identify said subtypes of said cancer type or in other words, pooling the genes that are most variably expressed into different clusters.

Step a' is also referred to as filtering. Filtering is carried out to select a subset of variably expressed gene across all samples. A gene is considered most variably expressed across all sets of gene expression data of all clinical samples referred to under a') if the standard deviation of the gene expression is higher across all sets of gene expression data in comparison to the standard deviation of any other gene. In one example the standard deviation is set to be 1.05. In another example, a gene is considered most variably expressed across all sets of gene expression data of all clinical samples referred to under a') if said gene has a higher variability in expression among all sets of expression data obtained from the clinical samples.

In general, cluster analysis permits the discovery of distinct and non-overlapping sub-populations within a larger population, the member items of each sub-population sharing some common features or properties. There are many methods to cluster which are known in the art; all of them are based on the computation of some type of geometrical distance between each sample in a collection which then be regrouped into clusters. The geometrical distance being a result for example of different variable expression.

In one example, the most 500 or 600 or 700 or 800 or 900 or 1000 variably expressed genes across all sets of gene expression data will be selected for clustering.

Issues to be addressed when clustering data include i) how to determine the number of clusters; and ii) how to assign confidence to the selected number of clusters, as well as to the induced cluster assignments. For example, consensus clustering provides a method to represent the consensus across multiple runs of a clustering algorithm, to determine the number of clusters in the data, and to assess the stability of the discovered clusters. The method can also be used to represent the consensus over multiple runs of a clustering algorithm with random restart (such as K-means, model-based Bayesian clustering, SOM, etc.), so as to account for its sensitivity to the initial conditions. Finally, it provides a visualization tool to inspect cluster number, membership, and boundaries.

In one example, the clustering algorithm for consensus clustering is hierarchical clustering with agglomerative linkage. More specifically, in one example, the clustering algorithm for consensus clustering is a hierarchical clustering with agglomerative linkage with Euclidean distance and with a sub-sampling ratio of between about 0.5 to 0.9, preferably 0.8 or at least 0.8, for 500, or 800 or 1000 or more than 500, or more than 800 or more than 1000 iterations. An example of consensus clustering that can be used herein has been described by. Monti, S., et al. (2003, Kluwer Academic Publishers, Printed in the Netherlands, Consensus Clustering—A re-sampling-based method for class discovery and visualization of gene expression microarray data).

Once different cancer subtype clusters have been identified the patient data in each cluster are compared with the phenotype of cancer which can be found in each cancer subtype cluster. For example, one group comprises patients having cancer at a more advanced stage and thus a poor prognosis compared to another subtype cluster with patients having a better prognosis. Whether the prognosis is death, survival, treatable with compound X or Y depends on the result of clustering of the initial data for a specific type of cancer. The result obtained can serve as guidance for a physician in making his decision on how to treat the patient.

In one example, assigning the set of gene expression data of the patient sample to a subtype cluster referred to under d) is carried out by:
  selecting a set of gene expression data from test subjects which correlate the best with the cancer phenotype assigned to each of the subtype clusters under b) for a given subtype cluster;
  subdividing said set of gene expression data of a clinical sample selected from all subtype clusters equally into at least two training groups;
  determining gene expression signatures within the at least two training groups which are characteristic for each of the subtype clusters previously determined; and
  comparing the set of gene expression data of a patient sample with the expression signatures for determining to which subtype cluster the patient sample is to be assigned.

In one example, an at least 50% or 60% or 70% or 75% match of the gene expression data of the patient sample with the expression signature of one of the subtype clusters assigns the patient sample to the respective subtype cluster. In other words, in case the gene expression data of the patient for whom the outcome of his or her disease is to be determined is most similar to the expression profile of one of the subtype clusters it will be assigned to this subtype cluster.

There are different statistical methods to assign the expression data of a patient to a specific subtype cluster. In one example, silhouette analysis is used to select sets of gene expression data from test subjects which correlate the best with the cancer phenotype assigned to each of the subtype clusters for a given subtype cluster.

Silhouette refers to a method of interpretation and validation of clusters of data. The technique provides a succinct graphical representation of how well each object lies within its cluster (Rousseeuw, P. J., 1987, Computational and Applied Mathematics, vol. 20, p. 53-65).

In one example, expression profiles having the highest silhouette values are selected from all subtype clusters to be subdivided into the at least two training groups.

Furthermore, a regression model, such as a linear or binary regression model can be used to determine gene expression signatures within one or both of the at least two training groups which are characteristic for each of the subtype clusters previously determined. Regression models are generally used to predict the outcome of a categorical (a variable that can take on a limited number of categories) criterion variable based on one or more predictor variables.

Figure 7A:
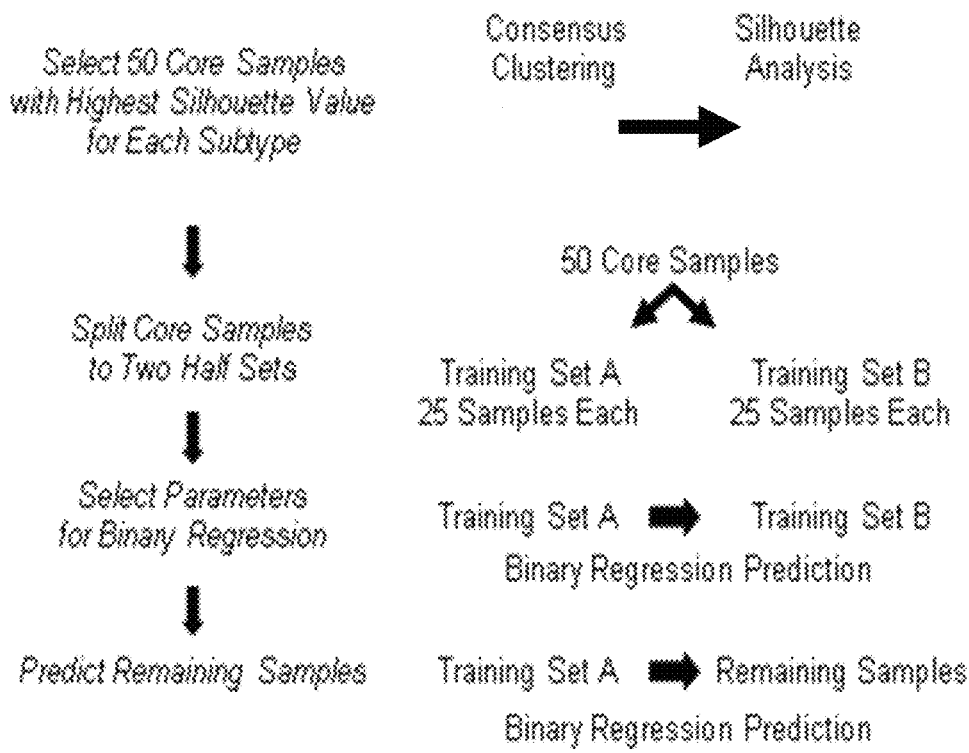
FIG. 7A illustrates the development of classification scheme.

A flowchart illustrating such a process is shown in FIG. 7A.

In one example, for determining to which subtype cluster the patient sample is to be assigned a Bayesian probit regression model can be used. A probit model is a type of regression where the dependent variable can only take two values, for example belonging to group a or b.

Finally, the epithelial-mesenchymal transition (EMT) signature can be determined by subjecting the results of the quantitative expression of the at least two markers characteristic for each subtype cluster identified under a) to a regression analysis, such as a logistic binary regression analysis.

The above method can be used for all types of cancer. In one example, the cancer includes, but is not limited to epithelial ovarian cancer (EOC), breast carcinoma, hepatocarcinoma, pancreatic carcinoma, glioblastoma multiforme (GBM), lung carcinoma, colorectal cancer and bladder carcinoma. In one example the cancer is more generally referred to a solid tumor type of cancer. The patient can be a mammal, wherein the mammal includes, but is not limited to humans.

In the following an example is provided illustrating the above method on the basis of a classification scheme generated for patients suffering or suspected to suffer from epithelial ovarian cancer. In this example multiple expression datasets were obtained each including expression microarray data of epithelial ovarian carcinoma derived from a given number of patients. The data were normalized and standardized as described above.

Before clustering is carried out a filtration of highly variably expressed genes across all samples is carried out. This filtering identified 1185 probesets corresponding to 941 genes which are listed in Gene List 1. This Gene List 1 can be used for clustering leading to the identification of the subtype clusters (molecular subtypes).

The result of such a clustering is shown in FIG. 5A. Clustering of 1538 samples using Gene List 1 results in five subtypes which are designated by the associated gene components. The five subtypes are the Epithelial-A (Epi-A) and Epithelial-B (Epi-B) tumor clusters exhibited expression of epithelial cell markers, such as CDH1 (E-cadherin), EPCAM, various keratin genes (KRTs) and CD24. The Mesenchymal (Mes) tumor subtype predominantly expressed fibroblastic/mesenchymal genes, such as PDGFRA, VCAM1, ZEB1, TWIST1, and extracellular matrix genes, including collagen and FN1. The Stem-like-A (Stem-A) and Stem-like-B (Stem-B) tumor clusters did not share many gene markers, but expressed typical markers for epithelial stem cells: LGR5 and PROM1 (CD133), respectively. Stem-A tumors also expressed more MYCN, NCAM, CDH2 (N-cadherin) and proliferation-related genes, suggesting neural characteristics. Epi-B and Mes tumors expressed inflammatory genes, such as multiple interferon down-stream genes, MHC class II genes and immunoglobulin genes.

Therefore, in another aspect of the present invention, it is referred to at least one or at least tow or at least three or at least four or all five group(s) selected from the group of genes belonging to one of the clusters including, but not limited to the group of genes shown in Gene List 2-Epi A, Gene List 2 Epi-B, Gene List 2-Mes, Gene List 2-Stem A or Gene List 2-Stem B.

After having clustered the samples into the five different groups it is now possible to determine to which of these groups any given sample of a patient belongs to. Once the sample has been assigned to one of the five groups it is possible to predict the outcome of the disease, such as epithelial ovarian cancer.

Therefore, in another aspect, the present invention refers to a method of estimating a clinical outcome of a patient suffering from epithelial ovarian cancer (EOC) wherein the method comprises:
a) providing or determining a set of expression data in a patient sample obtained from a patient suffering from epithelial ovarian cancer (EOC);
b) assigning the set of expression data derived from said patient sample to one of five subtype clusters for epithelial ovarian cancer (EOC),
wherein the first of the five subtype clusters of epithelial ovarian cancer (EOC) is characterized by the genes referred to in Gene List 2-Epi A;
wherein the second of the five subtype clusters of epithelial ovarian cancer (EOC) is characterized by the genes referred to in Gene List 2-EpiB;
wherein the third of the five subtype clusters of epithelial ovarian cancer (EOC) is characterized by the genes referred to in Gene List 2-Mes;
wherein the fourth of the five subtype clusters of epithelial ovarian cancer (EOC) is characterized by the genes referred to in Gene List 2-StemA;
wherein the fifth of the five subtype clusters of epithelial ovarian cancer (EOC) is characterized by the genes referred to in Gene List 2-StemB;
c) determining an EMT score for the patient sample; and
d) estimating the clinical outcome depending on any one of the five subtype clusters and the EMT score to which the patient sample is assigned.

In general, the prognosis, outcome or clinical outcome referred to herein refers to the overall probability of survival. The following Table 2 shows significant impact on overall survival of Stem-A and Epi-B signatures being independent prognostic factors from multivariate analysis.

As illustrated in Table 2, the effect of molecular subtyping on prognosis or determination of outcome was significant in both univariate and multivariate Cox regression analyses (Table 2). The results demonstrated robustness of the molecular classification scheme within the serous histotype and suggested that molecular subtyping is an independent prognostic factor for cancer patients, such as EOC patients.

TABLE 2

Univariate and multivariate Cox proportional hazards regression analysis for multiple clinical variables and tumor subtypes.

| Clinical Variables | Sample size (Total n = 537) | Univariate (HR, 95% CI) | p-value | Multivariate (HR, 95% CI) | p-value |
|---|---|---|---|---|---|
| Age (yr) | | | | | |
| <55 | 175 (32.47%) | 1 | | 1 | |
| >=55 | 364 (67.53%) | 1.403 (1.071-1.839) | 0.0141 | 1.285 (0.9781-1.687)* | 0.07173* |
| Stage | | | | | |
| I or II | 47 (8.72%) | 1 | | 1 | |
| III or IV | 492 (91.28%) | 3.907 (1.843-8.285) | 0.00038 | 3.429 (1.591-7.389)* | 0.00165* |
| Grade | | | | | |
| 1 | 17 (3.15%) | 1 | | 1 | |
| >=2 | 522 (96.85%) | 2.58 (0.9578-6.949) | 0.0608 | 1.365 (0.494-3.763)* | 0.54799* |
| Metastasis | | | | | |
| Primary | 500 (92.76%) | 1 | | 1 | |
| Metastasis | 39 (7.24%) | 1.349 (0.8323-2.185) | 0.224 | 1.391 (0.854-2.27)* | 0.1853* |
| Subtype | | | | | |
| Non Epi-A | 483 (89.61%) | 1 | | 1 | |
| Epi-A | 56 (10.39%) | 0.7103 (0.4498-1.122) | 0.142 | 0.9449 (0.5834-1.53)** | 0.8176** |
| Non Epi-B | 384 (71.24%) | 1 | | 1 | |
| Epi-B | 155 (28.76%) | 0.69 (0.5206-0.9144) | 0.0098 | 0.7347 (0.5532-0.976) | 0.033** |
| Non-Mes | 361 (66.98%) | 1 | | 1 | |
| Mes | 178 (33.02%) | 1.171 (0.907-1.513) | 0.225 | 1.01 (0.7771-1.324)** | 0.9164** |
| Non Stem-A | 411 (76.25%) | 1 | | 1 | |

TABLE 2-continued

Univariate and multivariate Cox proportional hazards regression analysis for multiple clinical variables and tumor subtypes.

| Clinical Variables | Sample size (Total n = 537) | Univariate (HR, 95% CI) | p-value | Multivariate (HR, 95% CI) | p-value |
|---|---|---|---|---|---|
| Stem-A | 128 (23.75%) | 1.417 (1.075-1.868) | 0.0135 | 1.382 (1.045-1.83)* | 0.0234* |
| Non Stem-B | 517 (95.92%) | 1 | | 1 | |
| Stem-B | 22 (4.08%) | 1.204 (0.6383-2.271) | 0.567 | 1.14 (0.6033-2.149)** | 0.6886** |

*Multivariate Cox regresion analysis of clinical variable with Stem-A subtype.
**For multivariate Cox regression, each subtype was independently analyzed with the other clinical variables (age, stage, grade, and metastasis) from the remaining subtypes.
Abbreviations:
Epi-A; Epithelial-A,
Epi-B; Epithelial-B,
Mes; Mesenchymal,
Stem-A; Stem-like-A,
Stem-B; Stem-like-B.

The five groups of genes provide a predictive framework that allows assigning data obtained from individual patients to one of the five groups and based on this assignment to make a prognosis regarding the clinical outcome of the cancer.

For example, as shown in the Kaplan-Meier analysis, Epi-A, Epi-B subtypes show better prognosis while Mes subtype are linked with poorer prognosis (FIG. 5C). Of the two groups with Stem-like marker gene expression, patients with Stem-B subtype showed intermediate prognosis, while patients with Stem-A subtype showed poorer prognosis similarly to Mes subtype (FIG. 5C). Thus, the probability of survival decreases in the following order EpiA=EpiB>StemB>Mes=StemA.

Assigning the set of expression data derived from said patient sample to one of five subtype clusters for epithelial ovarian cancer (EOC) can be carried out by methods known in the art. In one example assignment is carried out either a' by clustering, such as consensus clustering, the expression data derived from the patient sample together with the expression data which make up said five different subtype clusters of epithelial ovarian cancer (EOC) to determine to which group the expression data of the patient sample belongs; or b' by subjecting the expression data obtained from the patient sample together with the expression data which make up said five different subtype clusters of epithelial ovarian cancer (EOC) to a regression analysis, such as a binary regression analysis. Examples for a binary regression analysis comprise a logistic binary regression analysis.

Figure 26:
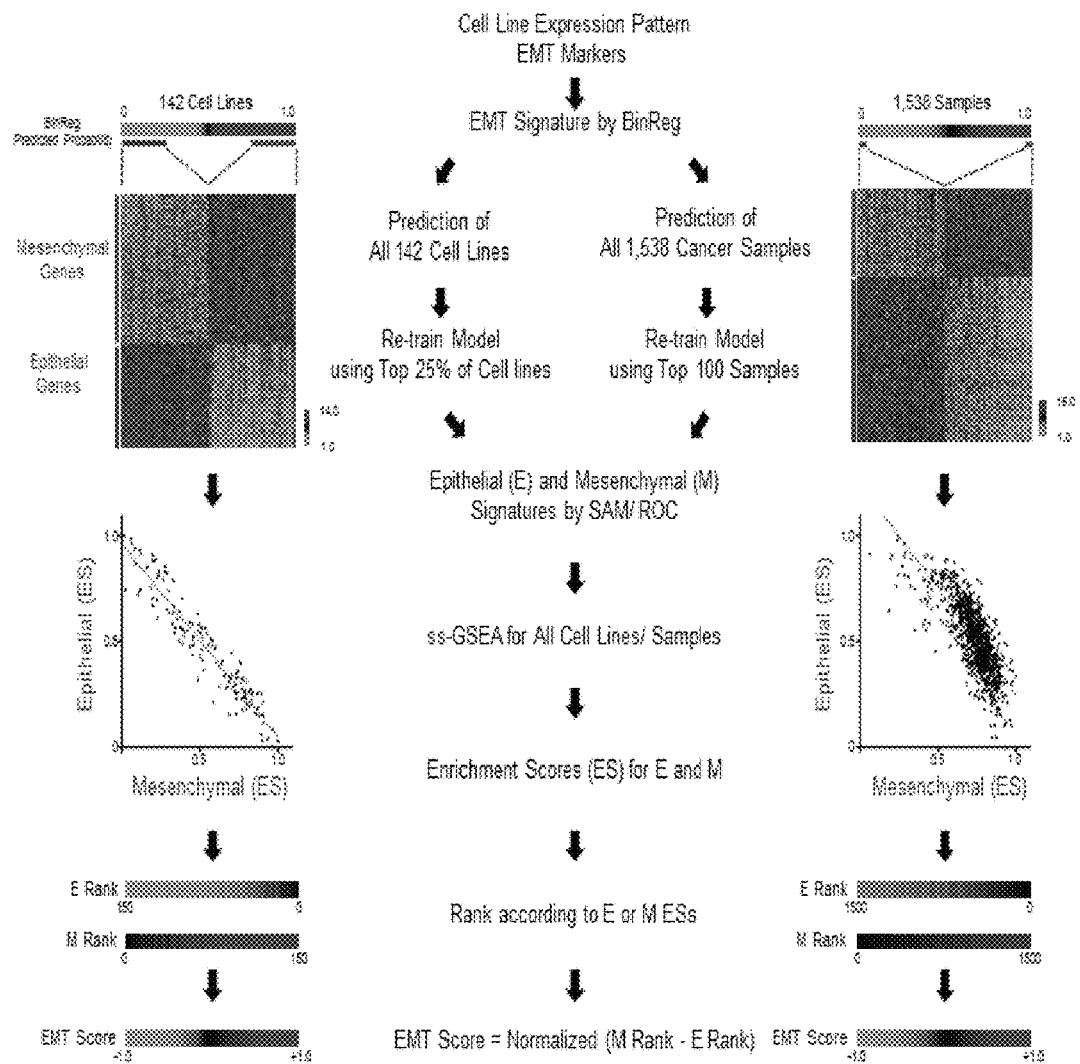
FIG. 26 shows the development of epithelial-mesenchymal transition signature. Expression of E- or N-cadherin on the cell surface of cultured ovarian cancer cell lines detected by immunofluorescent staining. Photographs by inverted microscopy are shown with cell line names. Shown are the photographs of two cell lines that represent each of epithelial (E-cadherin positive/N-cadherin negative), mesenchymal (E-cadherin negative/N-cadherin positive) or intermediate state (equal expression for both of E- and N-cadherins). The cell lines are aligned from the most epithelial, left, to the most mesenchymal, right. Upper and lower panels are to show E- and N-cadherin expression, respectively. (B) Assignment of epithelial or mesenchymal phenotype by scoring cell lines with positivity of E- and N-cadherins. Upper panel. Cadherin score. A subtraction of positivity for N-cadherin from that for E-cadherin was used as a cadherin score to reflect cellular epithelial-mesenchymal status. Cell lines are sorted according to the score. Lower panels. Heatmaps for E- and N-cadherin positivity. The color code for the positivity is shown on the right. Cell line names are shown underneath. The color font indicates the cell line subtype (grey=Epi-A, light grey=Epi-B, dark=Mes, dark grey=Stem-A and black=Stem-B). The cell lines with cadherin score above 2 were arbitrarily assigned to represent cells with epithelial state, while cells with mesenchymal state were defined by the cadherin score below 0. The asterisk indicates that OAW42 was not used for the signature generation, since it exhibits more mesenchymal phenotype in the transcriptome despite of the surface expression pattern of the cadherins (data not shown). (C) A gene signature to distinguish epithelial or mesenchymal state of cells, derived from cultured ovarian cancer cell lines with BinReg. Upper panel: The expression pattern of the EMT signature. The expression of a 50-gene signature is shown as a heatmap (dark=high and grey=low expression). Lower panel: A leave-one-out cross-validation of probabilities for the EMT phenotype (grey=epithelial, black=mesenchymal cells). The accuracy of this signature was 100.0% using 0.5 as a cutoff probability. A black bar indicates the mean value for each group. D and E. Prediction of epithelial or mesenchymal status of experimental models of EMT by BinReg with the gene signature derived from ovarian cancer cells. HMLER cells with experimental perturbations of E-cadherin expression by combinations of shRNAs (D: GSE9691). HMLE cells overexpressing each of multiple EMT inducers (TGF, Twist, Goosecoid=Gsc, and Snail) (E: GSE24202). Predicted probabilities are shown as bar plots with the experimental manipulations beneath the plots. Phenotypic changes by these gene manipulations coincide with altered predicted probability for the EMT signature.

In addition to assigning the expression data of a patient to one of the five specific subtype cluster the epithelial-mesenchymal score (EMT) score is determined. To determine an EMT score for a given type of cancer it is at first necessary to generate the basis for such a scoring system. FIG. 26 illustrates one example how such a system can develop. It can then be used to assign an EMT scoring to a given patient sample.

An EM scoring methodology of the epithelial-mesenchymal (EM) score can be developed to estimate the sample status for the epithelial or mesenchymal phenotype. A higher or lower EMT score indicates more of the mesenchymal or epithelial phenotype. The EMT score can be derived separately for clinical samples and cell lines. Using the cadherin score, a subtraction of N- from E-cadherin positivity on the cell surface detected by immunostaining, the cell lines can be assigned to the epithelial or mesenchymal phenotype and used to generate a gene expression signature using regression, such as BinReg regression model, so as to distinguish the epithelial, from mesenchymal phenotype. The resultant EM signature comprises a certain number of genes. The EM status can then predicted of clinical samples and remaining cell lines. To re-train the models, the top 100 tumors or the top 20% or 25% or 30% cell lines with the highest probabilities for epithelial or mesenchymal phenotype can be chosen and identified the highly correlated genes using the expression data. Afterwards each new sample can be assigned an individual epithelia-mesenchymal score by subtracting of the rank for mesenchymal from epithelial phenotype.

FIG. 26 illustrates such a method in which two paths for generating such an EMT scoring system are shown. One way uses cell lines while the other one uses the patient data which has been used to generate the subtype clusters.

As described above, for EMT scoring it was necessary to differentiate mesenchymal from epithelial cell types. Markes suitable for differentiating between mesenchymal and epithelial cells which are known in the art can be used. For example, markers for E-cadherin and N-cadherin can be used. The results of measuring the staining, such as immunostaining intensities for both markers are recorded (see e.g. FIG. 12A) and a cadherin-score is established by subtraction of the E-cadherin signal from the N-cadherin signal.

Using this scoring system an EMT scoring can be assigned to any given test sample from a patient. The EMT scoring is used together with the assignment to a specific subtype cluster to provide a prognosis regarding the clinical outcome of cancer.

Referring now to the example for epithelial ovarian cancer, the EMT score referred to under c) can be determined by a") computing an enrichment score by integration of the difference between the empirical cumulative distribution functions of genes from Gene List 3 and genes not in Gene List 3 for each set of expression data from the individual patient samples to determine the epithelial rank or mesenchymal rank of a sample; and b") determining the EMT score by subtracting the value, such as the normalized value, for the epithelial rank from the value, such as the normalized value, for the mesenchymal rank.

In another example, the EMT score referred to under c) for a patient cancer sample is determined by a") computing an enrichment score by integration of the difference between the empirical cumulative distribution functions of genes from Gene List 4 and genes not in Gene List 4 for each set of expression data from the individual patient cancer sample to determine the epithelial rank or mesenchymal rank of a sample; and b") determining the EMT score by subtracting the value, such as the normalized value, for the epithelial rank from the value, such as the normalized value, for the mesenchymal rank.

It is also noted that integration of the difference between the empirical cumulative distribution functions of genes from Gene List 3 or Gene List 4 and genes not in Gene List 3 or Gene List 4, respectively, for each set of expression data from the individual patient cancer sample, to determine the epithelial rank or mesenchymal rank of a sample can be carried out using single sample an enrichment analysis, such as gene set enrichment analysis (ss-GSEA).

Gene Set Enrichment Analysis (GSEA) (developed at the Broad Institute of MIT and Harvard) is a computational method that determines whether an a priori defined set of genes shows statistically significant, concordant differences between two biological states (e.g. phenotypes).

As previously mentioned when handling data obtained from different sources, barch effects can be removed using methods known in the art, such as ComBat.

In another aspect, the present invention is directed to a method of selecting model cancer cell lines for studying the effect of drugs. The method can include, but is not limited to firstly determining model cancer cell lines having an expression profile which is closes to the expression profile of a tumor specimen obtained from a patient suffering from said cancer; and secondly using said model cancer cell line to study the effect of pharmaceutical compositions which have or possibly show a therapeutic effect.

In another aspect, the present invention refers to a method of determining whether the epithelial mesenchymal score of a patient suffering from a cancer, such as epithelial ovarian cancer, can be changed by administering an EMT reversal agent to increase patients susceptibility for an anti-cancer treatment, wherein the method comprises classifying a tumor sample of said patient using a method of the present invention to determine the cancer subtype and EMT score; after determining the cancer subtype and EMT score determining whether a treatment with an EMT reversal agent is necessary to sensitize said patient to anti-cancer treatment.

The anti-cancer treatment referred to above can be any one of administering an anti-cancer drug, surgery, chemotherapy, or radiation therapy, or hormonal therapy, or a combination of these types of treatment.

For example, for ovarian cancer, such as epithelial ovarian cancer there are basically three forms of treatment. The primary one is surgery at which time the cancer is removed from the ovary and from as many other sites as is possible. Chemotherapy is the second important modality. This form of treatment uses drugs to kill the cancer cells. Taxene and/or platinum-based chemotherapy based anti-cancer drugs, such as carboplatin and paclitaxel are most often used for chemotherapy.

The other modality is radiation treatment, which is used in only certain instances. It utilizes high energy x-rays to kill cancer cells. Surgical treatment of ovarian cancer is best performed by a gynecologic oncologist who has been specially trained in the diagnosis and management of gynecologic malignancy. The treatment of ovarian cancer depends on the stage of the disease, the histologic cell type, and the patient's age and overall condition. The histologic cell type and the extent of disease based on the biopsies performed by the gynecologic oncologist during surgery (staging) are determined by the pathologist who analyzes tissues with a microscope. Based on the results of the method described herein it is now possible to determine a better course of action.

In another aspect, the present invention refers to a computer readable medium having stored therein a computer program comprising a set of executable instructions, when executed by a computer processor, controls the processor to perform the method according to the present invention.

In still another aspect, the present invention refers to a computer program comprising a set of executable instructions, when executed by a computer processor, controls the processor to perform the method according to the present invention.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Materials and Methods
Part A. Genome-scale Gene Expression Meta-analyses
Data Preprocessing of Affymetrix Expression Data
Epithelial ovarian cancer datasets were obtained from multiple data repositories such as Gene Expression Omnibus (GEO), Array Express, Expression Project for Oncology (ExpO), and The Cancel Genome Atlas (TCGA). Microarray data on Affymetrix U133A or U133 Plus 2 platform were utilized for analysis. Robust Multichip Average (RMA) normalization was performed separately on each dataset. The normalized data was compiled and subsequently standardized using ComBat {Johnson, 2007 #38} to remove batch effect. Removal of ovarian cancer cell lines, normal tissues and primary cultured normal cells from the standardized data yielded a dataset of 1,538 ovarian tumor samples. Eleven hundred and eighty-five probes corresponding to 941 genes were retained by applying threshold of standard deviation across all the samples greater than 1.05. The expression values of selected genes were normalized and centered with Cluster 3.0 and further processed to subtype identification.

Consensus Clustering

Consensus clustering (Monti, Savage et al. 2005, Blood, vol. 105, no. 5, pp. 1851) in Gene Pattern (Reich, Liefeld et al. 2006, Nat Genet, vol. 38, no. 5, pp. 500) was used to identify robust clusters that correspond to the distinct subgroups in epithelial ovarian cancer. As the clustering algorithm hierarchical clustering was chosen with agglomerative average linkage, with Euclidean distance and with subsampling ratio of 0.8 for 1000 iterations. The condition of Kmax=18 was employed since it gave a reasonable Gini index and purity with ~0.8 (data not shown).

Predictive Modeling and Validation by ClaNC

Silhouette analysis was performed using Matlab (ver. 7.8.0) to identify core samples that are defined as samples best representing their subtypes with positive silhouette width. Significance analysis of microarrays (SAM) and receiver-operative curve (ROC) were applied to determine the marker genes for each subtype and to assess the gene capability in distinguishing a subtype from the others [Tusher, Tibshirani et al., 2001, Proc Natl Acad Sci USA, vol. 98, no. 9, pp. 5116]. False discovery rate of zero and AUC threshold of >0.78 (up-regulated in the subtype) or <0.22 (down-regulated in the subtype) were used to filter out non-significant genes for SAM and for ROC, respectively. Based on these marker genes, ClaNC was applied to generate signatures for each subtype, and subsequently subtype predictive model of clinical samples (Dabney, 2006, Bioinformatics, vol. 22, no. 1, pp. 122). In order to validate the subtype prediction, ten-fold cross-validation was adopted to provide a sufficient estimation of the predictive model performance without the need of additional validation data. In ten-fold cross-validation, the 1,538 epithelial ovarian cancer samples were randomly partitioned into 10 sets each comprised 153-154 samples (Subramanian and Simon, 2011, Stat Med, vol. 30, no. 6, pp. 642). One set was used as a validation set (to be predicted) whereas the other 9 sets (1384 or 1385 samples) were used to build the predictive model. This process was repeated 10 times such that each set was used as validation set exactly once. This method minimized the bias introduced by the sample order and distribution when assessing the predictive model. Subtype predictions of all the validation sets were combined and compared against the subtype assignment by consensus clustering on all of the 1,538 samples.

Predictive Modeling and Validation by BinReg

Analysis of expression data based on a binary regression model using the BinReg ver. 2.0 was described previously (Mori, Rempel et al., 2008, Cancer Res, vol. 68, no. 20, pp. 8525; Gatza, Lucas et al., 2010, Proc Natl Acad Sci USA, vol. 107, no. 15, pp. 6994). Gene expression signatures were created by choosing the genes whose expression profiles across the training samples most highly correlated with the phenotype. Divide-and-conquer approach was adopted for generating signature for the different subtypes. In each subtype, a binary regression model was built that single out a subtype from the rest. The top 50 core samples were selected by their highest silhouette width of all the five subtypes, and subdivided them into two set of data, training set A and training set B. These training sets were utilized to determine appropriate condition/parameters for the binary regression model. Subsequently, the condition was used to predict the remaining samples by the training set A. To predict the status of the phenotype on a dataset, a Bayesian probit regression model was fitted that assigned the probability that a sample exhibited evidence of the phenotype, based on the concordance of its gene expression values with the signature (Gatza, Lucas et al., 2010, supra)

Single Sample Gene Set Enrichment Analysis

Single sample Gene Set Enrichment Analysis (ss-GSEA) was originally described in a previous study (Verhaak, Hoadley et al., 2010, Cancer Cell, vol. 17, no. 1, pp. 98). It is a statistic that computes, for each sample, the integration of the difference between the empirical cumulative distribution functions (ECDF) of genes in the signature and the genes not in the signature (Verhaak, Hoadley et al. 2010). Given a sample $S=\{x_1, x_2, \ldots x_i, \ldots, x_N\}$, where $x_i$ is the expression value of $i^{th}$ gene, N is the total number of genes, and a geneset G with $N_G$ number of genes, SS-GSEA computes the score by ES(G,S), firstly, convert the gene expression to ranks, i.e. $S=\{\gamma_1, \gamma_2, \ldots, \gamma_N\}$ based on their absolute expression, and rank ordered. Subsequently, SS-GSEA score ES(G,S) is calculated as $$ES(G, S) = \sum_i [P_G(G, S, i) - P_{NG}(G, S, i)]$$

Where $P_G(G,S,i)$ and $P_{NG}(G,S,i)$ are the ECDF of the genes in signature G and genes not in signature G respectively. The ECDF is computed using the equations $$P_G(G, S, i) = \sum_{r_j \in G, j \leq i}^{N} \frac{|\gamma_j|}{\sum_{\gamma_j \in G} |\gamma|}$$

$$P_{NG}(G, S, i) = \sum_{r_j \in G, j \leq i}^{N} \frac{1}{(N - N_G)}$$

$|\cdot|$ is the cardinality.

Statistical Analysis for Clinical Parameters

GraphPad Prism was used to examine statistical significance of clinical stage, primary or metastatic tumors, histological subtypes, or the malignant potential of each subtype by Fisher's exact test. For Kaplan-Meier analysis, the statistical significance was calculated by log-rank test.

Part B. In vitro EMT Modeling in Cancer Cell Lines

Cell Line Subtype Identification by Consensus Clustering

Four independent datasets for ovarian cancer cell lines from Duke University (42 cell lines), Kyoto University (37 cell lines), Singapore (34 cell lines) and National Laboratory (29 cell lines) were analyzed (Guan, Kuo et al., 2007, Clin Cancer Res, vol. 13, no. 19, pp. 5745; Matsumura, Huang et al., 2011, Genome Res, vol. 21, no. 1, pp. 74). The data for total of 142 cell lines were compiled and analyzed with the data of 1,142 core clinical samples in consensus clustering. Realizing that the identified subclass labeling for cell lines did not fully capture the pattern of clinical samples, this labeling was then used as tentative assignment for cell line subtypes for subsequent clustering analysis. After identification of the subtype-specific marker genes using the "cell-line only" expression data with SAM and ROC (Tusher, Tibshirani et al., 2001, Proc Natl Acad Sci USA, vol. 98, no. 9, pp. 5116), a consensus clustering was performed once more relying on the selected gene sets. This analysis yielded a stable subtype classification for the cell lines with reasonable similarity to that for clinical samples. Finally to confirm the expression similarity between cell lines and clinical samples for each subtype, BinReg and ClaNC were adopted to validate the subtype assignment of the cell lines (Dabney, 2006, supra; Gatza, Lucas et al., 2010, supra).

Determination of EMT Phenotype Category in Cancer Cell Lines

An ovarian cancer cell line library, termed SGOCL(42), consisting of 42 different ovarian cancer cell lines of serous, endometrioid, and undifferentiated histology was acquired via various sources and maintained in house. Detailed cell line names and growth conditions can be found in the following Table 3.

TABLE 3

Description of 42 ovarian cancer cell lines used in the study.

| Name | Histology | Media | Original Repository | Catalogue Number | Source |
|---|---|---|---|---|---|
| A2008 | Endometrioid | RPMI 1640 + 5% FBS | | | Kyoto U. |
| A2780 | Undifferentiated | RPMI 1640 + 10% FBS | ECACC | 93112519 | ECACC |
| BG1 | Poorly differentiated | DMEM + 10% FBS + Insulin (1 mg · mL-1) | | | Kyoto U. |
| C13 | Endometrioid | RPMI 1640 + 5% FBS (Iron-supplemented) | | | Kyoto U. |
| CAOV2 | Adenocarcinoma | RPMI + 10% FBS | | | Kyoto U. |
| CAOV3 | Serous | DMEM + 10% FBS | ATCC | HTB-75 | ATCC |
| CHI | Papillary cystadenocarcinoma | DMEM + 10% FBS + Insulin (10 mg · mL-1) + Hydrocortisone (0.5 mg · mL-1) | | | Kyoto U. |
| COLO720E | Adenocarcinoma | RPMI 1640 + 5-10% FBS | ECACC | 93072111 | ECACC |
| DOV13 | Adenocarcinoma | DMEM + 10% FBS | M.D. Anderson Cancer Center | | Kyoto U. |
| EFO21 | Dedifferentiated serous cystadenocarcinoma | RPMI 1640 + 20% FBS + 1 mM NaPy + 1x NEAA | DSMZ | ACC-235 | DSMZ |
| FUOV1 | Serous papillary adenocarcinoma | DMEM/Ham's F-12 (1:1) + 10% FBS | DSMZ | ACC-444 | DSMZ |
| Hey | Serous | RPMI 1640 + 10% FBS | | | Kyoto U. |
| HeyA8 | Serous | RPMI 1640 + 10% FBS | | | Kyoto U. |
| HeyC2 | Serous | RPMI 1640 + 10% FBS | | | Kyoto U. |
| IGROV1 | Endometrioid | RPMI 1640 + 10% FBS | NCI-Frederick | | Kyoto U. |
| JHOS2 | Serous cystadenocarcinoma | DMEM/Ham's F-12 (1:1) + 10% FBS + 0.1 mM NEAA | RIKEN | RCB1521 | Kyoto U. |
| JHOS3 | Serous cystadenocarcinoma | DMEM/Ham's F-12 (1:1) + 15% FBS + 0.1 mM NEAA | RIKEN | RCB1546 | Kyoto U. |
| JHOS4 | Serous cystadenocarcinoma | DMEM/Ham's F-12 (1:1) + 10% FBS + 0.1 mM NEAA | RIKEN | RCB1678 | Kyoto U. |
| OVCAR3 | Serous | RPMI 1640 + 20% FBS + 10 mg · mL-1 Insulin | ATCC | HTB-161 | ATCC |
| OAW28 | Cystadenocarcinoma | DMEM + 10% FBS + 20 IU · L-1 Insulin + 1 mM NaPy | ECACC | 85101601 | ECACC |
| OAW42 | Papillary serous cystadenocarcinoma | DMEM + 10% FBS + 20 IU · L -1 Insulin + 1 mM NaPy | ECACC | 85073102 | ECACC |
| OV17R | Adenocarcinoma | DMEM/Ham's F-12 (1:1) + 5% FBS + 0.4 mg · mL-1 Hydrocortisone + 10 mg · mL-1 Insulin | ECACC | 96020763 | ECACC |
| OV2008 | Serous cystadenocarcinoma | RPMI 1640 + 10% FBS (4 mM L-Glutamine + 1 mM NaPy + 1x NEAA)* | | | Kyoto U. |
| OV56 | Poorly differentiated | DMEM/Ham's F-12 (1:1) + 5% FBS + 0.5 mg · mL-1 Hydrocortisone + 10 mg · mL-1 Insulin | ECACC | 96020759 | ECACC |
| OV7 | Poorly differentiated | DMEM/ Ham's F-12 (1:1) + 5% FBS + 0.5 mg · mL-1 | ECACC | 96020764 | ECACC |

TABLE 3-continued

Description of 42 ovarian cancer cell lines used in the study.

| Name | Histology | Media | Original Repository | Catalogue Number | Source |
|---|---|---|---|---|---|
| OV90 | Serous | Hydrocortisone + 10 mg · mL-1 Insulin MCDB105 (1.5 mg · mL-1 Na2CO3)/M199 + 15% FBS (1:1) | ATCC | CRL-11732 | ATCC |
| ovary1847 (A1847) | Serous | RPMI 1640 + 10% FBS + 10 mg · mL-1 Insulin | | | Kyoto U. |
| OVCA420 | Serous | DMEM + 10% FBS | | | Kyoto U. |
| OVCA429 | Serous | DMEM + 10% FBS | | | Kyoto U. |
| OVCA432 | Serous | DMEM + 10% FBS | | | Kyoto U. |
| OVCA433 | Papillary serous cystadenocarcinoma | DMEM + 10% FBS | | | Kyoto U. |
| OVCAR10 | Poorly differentiated | | | | Kyoto U. |
| OVCAR2 | | RPMI 1640 + 10% FBS + Insulin (10 mg · mL-1) | | | Kyoto U. |
| OVCAR5 | Adenocarcinoma | RPMI 1640 + 10% FBS + Insulin (10 mg · mL-1) | NCI-Frederick | | Kyoto U. |
| OVCAR8 | Undifferentiated | RPMI + 10% FBS + Insulin (10 mg · mL-1) | NCI-Frederick | | Kyoto U. |
| OVK18 | Endometrioid | MEM + 10% FBS | RIKEN | RCB1903 | Kyoto U. |
| PEO1 | Poorly differentiated serous adenocarcinoma | RPMI 1640 + 10% FBS + Insulin (2.5 mg · mL-1) + 2 mM NaPy | CRT | PE Ovarian Adenocarcinoma Cell Line | CRT |
| PEO4 | Poorly differentiated serous adenocarcinoma | DMEM (HG) + 15% FBS + Insulin (2.5 mg · mL-1) + 1x NEAA | CRT | PE Ovarian Adenocarcinoma Cell Line | CRT |
| SKOV3 | Serous | DMEM (HG): DMEM (LG) (1:1) + 10% FBS | ATCC | HTB-77 | ATCC |
| TOV112D | Endometrioid | MCDB105 (1.5 mg · mL-1 Na2CO3)/M199 + 15% FBS (1:1) | ATCC | CRL-11731 | ATCC |
| TykNu | Undifferentiated | DMEM + 10% FCS | JCRB | JCRB0234.0 | Kyoto U. |
| UWB1.289 | Papillary serous | RPMI 1640/MEGM (Bullet Kit) (1:1) + 3% FBS | ATCC | CRL-2945 | ATCC |

Abbreviations:
ATCC: American Type Culture Collection
CRT: Cancer Research Technology (Cancer Research UK)
DSMZ: Deutsche Sammlung von Mikroorganismen and Zellkulturen
ECACC: European Collection of Cell Cultures
JCRB: Japanese Collection of Research Bioresources
Kyoto U.: Dr. Noriomi Matsumura Kyoto University (Matsumura, N., et al, Genome research, 2011, vol. 21, no. 1, pp. 74)
RIKEN: RIKEN BioResource Center The EMT phenotypes of each ovarian cancer cell line were characterized by morphological examinations (phase contrast imaging) and immunofluorescence staining for prototypic EMT markers. Cells were grown on glass coverslips until 70-80% confluence before fixing in cold acetone at −20° C. for 10 min followed by rehydration with PBS and blocking with 3% of BSA in PBS for 60 min. After washing with PBS, incubations with primary antibodies against E-cadherin (BD), N-cadherin (Takara), pan-cytokeratin (AE1/AE3, Dako), and vimentin (Dako) were performed at 37° C. for 1 hr. After washing with PBS, incubation with secondary antibodies conjugated with Alexa-488 (Invitrogen) were performed at room temperature for 1 hr in the dark. After washing with PBS, coverslips were subsequently mounted onto the glass slides with anti-fading mounting media. The staining results were read by three independent researchers (JPT, SWJ, and LYF). For E-cadherin and N-cadherin, only junctional stainings were regarded as positive. Cytoplasmic stainings of E-cadherin and N-cadherin were regarded as negative. A decision matrix was established to determine the EMT phenotype of each cell line into four categories: epithelial (E), intermediate epithelial (Int E), intermediate mesenchymal (Int M), and mesenchymal (M). In addition, the staining intensities were also documented as 0 (negative), 1 (weak positive), 2 (positive), and 3 (strong positive).

Quantification of EMT Status in Cancer Cell Lines

SGOCL(42) was grown in 10-cm tissue culture plates until 90% confluence before harvesting. Each cell line was duplicated. RNAs were extracted by using Qiazol (Qiagen) followed by clean-ups with miRNeasy columns (Qiagen). 500 ng of cell line RNAs were subjected for real-time PCR analysis for the expression levels of EMT genes. The expression levels of EMT markers were validated by using real-time quantitative PCR (qPCR) amplifications of 84 known molecules in EMT pathway (SABiosciences RT$^2$ Profiler EMT pathway, PAHS-090). The reactions were carried out according to the manufacturer's protocol by using 7900HT Fast Real-Time PCR System (Applied Biosystems). In brief, total RNAs were converted to cDNA by the First Stand Synthesis Kit. cDNA templates were mixed with the RV qPCR Master Mix. Equal volumes of mixtures were aliquot to the PCR plate (QIAGEN SA Biosciences RT$^2$ Profile EMT PCR Array) with PCR primers of genes of interest, 5 housekeeping genes (Beta-2-microglobulin, Hypoxanthine Phosphoribosyltransferase 1, Ribosomal Protein L13a, Glyceraldehyde-3-phosphate Dehydrogenase, Actin, beta) and 5 assay quality controls (1 human genomic DNA contamination, 2 reverse transcription control, 2 positive PCR control). Delta-Ct (dCt) and delta delta-Ct (ddCt) was calculated. Delta-Ct values were obtained by subtracting the averaged Ct values for all 5 housekeeping genes (HKG: B2M, HPRT1, RPL13A, GAPDH, ACTB) from the Ct value of the gene of interest (GOI). It can be expressed by the following formula: delta-Ct (GOI)=Ct (GOI)−Average Ct (HKG) whereby: delta-Ct (GOI): Differential threshold cycle (delta-Ct) of the gene of interest (GOD against that of the average of all 5 housekeeping genes. Ct (GOI): Threshold cycle (Ct) for the gene of interest (GOI); Ct (HKG): Threshold cycle (Ct) for the housekeeping gene (HKG)

Example: Delta-$Ct_{CTNNB1}$=$Ct_{CTNNB1}$−[($Ct_{B2M}$+$Ct_{HPRT1}$+$Ct_{RPL13A}$+$Ct_{GAPDH}$+$Ct_{ACTB}$)÷5]

Calculation of delta-delta-Ct: delta-delta-Ct values were obtained by subtracting the reference sample's delta-Ct value of the gene of interest from the sample's delta-Ct value of the same gene of interest.

Example: delta-delta-$Ct_{CTNNB1}$, the reference sample for this study used was PEO1 as it represents an epithelial ovarian carcinoma with positive immunofluorescence staining against epithelial markers (E-Cadherin and pan-cytokeratin) while negative against mesenchymal markers (N-Cadherin and vimentin). Delta-delta-$Ct_{CTNNB1}$ (SKOV-3)=delta-$Ct_{CTNNB1}$ (SKOV-3)−delta-$Ct_{CTNNB1}$ (PEO1).

EMT-Related Cell-based Functional Studies

Pipelines of EMT-related cell-based functional studies including migration assays, anoikis assays, spheroid formation assays, invasion and colony formation assays were established.

Migration assays were performed in a specially designed 96 well-format by seeding approximately 50,000 cells into the wells that have been pre-inserted with stoppers to occlude the center of the wells (Platypus Technology Oris Cell Migration Assays). In migration wells, stoppers were removed after reaching the desired incubation time to allow cell migration over night. In control wells, stoppers were not removed until reaching the migration endpoint. Quantitative readouts of migrations were accessed with two methods. For half of the plates, cells were stained with calcein-AM for 30 mins before subjecting to quantitative fluorescence reading by using a microplate reader (Tecan). For the other half of the plates, cells were fixed with 4% paraformaldehyde followed by permeabilization with 0.1% Triton X-100 and stained with phalloidin conjugated with FITC (Sigma-Aldrich). Images were then captured by using (microscope) at 4× followed by image analysis using metamorph software.

Anoikis resistance assays were performed by seeding $10^5$ cells into 6-well plates of either normal tissue culture plates (TCP; NUNC) or ultra-low attachment plates (ULA; Corning). Cells were incubated for 48 and 96 hrs before subjected for live-cell staining by using calcein AM/EthD-1 (CytoSelect) or subjected for MTT assays (CytoSelect). Fluorescence readouts for calceinAM and EthD-1 and absorbance readout for MTT were obtained by using a microplate reader (Tecan).

Epithelial-mesenchymal Score

A scoring methodology of the epithelial-mesenchymal (EM) score was developed to estimate the sample status for the epithelial or mesenchymal phenotype. A higher or lower EMT score indicates more of the mesenchymal or epithelial phenotype. The EMT score was derived separately for clinical samples and cell lines as below. Using the cadherin score, a subtraction of N- from E-cadherin positivity on the cell surface detected by immunostaining, the cell lines were assigned to the epithelial or mesenchymal phenotype and used to generate a gene expression signature using BinReg so as to distinguish the epithelial from mesenchymal phenotype. The resultant EM signature comprised 125 genes (data not shown). The EM status was then predicted of clinical samples and remaining cell lines by BinReg. To re-train the models, the top 100 tumors or the top 25% cell lines with the highest probabilities for epithelial or mesenchymal phenotype were chosen and identified the highly correlated genes using the expression data through SAM with q-value of 0 and ROC of 0.8. These procedures gave the gene lists of 693 probes for clinical samples (epithelial: 475 probes and mesenchymal: 218 probes; Gene List 4) and 989 probes for cell lines (epithelial: 550 probes and mesenchymal: 439 probes; Gene List 4). Importantly in both of clinical tumors and cell lines epithelial and mesenchymal genes included CDH1 and CDH2, respectively. Moreover, the strong correlations between the EMT score and the CDH1 or CDH2 expression value was observed (Cell-line Spearman p-value, CDH1: 5.96E-37, CDH2: 0.00000112, Tumor Spearman p-value, CDH1: 0, CDH2: 0). The ss-GSEA was then employed to compute the enrichment score of a clinical sample or a cell line based on the expression of epithelial- or mesenchymal signature genes. After ranking each sample according to the epithelial or mesenchymal enrichment score, the subtraction of the rank for mesenchymal from epithelial phenotype was defined as the epithelial-mesenchymal (EM) score.

Part C. Cell-based Small Molecule EMT Screening Assay

Maintenance of Mcherry Fluorescence-labeled NET-II Cells

Stably transfected mcherry fluorescence-labeled NET-II cells are maintained in DMEM supplemented with 10% fetal bovine serum (FBS, Thermo Scientific), 1 µg/mL puromycin (Sigma), 100 units/mL penicillin–100 units/mL streptomycin (1×pen-strep, Invitrogen) and 2 mM L-glutamine (Invitrogen).

Preparation of Compound Stock Plates

Test compounds were purchased from various vendors (Selleck Chemicals, Sigma Aldrich, SYNlthesis Med Chem, and Tocris Bioscience). For screening studies, test compounds at both 0.25 mM and 1.0 mM concentrations in DMSO are prepared, each occupying a single well in columns 2 to 11 of 96-well V-bottom plates (Greiner). For dose response studies, selected test compounds were prepared in duplicate wells and serial diluted in DMSO, starting a 1.0 mM concentration. Compound stock plates were stored at −20° C. and thawed at room temperature before use.

Spot Migration Assay

Figure 2:
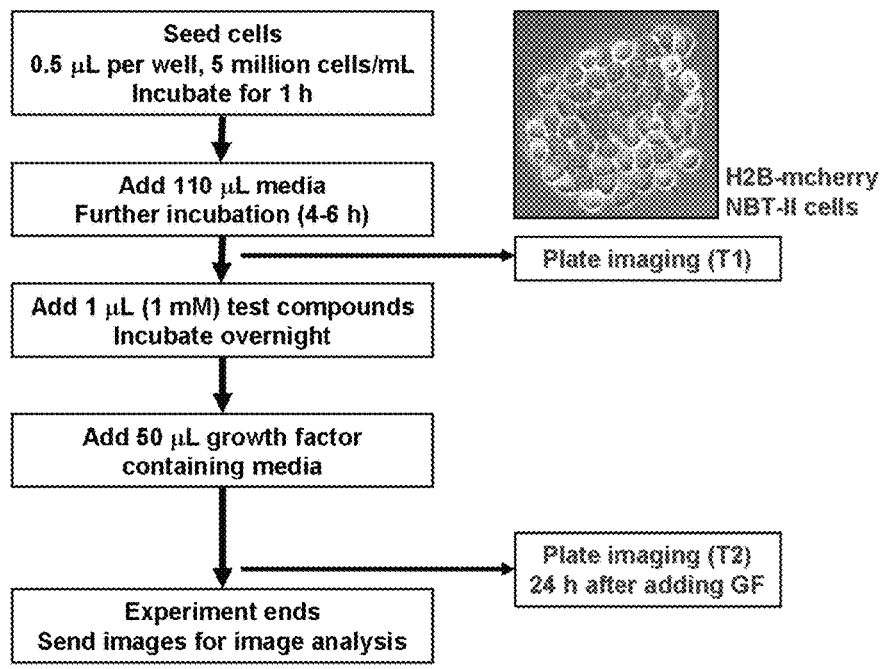
FIG. 2 shows a schematic of spot migration screening assay work flow.

A schematic for the spot migration assay is illustrated in FIG. 2. Cells were grown up to 80% confluency in tissue culture flasks prior to cell plating. Cells were first trypsinized, concentrated and re-suspended to a density of $5\times10^6$ cell/mL in $CO_2$ independent medium (Invitrogen) supplemented with 10% FBS. The cell suspension was then evenly aliquoted into the wells of 2 columns of a 96-well V-bottom plate. Using a robotic liquid handling station (Bravo, Agilent Technologies), 0.5 µL of cell suspension was transferred from the 2 columns of the cell suspension-loaded plate and deposited into the center of the wells of 2 columns of a 96-well clear bottom, black assay plate (Corning). This process was repeated six times so that all 96 wells of the assay plate were deposited with a cell suspension spot. The plate was then sealed to minimize evaporation of the cell suspension spots and transferred to a 37° C., 5% $CO_2$ incubator to allow for cells to attach to the culture surface. After one hour, the plate was gently washed with medium once to remove unattached cells, refreshed with 100 µL assay medium (DMEM supplemented with 10% FBS, 1× pen-strep and 2 mM L-glutamine), and then further incubated to allow for cell-cell contacts to establish in the cell colonies.

After 4 hours of incubation, the cell colonies for each well were imaged using a confocal microplate imager (MetaXpress Ultra, Molecular Devices) with 10× Plan Fluor objective, 561 nm laser excitation and 593/40 nm emission filter configuration. Four tiled, non-overlapping images were acquired around the center of each well, which were then stitched together during image analysis to generate a montage covering an area of 3.2 mm×3.2 mm. These images (T1) represent the initial state of the cell colonies before EMT induction.

After the T1 images are acquired, 1 µL of test compounds were transferred from compound stock plates and added to the assay plates. Appropriate negative controls (1 µL DMSO) and positive controls (1 µL 1.0 mM compound in DMSO) were also added into columns 1 and 12 of each assay plate respectively. the assay was adjusted to use AG1478, JNJ38877605 and BMS-536924 as reference positive control compounds for EGF, HGF and IGF-1 induced EMT respectively. The cultures were then further incubated overnight.

The next day, 50 µL of growth factor containing medium was added each well of the assay plates. For each of the EGF, HGF or IGF-1 induced EMT spot migration assays, the final growth factor concentrations was adjusted in each well to be 20 ng/mL EGF (Sigma), 4 ng/mL HGF (Calbiochem) or 150 ng/mL IGF-1 (R&D Systems), respectively. The cultures were then incubated for another 24 hours, to allow for EMT and sufficient cell motility/dispersion to occur in the cell colonies.

Finally, the cell colonies were imaged again using the confocal microplate imager as described above. These images (T2) represent the final state of the cell colonies after compound treatment and EMT induction. The acquired T1 and T2 image sets for each assay plate were then subjected to image analysis.

Image Analysis Routine

Acquired image sets were loaded into image analysis routine developed using Metamorph software. Briefly, a complete image of the entire cell colony in a well was first obtained by stitching the four tiled, non-overlapping images together. Image analysis consists of counting the cell number and measuring the area occupied by the cells. The positive nuclei were segmented using a wavelet decomposition scheme to remove the photonic noise and the inhomogeneous background. A watershed procedure was used to refine the result by separating the confluent nuclei. Also, segmented objects showing sizes smaller than that of a given threshold value was filtered off. Then, the nuclei segmentation was utilized to estimate the area of cell colonies. A morphological filter named close (combination of dilation and erosion) accurately perform the filling of the nuclei area. If some cells break out the colony, the close filter leads to different area containing cells. The biggest area was considered as the colony and other areas represent the outside cell islets. Each well was described by the cell number, the colony area and the cell islets area. The results were then exported.

Part D. EMT Reversal Assays

Maintenance of Ovarian Cell Lines

SKOV3, HEY and OVCAR-2 cells were maintained in RPMI (Invitrogen) supplemented with 10% fetal bovine serum (FBS, Thermo Scientific), 1 µg/mL puromycin (Sigma), 100 units/mL penicillin–100 units/mL streptomycin (1× pen-strep, Invitrogen) and 2 mM L-glutamine (Invitrogen).

Preparation of Compounds

AZD0530 and BIBF-1120 were purchased from Selleck Chemicals and SYN|thesis Med Chem respectively. DMSO was used as a vehicle to dissolve both compounds. A stock concentration of 10 mM was prepared for both compounds and stored at −20° C. and aliquots were thawed at room temperature before use.

EMT Reversal Assay

Cells were grown up to 80% confluency in tissue culture flasks prior to cell plating. Cells were first trypsinized, concentrated and re-suspended to a density of 1×10$^6$ cell/mL in RPMI supplemented with 10% FBS. For each cell lines, 1×10$^5$ cells were plated onto 100 mm cell culture treated dishes (Nunc) for each condition. The cells were then allowed to attach to the culture dish surface and grow overnight in 37° C., 5% $CO_2$ incubator. In drug conditions, the cells were then incubated with each of the compounds at a final concentration of 2 µM for 3 days to allow cell-cell contacts to establish in the dispersed culture. The medium was aspirated from the culture dishes and the cells were washed with PBS $Ca^{2+}$, $Mg^{2+}$ before they were snap-frozen with liquid nitrogen.

Western Blot and Semi Quantitative Analysis

Cells were lysed with RIPA buffer (Sigma) supplemented with protease inhibitor cocktail (Calbiochem) and phosphatase inhibitor cocktail (Roche). Protein concentration was measured using BCA (Pierce) protocol provided by the manufacturer. 8% polyacrylamide gels were used for the separation of proteins and transferred to PDVF membranes (Millipore). Membranes were blocked in 5% non-fat milk (Bio-rad) and incubated at 4 degree Celsius overnight with primary antibodies. E-cadherin antibody was purchased from BD laboratories, MMP13 antibody was purchased from Millipore and Tubulin was purchased from Sigma. The membranes were then incubated with HRP (Amersham) and developed with ECL (Millipore). The membranes were imaged using Gel documentation system with XTcooled Camera (Syngene). The raw intensity of the protein bands were quantified using GeneTools software (Syngene).

Results

Part A. Genome-scale Gene Expression Meta-analyses

Figure 3:
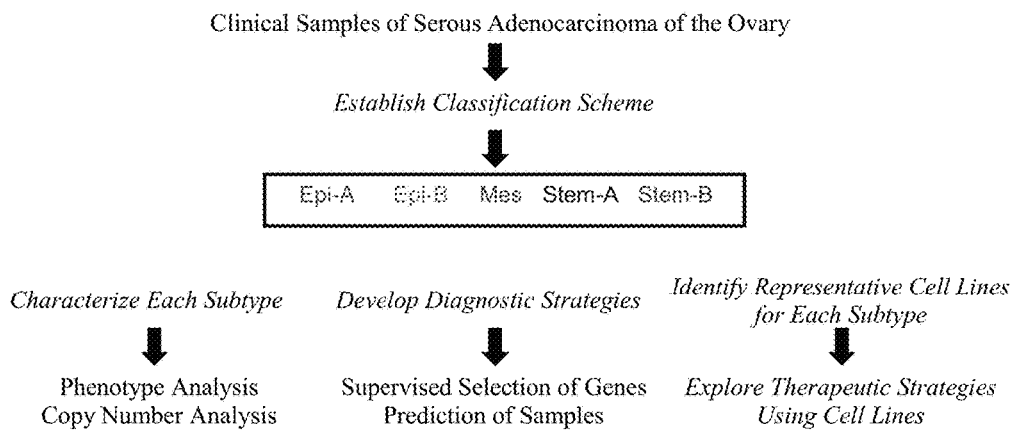
FIG. 3 illustrates integrative analyses for tumors and cell lines to define a novel therapeutic strategy for ovarian carcinoma.

Assessing the Molecular Heterogeneity of EOC and Identifying Clinically Relevant Subtypes Genome-scale gene expression meta-analysis was applied on gene expression profiles of epithelial ovarian cancer (EOC) obtained from publically available databases. The strategy was to firstly identify clinically relevant oncogenomic subtypes based on meta-analysis of expression data. These identified subtypes were further correlated with clinico-pathological factors, transcriptional characters and copy number aberrations. Subsequently, predictive models with supervised approaches were generated to develop gene expression based diagnostics. Representative cell lines for each subtype were identified, the cell line subtypes with in vitro phenotypes were correlated and those cell lines were used as a model to explore possible therapeutic options (FIG. 3).

Figure 4:
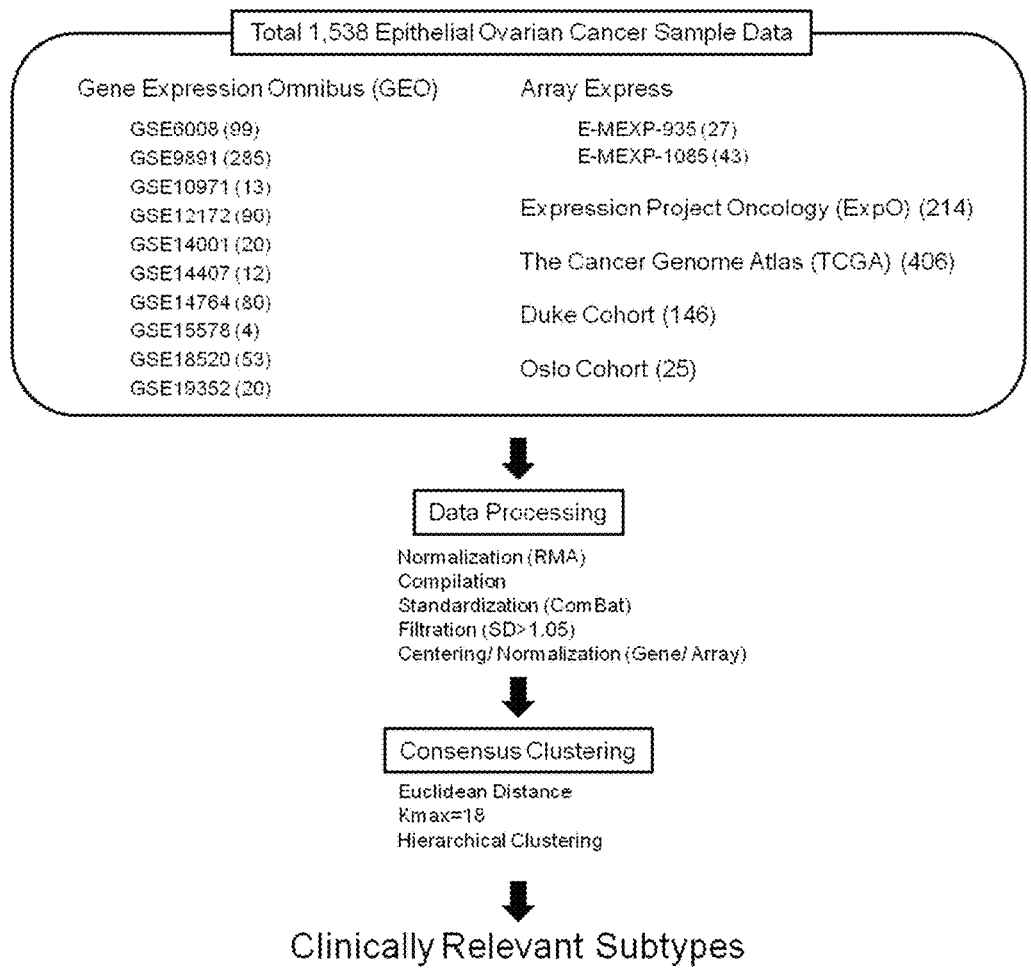
FIG. 4 shows sources of datasets and data processing scheme for investigating phenotypic complexity of EOC.

To investigate the phenotypic complexity of EOC, a large collection of gene expression data was utilized (n=1,538; serous: 1,244, mucinous: 25, clear cell: 25, endometrioid: 92 and others: 56 samples) derived from 17 independent studies (FIG. 4) (Hogdall, Christensen et al., 2003, Cancer, vol. 98, no. 1, pp. 66; Hendrix, Wu et 2006; Cancer Res, vol. 66, no. 3, pp. 1354; Hsu, Balakumaran et al., 2007, J Clin Oncol, vol. 25, no. 28, pp. 4350; Jochumsen, Tan et al., 2007, Int J Gynecol Cancer, vol 17, no. 5, pp. 979; Anglesio, Arnold et al., 2008, Mol Cancer Res, vol. 6, no. 11, pp. 1678; Tone, Begley et al., 2008, Clin Cancer Res, vol. 14, no. 13, pp. 4067; Tothill, Tinker et al., 2008, Clin Cancer Res, vol. 14, no. 16, pp. 5198; Bowen, Walker et al., 2009, BMC Med Genomics, vol. 2, pp. 71; Denkert, Budczies et al., 2009, J Pathol, vol. 218, no. 2, pp. 273; Mok, Bonome et al., 2009, Cancer Cell, vol. 16, no. 6, pp. 521; Pejovic, Pande et al., 2009, Transl Oncol, vol. 2, no. 4, pp. 341; Tung, Mok et al., 2009, Mod Pathol, vol. 22, no. 9, pp. 1243; Iorio, Ricci et al., 2010, Cancer Res, vol. 70, no. 5, pp. 2126).

Figure 5:
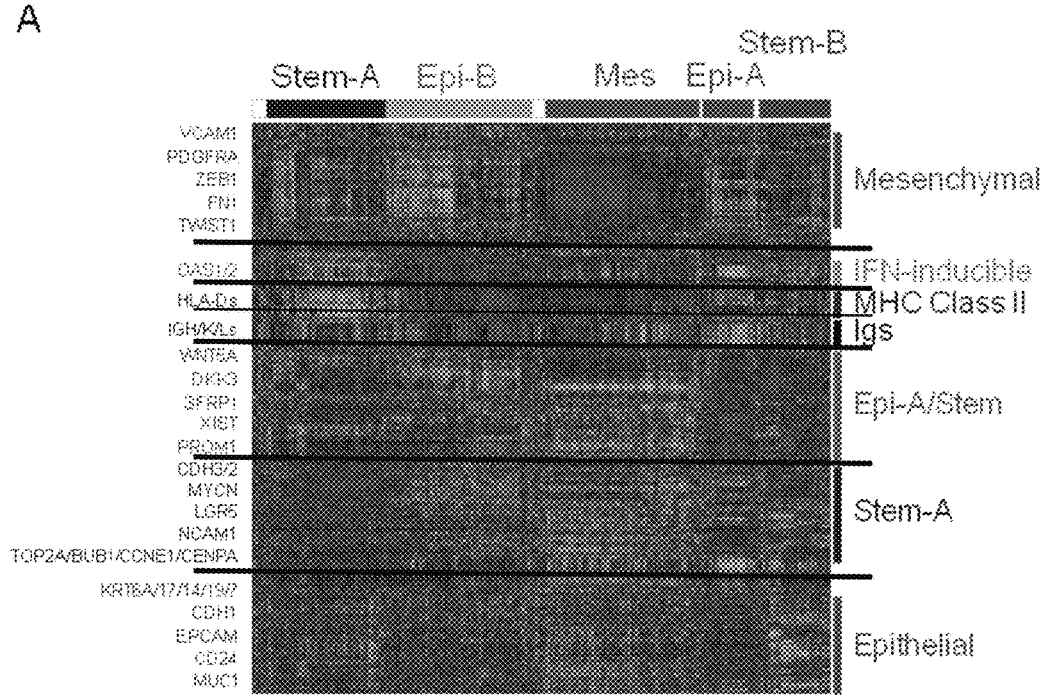
FIG. 5 (A) Gene expression heatmap for the five tumor clusters (dark=high; lighter=low expression). Consensus clustering of 1,538 samples identified five major subtypes, designated by the associated gene components. Note similarity between Epi-A/Stem-B subtype tumors and in the expression pattern of Epi-A/Stem genes and that between Epi-A/Epi-B subtypes for Epithelial genes. (B) Silhouette plot. Samples positive for the silhouette width (SW) in each subtype: Epi-A, 74.8% (101/135); Epi-B, 80.4% (315/392); Mes, 78.9% (325/412); Stem-A, 81.3% (256/315); and Stem-B, 76.7% (145/189). (C) Kaplan-Meier survival analysis based on the clusters. Among data for 1,538 patient samples, survival information for 845 samples was available (Duke: 143, GSE9891: 277, TCGA: 400 and Oslo: 25 samples) (Epi-A: 73, Epi-B: 233, Mes: 245, Stem-A: 190, Stem-B: 50 and others: 54 samples) and used for the Kaplan-Meier analysis. (D) Subtype-specific pathway enrichment. Heatmap shows subtype-specific ss-GSEA scores (false discovery rate (FDR) in significance analysis of microarrays (SAM) q=0%, receiver operation curve (ROC) >0.85) for 1,538 ovarian cancer samples. Gene sets are aligned in descending value of ROC. Samples are aligned by the subtype classification and SW. Dark color=positive SW (core samples); pale color=the samples classified, but negative SW.
Figure 5:
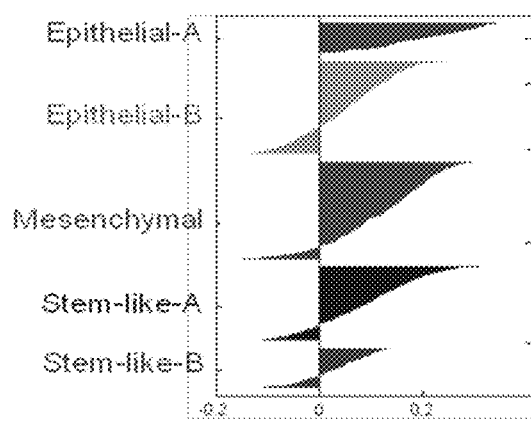
Figure 5:
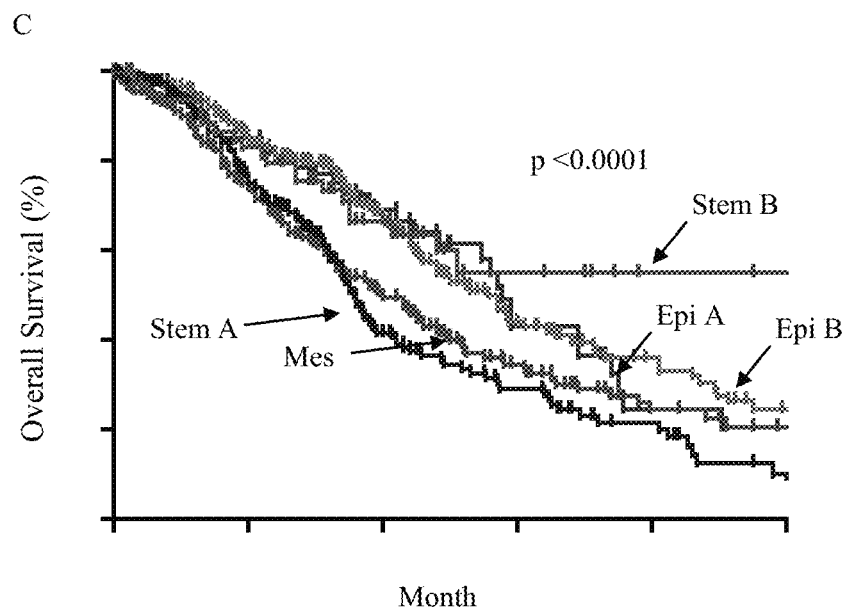
Figure 5:
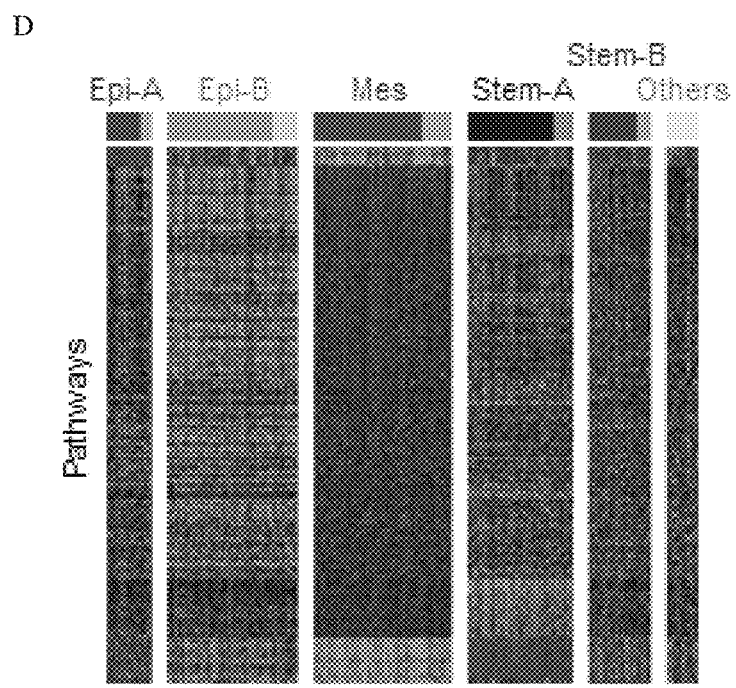

By performing consensus clustering of the assembled dataset, five predominant clusters characterized by distinct gene expression patterns were revealed (FIG. 5). Epithelial-A (Epi-A) and Epithelial-B (Epi-B) tumor clusters were characterized by epithelial cell marker expressions such as CDH1 (E-cadherin), EPCAM, various keratin genes (KRTs) and CD24. Mesenchymal tumor (Mes) subtype predominantly expresses fibroblastic/mesenchymal genes such as PDGFRA, VCAM1, ZEB1, TWIST1 and various extracellular matrices genes like collagen genes and FN1. Stem-like-A (Stem-A) and Stem-like-B (Stem-B) tumor clusters shared expresses LGR5 and PROM1 (CD133), typical markers for epithelial stem cells, respectively {Fodde, 2009 #30}. In addition, Stem-A tumors expressed proliferation-related genes as well as genes such as MYCN, NCAM, CDH2 (N-cadherin), implying their neural characters. Inflammatory genes, which were composed mainly by multiple interferon down-stream genes, MHC class II genes and immunoglobulin genes, were obviously detected in Epi-B and Mes tumors but rarely detected in the other subtypes (FIG. 5A). The silhouette plot confirmed the similarity of each tumor sample within a subtype, indicating robustness of the classification (FIG. 5B).

Our study exhibits robustness, it describes the molecular subtypes in details and provides clues for therapeutics intervention based on this novel stratification.

These identified subtypes were correlated with various clinico-pathological characters that are known to be important in ovarian cancer. Firstly, significance of the subtypes was investigated while correlated with patient outcomes. As shown in the Kaplan-Meier analysis, Epi-A, Epi-B subtypes show better prognosis while Mes subtype are linked with poorer prognosis (FIG. 5C). Of the two groups with Stem-like marker gene expression, patients with Stem-B subtype showed intermediate prognosis, while patients with Stem-A subtype showed poorer prognosis similarly to Mes subtype (FIG. 5C). It was confirmed that the tumors with the subtype were indeed characterized by epithelial, mesenchymal or stem-cell markers based on the Single Sample Gene Set Enrichment Analysis (ss-GSEA) (Verhaak, Hoadley et al., 2010, supra) with the literature-curated gene signatures for epithelial, mesenchymal and stem cells (FIG. 5D).

Figure 6:
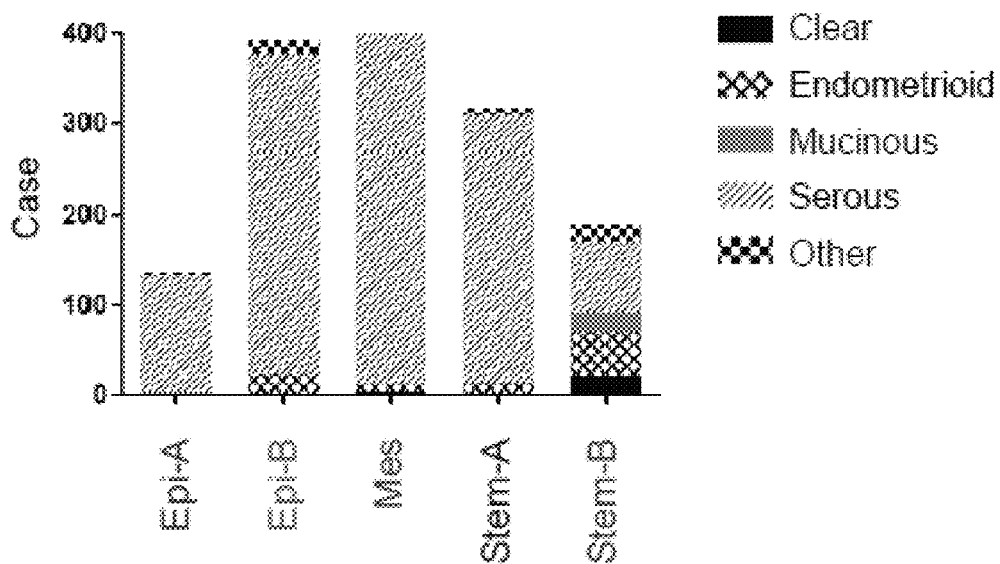
FIG. 6 (A) Relationship between expression subtypes with histological subtypes (upper panel) or the malignant potential (bottom panel) by histograms. Stem-B subtype had multiple histological characteristics. Most of low malignancy potential (LMP) tumors were classified as Epi-A subtype. (B) Kaplan-Meier survival analyses stratified by the clinical stage. Patients with stage I or II Stem-A ovarian carcinomas had significantly worse outcomes; Epi-A and Epi-B subtypes showed better prognoses; Stem-B cancers were no more benign at advanced stages. (C) Clinical features of subtypes in serous ovarian carcinomas without LMP tumors. Total 758 samples in this category were analyzed (Epi-A; 57, Epi-B; 227, Mes; 245, Stem-A; 188, and Stem-B; 41 samples). Upper panel. Kaplan-Meier analysis of serous ovarian carcinomas without LMP tumors. Lower panels. Relationship between expression subtypes with the clinical stages (left panel), and primary or metastatic tumors (right panel). Abbreviations: Epi-A; Epithelial-A, Epi-B; Epithelial-B, Mes; Mesenchymal, Stem-A; Stem-like-A, Stem-B; Stem-like-B, LMP; low malignant potential.
Figure 6:
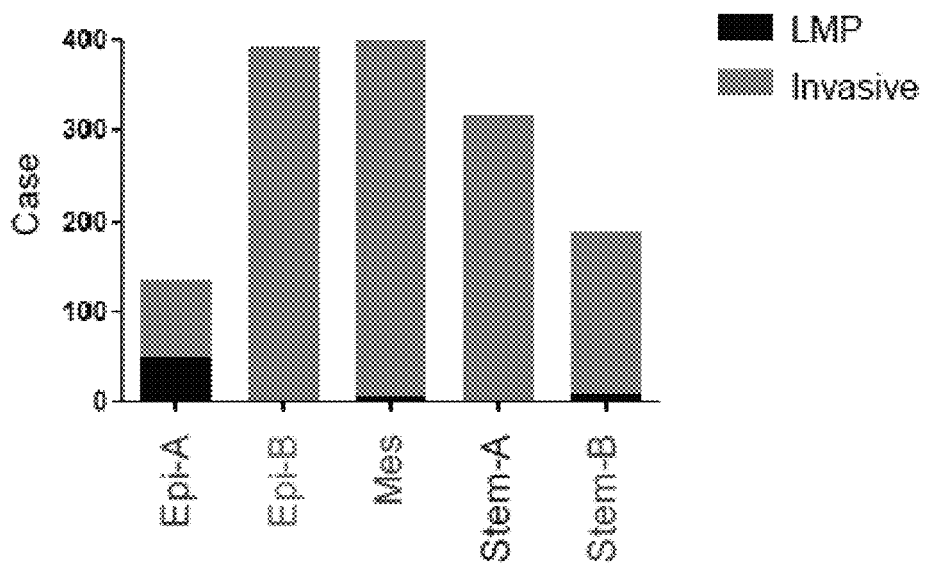
Figure 6:
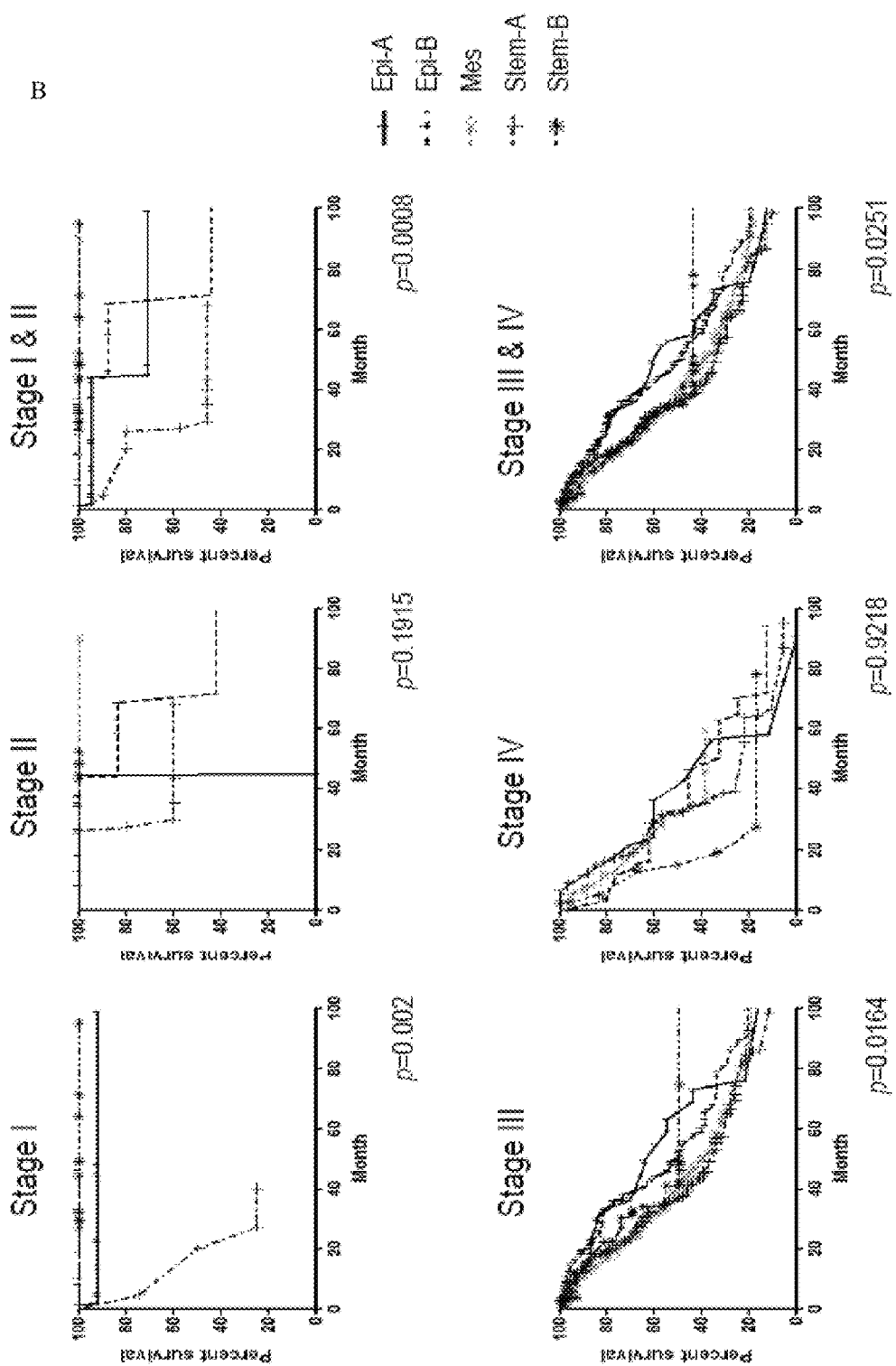
Figure 6:
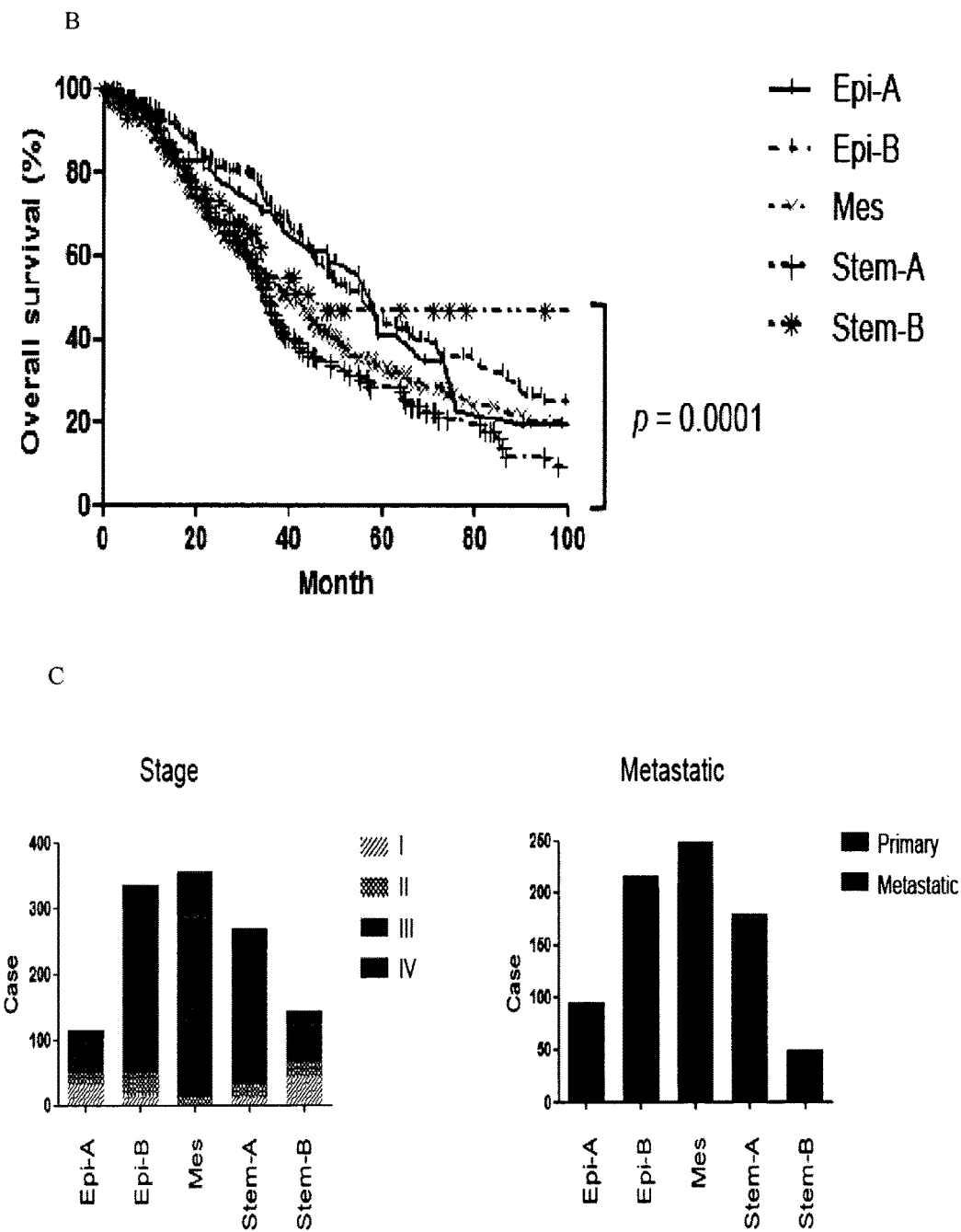

It was noted that serous adenocarcinoma histotype was identified in every subtype suggesting the molecular heterogeneity. Stem-B subtype consisted of multiple histologies and most of tumors with low malignancy potential are classified as Epi-A (FIG. 6A). It was found that Mes tumors were almost exclusively at more advanced stages (Stage III or IV) which could explain the worst prognosis on survival (FIG. 6C). The Epi-A and Epi-B subtypes generally had better prognosis in both early staged (I & II) and advanced staged (III & IV) diseases. Interestingly, the Stem-A subtype showed consistent poorer prognosis in both early staged (I & II) and advanced staged (III & IV) diseases, which indicated an aggressive phenotype associated with the stem cell-like property (FIGS. 6B and 6C). These results illustrated that the expression-based subtyping method could dissect the heterogeneity of ovarian adenocarcinoma and could also identify clinically relevant subtypes. Consistent with the notion that women of an advanced age have a higher risk among all ovarian cancer patient, the highest mean age was found in patients with Stem-A tumors (not Shown)

Development of a Predictive Framework for Ovarian Cancer Subtype Classification

Figure 7B:
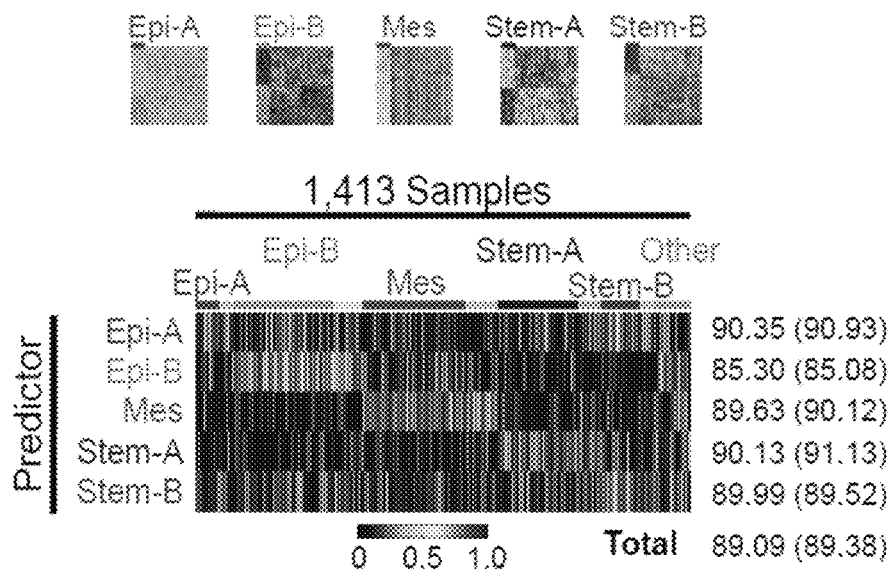
FIG. 7B illustrates a scheme of diagnostic subtype prediction based on Binary Regression model. For each subtype, 50 samples with the highest silhouette values in FIG. 5B were subdivided into training sets A and B, and predictive models were generated based on gene expression arrays of training set A. Multiple tests of predictions from training set A to training set B determined the best condition to perform Binary Regression analysis (BinReg). Defined condition was used to predict the status of the remaining samples. (B) shows diagnostic method to predict the ovarian cancer subtype based on Binary Regression model. Upper panels. Gene expression heatmap for subtype predictor. Expression of predictor genes: dark=high; lighter color=low. Bar=25 samples used to generate the subtype signature. Lower panel. Heatmap for predicted probabilities of subtype status of remaining samples. Dark=high; lighter color=low. Samples were aligned according to the subtype classification by consensus clustering (CC) and the silhouette width (SW). Deep color=positive SW (core samples); pale color=samples classified, but negative SW. Concordance (comparing the subtype assignment by CC of 1,538 samples against the predicted subtype by BinReg) is also shown. Samples with probability>0.5 for a subtype were deemed to be that subtype, whereas probability≤0.5 was deemed as the other subtype. The number in parenthesis indicates the concordance of the prediction against core samples. Subtype prediction of samples in five independent datasets (GSE19829, GSE20565, Japan Kyoto Ovarian Cancer cohort; JPKO, GSE26712 and GSE27651; total n=418). Concordance analyses using the additional independent data were used to validate the ovarian subtype signatures. The subtyping derived from CC of those validation datasets with 1,413 core samples from the initially compiled 1,538 samples was performed. Concordance was calculated by comparing the CC classification with the BinReg prediction. The Mes and Stem A subtypes still show the same trend for overall worst survival. Abbreviations: Epi-A; Epithelial-A, Epi-B; Mes; Mesenchymal, Stem-A; Stem-like-A, Stem-B; Stem-like-B.
Figure 7B:
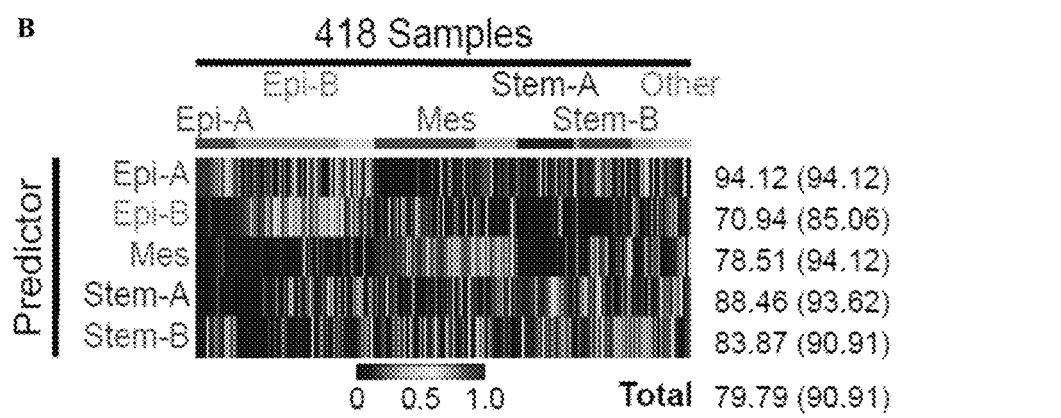
Figure 7B:
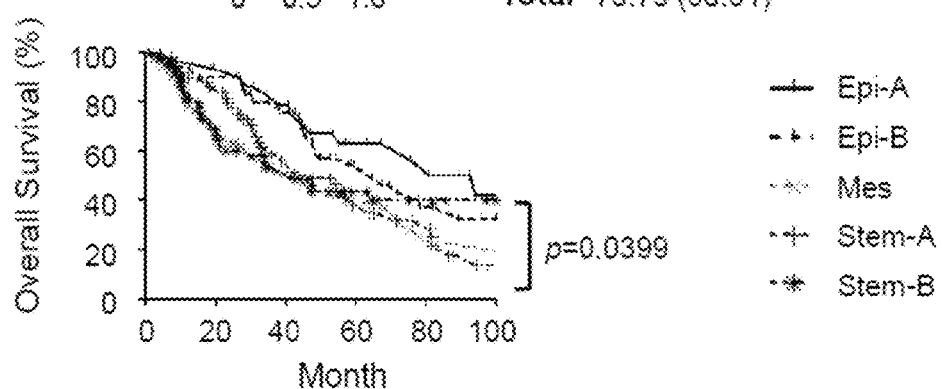

In order to obtain an effective classification strategy for future application, a classification scheme was subsequently developed representing a predictive framework whereby tumor samples can be quantitatively assigned to subgroups based on the patterns of gene expression (FIG. 7A). To overcome insufficient resolution in subtype status prediction of any independent cohort, it was set to develop a statistically sophisticated predictive model for subtype classification. From each subtype, 50 samples were selected with the highest silhouette values that were computed in FIG. 5B, subdivided into two training datasets A and B, and generated predictive models based on gene expression arrays of training set A. Multiple trials of Binary Regression analysis (BinReg) were performed by changing relevant parameters such as the number for metagenes and for genes in a metagene (Bild, Potti et al., 2006, Nat Rev Cancer, vol. 6, no. 9, pp. 735; Mori, Rempel et al., 2008, Cancer Res, vol. 68, no. 20, pp. 8525). The best condition to predict the status of the samples in the training set B was obtained, this defined condition was used to predict the status of all the remaining samples including the training dataset B (FIG. 7B). FIG. 7B(B) shows the heatmap for predicted probabilities for subtype status of the remaining samples. Comparison of the subtype predicted by BinReg with that classified by the consensus clustering (FIG. 5A) revealed overall 89.1% concordance for all the subtypes (89.4% for core samples), clearly indicating the powerful predictive capability of the method. To evaluate the extent to which such classifications are indeed robust, subtype prediction of samples in five independent datasets (GSE19829, GSE20565, Japan Kyoto Ovarian Cancer cohort; JPKO, GSE26712 and GSE27651; total n=418) which were not included in the meta-analysis, were investigated to evaluate the predictive capability as a more rigorous evaluation. In a separate analysis, the data of GSE20565 and JPKO were compiled with that of 1,142 core samples derived from the initial dataset of 1,538 samples and performed the consensus clustering. Afterwards concordance of those two different analytical methods was calculated. The high percentage of overall concordance (90.5% for GSE20565 and 83.6% for JPKO) for all the subtypes (FIG. 8D) clearly demonstrated robustness of this classification scheme as well as sound predictive capability of this predictive model.

Figure 8:
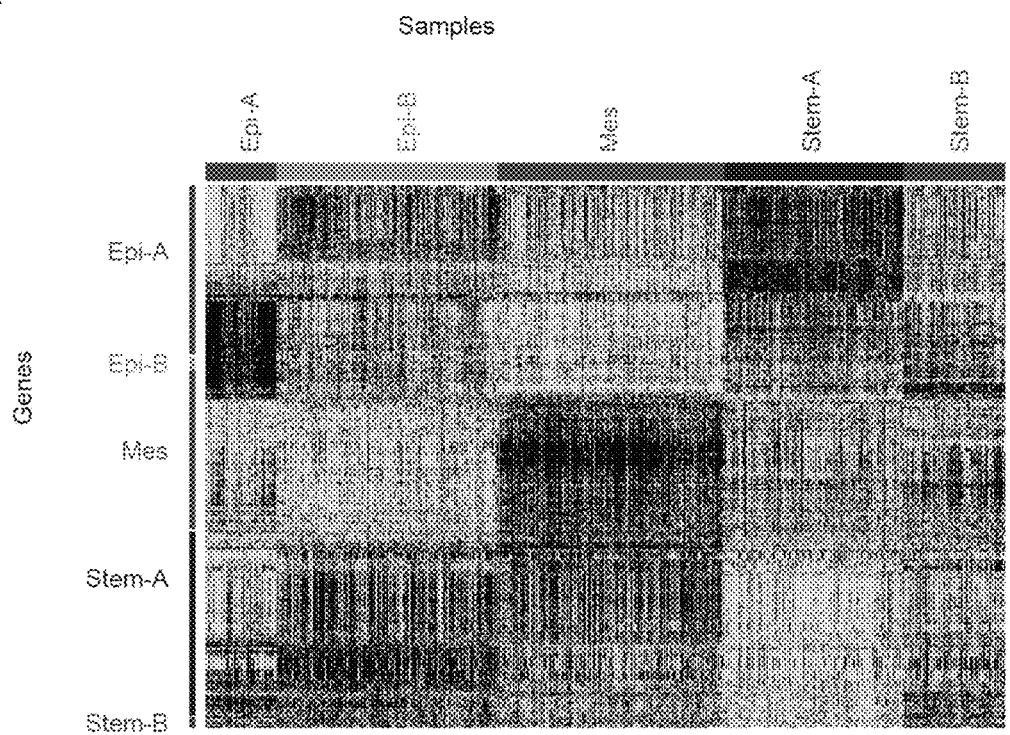
FIG. 8 shows diagnostic subtype prediction by SAM/ROC/ClaNC. (A) Gene expression heatmap of subtype-specific genes. Samples with positive silhouette values are aligned according to their subtype. Gene expression pattern is shown by heatmap (dark=high, lighter color=low expression). The subtype-specific genes were identified using significance analysis of microarrays (SAM) (false discovery rate; FDR q=0%) and receiver operating characteristic (ROC) (>0.78) {Tusher, 2001 #41}. (B) Left panels. Scheme of 10-fold cross-validation. 10-fold cross-validation was performed, in which the expression signatures from 90% samples were generated, the subtype status of the remaining 10% samples was predicted with the signatures by classification to nearest centroids (ClaNC), and these predictions were repeated 10 times. Data of 1,538 epithelial ovarian cancer (EOC) samples were randomly subdivided into 10 blocks of 154 or 153 sample data. Using data from 9 blocks (90% samples) (total 1,384 or 1,385 samples) as training data, subtype identification and subsequent gene selection were performed with consensus clustering (CC), silhouette analysis (SA), SAM and ROC. The remaining block (10% samples) was used as a validation set and the subtype of each sample was predicted by classification to nearest centroids (ClaNC). This process was repeated 10 times, combined predictions and performed Kaplan-Meier survival analysis. Right panels: An example of cross validation (the experiment #2). Gene expression heatmaps (dark=high, lighter color=low expression) and Kaplan-Meier survival analysis of the combined result at final stage are shown. (C) Concordance of the ClaNC prediction with the subtype status derived from consensus clustering. Colored bar=subtype status prediction of a sample. Samples are aligned according to the subtype classification by CC and SW. Deep color=positive SW; pale color=samples classified to a subtype but negative SW. Concordance (%) of the prediction with the subtype status derived from CC is also shown. The concordance was computed by comparing the subtype assignment by CC of 1,538 samples against the predicted subtype by ClaNC. The number in parenthesis indicates the accuracy of the prediction against core samples. This 10-fold cross validation showed an overall concordance of 72.4% for 1,538 samples. (D) Subtype prediction of samples in combined five independent datasets (GSE19829 [n=28], GSE20565 [n=95], Japan Kyoto Ovarian Cancer cohort; JPKO [n=67], GSE26712 [n=185] and GSE27651 [n=43]; total n=418). The subtype expression signatures were generated using all of the core samples (Epi-A: 101, Epi-B: 315, Mes: 325, Stem-A: 256 and Stem-B: 145). The genes were selected by SAM/ROC so that a subtype was distinguishable from the remaining samples. Subsequently, ClaNC was employed to predict the sample status. The concordance was computed by comparing the subtype assignment by CC of the samples against the predicted subtype. These independent cohorts showed a reasonable concordance of 80.1% (core samples: 89.6%) between the results derived from the prediction and the consensus clustering. Together, these results indicated the robustness of the classification scheme. Abbreviations: Epi-A; Epithelial-A, Epi-B; Epithelial-B, Mes; Mesenchymal, Stem-A; Stem-like-A, Stem-B; Stem-like-B.
Figure 8:
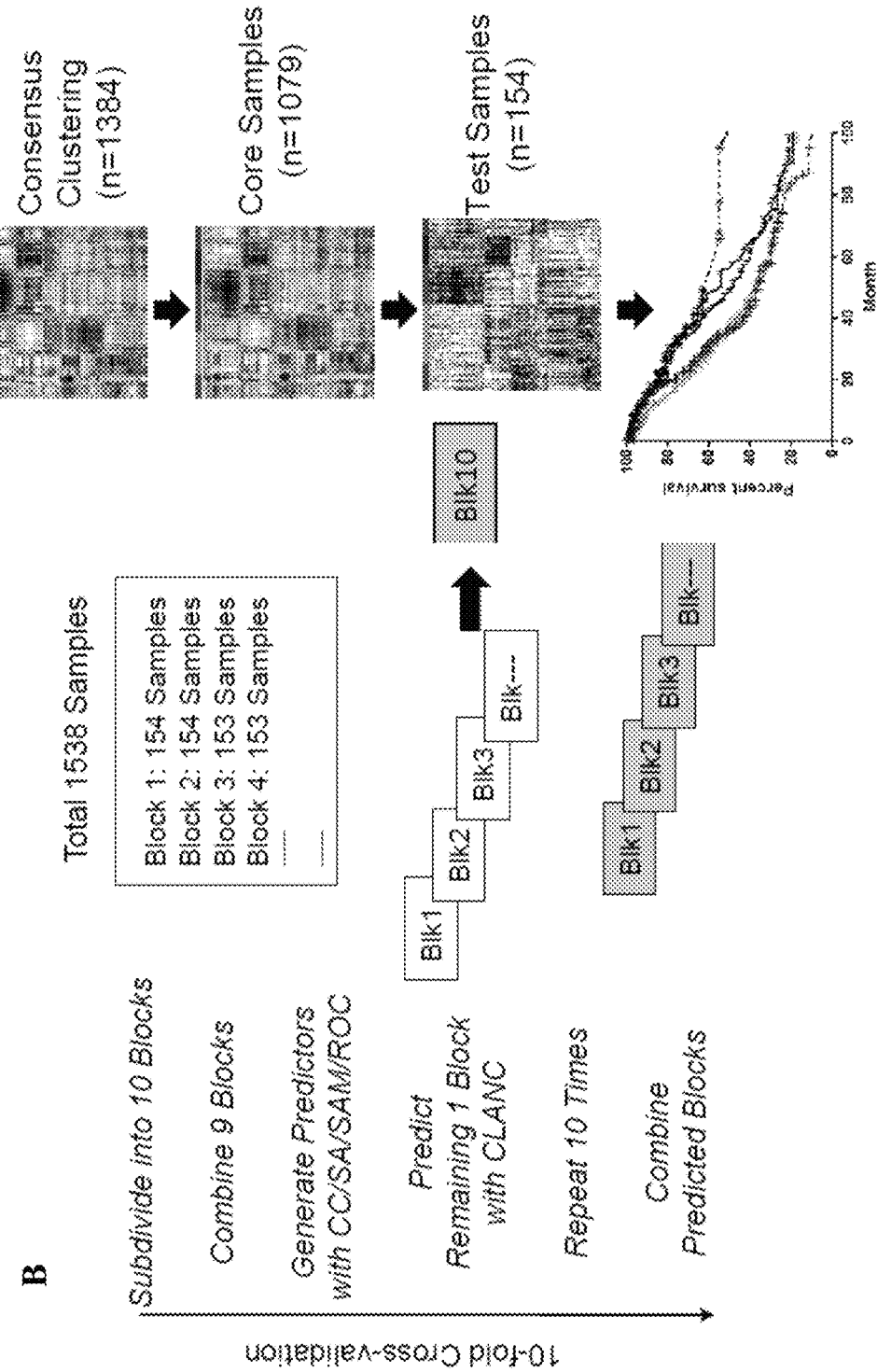
Figure 8:
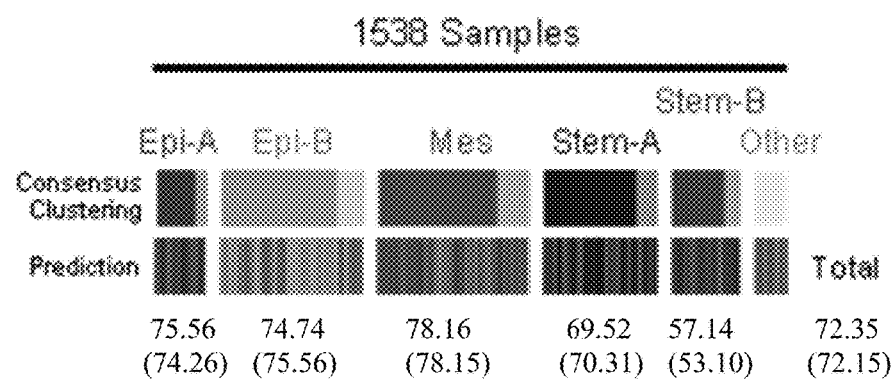
Figure 8:
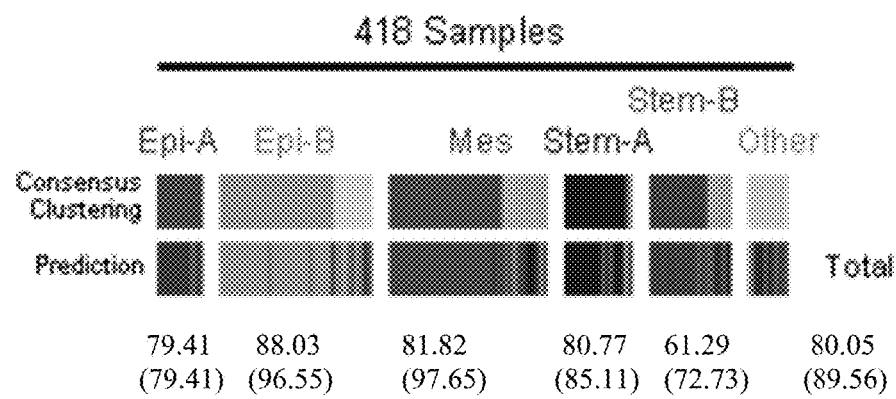

Robustness of the classification was further confirmed by an additional examination employing another statistical approach (FIG. 8). The gene signature to distinguish a subtype from the remaining subtypes was developed by supervised gene selection with SAM and ROC using all of 1,142 core samples (Epi-A: 101, Epi-B: 315, Mes: 325, Stem-A: 256 and Stem-B: 145) (FIG. 8A) (Tusher, Tibshirani et al. 2001). Three-dimensional visualization of the principal components of these selected genes for the all core samples revealed clearly distinguishable patterns for each subtype (data not shown). In order to know whether these genes have predictive capabilities, 10-fold cross validations were performed, in which the expression signatures from 90% samples in the same manner were generated, the subtype status of the remaining 10% samples with the signatures by ClaNC was predicted and the predictions were repeated 10 times (FIG. 8B) (Dabney, 2006, Bioinformatics, vol. 22, no. 1, pp. 122; Subramanian and Simon, 2011, Stat Med, vol. 3, no. 6, pp. 642). After compilation of 10 repeated results, the overall concordance for 1,538 samples was obtained as 72.4% (FIG. 8C). Furthermore, five independent datasets (GSE19829 [n=28], GSE20565 [n=95], Japan Kyoto Ovarian Cancer cohort; JPKO [n=67], GSE26712 [n=185] and GSE27651 [n=43]; total n=418) showed a reasonable concordance of 80.1% (core samples: 89.6%) between the results derived from the prediction and the consensus clustering using the gene signatures that were developed in FIG. 7B(B). Although the method relying on SAM/ROC/ClaNC showed slightly poorer predictive capability than that relying on BinReg (FIG. 7A), the observed concordance still demonstrates strong robustness of the classification scheme.

Part B. In vitro Modeling of Carcinoma Subtypes and EMT Phenotypes by Using an Ovarian Cancer Cell Line Library Identification of Cell Lines as Representatives of in vivo Tumors in Multiple Subtypes An important aspect of the development of a classification scheme is to establish a framework for facilitating the use of experimental systems, whether in vitro cell lines or xenografts, as models for the study of the in vivo cancers, so that cell line does truly reflect the underlying biology of the tumor. Expression studies of cultured breast cancer cell lines have indeed shown that these in vitro cells retain their subtype characteristics corresponding to those of the in vivo counterparts, therefore, the matched breast cell lines can be used for further study as representatives of in vivo tumors. In order to identify the cell-line counterparts of ovarian tumors, a co-clustering analysis was performed of a collection of total 142 cultured cell lines (Duke: GSE25429; 42, Kyoto: 37, National Laboratory: E-TABM-254; 29 and Singapore: 34 cell lines with redundancy in cell line names) with 1,142 of core tumor samples using the same clustering profiling method with the same tumor classifiers used in FIG. 5. This co-clustering resulted that all the cell lines were subdivided into 7 clusters (G1: 21, G5: 23, Epi-A: 1, Epi-B: 12, Mes: 33, Stem-A: 24 and Stem-B: 28 cell lines), among which at this time two clusters (G1 and G5) were excluded from the majority of tumor clusters and composed by predominantly cell lines. It was assumed that the expression signature for in vitro cultured ovarian cell-line subtype might to some extent differ from that of clinical tumors, one more round of consensus clustering was performed purely relying on the re-selected cell-line classifiers based on the first clustering result. Genes were selected that can distinguish each subtype from the remaining subtypes by SAM/ROC (data not shown). This double consensus clustering yielded five subtypes for the cell lines (Epi-A: 29, Epi-B: 10, Mes: 34, Stem-A: 42 and Stem-B: 27 cell lines) (FIG. 9A).

Figure 9:
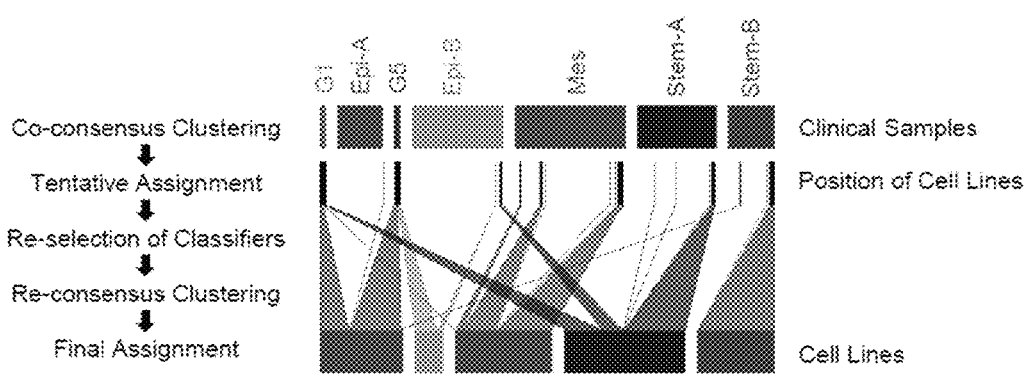
FIG. 9 (A) shows a schematic presentation for subtype classification of cell lines by consensus clustering. Data for total 142 of cell lines (Duke: 42, Kyoto: 37, National laboratory: 29 and Singapore: 34 cell lines with redundancy in cell line names) was analyzed together with 1,142 of core tumor samples in consensus clustering. Two-time consensus clustering coupled with re-selection of cell line classifiers finally identified five subtypes for the cell lines. Upper bars are to indicate the subtype status of clinical samples after the first consensus clustering. A lower bar underneath the upper bars indicates position of cell line sample with clinical tumor samples in the first clustering analysis. The cell line classes are shown by lower bars. Triangles are used to show the relation between the first and the second classifications. For example, all of 28 cell lines initially classified as Stem-B subtype were again classified in the same category, whilst a Stem-B cell line moved into Epithelial-A subclass. Likewise 10 cell lines of Group 1 (G1) and 17 of Group 5 (G5), appeared in the first clustering, fused to Epithelial-A subtype, while 10 of G1 and 8 of Epithelial-B moved to Stem-A subgroup. (B) Five subtypes in ovarian cancer cell line classification. Left panel; consensus clustering matrix (dark: high, white: low similarity), middle panel; gene expression heatmap (dark: high, lighter color: low expression), right panel; silhouette analysis for each subtype. (C) Prediction of clinical samples by cell line predictors using BinReg. Upper panels. Gene expression heatmaps for subtype predictors based on cell line expression data. The color map indicates high (dark color) or low (lighter color) expression of predictor genes. A bar indicates the cell line samples used for prediction to generate the subtype signature. The same labeling for cell lines in FIG. 9C was used for BinReg analysis. Middle panels. Predicted probability of core clinical samples for cell-line subtype predictor by BinReg analyses. Concordance of the prediction by cell line predictors with silhouette positive core sample status was also shown beneath the dot plots. Each subtype signature detected the difference between the corresponding subtype from the remaining tumor samples with statistical significance (all pair-wise Mann-Whitney test; p<0.0001). Lower panels. ROC analyses of subtype predictors. Overall accuracy of the prediction is shown by area under the ROC curve (AUC). Concordance of the subtype status derived from consensus clustering with the prediction based on the cell line subtype predictors was also shown in percentage. (D) Cell line names in the classification. Data sources of cell lines are Duke University (D), Kyoto University (K), Singapore (S) and National Laboratory (N). Many cell lines in Kyoto and Singapore collection are derived from Duke collection, while National Laboratory collection is totally independent of Kyoto, Duke or Singapore collection. Cell lines with negative silhouette width in FIG. 9B are shown with gray font. Note that Kyoto data included duplicated arrays for HEY.
Figure 9:
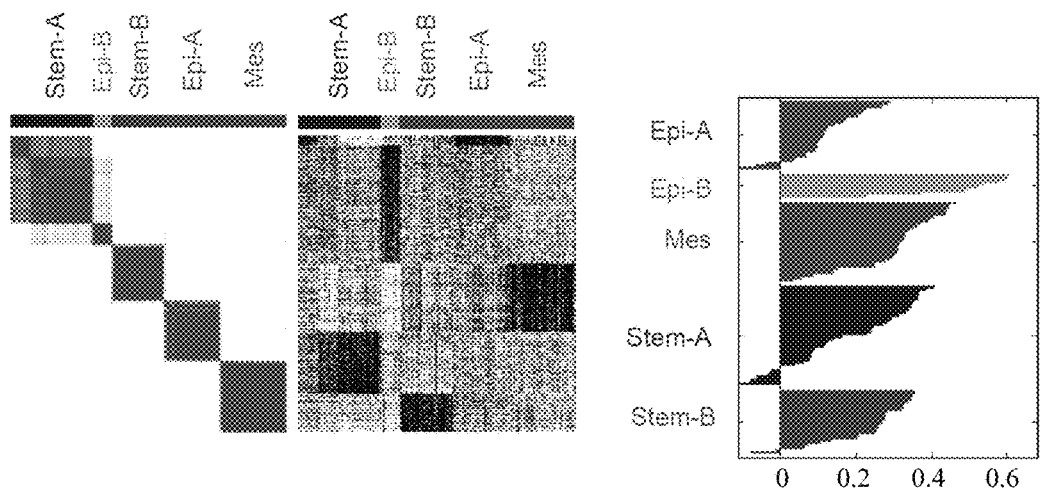
Figure 9:
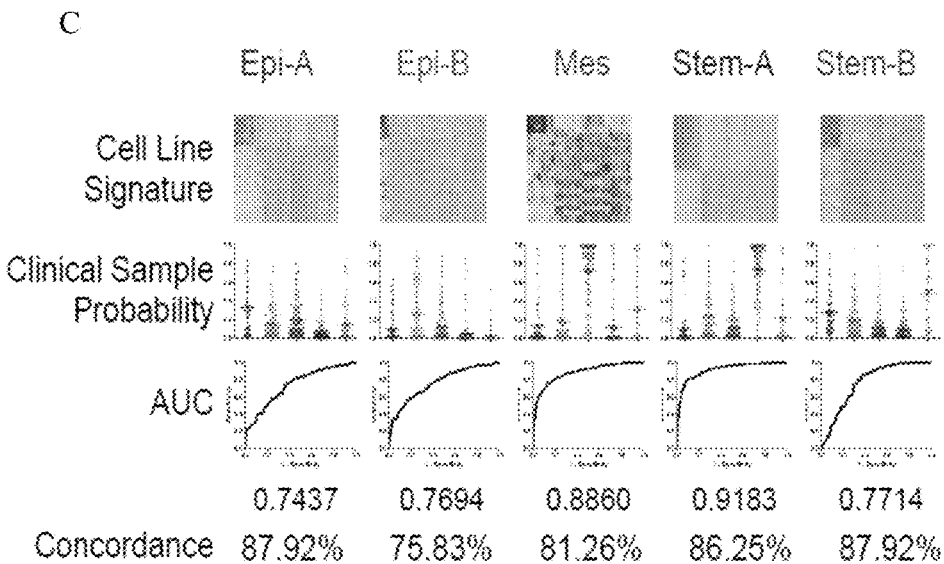

The similarity matrices and the silhouette values further supported the proper assignment of the cell line samples to corresponding subtypes (FIG. 9B). As shown in FIG. 9C, the cell-line subtype predictors were then developed based on the cell-line classification and applied to clinical data to estimate the similarity between in vivo tumors and in vitro cell lines in the gene expression pattern of the subtype predictors. The levels of accuracy of prediction between a cell-line classifier and a tumor subclass were tested with the area under curve (0.744 to 0.918) and concordance (75.8 to 87.9%), indicating similarity of cell lines and in vivo tumors in the expression (FIG. 9C). Finally, consistency of the classification in the cell-line names was confirmed across the different collections among Duke, Kyoto and Singapore cell lines (FIG. 9D). The analyses demonstrated that in vitro cancer cell lines may serve as a good experimental model system representing in vivo tumors classified as a given subtype.

Correlation of in vitro Cell Line Phenotypes with the Cell Line Subtypes

Figure 10:
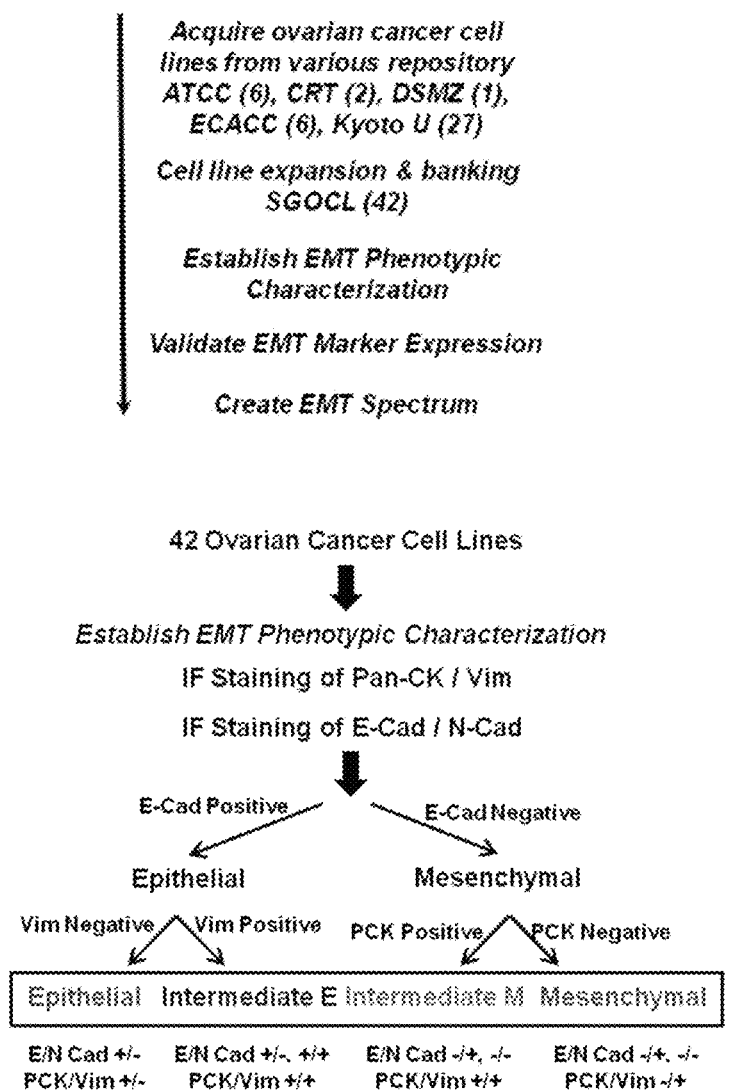
FIG. 10 shows (A) the EMT spectrum of the SOGCL A. Origin of the ovarian carcinoma cell lines and phenotypic characterization. (B) Immunostaining of one cell line representative of each subgroup. (C) Quantitative PCR of E-cadherin and Vimentin transcripts. (D) Expression values for E-cadherin, Pan-cytokeratin, N-cadherin and Vimentin for each subtype.
Figure 10:
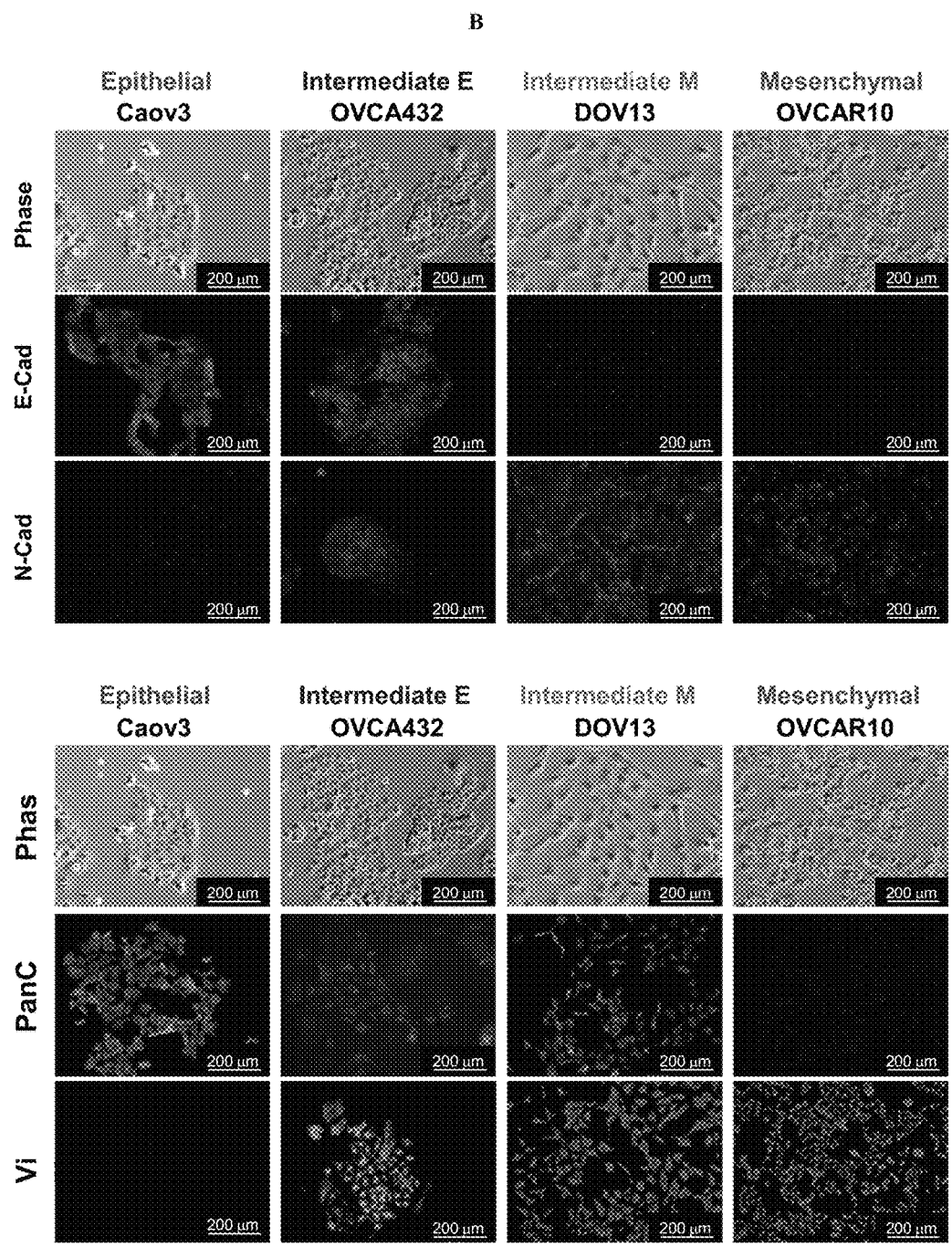
Figure 10:
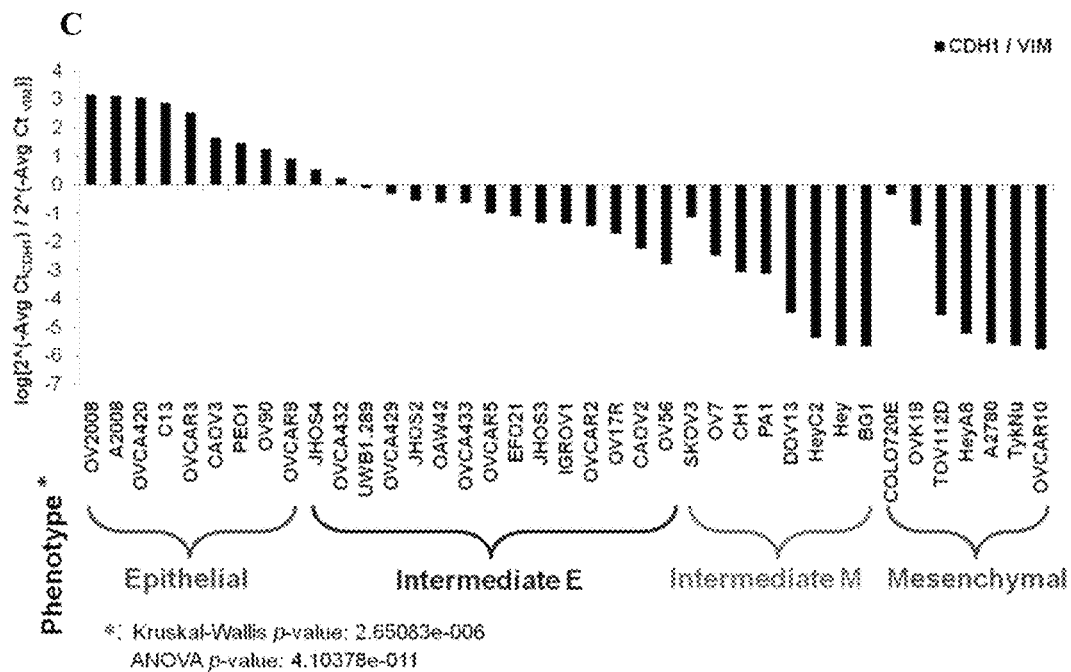
Figure 10:
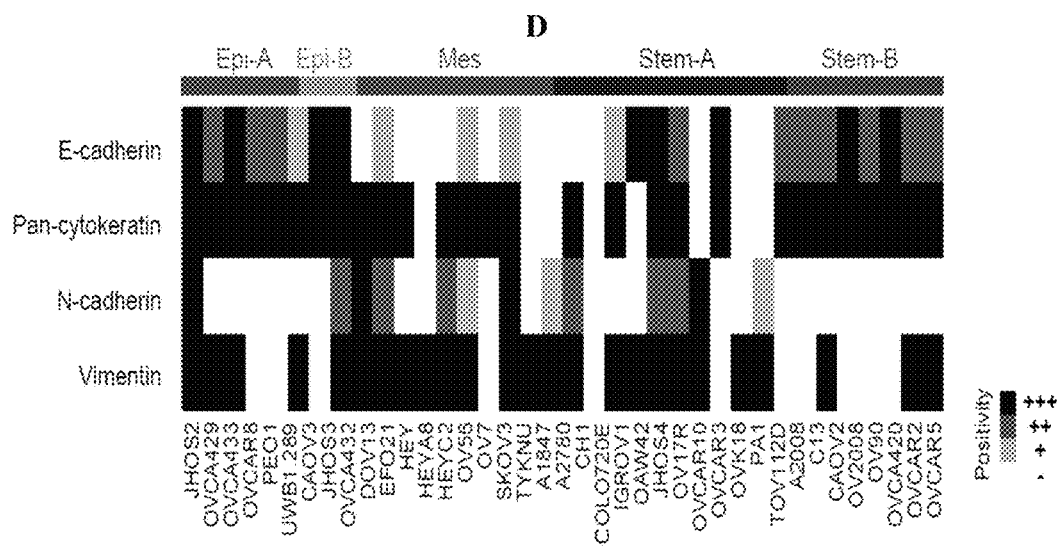

The subtype classifying signatures that were identified involved differential expression of genes that are regarded as epithelial-mesenchymal (EM) markers and EMT drivers. It was set to utilize an assemble of ovarian cancer cell line library, termed SGOCL(42), to model the entire spectrum of EMT. (FIG. 10A) In order to accurately model the heterogeneity, quantitative positioning of different EMT status/score is required. Established in vitro cancer cell lines can be regarded as snapshots of given phenotypic or molecular statuses representing different populations of in vivo tumors. Then examined the expressions of these markers was examined by using immunofluorescent stainings in cell lines (FIG. 10B). Based on the immunofluorescence staining pattern of E-cadherin, N-cadherin, pan-cytokeratin, and vimentin, a decision matrix was established to determine the EMT phenotype of each cell line. E-cadherin immunoreactivity was utilized to allocate the general epithelial (E-Cad positive) or mesenchymal (E-Cad negative) category. Subsequently, pan-cytokeratin and vimentin were utilized to determine the differentiation subcategory. Cells allocated into the epithelial category with negative vimentin immunoreactivity were designated as true epithelial (E). Cells allocated into the mesenchymal category with negative pan-cytokeratin immunoreactivity were designated as true mesenchymal (M). Those that co-express pan-cytokeratin and vimentin were designated as intermediates. Thus, SGOCL(42) was phenotypically characterized as four EMT categories: epithelial (E), intermediate epithelial (intermediate E), intermediate mesenchymal (intermediate M), mesenchymal (M).

In addition, the staining intensities were also documented as 0 (negative), 1 (weak positive), 2 (positive), and 3 (strong positive). The SGOCL(42) was subsequently ranked according to the quantitative PCR expression ratio of E-cadherin (CDH1) versus vimentin (VIM) within each EMT phenotype category. This categorization method created a quantitative EMT spectrum (FIG. 10C). This spectrum took into the considerations of both phenotypic and quantitative characterization which indicated that the expression patterns of epithelial-mesenchymal markers as well as major EMT drivers followed the EMT gradient.

Next the staining patterns were correlated with the subtypes identified. Epi-A, Epi-B and Stem-B cell lines were found to have positive stainings of E-cadherin, a epithelial marker; whereas the cell lines classified as Mes or Stem-A were characterized by immunopositivity for N-cadherin, a mesenchymal marker (FIG. 10D). The head-to-head matching between the oncogenomic subtypes and EMT phenotypes of SGOCL(42) also showed that most of the Mes and Stem-A lines were categorized as Intermediate M or M phenotype.

Figure 11:
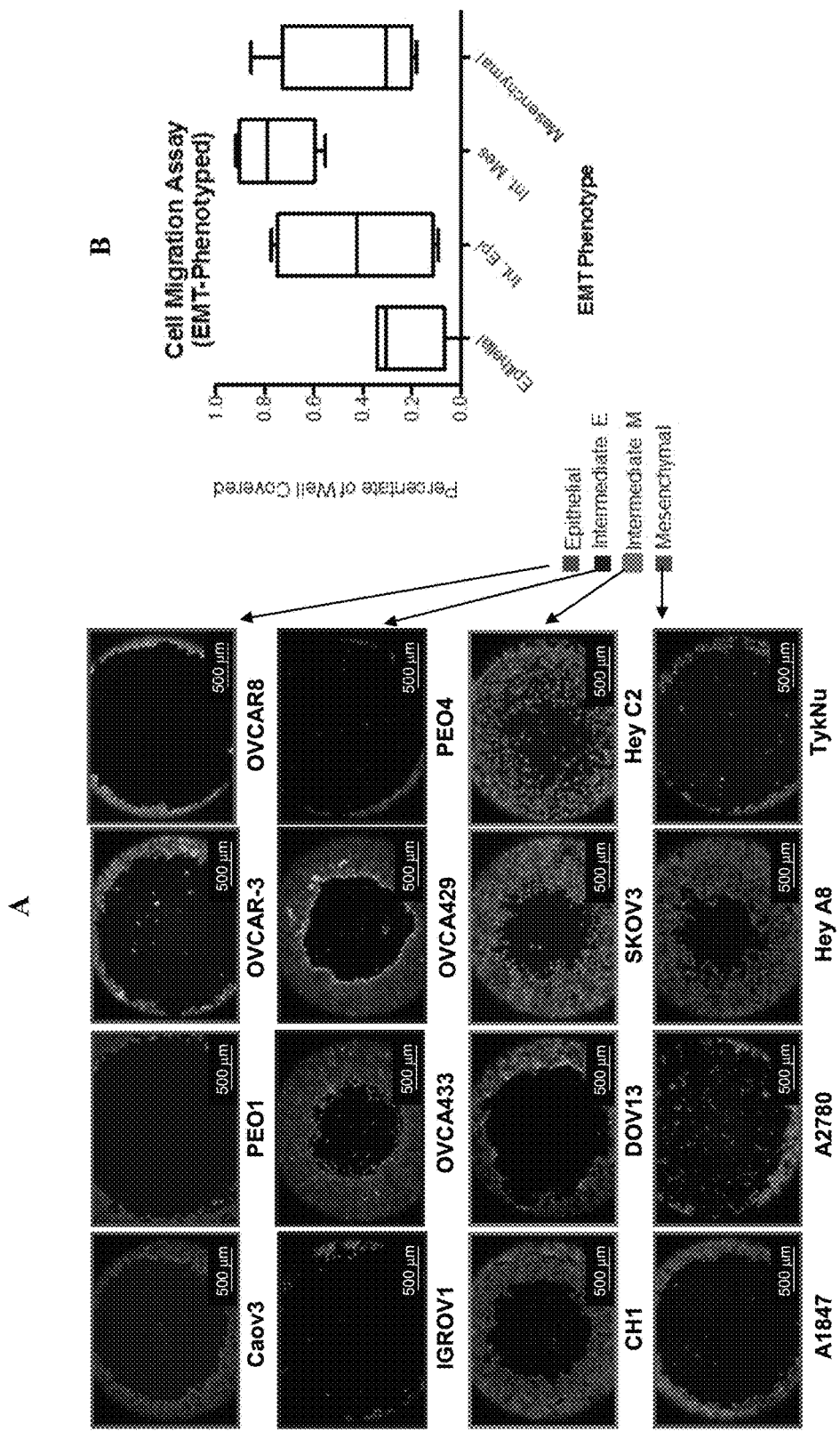
FIG. 11 illustrates characterization of the migratory, invasive, apoptotic and clonogenic properties of the SGOL42 cell lines. (A), (B) Migratory properties semi-quantitatively measured using the platypus technology Intermediate mesenchymal are significantly more migratory. (C)-(D) Two intermediate E and two intermediate M invade the matrigel. (E) Intermediate E (left) invade as cell collective while intermediate M (right) invade as solitary cells. (F) A significant number of cells undergo anoikis, however cell lines with intermediate M and M are more resistant. (G) Intermediate M cells all formed spheroids except DOV13.
Figure 11:
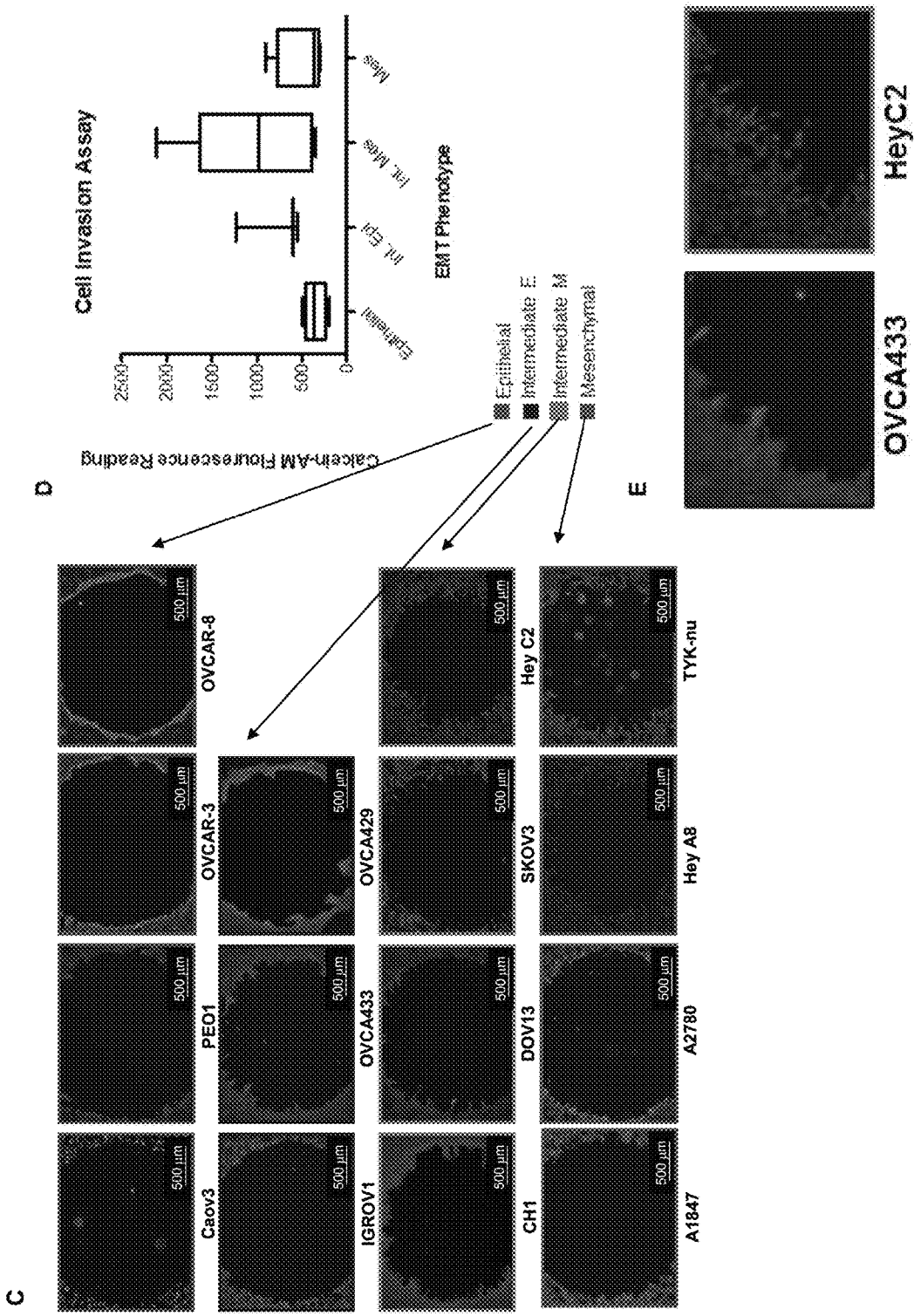
Figure 11:
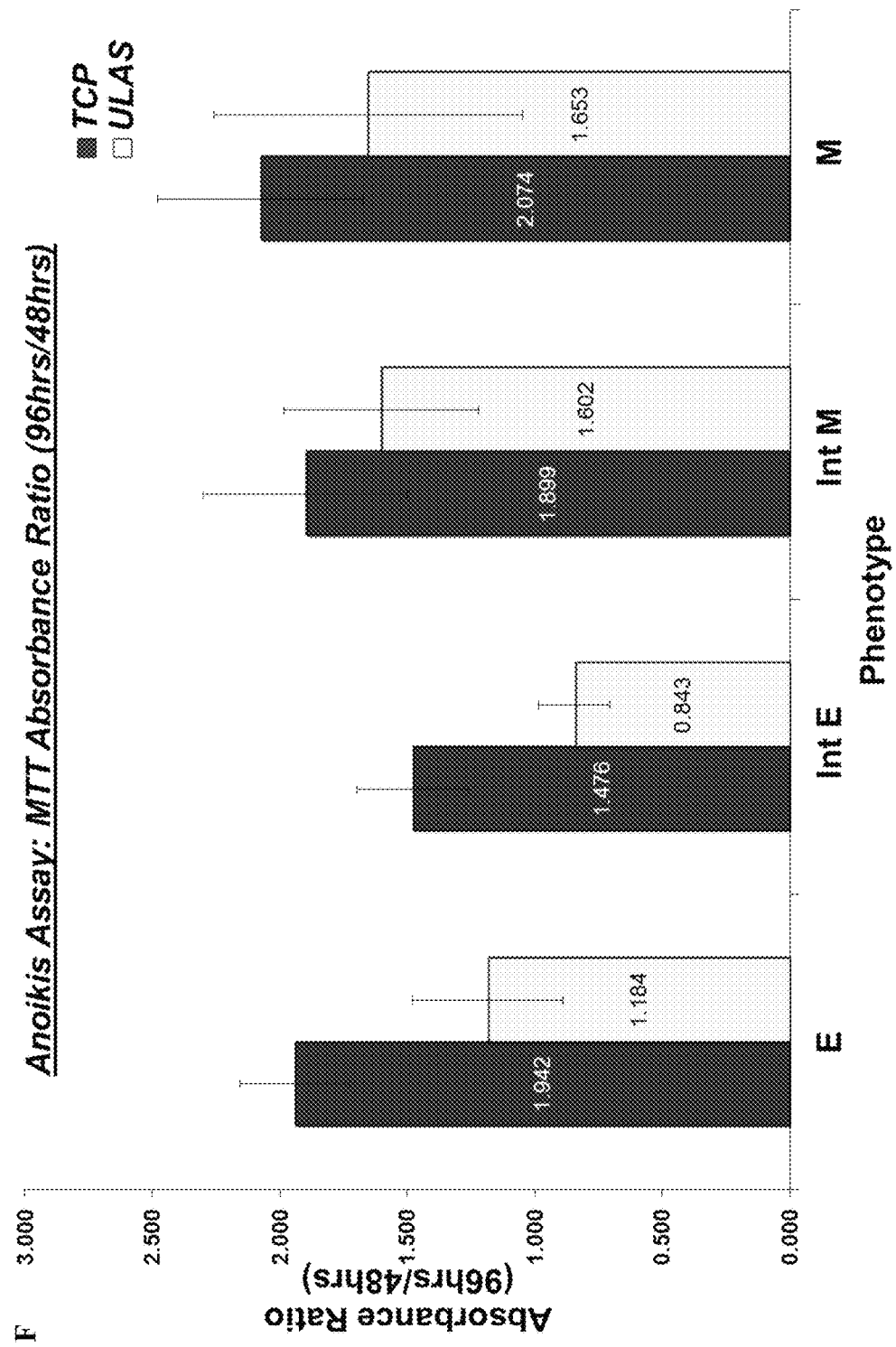
Figure 11:
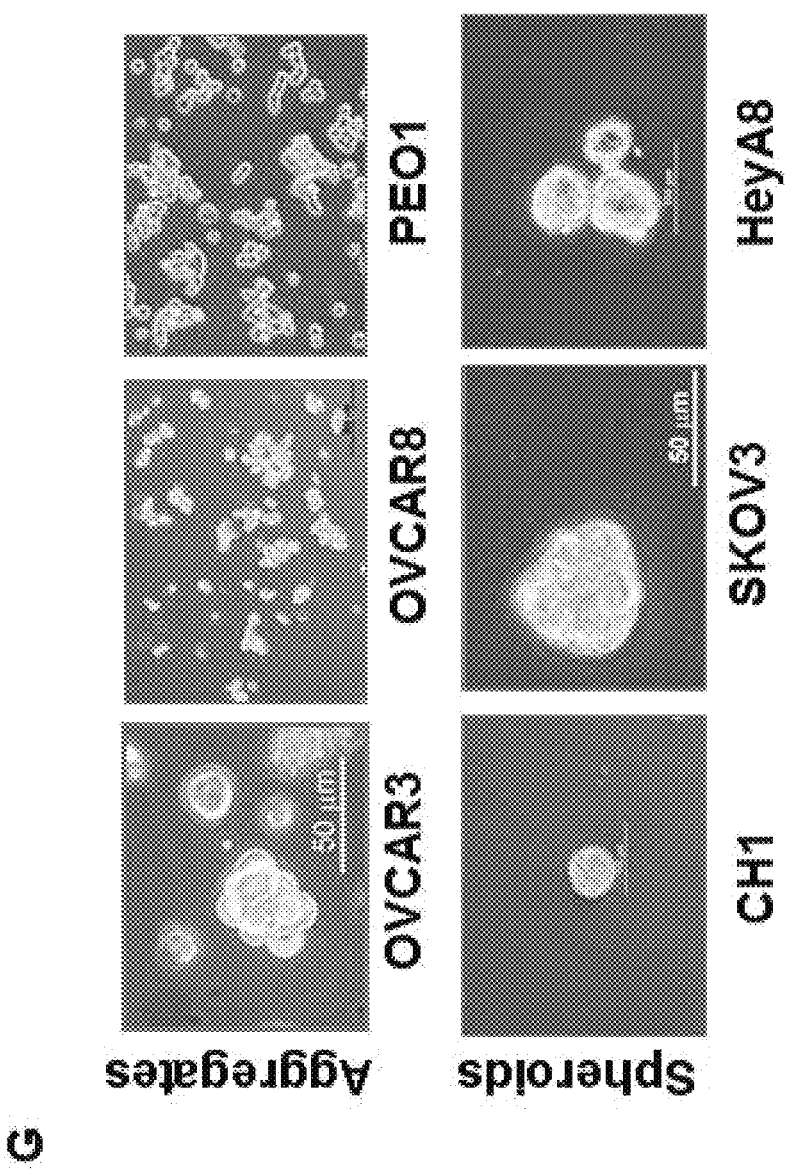

Cell Lines of Intermediate M or M Category Displayed More Aggressive in vitro Phenotypes Next the EMT-related functional differences were compared among the four EMT phenotypic categories in cell-based assays including migration, invasion, anoikis, and spheroid forming assays on a selected panel of cell lines from SGOCL(42). Firstly, the migratory abilities among EMT phenotypes were examined by using migration assays which detect the cell coverage of central migration zones created by silicon stoppers. After overnight migration, the Intermediate M phenotype covered most of the area of the migration zones (FIGS. 11A and B) compared to other phenotypes. In addition, invasiveness was also examined among these cell lines by measuring the number of cells penetrating into 3-D central invasion zones created by silicon stoppers subsequently filled with basement membrane extracts (BME). After 48 hr of incubation, two cell lines with Intermediate E and all four cell lines with Intermediate M phenotype showed significant invasion detected by fluorescence (FIGS. 11C and D). At the invasive front, we noticed that Intermediate E and Intermediate M displayed different invasive properties. Intermediate E displayed a collective movement while Intermediate M showed single cell movement forming radial spike (FIG. 11E). Furthermore, the ability of different EMT phenotypes to survive under anchorage independent conditions overtime were compared. In anoikis resistance assays, the viability between cells was measured which were grown on normal tissue culture treated surfaces (TCP) and low attachment suspension (ULAS) conditions using MTT assays. Generally, all four EMT phenotypes survived well in TCP conditions evident by the increase in the absorbance readings from 48 to 96 hrs (viability index greater than 1.0). In ULAS conditions, the viability dropped significantly in majority of the cell lines, indicating that the suspension conditions were not favorable for cell growth. However, the average viability index of Intermediate M and M phenotypes in ULAS conditions were still higher than those in E and Intermediate E (FIG. 11F), indicating that Intermediate M and M might be more resistant to anoikis. Interestingly, morphology differences were observed in ULAS conditions after 96 hr of incubation among EMT phenotypes. Majority of the tested cell lines formed 'grape-like' aggregates in ULAS conditions. Cell lines with Intermediate M phenotype all formed spheroids except DOV13 (FIG. 11G).

From these in vitro functional studies, it was concluded that cells harboring the Intermediate M phenotype was more prone to be migratory, invasive, anoikis resistant, and was more colony forming and spheroidogenic. These results indicated that the Intermediate M phenotype might represent an aggressive category in vitro.

From these in vitro functional studies, it was concluded that cells harboring the Intermediate M phenotype was more prone to be migratory, invasive, anoikis resistant, and was more colony forming and spheroidogenic. These results indicated that the Intermediate M phenotype represents a more aggressive category.

An Expression Profiling-based Epithelial-Mesenchymal Scoring System Developed in Ovarian Cancer Cell Lines (EMT Score)

Figure 12:
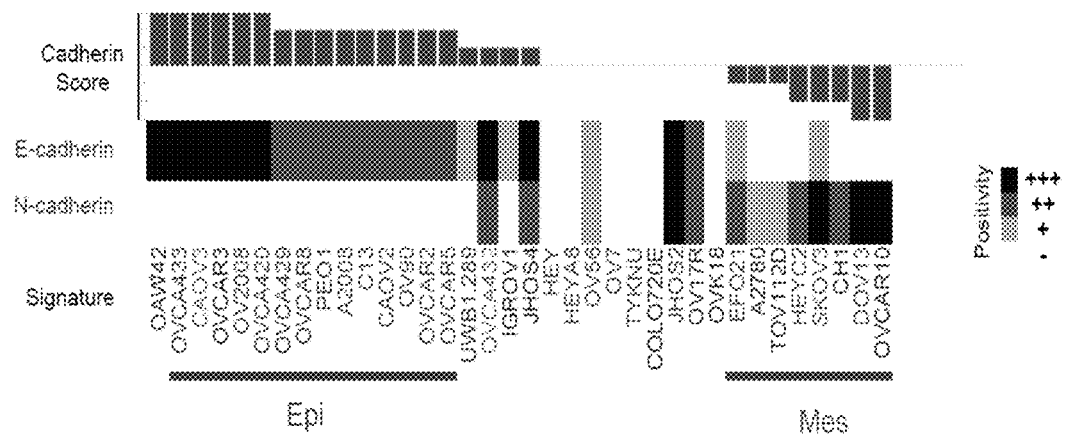
FIG. 12 illustrates the development of epithelial-mesenchymal transition signature based on cadherins expression of cultured cells. (A) Assignment of epithelial or mesenchymal phenotype by scoring cell lines with positivity of E- or N-cadherin on the cell surface. Upper panel. Cadherin score. A subtraction of N-cadherin from E-cadherin positivity was used as a score. Cell lines were sorted according to the score. Lower panel. Heatmap for E- or N-cadherin positivity. Cell line names are shown underneath. The color font indicates the cell line subclass (Green=Epi-A, light green=Epi-B, red=Mes, blue=Stem-A and purple=Stem-B). To generate the gene expression signature that can distinguish the cells with epithelial phenotype from those with mesenchymal phenotype, cell lines were selected with cadherin score above 2 (epithelial) or below 0 (mesenchymal). (B) A gene signature for epithelial-mesenchymal phenotype of ovarian cancer cells. Upper panel: the expression pattern of genes that distinguish epithelial from mesenchymal cells. The expression pattern of a 125-gene signature is shown as a heatmap (dark=high and lighter color=low expression). Lower panel: a leave-one-out cross-validation of probabilities for epithelial-mesenchymal phenotype (lighter color=epithelial, dark=mesenchymal cells). The accuracy of this signature was 100.0% using 0.5 as a cutoff probability. A bar indicates the mean value for each group. (C) Prediction of epithelial-mesenchymal phenotype of HMLER cells with different E-cadherin status by the gene signature derived from ovarian cancer cells. Predicted probabilities are shown as bar plots for epithelial and mesenchymal phenotype. Several manipulations of E-cadherin function are shown beneath the plots. Loss of E-cadherin expression or dominant-negative E-cadherin overexpression renders the HMLER cells more mesenchymal. The mesenchymal phenotype induced by loss of function of E-cadherin was recovered by simultaneously added beta-catenin knockdown. These phenotypic changes by the gene manipulations coincide with the alteration of mesenchymal predicted probability. (D) Prediction of epithelial-mesenchymal phenotype of the remaining ovarian cancer cell lines that were not used to generate the signature. Predicted probabilities were plotted according to the cell line subtype. A bar indicates the mean value for each group. (E) The epithelial-mesenchymal score and genes of clinical samples. ss-GSEA was used to estimate the status of a clinical tumor for epithelial and mesenchymal (EM) phenotype. A tumor was ranked according to the epithelial or mesenchymal phenotype. The rank for mesenchymal phenotype was subtracted from that for epithelial phenotype for each sample and designated it as an EMT score. The EMT score is shown in the heatmap (lighter color=epithelial, dark=mesenchymal phenotypes) with subtype information and the heatmap of the genes (lighter color=low, dark=high expression) used for SS-GSEA. (F) EMT score and the tumor subtype. EMT scores were plotted in the category of the tumor subtype. A dashed line is used to indicate the position of the median value of the EMT score. Epithelial and mesenchymal phenotypes were determined using this median as a cut-off value. Many of Epi-A, Epi-B and Stem-B tumors show epithelial phenotype (86.1%, 75.9% and 63.5%, respectively), while 83.2% of Stem-A and 66.2% of Mes ovarian cancers have mesenchymal phenotype.
Figure 12:
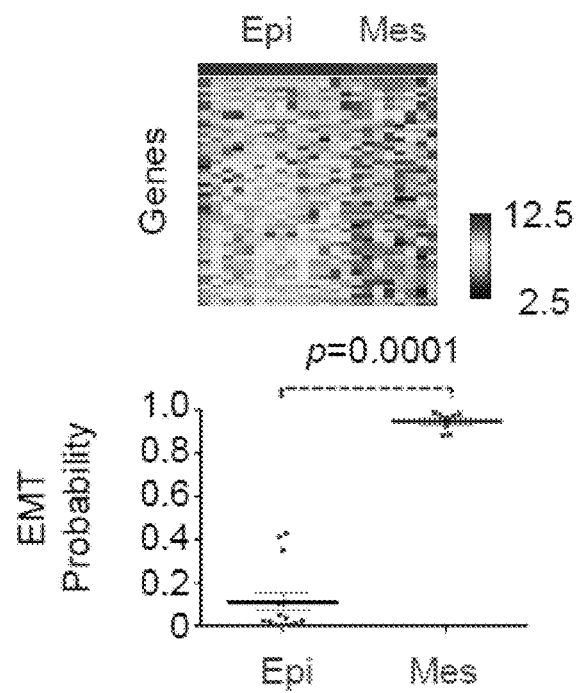
Figure 12:
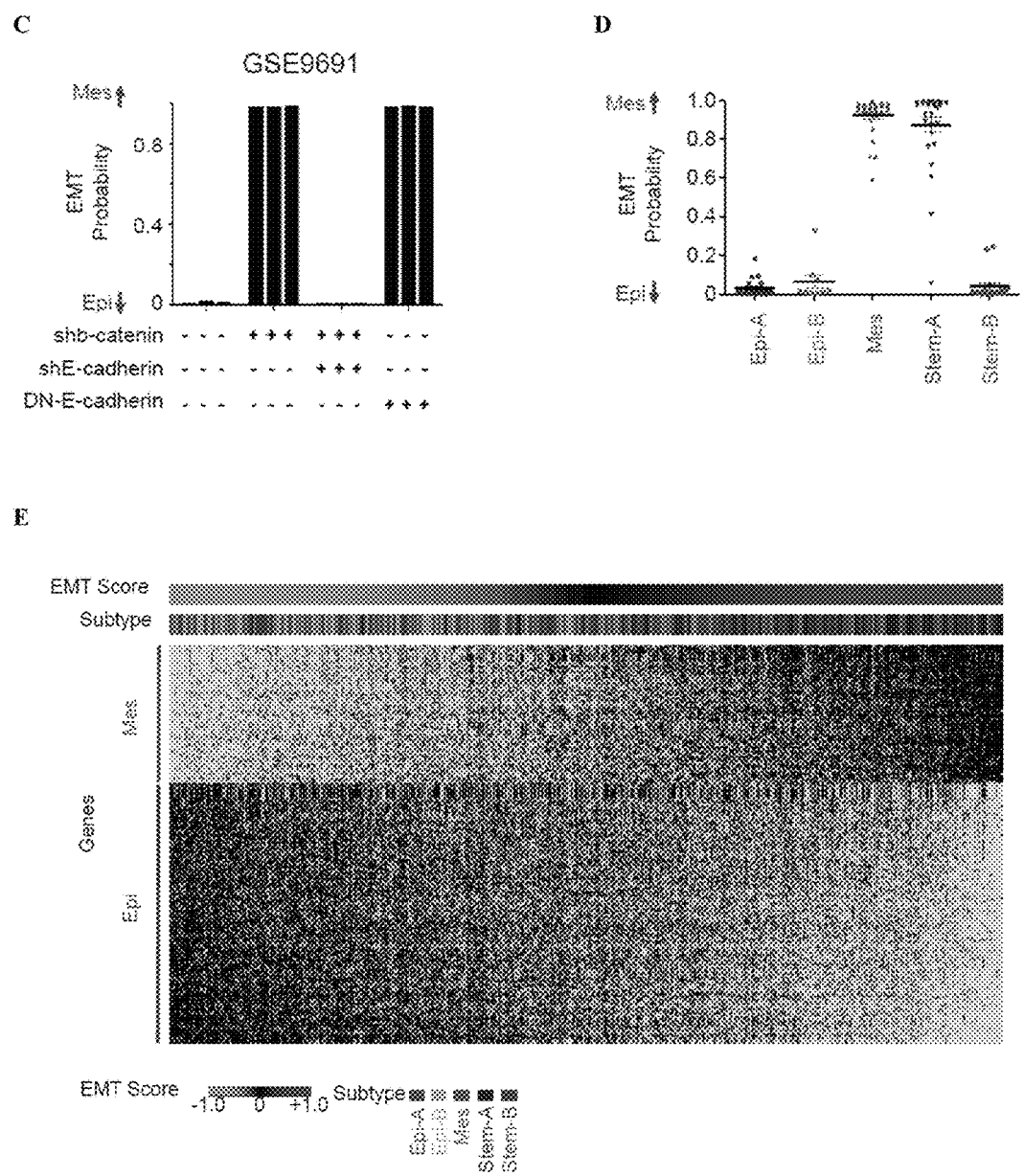
Figure 12:
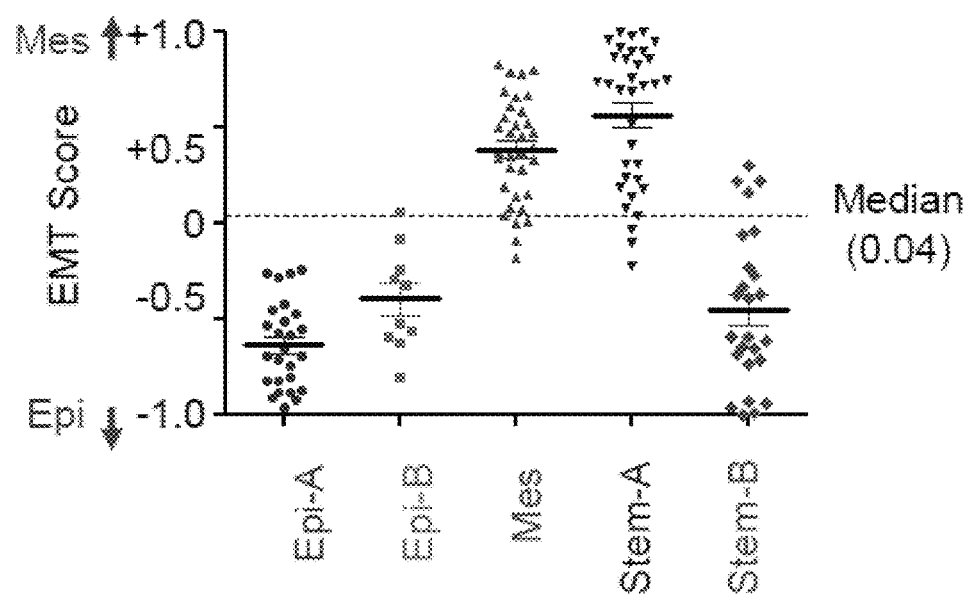

Since multiple EMT markers were detected as the subtype classifiers in the clinical tumor as well as cultured cell-lines, it was hypothesized that EMT has a significant impact on in vitro and in vivo behaviors and can be defined by a gene expression signature. Firstly, a scoring system was developed to quantify EMT status by using in vitro cell lines. 23 cell lines from SGOCL(42) were incorporated that included the 17 cell lines with epithelial phenotype (5 Epi-A, 1 Epi-B, 1 Stem-A and 8 Stem-B cell lines) and 8 cell lines with mesenchymal phenotype (4 Mes and 4 Stem-A cell lines) based on the cadherin score, that is the subtraction between E-cadherin and N-cadherin immunostaining intensities (FIGS. 12A and 12B). The EM expression signature derived contained CDH1 (E-cadherin) and CDH2 (N-cadherin) in the gene list and showed robustness in distinguishing epithelial from mesenchymal phenotype with a strong p-value (p=0.0001) in a leave-one-out cross validation study (FIG. 12B). The EM signature obtained from cultured ovarian cancer cell lines also accurately predicted the EM status in a model of EMT of cancer cells by silencing E-cadherin or introducing dominant negative E-cadherin, suggesting the EM expression signature could precisely reflect the cellular EM status (FIG. 12C). To validate the EM status prediction independently, the gene expression profilings of the remaining cell lines obtained from the meta-analysis that were not included in the signature generation were further utilized. The subtypes in cell lines could be perfectly categorized by this EM phenotype and EM expression signature (FIG. 12D). Epi-A, Epi-B, and Stem-B groups were predicted as epithelial status; Mes and Stem-A groups were predicted as mesenchymal status (FIG. 12D). It was thus possible to develop a scoring system to quantify the EM status, to create an EMT spectrum using the expression profiling of a panel of ovarian cancer cell lines, and to correlate with clinically relevant subtypes (FIGS. 12E and 12F).

Figure 27:
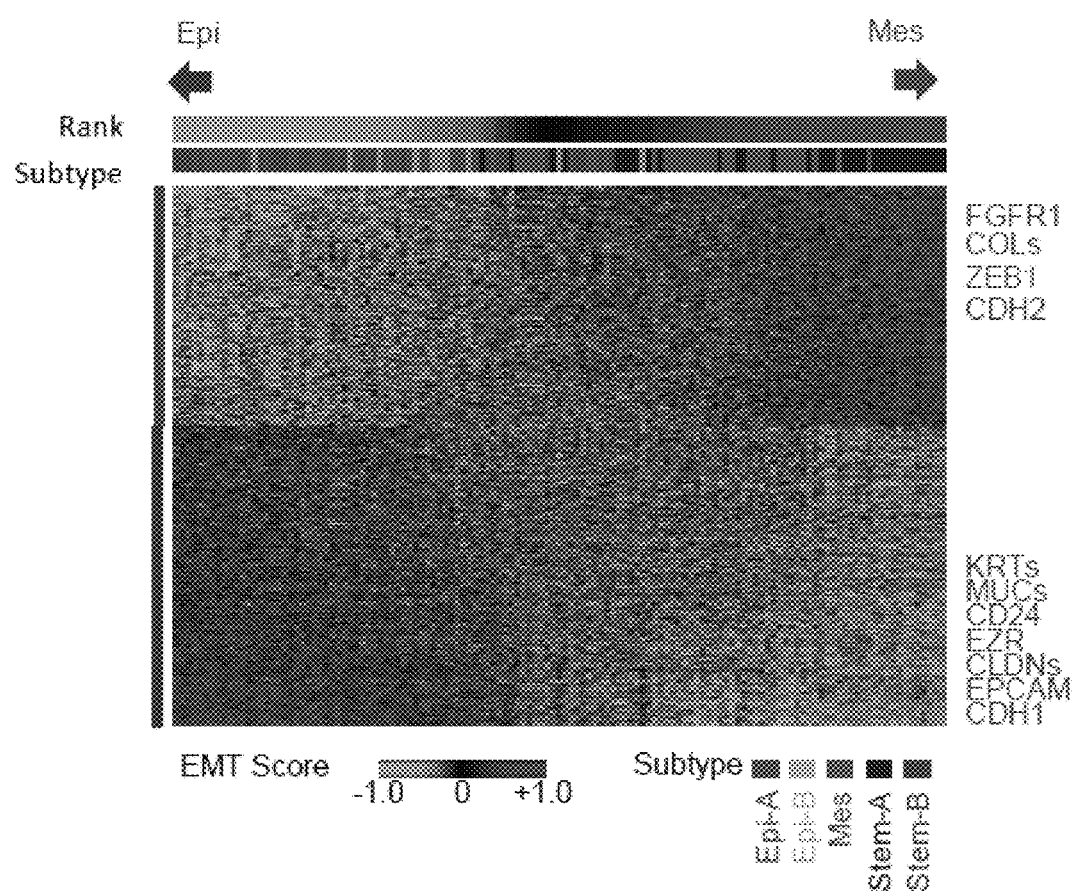
FIG. 27 shows the epithelial-mensenchymal score in cultured cell lines.

FIG. 27 shows EMT score and genes of cell lines. The EMT score was computed with the same method used for that of clinical samples and is shown in the heatmap (green=epithelial, red=mesenchymal phenotypes) with subtype information and the heatmap of the genes (green=low, red=high expression) used for ss-GSEA. F. Relation of EMT score and cell line subtype. The EMT score of the cell lines were plotted according to their subtype. Epithelial and mesenchymal phenotypes were assigned to each cell lines based on the median EMT score, indicated by the dashed line. All of the Epi-A cell lines exhibit epithelial phenotypes. 80.0% of Epi-B and 84.0% of Stem-B cell lines exhibit epithelial phenotypes. On the other hand, majority of Mes and Stem-A cell lines show mesenchymal phenotypes (82.4% and 91.2%, respectively).

Epithelial-mesenchymal Transition (EMT) Scoring

Using N-cadherin and E-cadherin positivity on the cell surface detected by immunostaining, the cell lines were assigned to the epithelial or mesenchymal phenotype and used to generate a gene expression signature by BinReg so as to distinguish the epithelial from mesenchymal phenotype of a sample. The resultant EMT signature comprised 50 genes significantly up- or down-regulated in the epithelial and mesenchymal phenotypes. The EMT status of clinical samples and remaining cell lines by BinReg was then predicted. The top 100 among 1,538 tumors or the 25% (35 or 36 among 142) cell lines with the highest probabilities for epithelial or mesenchymal phenotype were used to obtained the clinical samples- or cell line-specific EMT signature (i.e. significant up- or down-regulated genes in epithelial or mesenchymal phenotype) through SAM with q-value of 0 and ROC of 0.85. Based on the EMT signature, ss-GSEA was then employed to compute the enrichment score of a clinical sample or a cell line based on the expression of epithelial or mesenchymal signature genes. After ranking each sample according to the epithelial or mesenchymal enrichment score, the normalized subtraction of the rank for mesenchymal from epithelial phenotype was defined as the EMT score.

Figure 13:
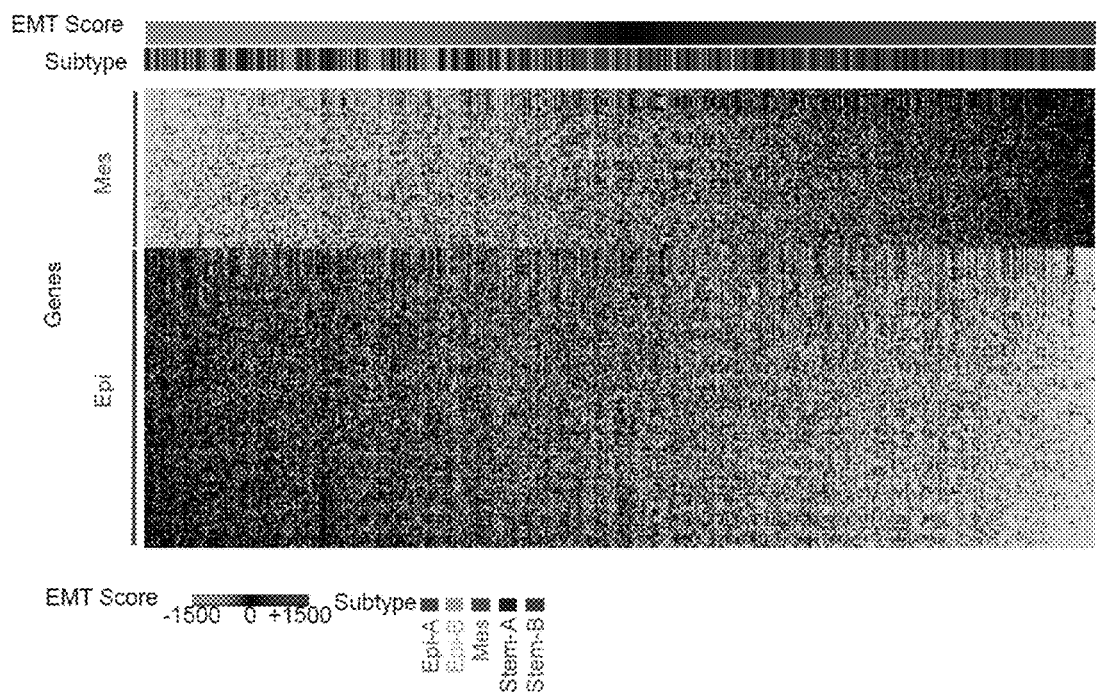
FIG. 13 (A) The epithelial-mesenchymal score and genes of clinical samples. ss-GSEA was used to estimate the status of a clinical tumor for epithelial and mesenchymal (EM) phenotype. A tumor was ranked according to the epithelial or mesenchymal phenotype. The rank for mesenchymal phenotype was subtracted from that for epithelial phenotype for each sample and designated as an EMT score. The EMT score is shown in the heatmap (lighter color=epithelial, dark=mesenchymal phenotypes) with subtype information and the heatmap of the genes (lighter color=low, dark=high expression) used for SS-GSEA. (B) EMT score and the tumor subtype. EMT scores were plotted in the category of the tumor subtype. A dashed line is used to indicate the position of the median value of the EMT score. Epithelial and mesenchymal phenotypes were determined using this median as a cut-off value. Many of Epi-A, Epi-B and Stem-B tumors show epithelial phenotype (86.1%, 75.9% and 63.5%, respectively), while 83.2% of Stem-A and 66.2% of Mes ovarian cancers have mesenchymal phenotype. (C) Validation was made with an independent collection of ovarian carcinoma samples, termed JPKO, and another publically available ovarian cancer expression dataset, termed GSE2056. (D) Epi-A and Epi-B tumors were classified to have epithelial phenotype (100% and 87.5%, respectively), while 89.47% of Stem-A and 89.65% of Mes tumors were classified as the mesenchymal phenotype.
Figure 13:
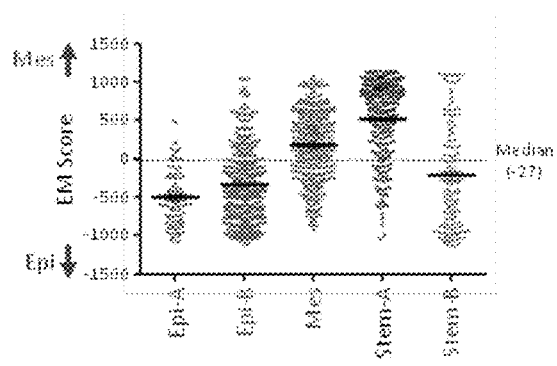
Figure 13:
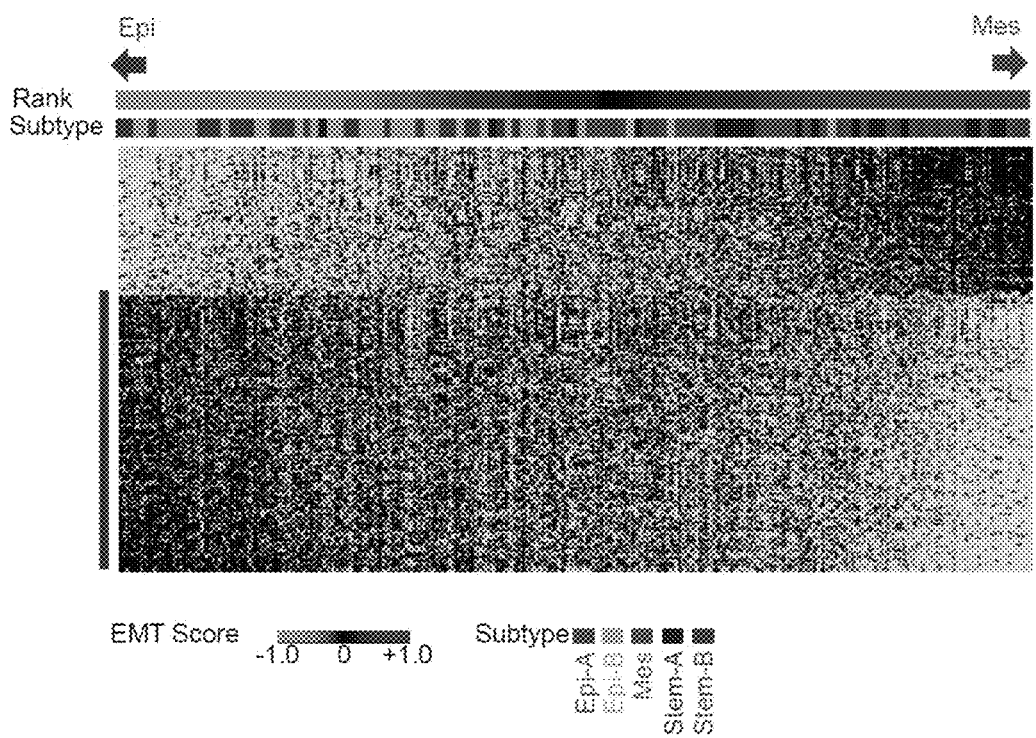
Figure 13:
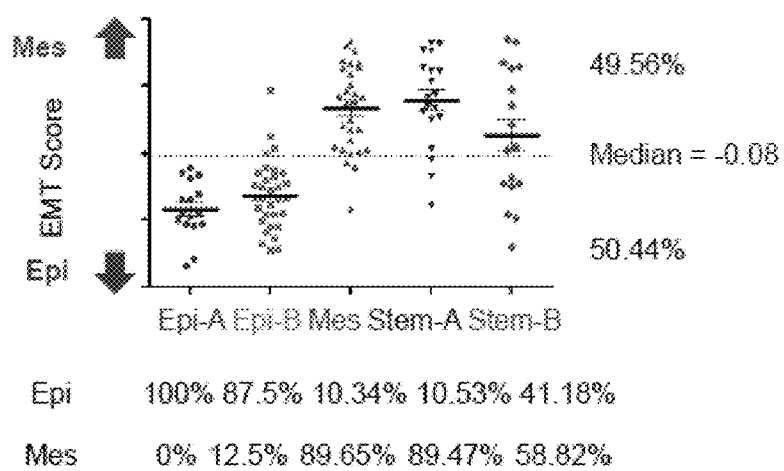

Application of Epithelial-mesenchymal Scoring System in Ovarian Carcinoma Samples To prove that this EM scoring system could be apply in clinical sample categorization, the cell line EM signature was applied in the meta-analysis data consisting of 1,538 ovarian cancer samples (FIGS. 13A and 13B). Using the median of the EMT score as a cut-off value, many of Epi-A, Epi-B and Stem-B tumors were classified to have epithelial phenotype (86.1%, 75.9% and 63.5%, respectively), while 83.2% of Stem-A and 66.2% of Mes ovarian cancers showed the mesenchymal phenotype. Importantly, since these clinical samples of Mes or Stem-A subtypes were found to have poorer survival outcomes, this indicated a correlation between a poor clinical outcome and the phenotypic mesenchymal character (FIG. 5). To further generate a robust prediction gene list, from the 1,538 meta-analysis samples, top 100 samples were selected from both epithelial and mesenchymal phenotypes designated by the cell line EM signature to re-train the dataset. An EMT Scoring Gene Signature was generated and subsequently validated the EM status prediction utilizing an independent collection of ovarian carcinoma samples, termed JPKO, and another publically available ovarian cancer expression dataset, termed GSE2056. As shown in FIG. 13D, Epi-A and Epi-B tumors were classified to have epithelial phenotype (100% and 87.5%, respectively), while 89.47% of Stem-A and 89.65% of Mes tumors were classified as the mesenchymal phenotype (FIGS. 13C and 13D). The Stem-B subtype was not significantly correlated with EM status. These results not only demonstrated that the EMT Scoring Gene Signature could robustly be applied for the prediction of epithelial or mesenchymal phenotype of independent tumor collections, but also supported the tight relationship between the ovarian cancer intrinsic subtype and the EM phenotype.

Key EMT Components Identified from CDH1, DDR1, ERBB3, and ZEB1 Signatures Might be Potential Novel Markers for Sub-classification of EOC.

Epithelial-mesenchymal transition (EMT), a crucial mechanism in development, has been known to promote carcinoma progression. Four genes, CDH1, DDR1, ERBB3 and ZEB 1 were utilized to generate EMT signatures. CDH1 codes for E-cadherin, the prototypical classical cadherin from the cadherin superfamily. E-cadherin is a calcium dependent cell-cell adhesion glycoprotein, which is the hallmark of EMT by the loss of its expression via mutation, promoter hypermethylation, or activation of its transcriptional suppressors. DDR1 codes for discoidin domain receptor 1, a receptor tyrosine kinase family member. Its autophosphorylation is achieved by collagens (type I to type VI). The expression of DDR1 is restricted to epithelial cells. DDR1 is significantly over-expressed in several human tumors from breast, ovarian, esophageal, and pediatric brain. ERBB3 codes for a member of the epidermal growth factor receptor (EGFR) family. It has a neuregulin binding domain but not an active kinase domain. It therefore can bind this ligand but not convey the signal into the cell through protein phosphorylation. However, it does form heterodimers with other EGF receptor family members which do have kinase activity. Heterodimerization leads to the activation of pathways which lead to cell proliferation or differentiation. Amplification of this gene and/or overexpression of its protein have been reported in numerous cancers, including prostate, bladder, and breast tumors. ZEB1 codes for Zinc finger E-box-binding homeobox 1, is a zinc finger transcription factor. ZEB 1 represses E-cadherin promoter and induces EMT by recruiting SMARCA4/BRG1. Therefore, these four markers, in combination, should be able to provide the sketch of the silhouette of EMT.

Figure 14:
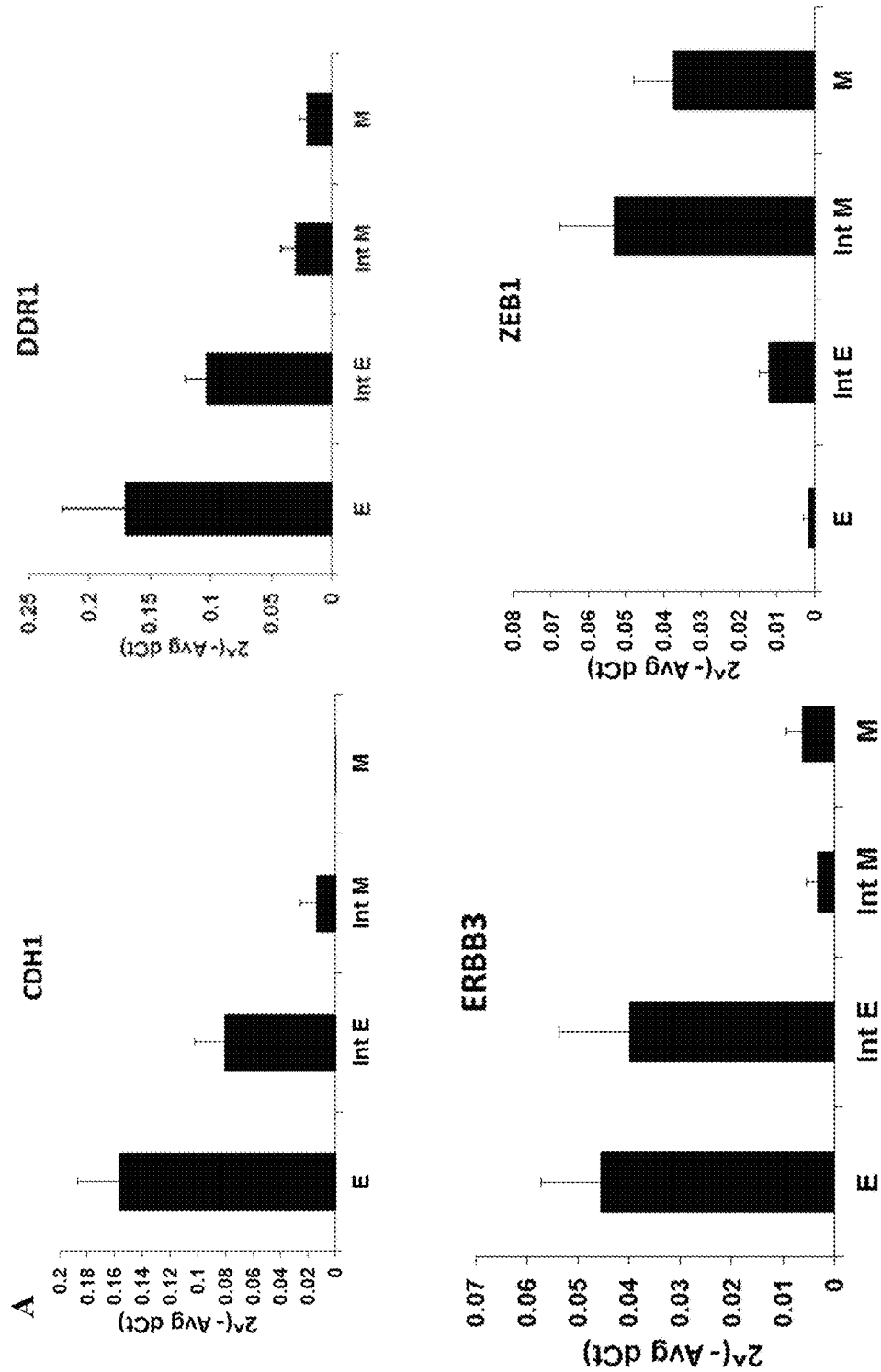
FIG. 14 (A) Relative expression level of the 4 genes (E-cadherin, DDR1, ERBB3 and ZEB1) across the four cell line subgroup. (B) 6 cell lines expressing high or low level of each of the 4 genes and the corresponding gene signatures to be used in the Venn diagram (C).
Figure 14:
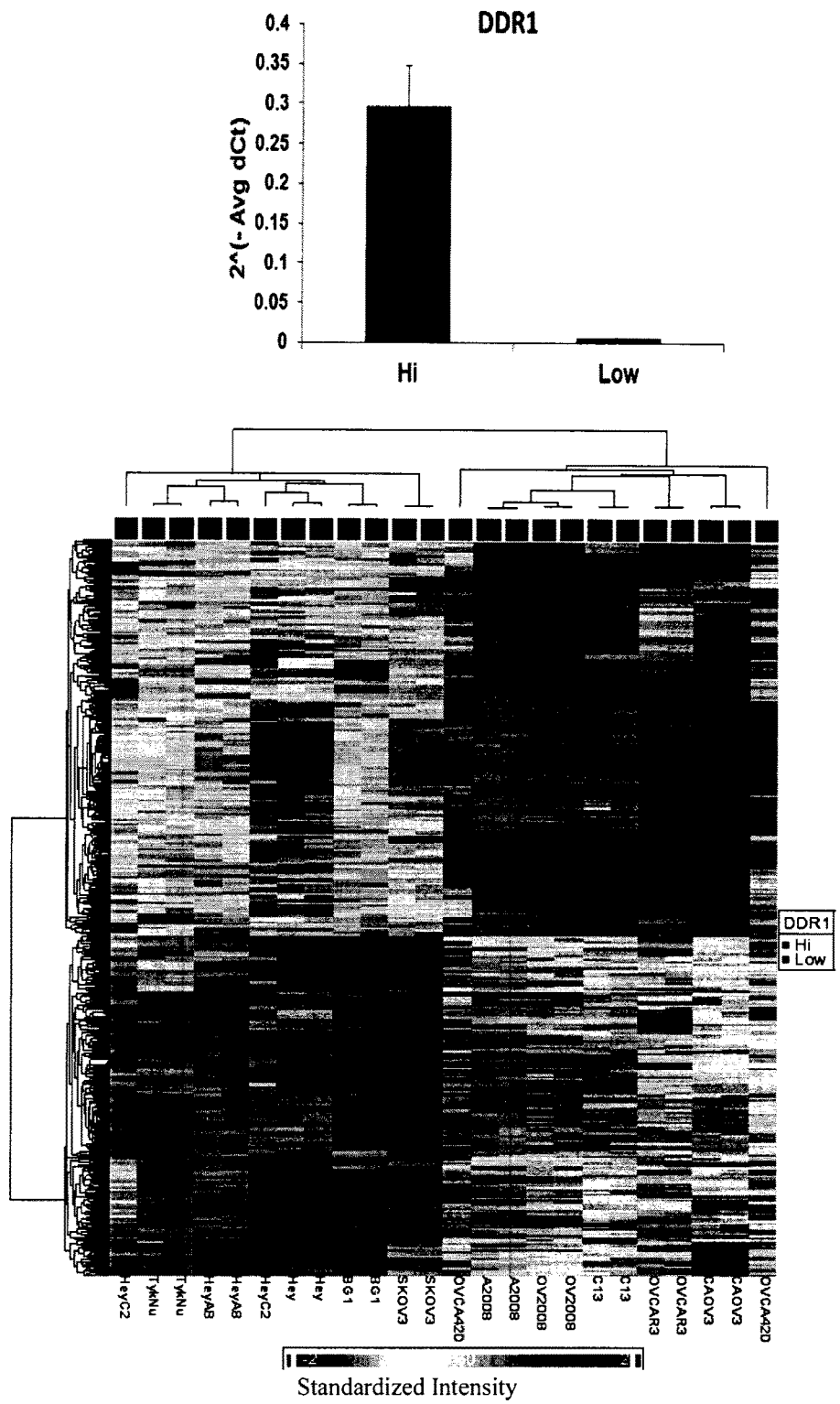
Figure 14:
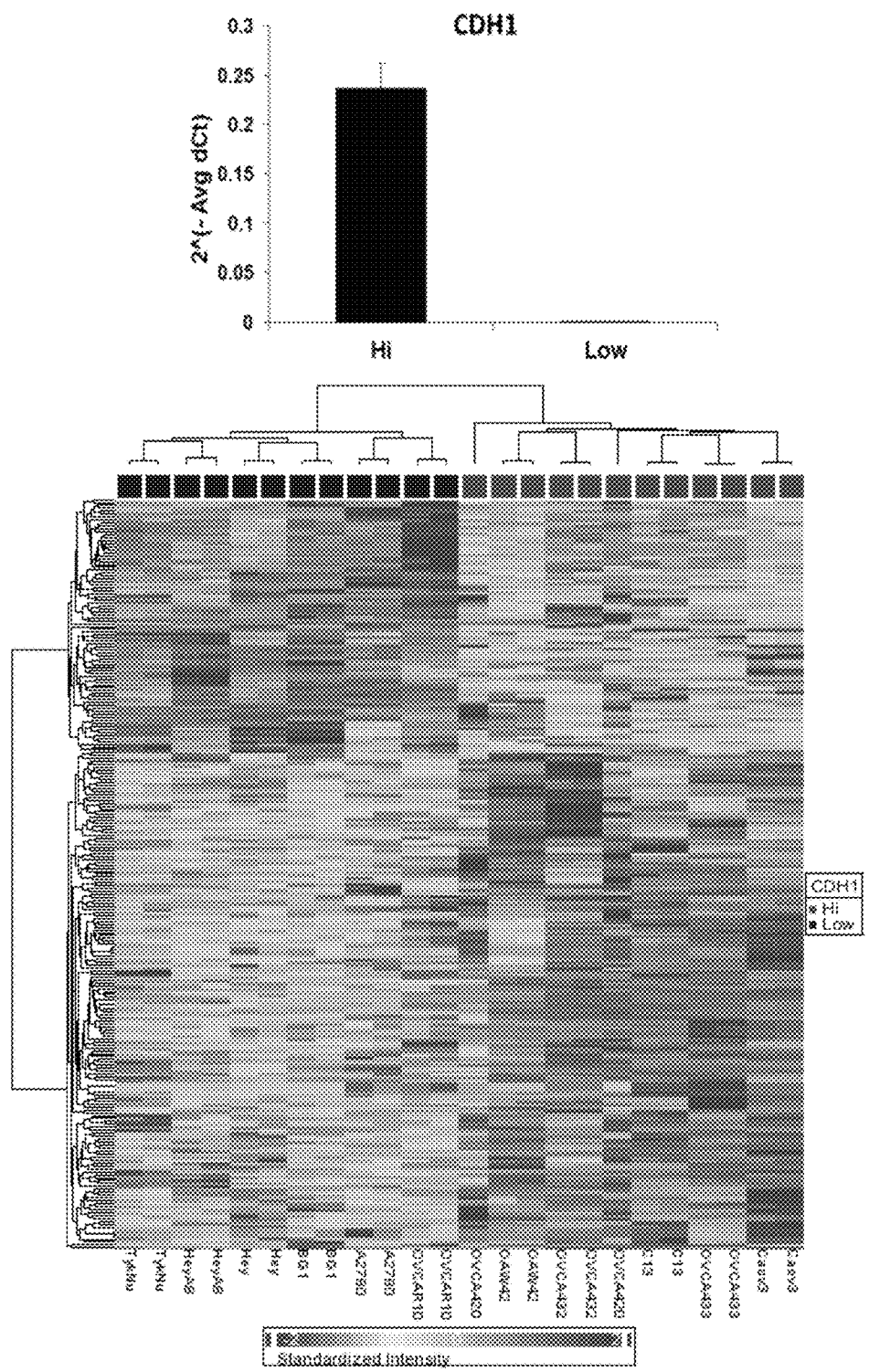
Figure 14:
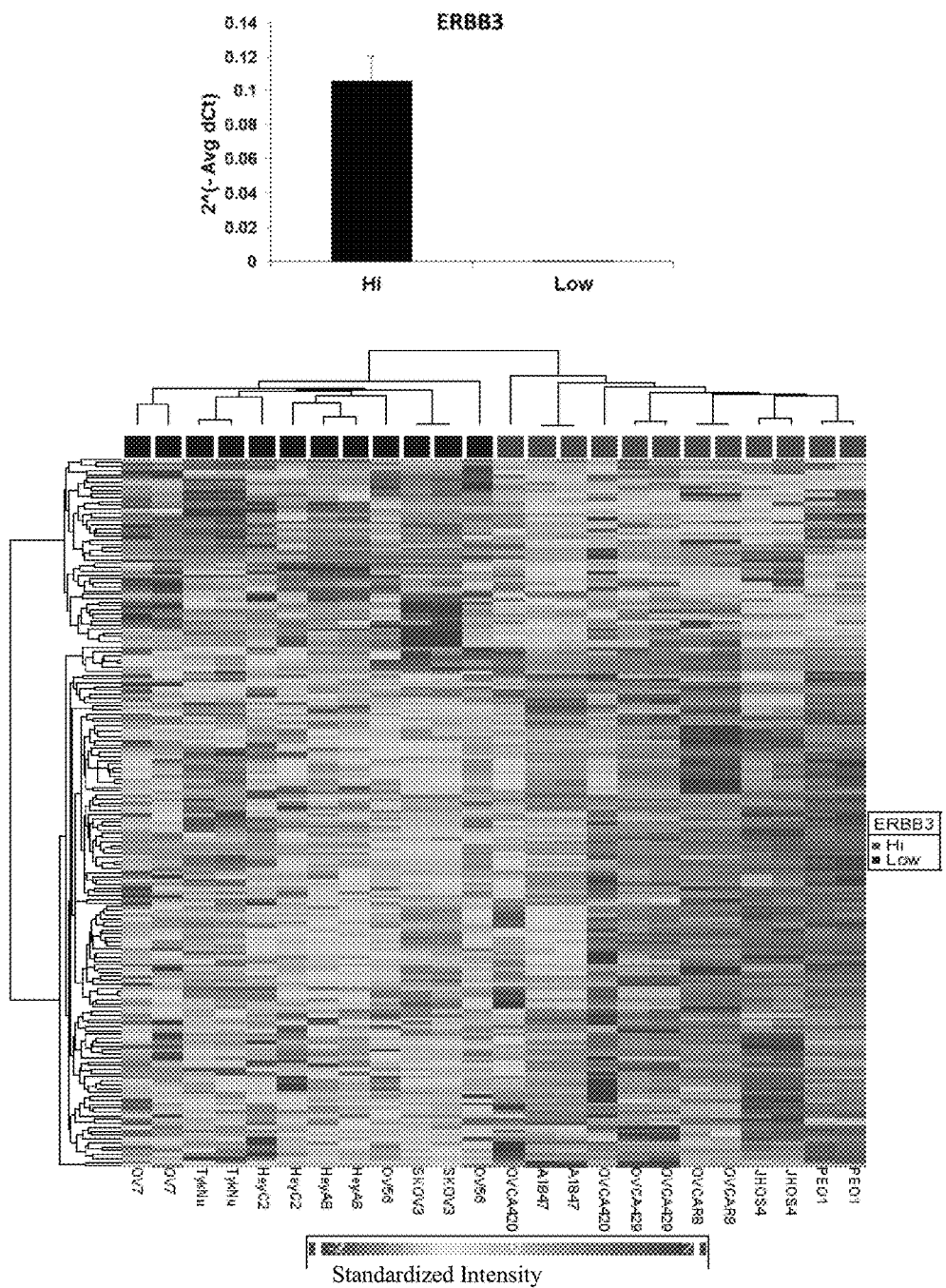
Figure 14:
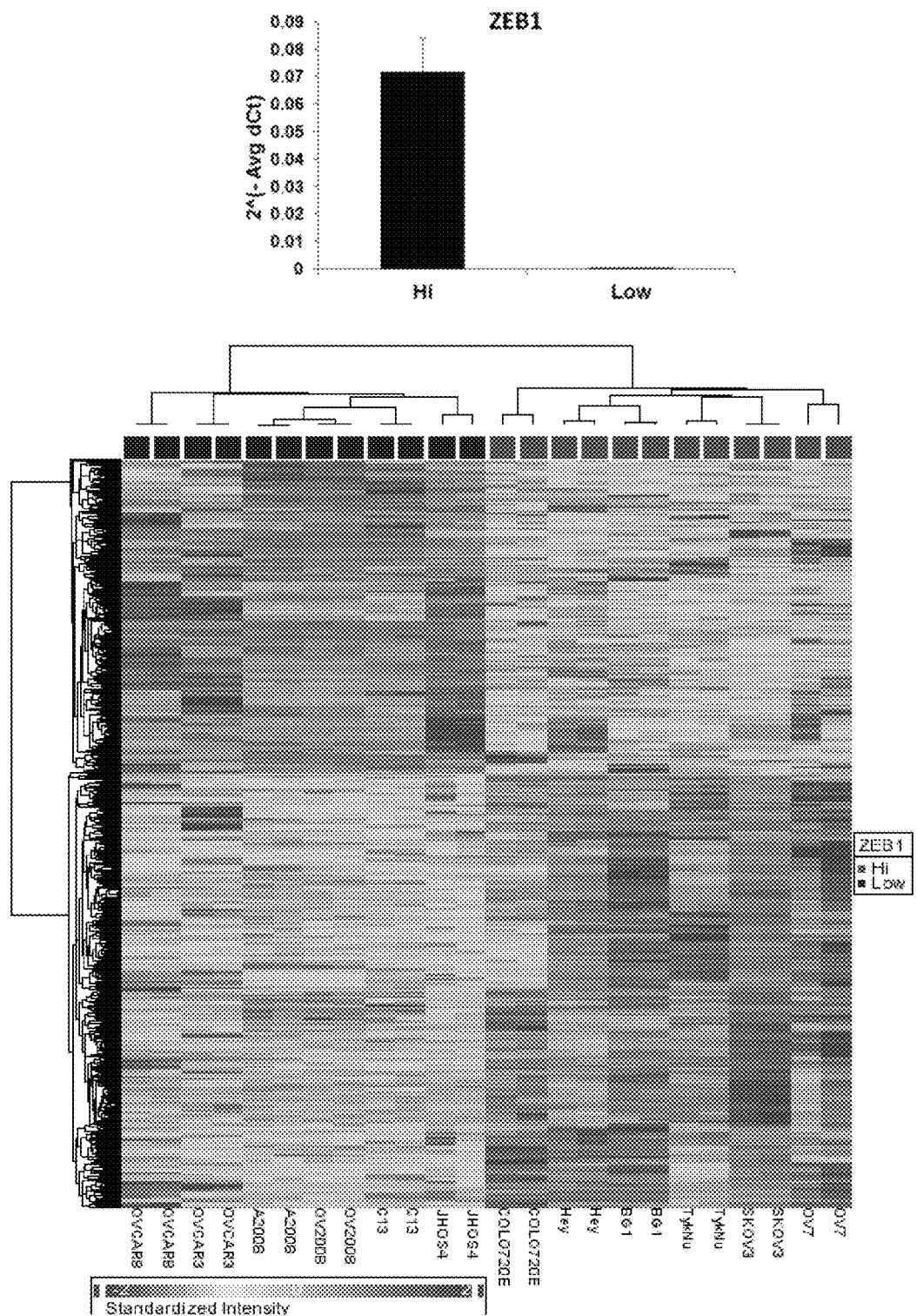
Figure 14:
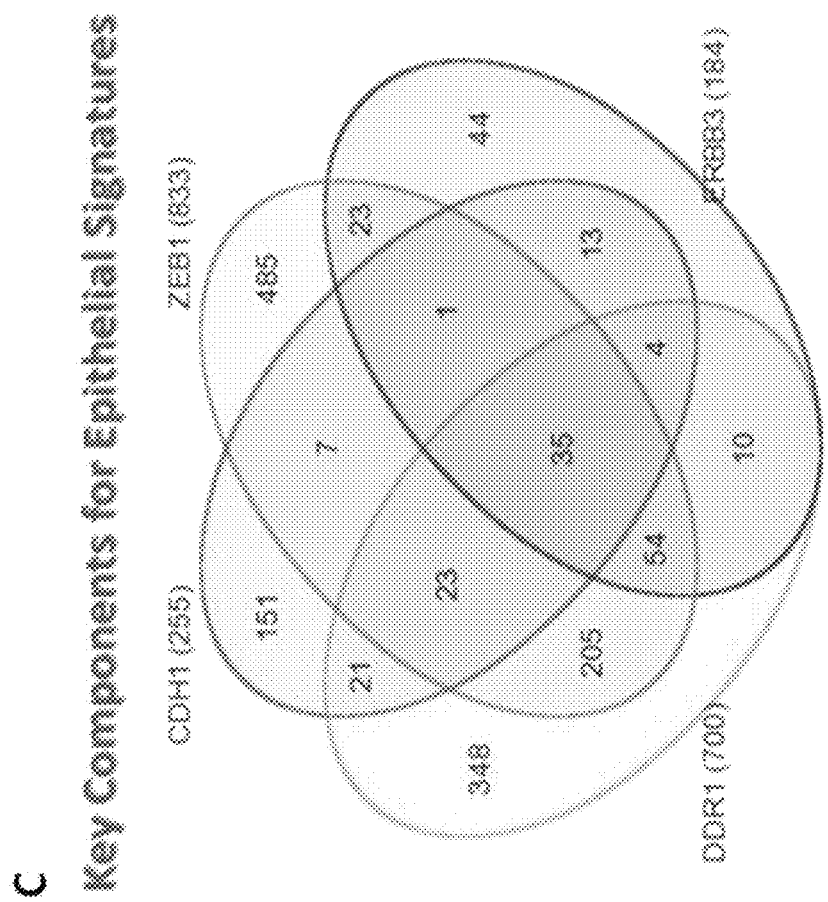

Quantitative real-time PCR (qPCR) was utilized to examine the expression patterns of CDH1, DDR1, ERBB3, and EMP3 in the panel of 42 ovarian cancer cell lines. The comparison of relative expression levels of these four genes among 42 cell lines were done via calculating ddCt. The expression levels of CDH1, DDR1, ERBB3 were found to be highest in ovarian cancer cell lines which harbor epithelial phenotypes. This confirms that CDH1, DDR1, ERBB3 expressions are linked to the EMT gradient (FIG. 14A). 6 cell lines were chosen with highest and 6 with lowest expressions of CDH1, DDR1, ERBB3, and ZEB1 respectively to generate signatures by using expression microarrays (FIG. 14B). Subsequently these four signatures were intersected by comparing the gene IDs using Venn diagram to search for commonly encountered genes, which it is believed are able to represent the key components in EMT (FIG. 14C). Among them, 14 genes (CDH1, CDH3, DDR1, EPCAM, ESRP1, ITGA5, JUP, MAL2, PKP1, PRSS8, SPINT1, ST14, VIM, ZEB1) have been shown to be involved in EMT; 19 genes (AP1M2, ARHGEF5, C19orf21, CD99L2, CTAGE6P, EMP3, GRHL1, GRHL2, HOOK1, LLGL2, LSR, MAP7, MYO5B, RAB25, S100A14, SLC44A2, SYDE1, TC2N, ZNF165) have not been reported to be involved in EMT by Pubmed search. Therefore, the method is robust enough to identify key EMT components that are well-known as well as novel ones.

Part C. Cell-based Small Molecule EMT Screening Assay

Image Analysis Parameters

As described above the images obtained from T1 and T2 were then sent for image analysis. Two parameters, "Cell Count" and "Cell Dispersion", are measured through the image segmentation routines. Briefly, the cell nuclei are segmented using a wavelet decomposition scheme, followed by a watershed procedure and size filtering as described previously. The final segmented objects or cell nuclei are then summed up to give the "Cell Count" of the analyzed well.

In addition, the X and Y coordinates of all cell nuclei are recorded and the average coordinates, which corresponds to the centre of the cell colony, is calculated. Finally, "Cell Dispersion" which is the standard deviation of the positions of all the cell nuclei in the analyzed well, is then calculated with respect to the centre of the cell colony.

Figure 18:
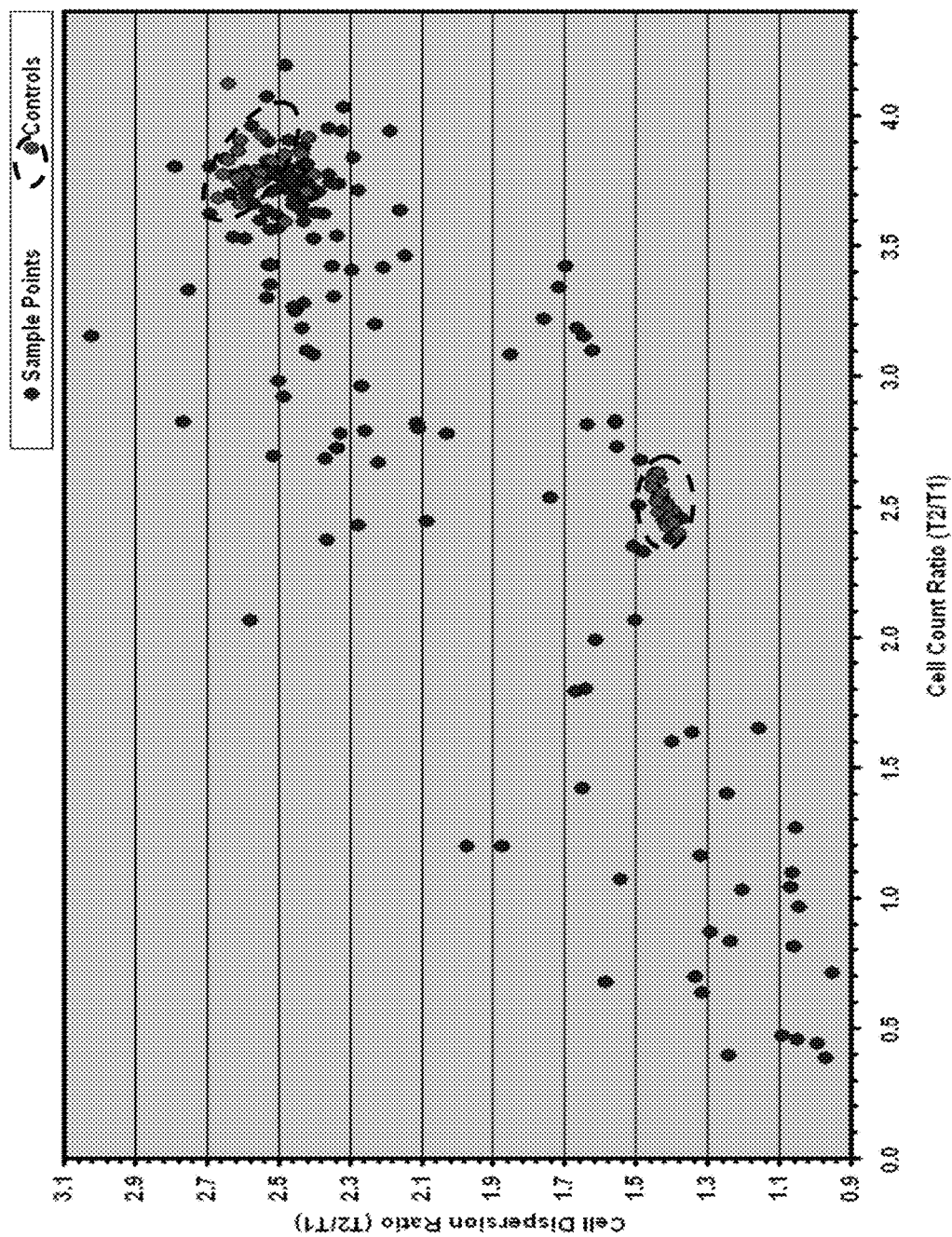
FIG. 18 Plot of Cell Dispersion ratio against Cell Count ratio of reference library compounds ("control" sample points encircled areas comprising control sample points as well as some "sample points").

By combining time-course imaging of T1 and T2, it was possible to obtain the derived measurements "Cell Count Ratio" and "Cell Dispersion Ratio", which correspond to the cell growth status and the cell migration/scattering status of each cell colony respectively (FIG. 18). The results generated from these two ratio parameters are used to assess the EMT inhibitory properties of the test compounds.

Assay Robustness Analysis

Figure 15:
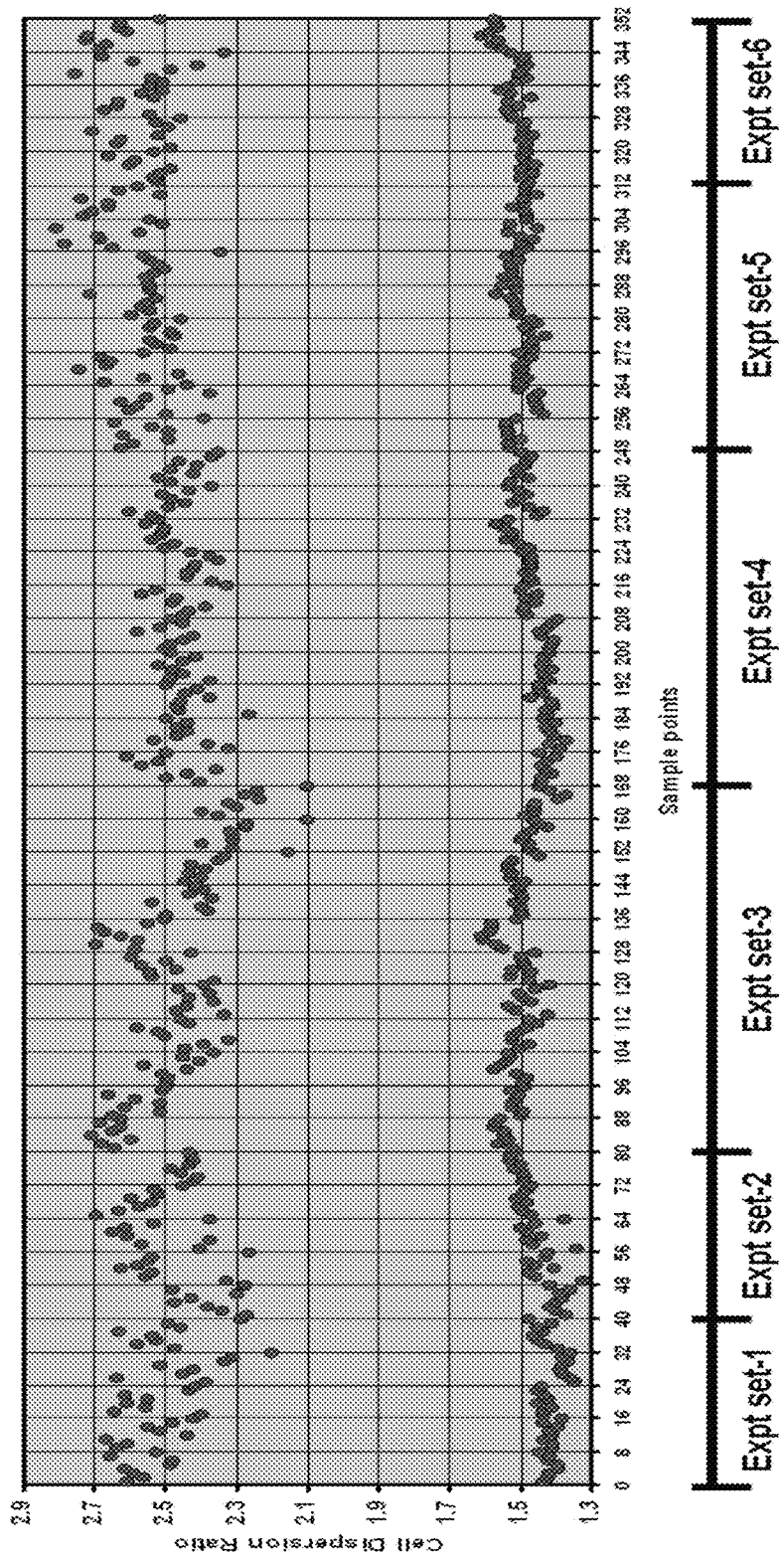
FIG. 15 Plot of Cell Dispersion ratio against sample number of all NegCtrl and PosCtrl conditions.
Figure 16:
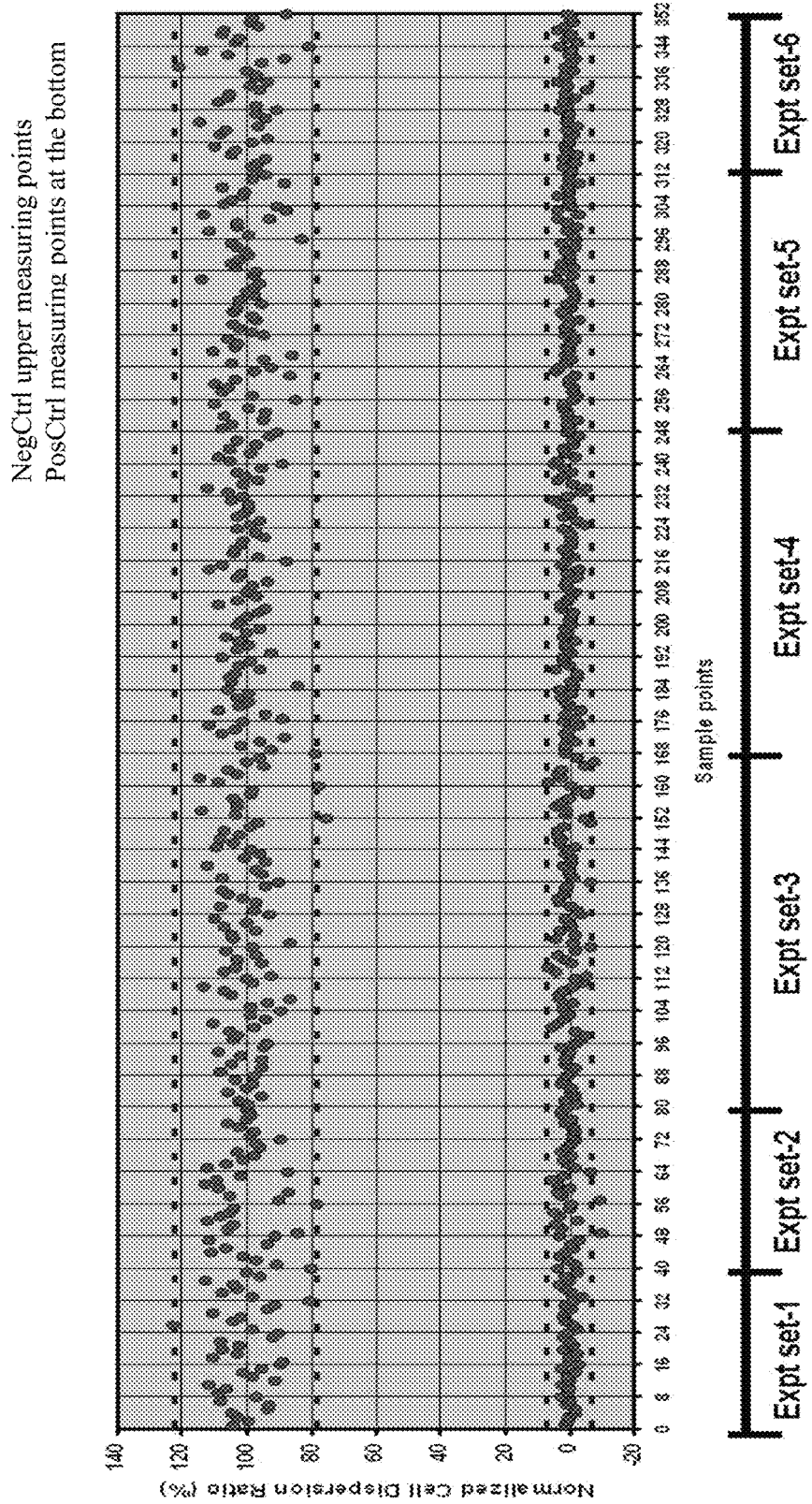
FIG. 16 Plot of Normalized Cell Dispersion ratio against sample number of all NegCtrl and PosCtrl conditions.
Figure 17:
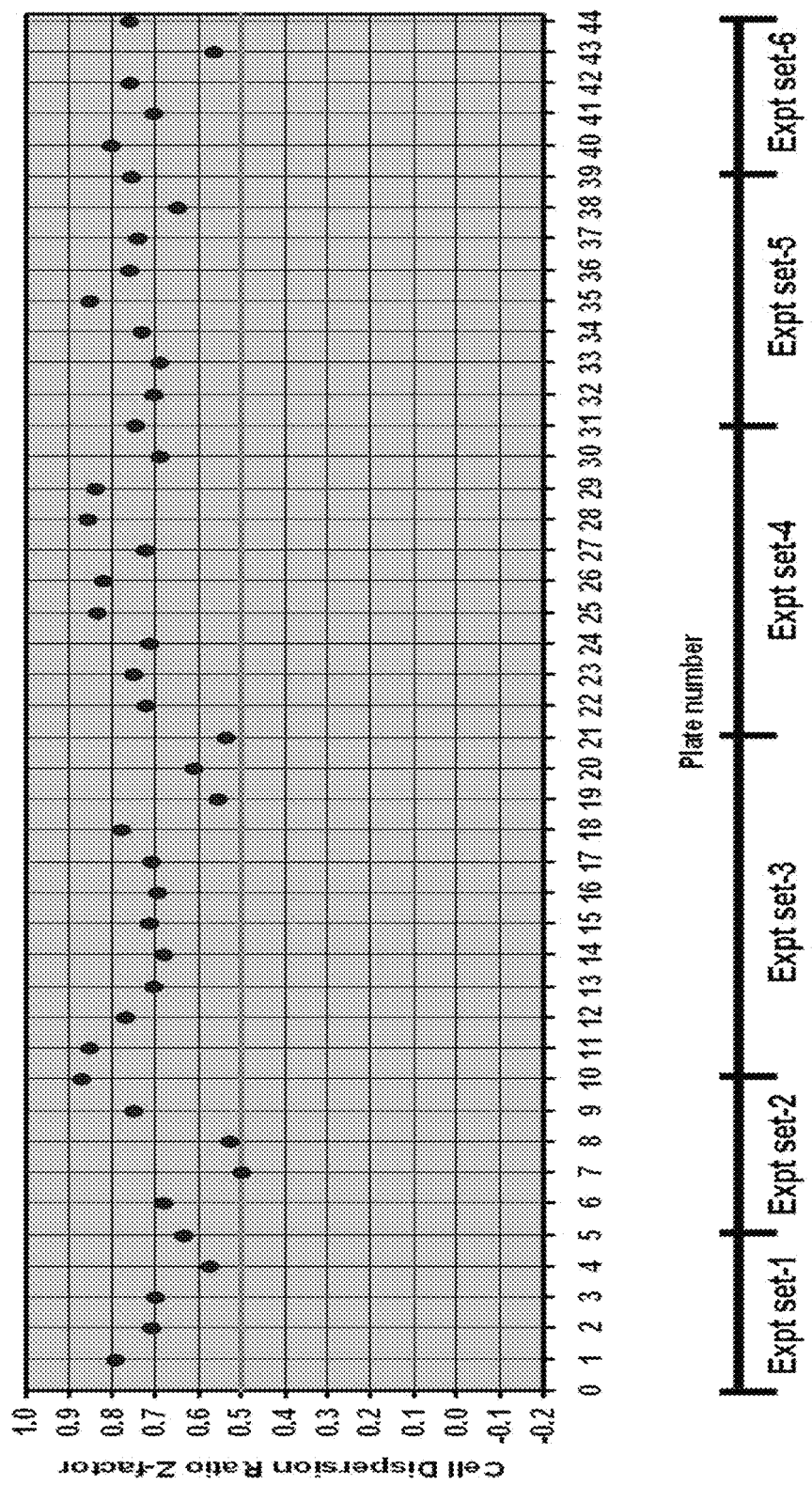
FIG. 17 Plot of Cell Dispersion ratio Z-factor statistics of NegCtrl vs. PosCtrl against plate number.

An example of 6 experiment sets done on different days is illustrated in FIGS. 15, 16 and 17. The Cell Dispersion ratio parameter is analyzed here to show the robustness of the assay in determining whether it can differentiate an EMT inhibited condition (i.e. PosCtrl condition) from an EMT uninhibited condition (i.e. NegCtrl condition):

For NegCtrl condition, [AG 1478]=0 microM and [EGF]= 20 ng/mL

For PosCtrl condition, [AG1478]=6.67 microM and [EGF]=20 ng/mL

Cell Dispersion ratio for NegCtrl condition is observed to be at 2.50±0.12 (FIG. 15)

Cell Dispersion ratio for PosCtrl condition is observed to be at 1.48±0.05 (FIG. 15)

Normalizing all plates to PosCtrl=0% and NegCtrl=100%

S.D. (normalized Cell Dispersion ratio for NegCtrl condition)=7.3% (FIG. 16)

S.D. (normalized Cell Dispersion ratio for PosCtrl condition)=2.3% (FIG. 17)

Lastly, the Cell Dispersion ratio Z-factor statistics of NegCtrl vs. PosCtrl conditions is found to be ≥0.5, demonstrating robustness of this assay (FIG. 17)

Hits Criteria Analysis

Figure 19:
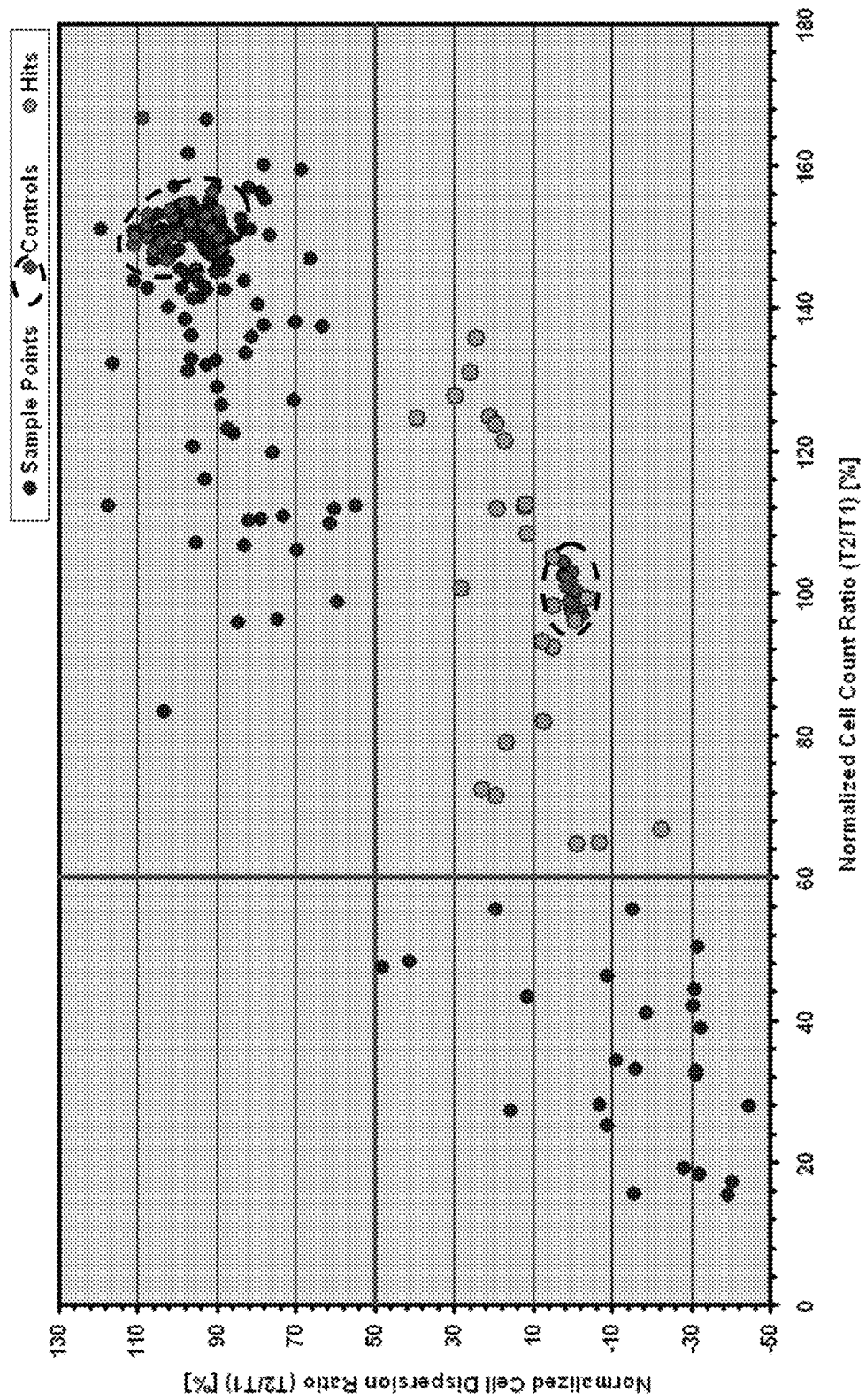
FIG. 19 Plot of Normalized Cell Dispersion ratio against Cell Count ratio of reference library compounds ("Hit" sample points lower right quadrant; "control" sample points encircled areas comprising control sample points as well as some "sample points").

The Tocris library set (Tocriscreen™ kinase inhibitor toolbox, Tocris Bioscience, Bristol, UK) was used as the reference to set the Threshold values for determining EMT inhibition in this assay. The Cell Dispersion ratio parameter in combination with the Cell Count ratio parameter were used in the analysis to select possible inhibitors of EMT. The Cell Count ratio was used to eliminate compounds that are cytotoxic to cells, or severely inhibit cell growth. By plotting Cell Dispersion ratio against Cell Count ratio together, it was possible to cluster sample points into the following observations (FIGS. 18 and 19):

Compound conditions that are cytotoxic to cells, and are severely inhibiting cell growth.

Compound conditions that inhibit cell dispersion, and do not severely inhibit cell growth.

Compound conditions that do not inhibit cell dispersion and cell growth.

Figure 20:
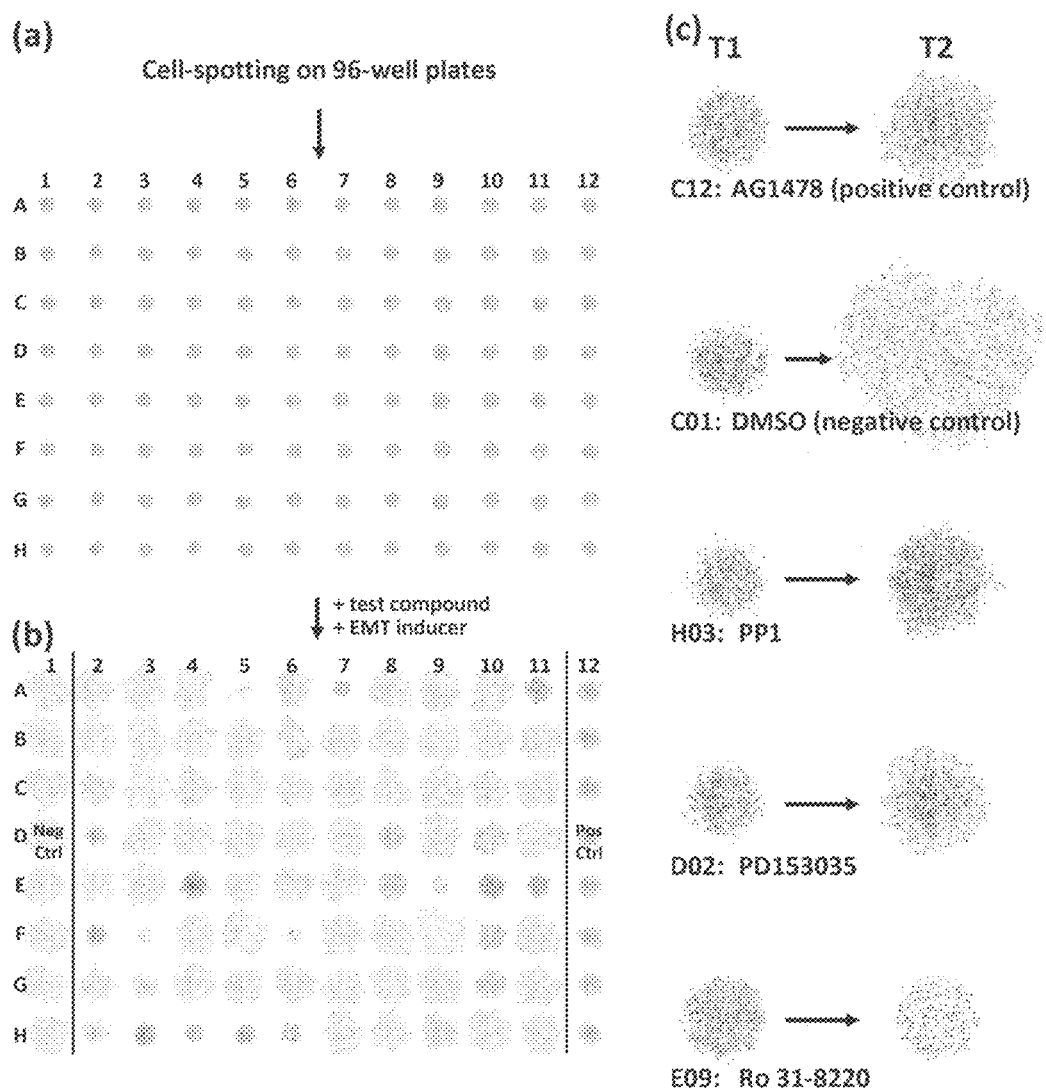
FIG. 20 (a) EMT screening assay image acquisition workflow. Robot-assisted plating of H2B-mcherry transfected NBT-II cells onto the well centers of 96-well plates. The initial plate image acquired at T1 serve as the baseline reference for calculation of Cell Count ratio and Cell Dispersion ratio for each well. The cells are then treated with test compounds overnight and further incubated for 24 h with a growth factor to induce EMT. (b) Final plate image acquired at T2, depicting dispersion response of cells 24 h after compounds and growth factor treatment. In the example shown, columns 2-11 are treated with 80 different test compounds at 6.67 µM in 0.67% DMSO and 20 ng/mL EGF. Column 1 serve as negative control wells treated with 0.67% DMSO and 20 ng/mL EGF, while column 12 serve as positive controls wells treated with 6.67 µM AG1478 in 0.67% DMSO and 20 ng/mL EGF. (c) Magnified images of selected wells from (b and c) acquired at T1 and T2. Wells C12, H03 and D02 are examples of cell colonies treated by compounds that can inhibit EGF initiated cell dispersion and do not severely inhibit cell growth. Well C01 is an example of a cell colony undergoing EGF induced EMT without any dispersion inhibition. Well E09 is an example of a cell colony treated by a growth inhibitory or toxic compound.

Normalizing all plates to Cell Dispersion ratio [PosCtrl=0% and NegCtrl=100%] and Cell Count ratio [PosCtrl=100%], it was possible to further resolve the clustering of the data points and apply the Threshold values to separate these clusters. In conclusion, the optimized hit selection criteria used to select for possible EMT inhibitors against EGF, HGF or IGF-1 induction are as follows:

Against EGF induction:
Sample Cell Count ratio≥1.5 (or ≥60% of PosCtrl Cell Count ratio), AND
Sample Cell Dispersion ratio≤50% of NegCtrl/PosCtrl Cell Dispersion ratios range Against HGF induction:
Sample Cell Count ratio≥1.5 (or ≥60% of PosCtrl Cell Count ratio), AND
Sample Cell Dispersion ratio≤50% of NegCtrl/PosCtrl Cell Dispersion ratios range And lastly, against IGF-1 induction:
Sample Cell Count ratio≥1.5 (or ≥85% of PosCtrl Cell Count ratio), AND
Sample Cell Dispersion ratio≤50% of NegCtrl/PosCtrl Cell Dispersion ratios range Compound Library Screening Test compounds were consolidated, formatted into compound library plates and tested in this spot migration assay to identify for possible EMT inhibitors. An example of the assay process of a typical spot migration assay is illustrated in FIG. 20. In this example, it was observed that the combined effect of the test compounds and EMT inducer (EGF in this example) on cell motility and proliferation can be grouped into the three classifications mentioned earlier, i.e.: (1) Compound conditions that are cytotoxic to cells, and are severely inhibiting cell growth; (2) Compound conditions that inhibit cell dispersion, and do not severely inhibit cell growth; and (3) Compound conditions that do not inhibit cell dispersion and cell growth (FIG. 21(b) and FIG. 21(c)).

Figure 21:
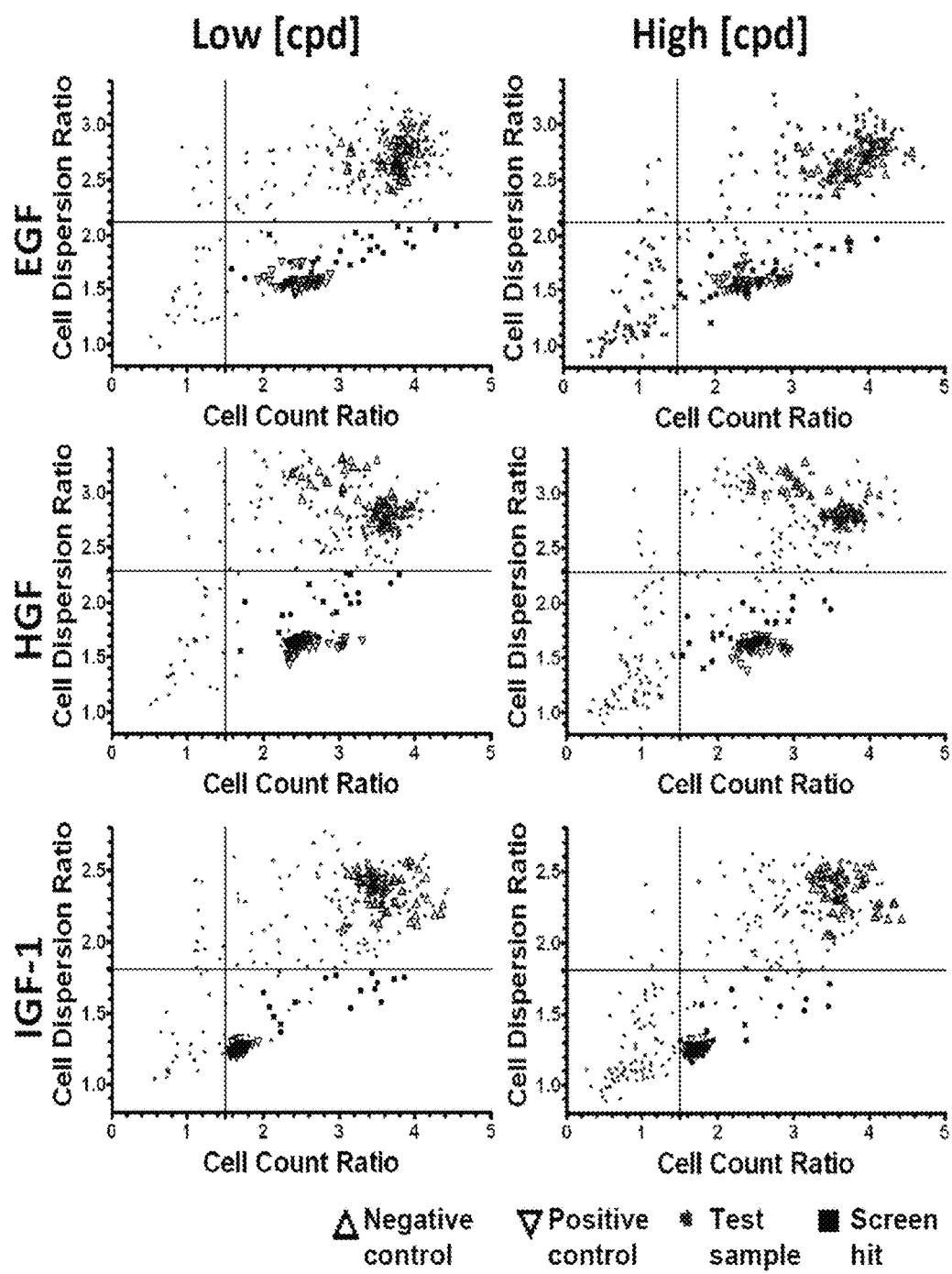
FIG. 21 Cell dispersion ratio vs. cell count ratio plots was plotted to illustrate the behavior of NBT-II treated with different test compounds and growth factors in this screening assay. Cell Dispersion Ratio (CDR) threshold is set at 50% CDR between Positive control CDR and negative control CDR. Cell Count Ratio threshold (CCR) is set as 1.5 growth rate. It was an interest to identify compounds that inhibit cell dispersion (i.e. less than CDR threshold) and do not severely inhibit cell growth (i.e. more than CCR threshold). To further refine the hits, the test compounds were run at a low and high concentration (1.67 microM and 6.67 microM respectively). Hit compounds (solid squares) were classified as test compounds that satisfy the CDR and CCR threshold criteria at both concentrations.

A collection of 269 compounds were eventually tested under EMT-activated conditions via induction with EGF, HGF or IGF-1. These compounds primarily consist of known inhibitors of various signaling pathways. The screening process is further refined to facilitate removal of weak motility inhibitors, and this can be done by screening the compounds at two concentrations of 1.67 μM and 6.67 μM (FIG. 21). The hit selection criteria defined previously for each growth factor condition is then applied. In general, compounds with weak motility inhibition effect will only show satisfactory cell dispersion inhibition at 6.67 μM but not at 1.67 μM. Conversely, some weak cytotoxic compounds may also exhibit satisfactory cell dispersion inhibition at 1.67 μM without severely inhibiting cell growth, but at higher 6.67 μM concentration, cellular toxicity is significant (Cell Count ratio≤1.5). We are therefore interested in selecting compounds that meet the hit selection criteria at both testing concentrations, which indicate that the compounds may exhibited good EMT inhibitory properties across a broad concentration range.

A total of 26 compounds satisfy the screening hit selection criteria and were subjected to further testing to generate dose response profile plots.

Dose Response Profile Generation for Initial Screening Hit Compounds

For dose response studies, compound plates containing serial diluted screening hit compounds were prepared as described previously. Complete spot migration assays were then performed with these compound plates. The Cell Dispersion ratio for every diluting concentration was then plotted in Prism software to generate the EMT dose response profile of the hit compounds against EGF, HGF or IGF-1 induction.

Figure 22:
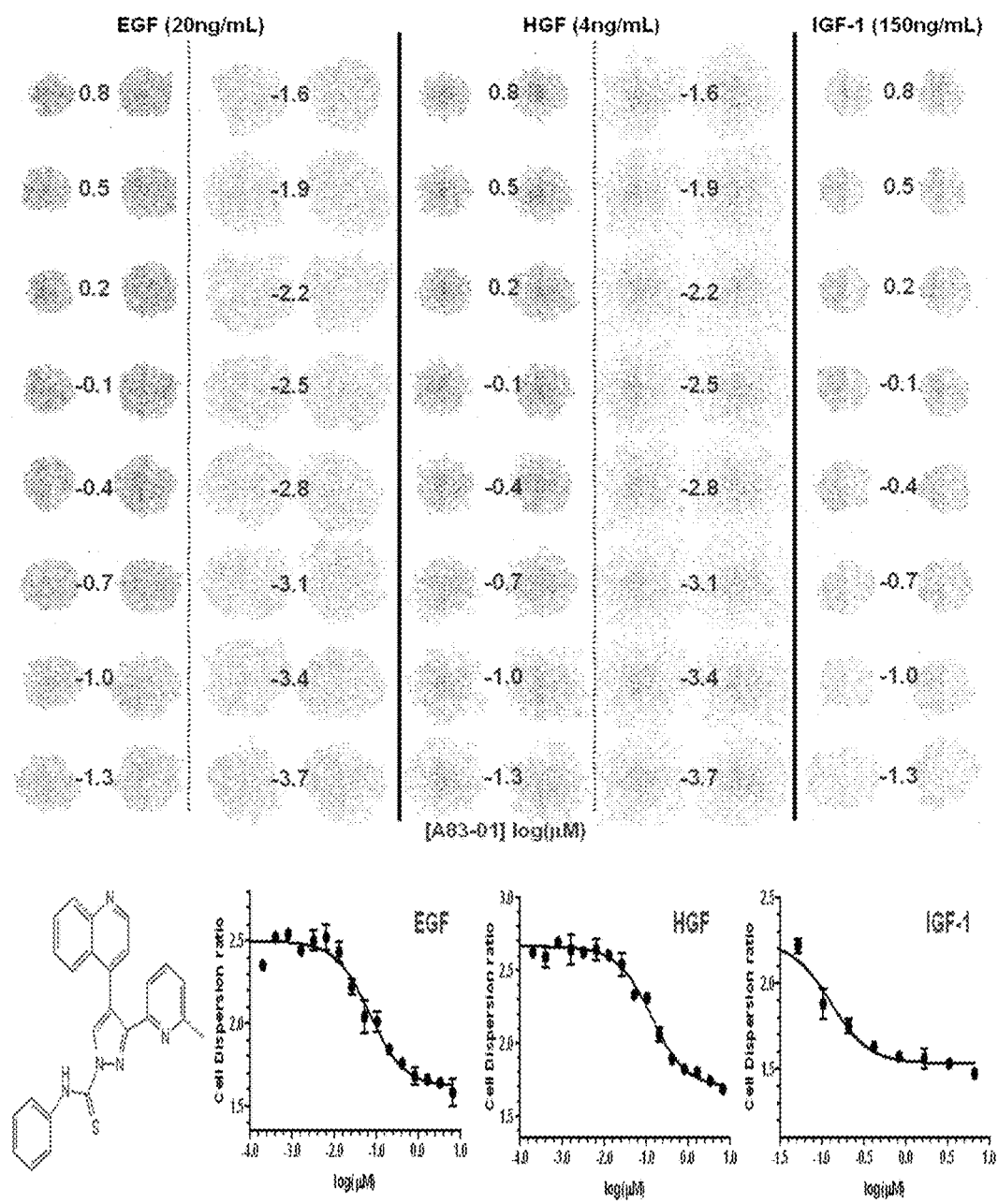
FIG. 22 Dose response profile of A83-01 against EMT induced by EGF, HGF or IGF-1.
Figure 23:
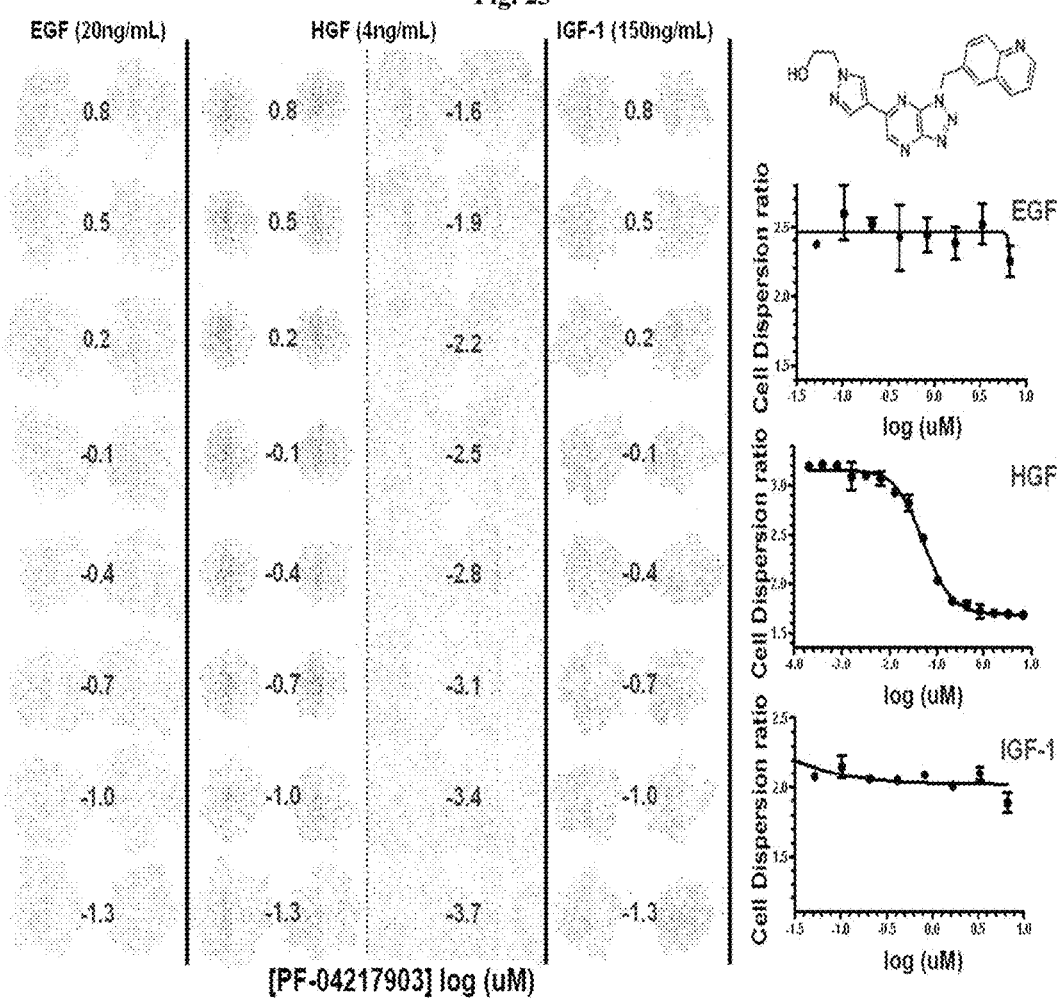
FIG. 23 Dose response profile of PF-04217903 against EMT induced by EGF, HGF or IGF-1.
Figure 24:
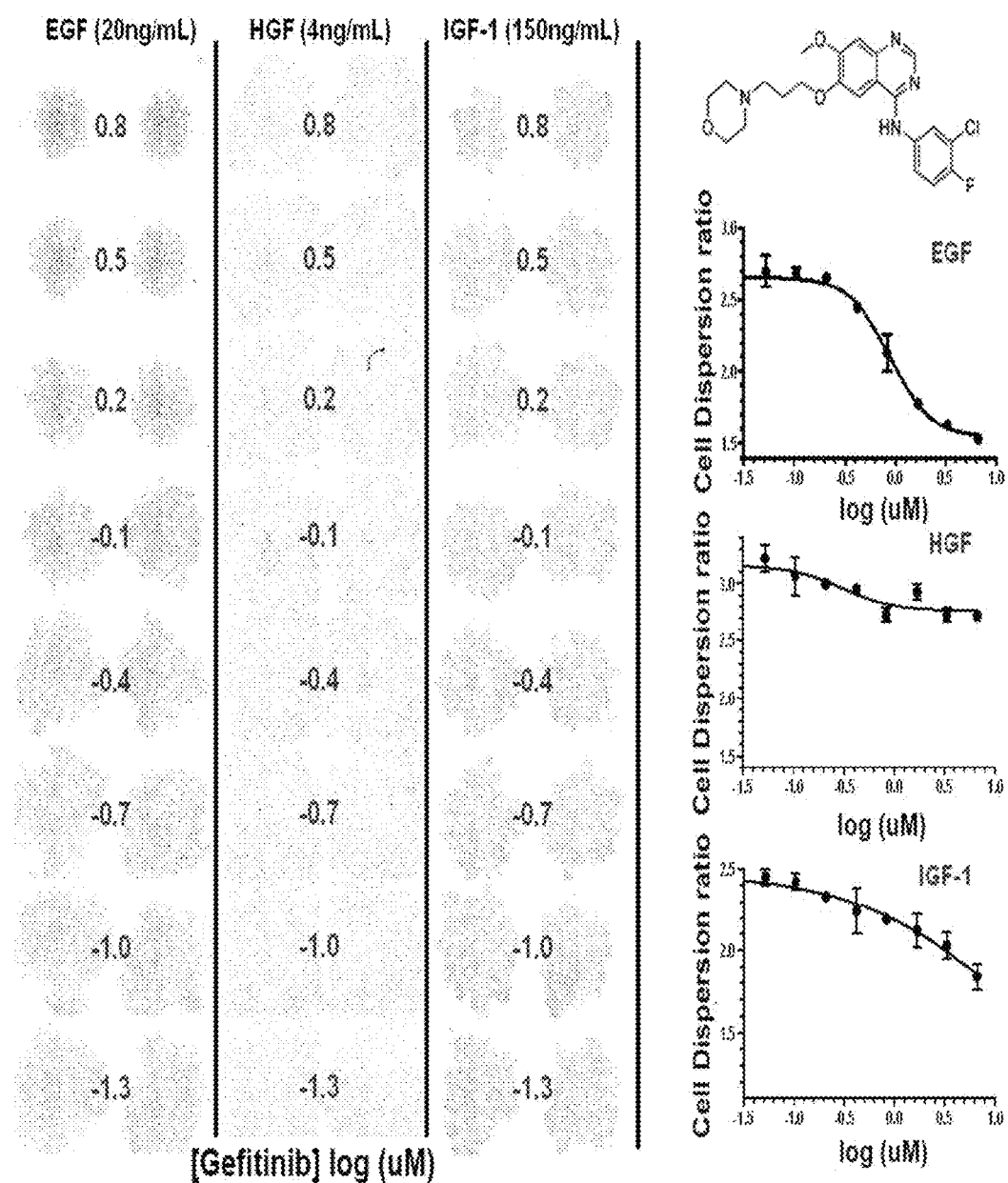
FIG. 24 Dose response profile of Gefitinib against EMT induced by EGF, HGF or IGF-1.

In general, the EMT spot migration assay has enabled us to identify compounds that compounds that are effective against all three growth factor signaling (FIG. 22 and Table 1) or compounds that can only inhibit specific growth factor signaling (FIG. 23, 24 and Table 1).

TABLE 1

Summary of inhibitor dose response against EMT induced by EGF, HGF or IGF-1.

| Name | ETC-ID | Cell Dispersion IC$_{50}$ (nM) | | |
| --- | --- | --- | --- | --- |
| | | EGF | HGF | IGF-1 |
| A83-01 | ETC-1677013 | 69 | 130 | 120 |
| AG 1478 | ETC-1676935 | 350 | — | — |
| AP1-2 | ETC-1676962 | 1300 | 970 | — |
| AZD 0530 | ETC-1692993 | 565 | 650 | 240 |
| AZD 6244 | ETC-1677316 | 840 | 471 | 534 |
| BMS 536924 | ETC-1681224 | 6600 | 2300 | 170 |
| CI-1040 | ETC-1677317 | 1000 | 820 | 1200 |
| D 4476 | ETC-1677010 | 1100 | 1400 | 1900 |
| Erlotinib | ETC-1677295 | 950 | — | — |
| GDC-0941 | ETC-1677322 | 740 | 380 | 490 |
| Gefitinib | ETC-1677294 | 880 | — | — |
| JNJ.38877605 | ETC-1677320 | — | 43 | — |
| Lapatinib | ETC-1677296 | 620 | — | — |
| LY 364947 | ETC-1677009 | 140 | 180 | 240 |
| MP-470 | ETC-1677344 | 510 | 970 | 580 |
| PD 0325901 | ETC-1677318 | 31 | 20 | 8.9 |
| PD 153035 | ETC-1676982 | 550 | — | — |
| PD 158780 | ETC-1676943 | 1200 | — | — |
| PF-04217903 | ETC-1677319 | — | 55 | — |
| PI-103 | ETC-1677327 | 680 | 380 | 400 |
| PIK-90 | ETC-1677325 | 950 | 400 | 620 |
| PP 1 | ETC-1676944 | 1725 | 2000 | 1200 |
| SB 431542 | ETC-1676933 | 1600 | 940 | 820 |

TABLE 1-continued

Summary of inhibitor dose response against
EMT induced by EGF, HGF or IGF-1.

| Name | ETC-ID | Cell Dispersion IC$_{50}$ (nM) | | |
|---|---|---|---|---|
| | | EGF | HGF | IGF-1 |
| SD-208 | ETC-1677008 | 85 | 110 | 150 |
| WHI-P 154 | ETC-1681221 | 590 | — | — |
| ZSTK 474 | ETC-1677331 | 850 | 410 | 660 |

Part D. EMT Reversal Assays

Based on their oncogenic subtypes and EMT categories, three cell lines were selected for EMT reversal assays. The three cell lines namely SKOV3, HEY and OVCAR-2 sub grouped into Mesenchymal, Intermediate M; Stem A, Intermediate M; and Stem B, Intermediate E; respectively were evaluated for their morphology and EMT markers after reversal. Two promising EMT inhibitors were identified, AZD0530 (potent inhibitor of Src kinase) from AstraZeneca and BIBF-1120 from Boehringer Ingelheim (potent inhibitor of VEGFR, PDGFR and FGFR) and went ahead with testing the three ovarian lines. These two inhibitors are currently used in phase 2 clinical trials.

Figure 25:
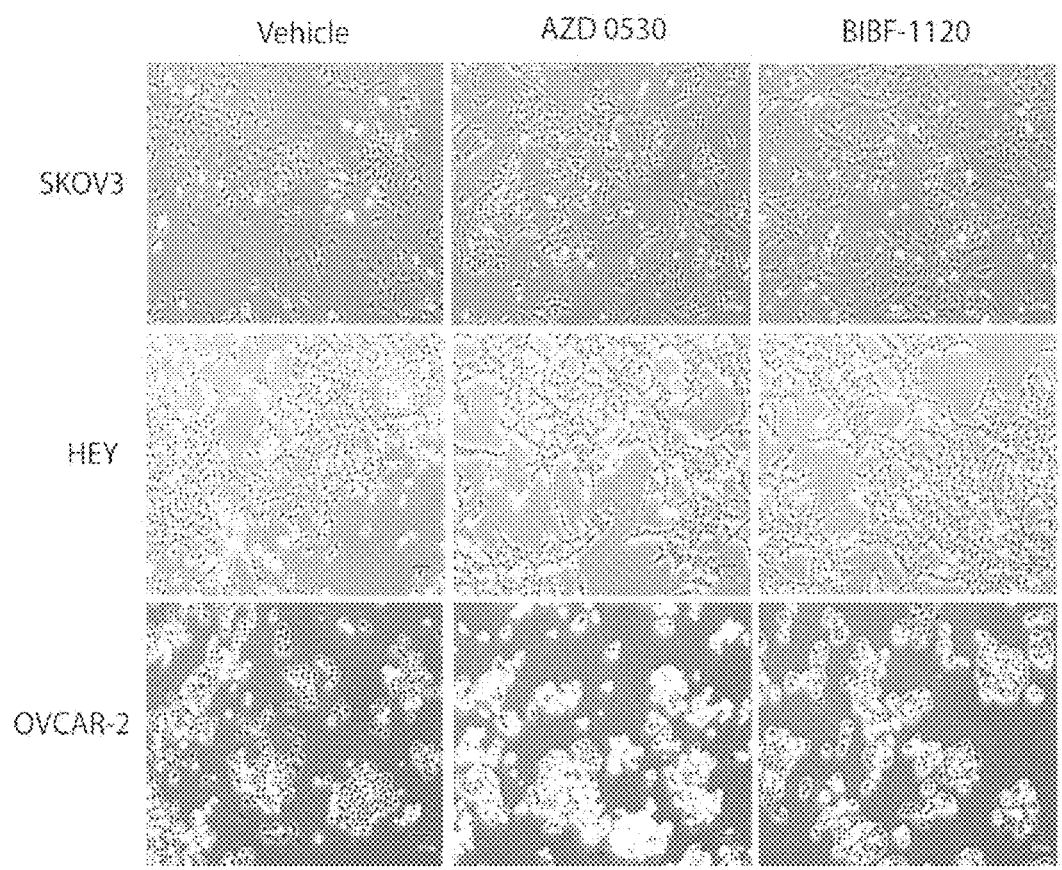
FIG. 25 shows morphology and Western blot analysis of SKOV3, HEY and OVCAR-2 after AZD0530 and BIBF-1120 treatment. (A) AZD0530 and BIBF-1120 restored epithelial morphology in SKOV3, HEY and OVCAR-2 as compared to DMSO (vehicle). (B) Western blot analysis of E-cadherin and MMP13 protein levels from each of the cell lines treated with 2 compounds and a control (v). Raw intensities of the western blot bands are measured and plotted into graphs. V: vehicle; AZD: AZD0530; BIBF: BIBF-1120.
Figure 25:
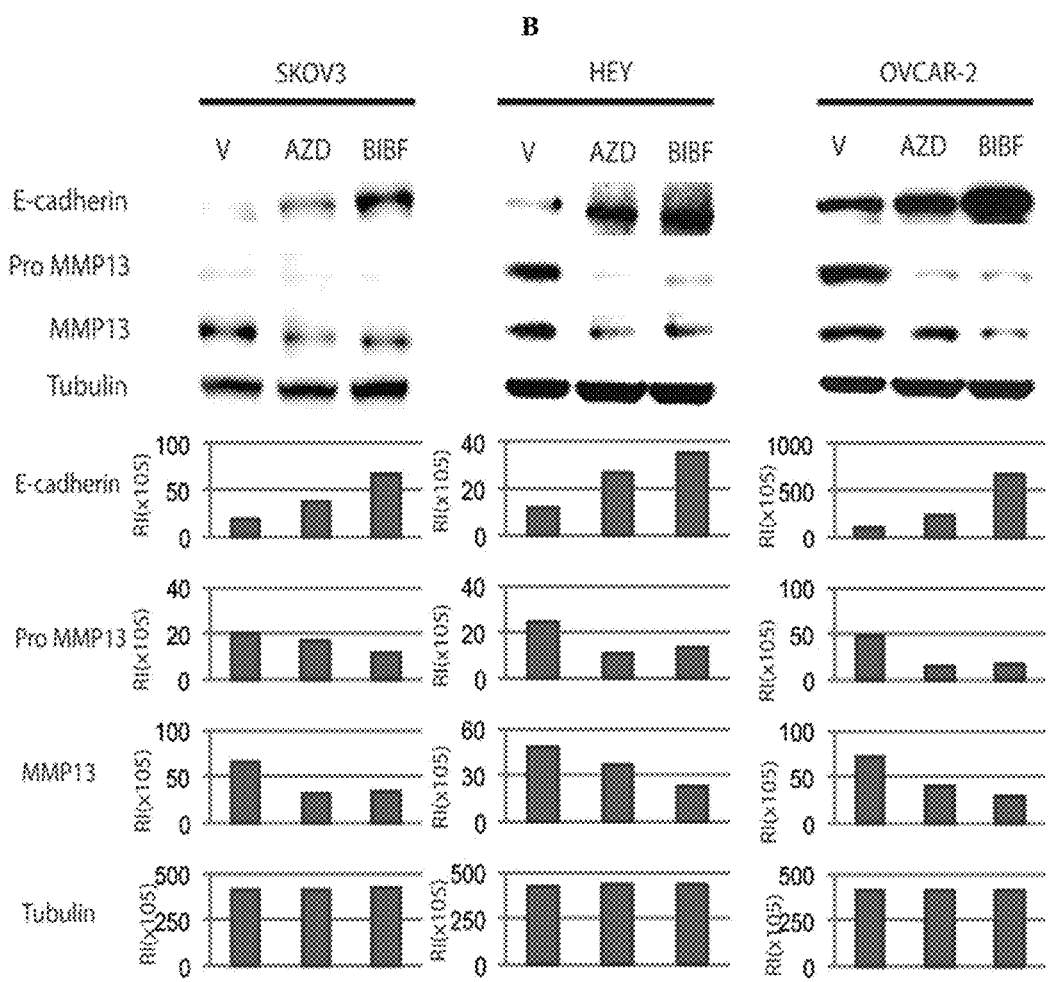

HEY and SKOV3 cells displayed a spindle-like dispersed phenotype while OVCAR-2 cells conferred a more epithelial-like morphology. Although the starting morphology was different for the three cell lines, compaction was markedly increased after treatment with small molecules AZD0530 and BIBF-1120 (FIG. 25A). HEY and SKOV3 cells restored the epithelioid-like morphology while OVCAR-2 cells formed tighter cobblestone-like cell colonies upon drug treatment. Along with the observed increased compaction, the three cell lines showed MET-like changes in protein expression. The addition of AZD 0530 and BIBF-1120 increased E-cadherin (epithelial marker) and reduced MMP13 (matrix metalloproteinase) protein levels (FIG. 25B). Semi-quantification of E-cadherin and MMP13 protein bands enabled comparison of the relative reversal profile of the two drugs on the three cell lines.

AZD0530 and BIBF-1120 increased E-cadherin levels to a different extent in the three cell lines. Treatment with BIBF-1120 resulted in marked increase of E-cadherin protein levels in all 3 cells lines while AZD0530 treatment showed a greater increase in E-cadherin protein levels in SKOV3 and HEY relative to OVCAR-2. Similar fashion was observed for reduction in MMP13 protein levels where AZD0530 treatment resulted in greater reduction of MMP13 protein levels in SKOV3 and HEY as compared to OVCAR-2. In conclusion, AZD0530 and BIBF-1120 showed similar reversal profile in SKOV3 and HEY cells while BIBF-1120 showed a relatively better reversal profile than AZD0530 in OVCAR-2 cells.

In this embodiment, the present study provides a technology to stratify individual ovarian carcinoma patients in one of 5 distinct subtypes and to assess an EMT score. These 2 parameters provide new surrogate markers to follow patients during the course of targeted therapy. A high content, high throughput cell-based screen has been designed to identify drugs interfering with the EMT status. This screening method permits to identify drugs in combination which can effectively reverse the EMT status. It is also used to define pathway interactions which overcome the therapeutic effect of single agent. Thus, it allows choosing the best combinations to circumvent the potential bypass mechanisms promoting activation of additional pathway not interfered with the prescribed drugs. Phosphoproteomic profiling of 42 ovarian carcinoma cell lines and of tumors will further help selecting appropriate drugs to reverse the EMT status. The reversal of the EMT status should alleviate resistance to conventional therapeutics. A therapeutic protocol can be designed to render ovarian cancer patient more sensitive to conventional therapeutics following administration of targeted EMT reversal therapeutics.

Gene List 1. Gene components used for the clustering.

| Affymetrix Probe ID | Gene Symbol | Gene Cluster |
|---|---|---|
| 201739_at | SGK1 | Not Assigned |
| 202499_s_at | SLC2A3 | Not Assigned |
| 202627_s_at | SERPINE1 | Not Assigned |
| 202628_s_at | SERPINE1 | Not Assigned |
| 202388_at | RGS2 | Not Assigned |
| 204472_at | GEM | Not Assigned |
| 201466_s_at | JUN | Not Assigned |
| 202672_s_at | ATF3 | Not Assigned |
| 201693_s_at | EGR1 | Not Assigned |
| 201694_s_at | EGR1 | Not Assigned |
| 202768_at | FOSB | Not Assigned |
| 201041_s_at | DUSP1 | Not Assigned |
| 209189_at | FOS | Not Assigned |
| 206115_at | EGR3 | Not Assigned |
| 201289_at | CYR61 | Not Assigned |
| 210764_s_at | CYR61 | Not Assigned |
| 209101_at | CTGF | Not Assigned |
| 221841_s_at | KLF4 | Not Assigned |
| 204621_s_at | NR4A2 | Not Assigned |
| 204622_x_at | NR4A2 | Not Assigned |
| 216248_s_at | NR4A2 | Not Assigned |
| 204018_x_at | HBA1 /// HBA2 | Not Assigned |
| 211699_x_at | HBA1 /// HBA2 | Not Assigned |
| 209458_x_at | HBA1 /// HBA2 | Not Assigned |
| 211745_x_at | HBA1 /// HBA2 | Not Assigned |
| 217414_x_at | HBA1 /// HBA2 | Not Assigned |
| 214414_x_at | HBA1 /// HBA2 | Not Assigned |
| 209116_x_at | HBB | Not Assigned |
| 211696_x_at | HBB | Not Assigned |

-continued

| Gene List 1. Gene components used for the clustering. | | |
|---|---|---|
| Affymetrix Probe ID | Gene Symbol | Gene Cluster |
| 217232_x_at | HBB | Not Assigned |
| 205239_at | AREG | Not Assigned |
| 201631_s_at | IER3 | Not Assigned |
| 209457_at | DUSP5 | Not Assigned |
| 36711_at | MAFF | Not Assigned |
| 218541_s_at | C8orf4 | Not Assigned |
| 201645_at | TNC | Mesenchymal |
| 205206_at | KAL1 | Mesenchymal |
| 201430_s_at | DPYSL3 | Mesenchymal |
| 201431_s_at | DPYSL3 | Mesenchymal |
| 201860_s_at | PLAT | Mesenchymal |
| 204457_s_at | GAS1 | Mesenchymal |
| 202157_s_at | CUGBP2 | Mesenchymal |
| 202391_at | BASP1 | Mesenchymal |
| 203066_at | GALNAC4S-6ST | Mesenchymal |
| 212012_at | PXDN | Mesenchymal |
| 212013_at | PXDN | Mesenchymal |
| 202435_s_at | CYP1B1 | Mesenchymal |
| 202436_s_at | CYP1B1 | Mesenchymal |
| 202437_s_at | CYP1B1 | Mesenchymal |
| 203180_at | ALDH1A3 | Mesenchymal |
| 205433_at | BCHE | Mesenchymal |
| 203548_s_at | LPL | Mesenchymal |
| 203549_s_at | LPL | Mesenchymal |
| 203980_at | FABP4 | Mesenchymal |
| 209612_s_at | ADH1B | Mesenchymal |
| 209613_s_at | ADH1B | Mesenchymal |
| 206488_s_at | CD36 | Mesenchymal |
| 209555_s_at | CD36 | Mesenchymal |
| 213524_s_at | G0S2 | Mesenchymal |
| 211726_s_at | FMO2 | Mesenchymal |
| 201787_at | FBLN1 /// LOC100133843 | Mesenchymal |
| 202994_s_at | FBLN1 | Mesenchymal |
| 202995_s_at | FBLN1 | Mesenchymal |
| 201286_at | SDC1 | Mesenchymal |
| 201287_s_at | SDC1 | Mesenchymal |
| 202363_at | SPOCK1 | Mesenchymal |
| 218002_s_at | CXCL14 | Mesenchymal |
| 205559_s_at | PCSK5 | Mesenchymal |
| 202274_at | ACTG2 | Mesenchymal |
| 202555_s_at | MYLK | Mesenchymal |
| 201058_s_at | MYL9 | Mesenchymal |
| 204083_s_at | TPM2 | Mesenchymal |
| 201667_at | GJA1 | Mesenchymal |
| 206227_at | CILP | Mesenchymal |
| 205226_at | PDGFRL | Mesenchymal |
| 201215_at | PLS3 | Mesenchymal |
| 203058_s_at | PAPSS2 | Mesenchymal |
| 203060_s_at | PAPSS2 | Mesenchymal |
| 203903_s_at | HEPH | Mesenchymal |
| 203477_at | COL15A1 | Mesenchymal |
| 202202_s_at | LAMA4 | Mesenchymal |
| 202007_at | NID1 | Mesenchymal |
| 204114_at | NID2 | Mesenchymal |
| 201505_at | LAMB1 | Mesenchymal |
| 211651_s_at | LAMB1 | Mesenchymal |
| 213429_at | — | Mesenchymal |
| 204955_at | SRPX | Mesenchymal |
| 208782_at | FSTL1 | Mesenchymal |
| 210762_s_at | DLC1 | Mesenchymal |
| 212298_at | NRP1 | Mesenchymal |
| 201506_at | TGFBI | Mesenchymal |
| 203868_s_at | VCAM1 | Mesenchymal |
| 209732_at | CLEC2B | Mesenchymal |
| 201616_s_at | CALD1 | Mesenchymal |
| 201617_x_at | CALD1 | Mesenchymal |
| 201108_s_at | THBS1 | Mesenchymal |
| 201109_s_at | THBS1 | Mesenchymal |
| 201110_s_at | THBS1 | Mesenchymal |
| 200974_at | ACTA2 | Mesenchymal |
| 205547_s_at | TAGLN | Mesenchymal |
| 209621_s_at | PDLIM3 | Mesenchymal |
| 204051_s_at | SFRP4 | Mesenchymal |
| 204052_s_at | SFRP4 | Mesenchymal |
| 204135_at | FILIP1L | Mesenchymal |

-continued

| Gene List 1. Gene components used for the clustering. | | |
|---|---|---|
| Affymetrix Probe ID | Gene Symbol | Gene Cluster |
| 203131_at | PDGFRA | Mesenchymal |
| 207172_s_at | CDH11 | Mesenchymal |
| 207173_x_at | CDH11 | Mesenchymal |
| 202283_at | SERPINF1 | Mesenchymal |
| 201893_x_at | DCN | Mesenchymal |
| 211813_x_at | DCN | Mesenchymal |
| 211896_s_at | DCN | Mesenchymal |
| 209335_at | DCN | Mesenchymal |
| 206101_at | ECM2 | Mesenchymal |
| 212764_at | ZEB1 | Mesenchymal |
| 218656_s_at | LHFP | Mesenchymal |
| 210139_s_at | PMP22 | Mesenchymal |
| 204337_at | RGS4 | Mesenchymal |
| 208131_s_at | PTGIS | Mesenchymal |
| 203570_at | LOXL1 | Mesenchymal |
| 204463_s_at | EDNRA | Mesenchymal |
| 204464_s_at | EDNRA | Mesenchymal |
| 201149_s_at | TIMP3 | Mesenchymal |
| 201147_s_at | TIMP3 | Mesenchymal |
| 201150_s_at | TIMP3 | Mesenchymal |
| 206439_at | EPYC | Mesenchymal |
| 205422_s_at | ITGBL1 | Mesenchymal |
| 205941_s_at | COL10A1 | Mesenchymal |
| 217428_s_at | COL10A1 | Mesenchymal |
| 203876_s_at | MMP11 | Mesenchymal |
| 203878_s_at | MMP11 | Mesenchymal |
| 213909_at | LRRC15 | Mesenchymal |
| 213338_at | TMEM158 | Mesenchymal |
| 205479_s_at | PLAU | Mesenchymal |
| 211668_s_at | PLAU | Mesenchymal |
| 218468_s_at | GREM1 | Mesenchymal |
| 218469_at | GREM1 | Mesenchymal |
| 204589_at | NUAK1 | Mesenchymal |
| 202765_s_at | FBN1 | Mesenchymal |
| 202766_s_at | FBN1 | Mesenchymal |
| 213139_at | SNAI2 | Mesenchymal |
| 201069_at | MMP2 | Mesenchymal |
| 201792_at | AEBP1 | Mesenchymal |
| 201438_at | COL6A3 | Mesenchymal |
| 200665_s_at | SPARC | Mesenchymal |
| 212667_at | SPARC | Mesenchymal |
| 202403_s_at | COL1A2 | Mesenchymal |
| 202404_s_at | COL1A2 | Mesenchymal |
| 202310_s_at | COL1A1 | Mesenchymal |
| 202311_s_at | COL1A1 | Mesenchymal |
| 201852_x_at | COL3A1 | Mesenchymal |
| 215076_s_at | COL3A1 | Mesenchymal |
| 211161_s_at | COL3A1 | Mesenchymal |
| 203325_s_at | COL5A1 | Mesenchymal |
| 212488_at | COL5A1 | Mesenchymal |
| 212489_at | COL5A1 | Mesenchymal |
| 221729_at | COL5A2 | Mesenchymal |
| 221730_at | COL5A2 | Mesenchymal |
| 201744_s_at | LUM | Mesenchymal |
| 202450_s_at | CTSK | Mesenchymal |
| 203083_at | THBS2 | Mesenchymal |
| 211719_x_at | FN1 | Mesenchymal |
| 212464_s_at | FN1 | Mesenchymal |
| 210495_x_at | FN1 | Mesenchymal |
| 216442_x_at | FN1 | Mesenchymal |
| 209955_s_at | FAP | Mesenchymal |
| 210511_s_at | INHBA | Mesenchymal |
| 204320_at | COL11A1 | Mesenchymal |
| 37892_at | COL11A1 | Mesenchymal |
| 210809_s_at | POSTN | Mesenchymal |
| 204619_s_at | VCAN | Mesenchymal |
| 204620_s_at | VCAN | Mesenchymal |
| 221731_x_at | VCAN | Mesenchymal |
| 211571_s_at | VCAN | Mesenchymal |
| 215646_s_at | VCAN | Mesenchymal |
| 213790_at | ADAM12 | Mesenchymal |
| 219087_at | ASPN | Mesenchymal |
| 221541_at | CRISPLD2 | Mesenchymal |
| 217430_x_at | COL1A1 | Mesenchymal |
| 221019_s_at | COLEC12 | Mesenchymal |

-continued

| Gene List 1. Gene components used for the clustering. | | |
|---|---|---|
| Affymetrix Probe ID | Gene Symbol | Gene Cluster |
| 204298_s_at | LOX | Mesenchymal |
| 215446_s_at | LOX | Mesenchymal |
| 202465_at | PCOLCE | Mesenchymal |
| 209156_s_at | COL6A2 | Mesenchymal |
| 213428_s_at | COL6A1 | Mesenchymal |
| 209651_at | TGFB1I1 | Mesenchymal |
| 213905_x_at | BGN | Mesenchymal |
| 209687_at | CXCL12 | Mesenchymal |
| 218162_at | OLFML3 | Mesenchymal |
| 205943_at | TDO2 | Mesenchymal |
| 206025_s_at | TNFAIP6 | Mesenchymal |
| 206026_s_at | TNFAIP6 | Mesenchymal |
| 202998_s_at | LOXL2 | Mesenchymal |
| 211980_at | COL4A1 | Mesenchymal |
| 211981_at | COL4A1 | Mesenchymal |
| 213943_at | TWIST1 | Mesenchymal |
| 221911_at | ETV1 | Mesenchymal |
| 212473_s_at | MICAL2 | Mesenchymal |
| 202237_at | NNMT | Mesenchymal |
| 202238_s_at | NNMT | Mesenchymal |
| 212344_at | SULF1 | Mesenchymal |
| 212353_at | SULF1 | Mesenchymal |
| 212354_at | SULF1 | Mesenchymal |
| 208747_s_at | C1S | Mesenchymal |
| 212067_s_at | C1R | Mesenchymal |
| 205713_s_at | COMP | Mesenchymal |
| 221900_at | COL8A2 | Mesenchymal |
| 209758_s_at | MFAP5 | Mesenchymal |
| 213764_s_at | MFAP5 | Mesenchymal |
| 213765_at | MFAP5 | Mesenchymal |
| 209496_at | RARRES2 | Mesenchymal |
| 208850_s_at | THY1 | Mesenchymal |
| 213869_x_at | THY1 | Mesenchymal |
| 209540_at | IGF1 | Mesenchymal |
| 209541_at | IGF1 | Mesenchymal |
| 209542_x_at | IGF1 | Mesenchymal |
| 222288_at | — | Mesenchymal |
| 219304_s_at | PDGFD | Mesenchymal |
| 219935_at | ADAMTS5 | Mesenchymal |
| 218723_s_at | C13orf15 | Mesenchymal |
| 202458_at | PRSS23 | Not Assigned |
| 219773_at | NOX4 | Not Assigned |
| 203817_at | GUCY1B3 | Not Assigned |
| 221942_s_at | GUCY1A3 | Not Assigned |
| 212942_at | KIAA1199 | Not Assigned |
| 209596_at | MXRA5 | Not Assigned |
| 219454_at | EGFL6 | Not Assigned |
| 202619_s_at | PLOD2 | Not Assigned |
| 202620_s_at | PLOD2 | Not Assigned |
| 201313_at | ENO2 | Not Assigned |
| 201849_at | BNIP3 | Not Assigned |
| 202887_s_at | DDIT4 | Not Assigned |
| 202912_at | ADM | Not Assigned |
| 204595_s_at | STC1 | Not Assigned |
| 204597_x_at | STC1 | Not Assigned |
| 210095_s_at | IGFBP3 | Not Assigned |
| 212143_s_at | IGFBP3 | Not Assigned |
| 204475_at | MMP1 | Not Assigned |
| 209301_at | CA2 | Not Assigned |
| 209267_s_at | SLC39A8 | Not Assigned |
| 219869_s_at | SLC39A8 | Not Assigned |
| 205542_at | STEAP1 | Not Assigned |
| 204259_at | MMP7 | Not Assigned |
| 209875_s_at | SPP1 | Not Assigned |
| 204285_s_at | PMAIP1 | Not Assigned |
| 205590_at | RASGRP1 | Not Assigned |
| 209277_at | TFPI2 | Not Assigned |
| 209278_s_at | TFPI2 | Not Assigned |
| 205534_at | PCDH7 | Not Assigned |
| 204932_at | TNFRSF11B | Not Assigned |
| 204933_s_at | TNFRSF11B | Not Assigned |
| 217143_s_at | TRA@ /// TRD@ | Not Assigned |
| 202888_s_at | ANPEP | Not Assigned |
| 204198_s_at | RUNX3 | Not Assigned |
| 202018_s_at | LTF | Not Assigned |

-continued

| Gene List 1. Gene components used for the clustering. | | |
|---|---|---|
| Affymetrix Probe ID | Gene Symbol | Gene Cluster |
| 202376_at | SERPINA3 | Not Assigned |
| 209443_at | SERPINA5 | Not Assigned |
| 202917_s_at | S100A8 | Not Assigned |
| 203535_at | S100A9 | Not Assigned |
| 205916_at | S100A7 | Not Assigned |
| 203691_at | PI3 | Not Assigned |
| 41469_at | PI3 | Not Assigned |
| 206157_at | PTX3 | Not Assigned |
| 206336_at | CXCL6 | Not Assigned |
| 202859_x_at | IL8 | Not Assigned |
| 211506_s_at | IL8 | Not Assigned |
| 204470_at | CXCL1 | Not Assigned |
| 209774_x_at | CXCL2 | Not Assigned |
| 214974_x_at | CXCL5 | Not Assigned |
| 204099_at | SMARCD3 | Not Assigned |
| 206859_s_at | PAEP | Not Assigned |
| 206697_s_at | HP /// HPR | Not Assigned |
| 208470_s_at | HP /// HPR | Not Assigned |
| 208451_s_at | C4A /// C4B | Not Assigned |
| 214428_x_at | C4A /// C4B | Not Assigned |
| 205844_at | VNN1 | Not Assigned |
| 212531_at | LCN2 | Not Assigned |
| 219630_at | PDZK1IP1 | Not Assigned |
| 214456_x_at | SAA1 /// SAA2 | Not Assigned |
| 217966_s_at | FAM129A | Not Assigned |
| 217967_s_at | FAM129A | Not Assigned |
| 200633_at | UBB | Not Assigned |
| 200799_at | HSPA1A | Not Assigned |
| 201348_at | GPX3 | Not Assigned |
| 214091_s_at | GPX3 | Not Assigned |
| 209283_at | CRYAB | Not Assigned |
| 208396_s_at | PDE1A | Not Assigned |
| 204971_at | CSTA | Not Assigned |
| 206391_at | RARRES1 | Not Assigned |
| 206392_s_at | RARRES1 | Not Assigned |
| 221872_at | RARRES1 | Not Assigned |
| 218729_at | LXN | Not Assigned |
| 201641_at | BST2 | IFN Inducible |
| 201601_x_at | IFITM1 | IFN Inducible |
| 214022_s_at | IFITM1 | IFN Inducible |
| 204698_at | ISG20 | IFN Inducible |
| 202307_s_at | TAP1 | IFN Inducible |
| 204279_at | PSMB9 | IFN Inducible |
| 206082_at | HCP5 | IFN Inducible |
| 202269_x_at | GBP1 | IFN Inducible |
| 202270_at | GBP1 | IFN Inducible |
| 204533_at | CXCL10 | IFN Inducible |
| 210163_at | CXCL11 | IFN Inducible |
| 211122_s_at | CXCL11 | IFN Inducible |
| 209969_s_at | STAT1 | IFN Inducible |
| 214038_at | CCL8 | IFN Inducible |
| 204994_at | MX2 | IFN Inducible |
| 202411_at | IFI27 | IFN Inducible |
| 205569_at | LAMP3 | IFN Inducible |
| 202869_at | OAS1 | IFN Inducible |
| 205552_s_at | OAS1 | IFN Inducible |
| 204972_at | OAS2 | IFN Inducible |
| 204415_at | IFI6 | IFN Inducible |
| 205483_s_at | ISG15 | IFN Inducible |
| 202086_at | MX1 | IFN Inducible |
| 204439_at | IFI44L | IFN Inducible |
| 214453_s_at | IFI44 | IFN Inducible |
| 203153_at | IFIT1 | IFN Inducible |
| 213797_at | RSAD2 | IFN Inducible |
| 218943_s_at | DDX58 | IFN Inducible |
| 219209_at | IFIH1 | IFN Inducible |
| 219863_at | HERC5 | IFN Inducible |
| 214059_at | IFI44 | IFN Inducible |
| 210029_at | IDO1 | IFN Inducible |
| 205992_s_at | IL15 | IFN Inducible |
| 202687_s_at | TNFSF10 | IFN Inducible |
| 202688_at | TNFSF10 | IFN Inducible |
| 214329_x_at | TNFSF10 | IFN Inducible |
| 202357_s_at | C2 /// CFB | IFN Inducible |
| 217767_at | C3 | IFN Inducible |

-continued

Gene List 1. Gene components used for the clustering.

| Affymetrix Probe ID | Gene Symbol | Gene Cluster |
|---|---|---|
| 206332_s_at | IFI16 | IFN Inducible |
| 208966_x_at | IFI16 | IFN Inducible |
| 208965_s_at | IFI16 | IFN Inducible |
| 204070_at | RARRES3 | IFN Inducible |
| 219684_at | RTP4 | IFN Inducible |
| 219403_s_at | HPSE | Not Assigned |
| 204745_x_at | MT1G | Not Assigned |
| 206461_x_at | MT1H | Not Assigned |
| 208581_x_at | MT1X | Not Assigned |
| 213629_x_at | MT1F | Not Assigned |
| 217165_x_at | MT1F | Not Assigned |
| 212859_x_at | MT1E | Not Assigned |
| 217546_at | MT1M | Not Assigned |
| 204897_at | PTGER4 | Not Assigned |
| 201963_at | ACSL1 | Not Assigned |
| 201141_at | GPNMB | Not Assigned |
| 218559_s_at | MAFB | Not Assigned |
| 204446_s_at | ALOX5 | MHC Class II |
| 203381_s_at | APOE | MHC Class II |
| 203382_s_at | APOE | MHC Class II |
| 204416_x_at | APOC1 | MHC Class II |
| 202957_at | HCLS1 | MHC Class II |
| 204174_at | ALOX5AP | MHC Class II |
| 204006_s_at | FCGR3A /// FCGR3B | MHC Class II |
| 202803_s_at | ITGB2 | MHC Class II |
| 206584_at | LY96 | MHC Class II |
| 201858_s_at | SRGN | MHC Class II |
| 201859_at | SRGN | MHC Class II |
| 201743_at | CD14 | MHC Class II |
| 201721_s_at | LAPTM5 | MHC Class II |
| 204122_at | TYROBP | MHC Class II |
| 202953_at | C1QB | MHC Class II |
| 218232_at | C1QA | MHC Class II |
| 203645_s_at | CD163 | MHC Class II |
| 215049_x_at | CD163 | MHC Class II |
| 219607_s_at | MS4A4A | MHC Class II |
| 212587_s_at | PTPRC | MHC Class II |
| 211742_s_at | EVI2B | MHC Class II |
| 212588_at | PTPRC | MHC Class II |
| 220330_s_at | SAMSN1 | MHC Class II |
| 210889_s_at | FCGR2B | MHC Class II |
| 202902_s_at | CTSS | MHC Class II |
| 213975_s_at | LYZ | MHC Class II |
| 205890_s_at | GABBR1 /// UBD | MHC Class II |
| 205242_at | CXCL13 | MHC Class II |
| 203915_at | CXCL9 | MHC Class II |
| 1405_i_at | CCL5 | MHC Class II |
| 204655_at | CCL5 | MHC Class II |
| 210915_x_at | TRBC1 | MHC Class II |
| 211796_s_at | TRBC1 /// TRBC2 | MHC Class II |
| 34210_at | CD52 | MHC Class II |
| 202748_at | GBP2 | MHC Class II |
| 204646_at | DPYD | MHC Class II |
| 211368_s_at | CASP1 | MHC Class II |
| 213293_s_at | TRIM22 | MHC Class II |
| 217995_at | SQRDL | MHC Class II |
| 201137_s_at | HLA-DPB1 | MHC Class II |
| 209619_at | CD74 | MHC Class II |
| 204670_x_at | HLA-DRB1 /// HLA-DRB4 | MHC Class II |
| 208306_x_at | — | MHC Class II |
| 209312_x_at | HLA-DRB1 /// HLA-DRB4 /// HLA-DRB5 | MHC Class II |
| 215193_x_at | HLA-DRB1 /// HLA-DRB3 /// HLA-DRB4 | MHC Class II |
| 208894_at | HLA-DRA | MHC Class II |
| 210982_s_at | HLA-DRA | MHC Class II |
| 217478_s_at | HLA-DMA | MHC Class II |
| 211990_at | HLA-DPA1 | MHC Class II |
| 211991_s_at | HLA-DPA1 | MHC Class II |
| 209823_x_at | HLA-DQB1 | MHC Class II |
| 211656_x_at | HLA-DQB1 | MHC Class II |
| 212671_s_at | HLA-DQA1 /// HLA-DQA2 | MHC Class II |
| 213537_at | HLA-DPA1 | MHC Class II |
| 211654_x_at | HLA-DQB1 | MHC Class II |
| 212998_x_at | HLA-DQB1 | MHC Class II |
| 202988_s_at | RGS1 | MHC Class II |
| 216834_at | RGS1 | MHC Class II |

Gene List 1. Gene components used for the clustering.

| Affymetrix Probe ID | Gene Symbol | Gene Cluster |
| --- | --- | --- |
| 209795_at | CD69 | MHC Class II |
| 204580_at | MMP12 | Not Assigned |
| 203936_s_at | MMP9 | Not Assigned |
| 206134_at | ADAMDEC1 | Not Assigned |
| 202638_s_at | ICAM1 | Not Assigned |
| 203828_s_at | IL32 | Not Assigned |
| 216598_s_at | CCL2 | Not Assigned |
| 205476_at | CCL20 | Not Assigned |
| 210538_s_at | BIRC3 | Not Assigned |
| 215223_s_at | SOD2 | Not Assigned |
| 216841_s_at | SOD2 | Not Assigned |
| 217388_s_at | KYNU | Not Assigned |
| 205267_at | POU2AF1 | Immunoglobulin |
| 211634_x_at | IGHM /// LOC100133862 | Immunoglobulin |
| 211635_x_at | IGH@ /// IGHA1 /// IGHA2 /// IGHG1 /// IGHG3 /// IGHM /// IGHV1OR15-5 /// IGHV4-31 /// IGHV7-81 /// LOC642131 | Immunoglobulin |
| 209374_s_at | IGHM | Immunoglobulin |
| 214916_x_at | IGH@ /// IGHA1 /// IGHA2 /// IGHD /// IGHG1 /// IGHG2 /// IGHG3 /// IGHM /// IGHV3-23 /// IGHV4-31 /// LOC100126583 | Immunoglobulin |
| 211798_x_at | IGLJ3 | Immunoglobulin |
| 211881_x_at | IGLJ3 | Immunoglobulin |
| 216853_x_at | IGLV3-19 | Immunoglobulin |
| 211637_x_at | IGH@ /// IGHA1 /// IGHA2 /// IGHD /// IGHG1 /// IGHG3 /// IGHG4 /// IGHM /// IGHV3-23 /// IGHV4-31 /// LOC100126583 /// LOC642131 /// LOC652128 /// VSIG6 | Immunoglobulin |
| 216491_x_at | IGHM | Immunoglobulin |
| 211650_x_at | IGHA1 /// IGHD /// IGHG1 /// IGHG3 /// IGHM /// IGHV3-23 /// IGHV4-31 /// LOC100126583 | Immunoglobulin |
| 216510_x_at | IGHA1 /// IGHD /// IGHG1 /// IGHM /// IGHV3-23 /// IGHV4-31 | Immunoglobulin |
| 216557_x_at | IGH@ /// IGHA1 /// IGHG1 /// IGHG3 /// IGHM /// IGHV3-23 /// IGHV4-31 | Immunoglobulin |
| 217281_x_at | IGH@ /// IGHA1 /// IGHA2 /// IGHG1 /// IGHG2 /// IGHG3 /// IGHM /// IGHV4-31 /// LOC100126583 /// LOC652494 | Immunoglobulin |
| 211643_x_at | IGK@ /// IGKV3-20 /// IGKV3D-11 /// IGKV3D-15 /// LOC440871 | Immunoglobulin |
| 211644_x_at | IGK@ /// IGKC /// IGKV3-20 /// IGKV3D-11 /// IGKV3D-15 /// LOC440871 | Immunoglobulin |
| 211645_x_at | — | Immunoglobulin |
| 216401_x_at | LOC652493 | Immunoglobulin |
| 217378_x_at | LOC100130100 | Immunoglobulin |
| 216207_x_at | IGKC /// IGKV1-5 /// LOC100130100 /// LOC647506 /// LOC650405 /// LOC652493 /// LOC652694 | Immunoglobulin |
| 217480_x_at | IGKV1OR15-118 | Immunoglobulin |
| 216576_x_at | IGKC /// IGKV1-5 /// LOC647506 /// LOC652694 | Immunoglobulin |
| 215176_x_at | LOC100130100 | Immunoglobulin |
| 217157_x_at | IGK@ /// IGKC /// LOC647506 /// LOC650405 /// LOC652493 | Immunoglobulin |
| 216984_x_at | IGLV2-11 /// IGLV2-18 /// IGLV2-23 | Immunoglobulin |
| 217148_x_at | IGL@ | Immunoglobulin |
| 217235_x_at | IGL@ /// IGLC1 /// IGLV2-11 /// IGLV2-18 /// IGLV2-23 | Immunoglobulin |
| 214973_x_at | IGHD | Immunoglobulin |
| 217179_x_at | — | Immunoglobulin |
| 217227_x_at | IGL@ | Immunoglobulin |
| 217258_x_at | IGL@ | Immunoglobulin |
| 214768_x_at | FAM20B | Immunoglobulin |
| 214777_at | IGKV4-1 | Immunoglobulin |
| 212592_at | IGJ | Immunoglobulin |
| 209138_x_at | IGL@ | Immunoglobulin |
| 215121_x_at | IGL@ | Immunoglobulin |
| 214677_x_at | IGL@ | Immunoglobulin |
| 215379_x_at | IGL@ | Immunoglobulin |
| 214669_x_at | IGKC | Immunoglobulin |
| 214836_x_at | IGKC | Immunoglobulin |

Gene List 1. Gene components used for the clustering.

| Affymetrix Probe ID | Gene Symbol | Gene Cluster |
| --- | --- | --- |
| 211430_s_at | IGH@ /// IGHG1 /// IGHG2 /// IGHM /// IGHV4-31 | Immunoglobulin |
| 221651_x_at | IGK@ /// IGKC | Immunoglobulin |
| 221671_x_at | IGK@ /// IGKC | Immunoglobulin |
| 215946_x_at | IGLL3 | Immunoglobulin |
| 217022_s_at | IGH@ /// IGHA1 /// IGHA2 /// LOC100126583 | Immunoglobulin |
| 215214_at | IGL@ | Immunoglobulin |
| 216560_x_at | IGL@ | Immunoglobulin |
| 203290_at | HLA-DQA1 | Not Assigned |
| 221491_x_at | HLA-DRB1 /// HLA-DRB3 /// HLA-DRB4 /// HLA-DRB5 /// LOC100133484 /// LOC100133661 /// LOC731718 | Not Assigned |
| 209480_at | HLA-DQB1 | Not Assigned |
| 213831_at | HLA-DQA1 | Not Assigned |
| 212999_x_at | HLA-DQB1 | Not Assigned |
| 219759_at | ERAP2 | Not Assigned |
| 209728_at | HLA-DRB4 | Not Assigned |
| 204836_at | GLDC | Not Assigned |
| 210785_s_at | C1orf38 | Not Assigned |
| 211663_x_at | PTGDS | Not Assigned |
| 211748_x_at | PTGDS | Not Assigned |
| 212187_x_at | PTGDS | Not Assigned |
| 201008_s_at | TXNIP | Stem-A/B |
| 201983_s_at | EGFR | Stem-A/B |
| 208146_s_at | CPVL | Stem-A/B |
| 213385_at | CHN2 | Stem-A/B |
| 201842_s_at | EFEMP1 | Stem-A/B |
| 201843_s_at | EFEMP1 | Stem-A/B |
| 202291_s_at | MGP | Stem-A/B |
| 202746_at | ITM2A | Stem-A/B |
| 213258_at | TFPI | Stem-A/B |
| 211597_s_at | HOPX | Stem-A/B |
| 201280_s_at | DAB2 | Stem-A/B |
| 203305_at | F13A1 | Stem-A/B |
| 204438_at | MRC1 /// MRC1L1 | Stem-A/B |
| 204112_s_at | HNMT | Stem-A/B |
| 212063_at | CD44 | Stem-A/B |
| 211675_s_at | MDFIC | Stem-A/B |
| 221760_at | MAN1A1 | Stem-A/B |
| 209392_at | ENPP2 | Stem-A/B |
| 204235_s_at | GULP1 | Stem-A/B |
| 204237_at | GULP1 | Stem-A/B |
| 203323_at | CAV2 | Stem-A/B |
| 203324_s_at | CAV2 | Stem-A/B |
| 203065_s_at | CAV1 | Stem-A/B |
| 212097_at | CAV1 | Stem-A/B |
| 203476_at | TPBG | Stem-A/B |
| 203939_at | NT5E | Stem-A/B |
| 213800_at | CFH | Stem-A/B |
| 215388_s_at | CFH /// CFHR1 | Stem-A/B |
| 201579_at | FAT1 | Stem-A/B |
| 209487_at | RBPMS | Stem-A/B |
| 209488_s_at | RBPMS | Stem-A/B |
| 219049_at | CSGALNACT1 | Stem-A/B |
| 206858_s_at | HOXC6 | Stem-A/B |
| 201565_s_at | ID2 | Stem-A/B |
| 207826_s_at | ID3 | Stem-A/B |
| 208937_s_at | ID1 | Stem-A/B |
| 201162_at | IGFBP7 | Stem-A/B |
| 201426_s_at | VIM | Stem-A/B |
| 201508_at | IGFBP4 | Stem-A/B |
| 201185_at | HTRA1 | Stem-A/B |
| 207191_s_at | ISLR | Stem-A/B |
| 202975_s_at | RHOBTB3 | Stem-A/B |
| 202976_s_at | RHOBTB3 | Stem-A/B |
| 204749_at | NAP1L3 | Stem-A/B |
| 214247_s_at | DKK3 | Stem-A/B |
| 219463_at | C20orf103 | Stem-A/B |
| 209505_at | NR2F1 | Stem-A/B |
| 202149_at | NEDD9 | Stem-A/B |
| 212154_at | SDC2 | Stem-A/B |
| 212158_at | SDC2 | Stem-A/B |
| 221933_at | NLGN4X | Stem-A/B |
| 205381_at | LRRC17 | Stem-A/B |

-continued

| Gene List 1. Gene components used for the clustering. | | |
|---|---|---|
| Affymetrix Probe ID | Gene Symbol | Gene Cluster |
| 203789_s_at | SEMA3C | Stem-A/B |
| 212915_at | PDZRN3 | Stem-A/B |
| 202036_s_at | SFRP1 | Stem-A/B |
| 202037_s_at | SFRP1 | Stem-A/B |
| 202609_at | EPS8 | Stem-A/B |
| 203881_s_at | DMD | Stem-A/B |
| 213397_x_at | RNASE4 | Stem-A/B |
| 203680_at | PRKAR2B | Stem-A/B |
| 202920_at | ANK2 | Stem-A/B |
| 202992_at | C7 | Stem-A/B |
| 204719_at | ABCA8 | Stem-A/B |
| 204359_at | FLRT2 | Stem-A/B |
| 212865_s_at | COL14A1 | Stem-A/B |
| 218730_s_at | OGN | Stem-A/B |
| 209469_at | GPM6A | Stem-A/B |
| 203304_at | BAMBI | Stem-A/B |
| 204041_at | MAOB | Stem-A/B |
| 203824_at | TSPAN8 | Stem-A/B |
| 204931_at | TCF21 | Stem-A/B |
| 209242_at | PEG3 | Stem-A/B |
| 209243_s_at | PEG3 /// ZIM2 | Stem-A/B |
| 204548_at | STAR | Stem-A/B |
| 220102_at | FOXL2 | Stem-A/B |
| 209560_s_at | DLK1 | Stem-A/B |
| 219873_at | COLEC11 | Stem-A/B |
| 216733_s_at | GATM | Stem-A/B |
| 214079_at | DHRS2 | Stem-A/B |
| 215506_s_at | DIRAS3 | Stem-A/B |
| 218974_at | SOBP | Stem-A/B |
| 212224_at | ALDH1A1 | Stem-A/B |
| 205990_s_at | WNT5A | Stem-A/B |
| 213425_at | WNT5A | Stem-A/B |
| 209822_s_at | VLDLR | Stem-A/B |
| 212190_at | SERPINE2 | Stem-A/B |
| 209894_at | LEPR | Stem-A/B |
| 207002_s_at | PLAGL1 | Stem-A/B |
| 209318_x_at | PLAGL1 | Stem-A/B |
| 215016_x_at | DST | Stem-A/B |
| 202948_at | IL1R1 | Epi-A/Stem-B |
| 203854_at | CFI | Epi-A/Stem-B |
| 204201_s_at | PTPN13 | Epi-A/Stem-B |
| 204872_at | TLE4 | Epi-A/Stem-B |
| 212188_at | KCTD12 | Epi-A/Stem-B |
| 212192_at | KCTD12 | Epi-A/Stem-B |
| 213093_at | PRKCA | Epi-A/Stem-B |
| 214218_s_at | XIST | Epi-A/Stem-B |
| 221728_x_at | XIST | Epi-A/Stem-B |
| 207480_s_at | MEIS2 | Epi-A/Stem-B |
| 210002_at | GATA6 | Epi-A/Stem-B |
| 214945_at | FAM153A /// FAM153B /// FAM153C | Epi-A/Stem-B |
| 213094_at | GPR126 | Epi-A/Stem-B |
| 218326_s_at | LGR4 | Epi-A/Stem-B |
| 202342_s_at | TRIM2 | Not Assigned |
| 205442_at | MFAP3L | Not Assigned |
| 205453_at | HOXB2 | Not Assigned |
| 205366_s_at | HOXB6 | Not Assigned |
| 204779_s_at | HOXB7 | Not Assigned |
| 216973_s_at | HOXB7 | Not Assigned |
| 211538_s_at | HSPA2 | Not Assigned |
| 203924_at | GSTA1 | Not Assigned |
| 204151_x_at | AKR1C1 | Not Assigned |
| 209699_x_at | AKR1C2 | Not Assigned |
| 211653_x_at | AKR1C2 | Not Assigned |
| 209160_at | AKR1C3 | Not Assigned |
| 202554_s_at | GSTM3 | Not Assigned |
| 205799_s_at | SLC3A1 | Not Assigned |
| 206268_at | LEFTY1 | Not Assigned |
| 206561_s_at | AKR1B10 | Not Assigned |
| 205403_at | IL1R2 | Not Assigned |
| 219564_at | KCNJ16 | Not Assigned |
| 203961_at | NEBL | Not Assigned |
| 203962_s_at | NEBL | Not Assigned |
| 212328_at | LIMCH1 | Not Assigned |
| 204364_s_at | REEP1 | Not Assigned |
| 221523_s_at | RRAGD | Not Assigned |

-continued

| Gene List 1. Gene components used for the clustering. | | |
|---|---|---|
| Affymetrix Probe ID | Gene Symbol | Gene Cluster |
| 219789_at | NPR3 | Not Assigned |
| 201340_s_at | ENC1 | Not Assigned |
| 201939_at | PLK2 | Not Assigned |
| 208711_s_at | CCND1 | Not Assigned |
| 208712_at | CCND1 | Not Assigned |
| 205680_at | MMP10 | Not Assigned |
| 206228_at | PAX2 | Not Assigned |
| 205997_at | ADAM28 | Not Assigned |
| 202478_at | TRIB2 | Not Assigned |
| 204011_at | SPRY2 | Not Assigned |
| 212558_at | SPRY1 | Not Assigned |
| 208891_at | DUSP6 | Not Assigned |
| 208892_s_at | DUSP6 | Not Assigned |
| 208893_s_at | DUSP6 | Not Assigned |
| 204014_at | DUSP4 | Not Assigned |
| 213462_at | NPAS2 | Not Assigned |
| 39549_at | NPAS2 | Not Assigned |
| 219230_at | TMEM100 | Not Assigned |
| 217996_at | PHLDA1 | Not Assigned |
| 217997_at | PHLDA1 | Not Assigned |
| 209030_s_at | CADM1 | Not Assigned |
| 209031_at | CADM1 | Not Assigned |
| 213479_at | NPTX2 | Not Assigned |
| 213131_at | OLFM1 | Not Assigned |
| 202068_s_at | LDLR | Not Assigned |
| 201925_s_at | CD55 | Not Assigned |
| 201926_s_at | CD55 | Not Assigned |
| 218960_at | TMPRSS4 | Not Assigned |
| 205328_at | CLDN10 | Not Assigned |
| 209803_s_at | PHLDA2 | Not Assigned |
| 205174_s_at | QPCT | Not Assigned |
| 202833_s_at | SERPINA1 | Not Assigned |
| 211429_s_at | SERPINA1 | Not Assigned |
| 205016_at | TGFA | Not Assigned |
| 211026_s_at | MGLL | Not Assigned |
| 209529_at | PPAP2C | Not Assigned |
| 218963_s_at | KRT23 | Not Assigned |
| 213432_at | MUC5B | Not Assigned |
| 219857_at | C10orf81 | Not Assigned |
| 201468_s_at | NQO1 | Not Assigned |
| 210519_s_at | NQO1 | Not Assigned |
| 202489_s_at | FXYD3 | Not Assigned |
| 209498_at | CEACAM1 | Not Assigned |
| 202712_s_at | CKMT1A /// CKMT1B | Not Assigned |
| 33322_i_at | SFN | Not Assigned |
| 33323_r_at | SFN | Not Assigned |
| 203963_at | CA12 | Not Assigned |
| 214164_x_at | CA12 | Not Assigned |
| 215867_x_at | CA12 | Not Assigned |
| 203510_at | MET | Epi-A/Stem-B |
| 204304_s_at | PROM1 | Epi-A/Stem-B |
| 213664_at | SLC1A1 | Epi-A/Stem-B |
| 204363_at | F3 | Not Assigned |
| 209373_at | MALL | Not Assigned |
| 203108_at | GPRC5A | Not Assigned |
| 212444_at | — | Not Assigned |
| 218309_at | CAMK2N1 | Not Assigned |
| 204351_at | S100P | Not Assigned |
| 201884_at | CEACAM5 | Not Assigned |
| 203757_s_at | CEACAM6 | Not Assigned |
| 211657_at | CEACAM6 | Not Assigned |
| 205009_at | TFF1 | Not Assigned |
| 206239_s_at | SPINK1 | Not Assigned |
| 212768_s_at | OLFM4 | Not Assigned |
| 203908_at | SLC4A4 | Not Assigned |
| 204623_at | TFF3 | Not Assigned |
| 209173_at | AGR2 | Not Assigned |
| 215108_x_at | TOX3 | Not Assigned |
| 214774_x_at | TOX3 | Not Assigned |
| 216623_x_at | TOX3 | Not Assigned |
| 209114_at | TSPAN1 | Not Assigned |
| 219508_at | GCNT3 | Not Assigned |
| 221577_x_at | GDF15 | Not Assigned |
| 205765_at | CYP3A5 | Not Assigned |
| 214234_s_at | CYP3A5 | Not Assigned |

Gene List 1. Gene components used for the clustering.

| Affymetrix Probe ID | Gene Symbol | Gene Cluster |
| --- | --- | --- |
| 214235_at | CYP3A5 | Not Assigned |
| 205597_at | SLC44A4 | Not Assigned |
| 219580_s_at | TMC5 | Not Assigned |
| 204855_at | SERPINB5 | Not Assigned |
| 218796_at | FERMT1 | Not Assigned |
| 218976_at | DNAJC12 | Not Assigned |
| 213506_at | F2RL1 | Not Assigned |
| 203717_at | DPP4 | Not Assigned |
| 211478_s_at | DPP4 | Not Assigned |
| 222108_at | AMIGO2 | Not Assigned |
| 205044_at | GABRP | Not Assigned |
| 204664_at | ALPP | Not Assigned |
| 217109_at | MUC4 | Not Assigned |
| 217110_s_at | MUC4 | Not Assigned |
| 39248_at | AQP3 | Not Assigned |
| 203240_at | FCGBP /// LOC100133944 | Not Assigned |
| 205898_at | CX3CR1 | Not Assigned |
| 205668_at | LY75 | Not Assigned |
| 218322_s_at | ACSL5 | Not Assigned |
| 212543_at | AIM1 | Not Assigned |
| 219014_at | PLAC8 | Not Assigned |
| 206100_at | CPM | Not Assigned |
| 205043_at | CFTR | Not Assigned |
| 218435_at | DNAJC15 | Not Assigned |
| 203559_s_at | ABP1 | Not Assigned |
| 220532_s_at | TMEM176B | Not Assigned |
| 203913_s_at | HPGD | Not Assigned |
| 203914_x_at | HPGD | Not Assigned |
| 211548_s_at | HPGD | Not Assigned |
| 201116_s_at | CPE | Not Assigned |
| 201117_s_at | CPE | Not Assigned |
| 201540_at | FHL1 | Not Assigned |
| 210299_s_at | FHL1 | Not Assigned |
| 209763_at | CHRDL1 | Not Assigned |
| 210517_s_at | AKAP12 | Not Assigned |
| 204223_at | PRELP | Not Assigned |
| 219778_at | ZFPM2 | Not Assigned |
| 207808_s_at | PROS1 | Not Assigned |
| 218901_at | PLSCR4 | Not Assigned |
| 204948_s_at | FST | Not Assigned |
| 213265_at | PGA3 /// PGA4 /// PGA5 | Not Assigned |
| 217889_s_at | CYBRD1 | Not Assigned |
| 212816_s_at | CBS | Not Assigned |
| 222242_s_at | KLK5 | Not Assigned |
| 201746_at | TP53 | Stem-A |
| 201123_s_at | EIF5A | Stem-A |
| 205048_s_at | PSPH | Stem-A |
| 208719_s_at | DDX17 | Stem-A |
| 207016_s_at | ALDH1A2 | Stem-A |
| 200951_s_at | CCND2 | Stem-A |
| 200953_s_at | CCND2 | Stem-A |
| 203408_s_at | SATB1 | Stem-A |
| 205110_s_at | FGF13 | Stem-A |
| 209598_at | PNMA2 | Stem-A |
| 212233_at | MAP1B | Stem-A |
| 204529_s_at | TOX | Stem-A |
| 206172_at | IL13RA2 | Stem-A |
| 203705_s_at | FZD7 | Stem-A |
| 203706_s_at | FZD7 | Stem-A |
| 204983_s_at | GPC4 | Stem-A |
| 204984_at | GPC4 | Stem-A |
| 203895_at | PLCB4 | Stem-A |
| 207030_s_at | CSRP2 | Stem-A |
| 205932_s_at | MSX1 | Stem-A |
| 202965_s_at | CAPN6 | Stem-A |
| 213110_s_at | COL4A5 | Stem-A |
| 203184_at | FBN2 | Stem-A |
| 204400_at | EFS | Stem-A |
| 202016_at | MEST | Stem-A |
| 201310_s_at | C5orf13 | Stem-A |
| 203417_at | MFAP2 | Stem-A |
| 210220_at | FZD2 | Stem-A |
| 211071_s_at | MLLT11 | Stem-A |
| 204913_s_at | SOX11 | Stem-A |
| 204914_s_at | SOX11 | Stem-A |

Gene List 1. Gene components used for the clustering.

| Affymetrix Probe ID | Gene Symbol | Gene Cluster |
|---|---|---|
| 204915_s_at | SOX11 | Stem-A |
| 205122_at | TMEFF1 | Stem-A |
| 205347_s_at | TMSB15A | Stem-A |
| 214023_x_at | TUBB2B | Stem-A |
| 204724_s_at | COL9A3 | Stem-A |
| 205471_s_at | DACH1 | Stem-A |
| 205472_s_at | DACH1 | Stem-A |
| 212850_s_at | LRP4 | Stem-A |
| 214761_at | ZNF423 | Stem-A |
| 209757_s_at | MYCN | Stem-A |
| 211276_at | TCEAL2 | Stem-A |
| 218332_at | BEX1 | Stem-A |
| 206857_s_at | FKBP1B | Stem-A |
| 203256_at | CDH3 | Stem-A |
| 221958_s_at | GPR177 | Stem-A |
| 219250_s_at | FLRT3 | Stem-A |
| 213348_at | CDKN1C | Stem-A |
| 204141_at | TUBB2A | Stem-A |
| 211959_at | IGFBP5 | Stem-A |
| 212977_at | CXCR7 | Stem-A |
| 219410_at | TMEM45A | Stem-A |
| 221024_s_at | SLC2A10 | Stem-A |
| 209355_s_at | PPAP2B | Stem-A |
| 209220_at | GPC3 | Stem-A |
| 44783_s_at | HEY1 | Stem-A |
| 203697_at | FRZB | Stem-A |
| 203698_s_at | FRZB | Stem-A |
| 209656_s_at | TMEM47 | Stem-A |
| 209897_s_at | SLIT2 | Stem-A |
| 213568_at | OSR2 | Stem-A |
| 204073_s_at | C11orf9 | Stem-A |
| 204379_s_at | FGFR3 | Stem-A |
| 202409_at | IGF2 /// INS-IGF2 | Stem-A |
| 202410_x_at | IGF2 /// INS-IGF2 | Stem-A |
| 210881_s_at | IGF2 /// INS-IGF2 | Stem-A |
| 202242_at | TSPAN7 | Stem-A |
| 203627_at | IGF1R | Stem-A |
| 203628_at | IGF1R | Stem-A |
| 208025_s_at | HMGA2 | Stem-A |
| 218847_at | IGF2BP2 | Stem-A |
| 221004_s_at | ITM2C | Stem-A |
| 221245_s_at | FZD5 | Stem-A |
| 209035_at | MDK | Stem-A |
| 214390_s_at | BCAT1 | Stem-A |
| 214452_at | BCAT1 | Stem-A |
| 205619_s_at | MEOX1 | Stem-A |
| 202668_at | EFNB2 | Stem-A |
| 202669_s_at | EFNB2 | Stem-A |
| 206953_s_at | LPHN2 | Stem-A |
| 213325_at | PVRL3 | Stem-A |
| 205901_at | PNOC | Stem-A |
| 205402_x_at | PRSS2 | Stem-A |
| 202718_at | IGFBP2 | Stem-A |
| 204450_x_at | APOA1 | Stem-A |
| 217073_x_at | APOA1 | Stem-A |
| 204105_s_at | NRCAM | Stem-A |
| 205549_at | PCP4 | Stem-A |
| 209590_at | BMP7 | Stem-A |
| 209591_s_at | BMP7 | Stem-A |
| 212843_at | NCAM1 | Stem-A |
| 218824_at | PNMAL1 | Stem-A |
| 206987_x_at | FGF18 | Stem-A |
| 211029_x_at | FGF18 | Stem-A |
| 209552_at | PAX8 | Stem-A |
| 213917_at | PAX8 | Stem-A |
| 214528_s_at | PAX8 | Stem-A |
| 221950_at | EMX2 | Stem-A |
| 203849_s_at | KIF1A | Stem-A |
| 213622_at | COL9A2 | Stem-A |
| 206772_at | PTH2R | Stem-A |
| 220167_s_at | LOC729355 /// TP53TG3 | Stem-A |
| 214373_at | — | Stem-A |
| 214157_at | GNAS | Stem-A |
| 204784_s_at | MLF1 | Stem-A |
| 213122_at | TSPYL5 | Stem-A |

-continued

| Gene List 1. Gene components used for the clustering. | | |
|---|---|---|
| Affymetrix Probe ID | Gene Symbol | Gene Cluster |
| 212092_at | PEG10 | Stem-A |
| 212094_at | PEG10 | Stem-A |
| 219743_at | HEY2 | Stem-A |
| 203638_s_at | FGFR2 | Stem-A |
| 208228_s_at | FGFR2 | Stem-A |
| 214053_at | ERBB4 | Stem-A |
| 219132_at | PELI2 | Stem-A |
| 205358_at | GRIA2 | Stem-A |
| 210393_at | LGR5 | Stem-A |
| 213880_at | LGR5 | Stem-A |
| 205413_at | MPPED2 | Stem-A |
| 215692_s_at | MPPED2 | Stem-A |
| 204069_at | MEIS1 | Stem-A |
| 211596_s_at | LRIG1 | Stem-A |
| 219993_at | SOX17 | Stem-A |
| 221884_at | EVI1 | Stem-A |
| 204602_at | DKK1 | Stem-A |
| 204712_at | WIF1 | Stem-A |
| 205278_at | GAD1 | Stem-A |
| 206224_at | CST1 | Stem-A |
| 204748_at | PTGS2 | Stem-A |
| 210145_at | PLA2G4A | Stem-A |
| 213222_at | PLCB1 | Stem-A |
| 201522_x_at | SNRPN /// SNURF | Stem-A |
| 206042_x_at | SNRPN /// SNURF | Stem-A |
| 221974_at | IPW | Stem-A |
| 209550_at | NDN | Stem-A |
| 205541_s_at | GSPT2 | Stem-A |
| 209228_x_at | TUSC3 | Stem-A |
| 213423_x_at | TUSC3 | Stem-A |
| 215440_s_at | BEX4 | Stem-A |
| 203130_s_at | KIF5C | Stem-A |
| 203423_at | RBP1 | Stem-A |
| 203889_at | SCG5 | Stem-A |
| 207717_s_at | PKP2 | Stem-A |
| 209569_x_at | D4S234E | Stem-A |
| 209570_s_at | D4S234E | Stem-A |
| 209459_s_at | ABAT | Stem-A |
| 200962_at | RPL31 | Stem-A |
| 202431_s_at | MYC | Stem-A |
| 209291_at | ID4 | Stem-A |
| 209292_at | ID4 | Stem-A |
| 209293_x_at | ID4 | Stem-A |
| 209582_s_at | CD200 | Stem-A |
| 209583_s_at | CD200 | Stem-A |
| 201578_at | PODXL | Stem-A |
| 219764_at | FZD10 | Stem-A |
| 203440_at | CDH2 | Stem-A |
| 206002_at | GPR64 | Stem-A |
| 222325_at | — | Stem-A |
| 221558_s_at | LEF1 | Stem-A |
| 213456_at | SOSTDC1 | Stem-A |
| 209504_s_at | PLEKHB1 | Stem-A |
| 58916_at | KCTD14 | Stem-A |
| 209921_at | SLC7A11 | Stem-A |
| 217678_at | SLC7A11 | Stem-A |
| 213849_s_at | PPP2R2B | Stem-A |
| 205186_at | DNALI1 | Stem-A |
| 206197_at | NME5 | Stem-A |
| 218876_at | TPPP3 | Stem-A |
| 220269_at | ZBBX | Stem-A |
| 220168_at | CASC1 | Stem-A |
| 222271_at | — | Stem-A |
| 221185_s_at | IQCG | Stem-A |
| 205625_s_at | CALB1 | Stem-A |
| 205626_s_at | CALB1 | Stem-A |
| 204614_at | SERPINB2 | Stem-A |
| 206404_at | FGF9 | Stem-A |
| 209904_at | TNNC1 | Stem-A |
| 219529_at | CLIC3 | Stem-A |
| 214321_at | NOV | Stem-A |
| 201242_s_at | ATP1B1 | Stem-A |
| 206291_at | NTS | Stem-A |
| 205342_s_at | SULT1C2 | Stem-A |
| 211470_s_at | SULT1C2 | Stem-A |

-continued

| Gene List 1. Gene components used for the clustering. | | |
|---|---|---|
| Affymetrix Probe ID | Gene Symbol | Gene Cluster |
| 201387_s_at | UCHL1 | Stem-A |
| 209406_at | BAG2 | Stem-A |
| 205229_s_at | COCH | Stem-A |
| 218888_s_at | NETO2 | Stem-A |
| 204159_at | CDKN2C | Stem-A |
| 206632_s_at | APOBEC3B | Stem-A |
| 203560_at | GGH | Stem-A |
| 206023_at | NMU | Stem-A |
| 201890_at | RRM2 | Stem-A |
| 209773_s_at | RRM2 | Stem-A |
| 201291_s_at | TOP2A | Stem-A |
| 201292_at | TOP2A | Stem-A |
| 203764_at | DLGAP5 | Stem-A |
| 209714_s_at | CDKN3 | Stem-A |
| 202870_s_at | CDC20 | Stem-A |
| 204822_at | TTK | Stem-A |
| 204962_s_at | CENPA | Stem-A |
| 210052_s_at | TPX2 | Stem-A |
| 209642_at | BUB1 | Stem-A |
| 219918_s_at | ASPM | Stem-A |
| 210559_s_at | CDC2 | Stem-A |
| 218009_s_at | PRC1 | Stem-A |
| 218542_at | CEP55 | Stem-A |
| 219148_at | PBK | Stem-A |
| 207039_at | CDKN2A | Stem-A |
| 209644_x_at | CDKN2A | Stem-A |
| 213523_at | CCNE1 | Stem-A |
| 213872_at | C6orf62 | Stem-A |
| 220892_s_at | PSAT1 | Stem-A |
| 209122_at | ADFP | Stem-A |
| 218454_at | PLBD1 | Stem-A |
| 202350_s_at | MATN2 | Stem-A |
| 206698_at | XK | Stem-A |
| 207469_s_at | PIR | Stem-A |
| 220994_s_at | STXBP6 | Stem-A |
| 203819_s_at | IGF2BP3 | Stem-A |
| 203820_s_at | IGF2BP3 | Stem-A |
| 33767_at | NEFH | Stem-A |
| 206640_x_at | GAGE12C /// GAGE12D /// GAGE12E /// GAGE12F /// GAGE12G /// GAGE12H /// GAGE12I /// GAGE2A /// GAGE2C /// GAGE4 /// GAGE5 /// GAGE6 /// GAGE7 | Stem-A |
| 208235_x_at | GAGE12F /// GAGE12G /// GAGE12I /// GAGE7 | Stem-A |
| 207086_x_at | GAGE1 /// GAGE12C /// GAGE12D /// GAGE12E /// GAGE12F /// GAGE12G /// GAGE12H /// GAGE12I /// GAGE12J /// GAGE2A /// GAGE2C /// GAGE2D /// GAGE2E /// GAGE4 /// GAGE5 /// GAGE6 /// GAGE7 /// GAGE8 | Stem-A |
| 208155_x_at | GAGE1 /// GAGE12F /// GAGE12G /// GAGE12I /// GAGE12J /// GAGE4 /// GAGE5 /// GAGE6 /// GAGE7 | Stem-A |
| 207663_x_at | GAGE3 | Stem-A |
| 207739_s_at | GAGE1 /// GAGE12F /// GAGE12G /// GAGE12I /// GAGE12J /// GAGE2A /// GAGE2B /// GAGE2C /// GAGE2D /// GAGE2E /// GAGE3 /// GAGE4 /// GAGE5 /// GAGE6 /// GAGE7 /// GAGE8 | Stem-A |
| 210503_at | MAGEA11 | Stem-A |
| 214254_at | MAGEA4 | Stem-A |
| 209942_x_at | MAGEA3 | Stem-A |
| 214612_x_at | MAGEA6 | Stem-A |
| 210546_x_at | CTAG1A /// CTAG1B | Stem-A |
| 211674_x_at | CTAG1A /// CTAG1B | Stem-A |
| 210394_x_at | SSX4 /// SSX4B | Stem-A |
| 214183_s_at | TKTL1 | Stem-A |
| 210445_at | FABP6 | Stem-A |
| 204424_s_at | LMO3 | Stem-A |
| 206018_at | FOXG1 | Stem-A |
| 206373_at | ZIC1 | Stem-A |
| 213844_at | HOXA5 | Stem-A |
| 213150_at | HOXA10 | Stem-A |
| 214651_s_at | HOXA9 | Stem-A |
| 218625_at | NRN1 | Stem-A |

Gene List 1. Gene components used for the clustering.

| Affymetrix Probe ID | Gene Symbol | Gene Cluster |
|---|---|---|
| 221690_s_at | NLRP2 | Stem-A |
| 219288_at | C3orf14 | Stem-A |
| 200832_s_at | SCD | Stem-A |
| 219215_s_at | SLC39A4 | Stem-A |
| 209398_at | HIST1H1C | Stem-A |
| 202708_s_at | HIST2H2BE | Stem-A |
| 214290_s_at | HIST2H2AA3 /// HIST2H2AA4 | Stem-A |
| 218280_x_at | HIST2H2AA3 /// HIST2H2AA4 | Stem-A |
| 209911_x_at | HIST1H2BD | Stem-A |
| 208579_x_at | H2BFS | Stem-A |
| 215071_s_at | HIST1H2AC | Stem-A |
| 206110_at | — | Stem-A |
| 210387_at | HIST1H2BG | Stem-A |
| 214469_at | HIST1H2AE | Stem-A |
| 203815_at | GSTT1 | Not Assigned |
| 201042_at | TGM2 | Epithelial |
| 202856_s_at | SLC16A3 | Epithelial |
| 211564_s_at | PDLIM4 | Epithelial |
| 203074_at | ANXA8 /// ANXA8L1 /// ANXA8L2 | Epithelial |
| 206595_at | CST6 | Epithelial |
| 215704_at | FLG | Epithelial |
| 204584_at | L1CAM | Epithelial |
| 205258_at | INHBB | Epithelial |
| 201820_at | KRT5 | Epithelial |
| 209125_at | KRT6A | Epithelial |
| 205157_s_at | KRT17 | Epithelial |
| 212236_x_at | KRT17 | Epithelial |
| 209351_at | KRT14 | Epithelial |
| 205081_at | CRIP1 | Epithelial |
| 203726_s_at | LAMA3 | Epithelial |
| 202267_at | LAMC2 | Epithelial |
| 209270_at | LAMB3 | Epithelial |
| 203407_at | PPL | Epithelial |
| 202504_at | TRIM29 | Epithelial |
| 212992_at | AHNAK2 | Epithelial |
| 205780_at | BIK | Epithelial |
| 206884_s_at | SCEL | Epithelial |
| 210064_s_at | UPK1B | Epithelial |
| 210065_s_at | UPK1B | Epithelial |
| 203186_s_at | S100A4 | Epithelial |
| 204268_at | S100A2 | Epithelial |
| 217728_at | S100A6 | Epithelial |
| 203571_s_at | C10orf116 | Epithelial |
| 218677_at | S100A14 | Epithelial |
| 202286_s_at | TACSTD2 | Epithelial |
| 209016_s_at | KRT7 | Epithelial |
| 201650_at | KRT19 | Epithelial |
| 217744_s_at | PERP | Epithelial |
| 218186_at | RAB25 | Epithelial |
| 215729_s_at | VGLL1 | Epithelial |
| 213240_s_at | KRT4 | Epithelial |
| 219476_at | C1orf116 | Epithelial |
| 201012_at | ANXA1 | Epithelial |
| 209386_at | TM4SF1 | Epithelial |
| 209387_s_at | TM4SF1 | Epithelial |
| 215034_s_at | TM4SF1 | Epithelial |
| 209369_at | ANXA3 | Epithelial |
| 201324_at | EMP1 | Epithelial |
| 201325_s_at | EMP1 | Epithelial |
| 202206_at | ARL4C | Epithelial |
| 202207_at | ARL4C | Epithelial |
| 203910_at | ARHGAP29 | Epithelial |
| 218182_s_at | CLDN1 | Epithelial |
| 220332_at | CLDN16 | Epithelial |
| 204777_s_at | MAL | Epithelial |
| 204751_x_at | DSC2 | Epithelial |
| 205532_s_at | CDH6 | Epithelial |
| 210602_s_at | CDH6 | Epithelial |
| 214803_at | — | Epithelial |
| 219274_at | TSPAN12 | Epithelial |
| 206658_at | UPK3B | Epithelial |
| 202524_s_at | SPOCK2 | Epithelial |
| 219836_at | ZBED2 | Epithelial |
| 213317_at | CLIC5 | Epithelial |
| 219866_at | CLIC5 | Epithelial |

Gene List 1. Gene components used for the clustering.

| Affymetrix Probe ID | Gene Symbol | Gene Cluster |
|---|---|---|
| 206825_at | OXTR | Epithelial |
| 220979_s_at | ST6GALNAC5 | Epithelial |
| 219064_at | ITIH5 | Epithelial |
| 222162_s_at | ADAMTS1 | Epithelial |
| 201951_at | ALCAM | Not Assigned |
| 201952_at | ALCAM | Not Assigned |
| 209781_s_at | KHDRBS3 | Not Assigned |
| 202233_s_at | UQCRH | Not Assigned |
| 209167_at | GPM6B | Not Assigned |
| 209170_s_at | GPM6B | Not Assigned |
| 219497_s_at | BCL11A | Not Assigned |
| 209465_x_at | PTN | Not Assigned |
| 209466_x_at | PTN | Not Assigned |
| 211737_x_at | PTN | Not Assigned |
| 218502_s_at | TRPS1 | Epithelial |
| 201131_s_at | CDH1 | Epithelial |
| 201839_s_at | EPCAM | Epithelial |
| 203397_s_at | GALNT3 | Epithelial |
| 203453_at | SCNN1A | Epithelial |
| 202525_at | PRSS8 | Epithelial |
| 202454_s_at | ERBB3 | Epithelial |
| 219121_s_at | ESRP1 | Epithelial |
| 208650_s_at | CD24 | Epithelial |
| 209772_s_at | CD24 | Epithelial |
| 208651_x_at | CD24 | Epithelial |
| 209771_x_at | CD24 | Epithelial |
| 216379_x_at | CD24 | Epithelial |
| 266_s_at | CD24 | Epithelial |
| 204653_at | TFAP2A | Epithelial |
| 218806_s_at | VAV3 | Epithelial |
| 218807_at | VAV3 | Epithelial |
| 219768_at | VTCN1 | Epithelial |
| 202935_s_at | SOX9 | Not Assigned |
| 202936_s_at | SOX9 | Not Assigned |
| 204542_at | ST6GALNAC2 | Not Assigned |
| 204990_s_at | ITGB4 | Not Assigned |
| 207547_s_at | FAM107A | Not Assigned |
| 209074_s_at | FAM107A | Not Assigned |
| 208791_at | CLU | Not Assigned |
| 208792_s_at | CLU | Not Assigned |
| 222043_at | CLU | Not Assigned |
| 203021_at | SLPI | Not Assigned |
| 203892_at | WFDC2 | Not Assigned |
| 203953_s_at | CLDN3 | Not Assigned |
| 202510_s_at | TNFAIP2 | Not Assigned |
| 207847_s_at | MUC1 | Not Assigned |
| 213693_s_at | MUC1 | Not Assigned |
| 204846_at | CP | Not Assigned |
| 214282_at | — | Not Assigned |
| 209395_at | CHI3L1 | Not Assigned |
| 209396_s_at | CHI3L1 | Not Assigned |
| 210096_at | CYP4B1 | Not Assigned |
| 204733_at | KLK6 | Not Assigned |
| 205778_at | KLK7 | Not Assigned |
| 206125_s_at | KLK8 | Not Assigned |
| 205470_s_at | KLK11 | Not Assigned |
| 209792_s_at | KLK10 | Not Assigned |
| 204124_at | SLC34A2 | Not Assigned |
| 220196_at | MUC16 | Not Assigned |
| 205334_at | S100A1 | Not Assigned |
| 32625_at | NPR1 | Not Assigned |
| 205363_at | BBOX1 | Not Assigned |
| 214844_s_at | DOK5 | Not Assigned |
| 203661_s_at | TMOD1 | Not Assigned |
| 203662_s_at | TMOD1 | Not Assigned |
| 221530_s_at | BHLHE41 | Not Assigned |
| 209437_s_at | SPON1 | Not Assigned |
| 209436_at | SPON1 | Not Assigned |
| 213994_s_at | SPON1 | Not Assigned |
| 213993_at | SPON1 | Not Assigned |
| 204437_s_at | FOLR1 | Not Assigned |
| 204885_s_at | MSLN | Not Assigned |
| 205473_at | ATP6V1B1 | Not Assigned |
| 220177_s_at | TMPRSS3 | Not Assigned |
| 219440_at | RAI2 | Not Assigned |

-continued

| Gene List 1. Gene components used for the clustering. | | |
|---|---|---|
| Affymetrix Probe ID | Gene Symbol | Gene Cluster |
| 208498_s_at | AMY1A /// AMY1B /// AMY1C /// AMY2A /// AMY2B | Not Assigned |
| 222139_at | KIAA1466 | Not Assigned |
| 222281_s_at | — | Not Assigned |
| 222334_at | — | Not Assigned |
| 204537_s_at | GABRE | Not Assigned |
| 209493_at | PDZD2 | Not Assigned |
| 204942_s_at | ALDH3B2 | Not Assigned |
| 205286_at | TFAP2C | Not Assigned |
| 210397_at | DEFB1 | Not Assigned |
| 216615_s_at | HTR3A | Not Assigned |
| 217002_s_at | HTR3A | Not Assigned |
| 214657_s_at | NCRNA00084 | Not Assigned |
| 219153_s_at | THSD4 | Not Assigned |
| 205097_at | SLC26A2 | Not Assigned |
| 206022_at | NDP | Not Assigned |
| 211685_s_at | NCALD | Not Assigned |
| 204591_at | CHL1 | Not Assigned |
| 219932_at | SLC27A6 | Not Assigned |
| 207802_at | CRISP3 | Not Assigned |
| 203780_at | MPZL2 | Not Assigned |
| 213285_at | TMEM30B | Not Assigned |
| 212560_at | SORL1 | Not Assigned |
| 205316_at | SLC15A2 | Not Assigned |
| 205225_at | ESR1 | Not Assigned |
| 209692_at | EYA2 | Not Assigned |
| 219850_s_at | EHF | Not Assigned |
| 207910_at | SCGB1D1 | Not Assigned |
| 206378_at | SCGB2A2 | Not Assigned |
| 205979_at | SCGB2A1 | Not Assigned |
| 206799_at | SCGB1D2 | Not Assigned |
| 218857_s_at | ASRGL1 | Not Assigned |
| 218858_at | DEPDC6 | Not Assigned |
| 205432_at | OVGP1 | Not Assigned |
| 205862_at | GREB1 | Not Assigned |
| 218211_s_at | MLPH | Not Assigned |
| 218692_at | GOLSYN | Not Assigned |
| 218804_at | ANO1 | Not Assigned |
| 212805_at | PRUNE2 | Not Assigned |
| 218736_s_at | PALMD | Not Assigned |
| 219359_at | ATHL1 | Not Assigned |
| 205830_at | CLGN | Not Assigned |
| 205899_at | CCNA1 | Not Assigned |
| 205833_s_at | PART1 | Not Assigned |
| 212909_at | LYPD1 | Not Assigned |
| 213273_at | ODZ4 | Not Assigned |
| 205969_at | AADAC | Not Assigned |
| 210861_s_at | WISP3 | Not Assigned |
| 202575_at | CRABP2 | Not Assigned |
| 205350_at | CRABP1 | Not Assigned |
| 203786_s_at | TPD52L1 | Not Assigned |
| 210372_s_at | TPD52L1 | Not Assigned |
| 207076_s_at | ASS1 | Not Assigned |
| 203632_s_at | GPRC5B | Not Assigned |
| 206067_s_at | WT1 | Not Assigned |
| 216953_s_at | WT1 | Not Assigned |
| 205127_at | PTGS1 | Not Assigned |
| 205128_x_at | PTGS1 | Not Assigned |
| 215813_s_at | PTGS1 | Not Assigned |
| 205975_s_at | HOXD1 | Not Assigned |
| 205522_at | HOXD4 | Not Assigned |
| 206601_s_at | HOXD3 | Not Assigned |
| 219867_at | CHODL | Not Assigned |
| 220816_at | LPAR3 | Not Assigned |
| 209201_x_at | CXCR4 | Not Assigned |
| 211919_s_at | CXCR4 | Not Assigned |
| 217028_at | CXCR4 | Not Assigned |
| 204086_at | PRAME | Not Assigned |
| 220051_at | PRSS21 | Not Assigned |
| 220179_at | DPEP3 | Not Assigned |
| 213201_s_at | TNNT1 | Not Assigned |
| 208383_s_at | PCK1 | Not Assigned |
| 213921_at | SST | Not Assigned |
| 211343_s_at | COL13A1 | Not Assigned |

| Index | Probe | Gene | Category |
|---|---|---|---|
| | | Gene List 2 - EpiA | |
| 1 | 211430_s_at | IGH@ /// IGHG1 /// IGHG2 /// IGHM /// IGHV4-31 | EpiA_Dn |
| 2 | 214677_x_at | IGL@ | EpiA_Dn |
| 3 | 209138_x_at | IGL@ | EpiA_Dn |
| 4 | 221651_x_at | IGK@ /// IGKC | EpiA_Dn |
| 5 | 221671_x_at | IGK@ /// IGKC | EpiA_Dn |
| 6 | 217022_s_at | IGH@ /// IGHA1 /// IGHA2 /// LOC100126583 | EpiA_Dn |
| 7 | 215121_x_at | IGL@ | EpiA_Dn |
| 8 | 215176_x_at | LOC100130100 | EpiA_Dn |
| 9 | 214669_x_at | IGKC | EpiA_Dn |
| 10 | 209687_at | CXCL12 | EpiA_Dn |
| 11 | 203417_at | MFAP2 | EpiA_Dn |
| 12 | 214836_x_at | IGKC | EpiA_Dn |
| 13 | 209541_at | IGF1 | EpiA_Dn |
| 14 | 203381_s_at | APOE | EpiA_Dn |
| 15 | 201147_s_at | TIMP3 | EpiA_Dn |
| 16 | 209122_at | ADFP | EpiA_Dn |
| 17 | 201150_s_at | TMP3 | EpiA_Dn |
| 18 | 203382_s_at | APOE | EpiA_Dn |
| 19 | 204320_at | COL11A1 | EpiA_Dn |
| 20 | 215446_s_at | LOX | EpiA_Dn |
| 21 | 203560_at | GGH | EpiA_Dn |
| 22 | 209540_at | IGF1 | EpiA_Dn |
| 23 | 221541_at | CRISPLD2 | EpiA_Dn |
| 24 | 201149_s_at | TIMP3 | EpiA_Dn |
| 25 | 219410_at | TMEM45A | EpiA_Dn |
| 26 | 205347_s_at | TMSB15A | EpiA_Dn |
| 27 | 209542_x_at | IGF1 | EpiA_Dn |
| 28 | 204298_s_at | LOX | EpiA_Dn |
| 29 | 218454_at | PLBD1 | EpiA_Dn |
| 30 | 218559_s_at | MAFB | EpiA_Dn |
| 31 | 213187_x_at | FTL | EpiA_Dn |
| 32 | 201148_s_at | TIMP3 | EpiA_Dn |
| 33 | 218888_s_at | NETO2 | EpiA_Dn |
| 34 | 212365_at | MYO1B | EpiA_Dn |
| 35 | 211577_s_at | IGF1 | EpiA_Dn |
| 36 | 209708_at | MOXD1 | EpiA_Dn |
| 37 | 203666_at | CXCL12 | EpiA_Dn |
| 38 | 221766_s_at | FAM46A | EpiA_Dn |
| 39 | 209209_s_at | FERMT2 | EpiA_Dn |
| 40 | 216044_x_at | FAM69A | EpiA_Dn |
| 41 | 201050_at | PLD3 | EpiA_Dn |
| 42 | 212884_x_at | APOE | EpiA_Dn |
| 43 | 213125_at | OLFML2B | EpiA_Dn |
| 44 | 218223_s_at | PLEKHO1 | EpiA_Dn |
| 45 | 206028_s_at | MERTK | EpiA_Dn |
| 46 | 202619_s_at | PLOD2 | EpiA_Dn |
| 47 | 210052_s_at | TPX2 | EpiA_Dn |
| 48 | 209210_s_at | FERMT2 | EpiA_Dn |
| 49 | 205304_s_at | KCNJ8 | EpiA_Dn |
| 50 | 214845_s_at | CALU | EpiA_Dn |
| 51 | 203300_x_at | AP1S2 | EpiA_Dn |
| 52 | 200783_s_at | STMN1 | EpiA_Dn |
| 53 | 209198_s_at | SYT11 | EpiA_Dn |
| 54 | 219479_at | KDELC1 | EpiA_Dn |
| 55 | 202273_at | PDGFRB | EpiA_Dn |
| 56 | 221210_s_at | NPL | EpiA_Dn |
| 57 | 207426_s_at | TNFSF4 | EpiA_Dn |
| 58 | 218193_s_at | GOLT1B | EpiA_Dn |
| 59 | 201559_s_at | CLIC4 | EpiA_Dn |
| 60 | 212788_x_at | FTL | EpiA_Dn |
| 61 | 212279_at | TMEM97 | EpiA_Dn |
| 62 | 200866_s_at | PSAP | EpiA_Dn |
| 63 | 201212_at | LGMN | EpiA_Dn |
| 64 | 209365_s_at | ECM1 | EpiA_Dn |
| 65 | 204415_at | IFI6 | EpiA_Dn |
| 66 | 208962_s_at | FADS1 | EpiA_Dn |
| 67 | 204203_at | CEBPG | EpiA_Dn |
| 68 | 209882_at | RIT1 | EpiA_Dn |
| 69 | 212396_s_at | KIAA0090 | EpiA_Dn |
| 70 | 207390_s_at | SMTN | EpiA_Dn |
| 71 | 209325_s_at | RGS16 | EpiA_Dn |
| 72 | 202558_s_at | HSPA13 | EpiA_Dn |
| 73 | 210568_s_at | RECQL | EpiA_Dn |
| 74 | 200744_s_at | GNB1 | EpiA_Dn |
| 75 | 200756_x_at | CALU | EpiA_Dn |
| 76 | 221269_s_at | SH3BGRL3 | EpiA_Dn |
| 77 | 202747_s_at | ITM2A | EpiA_Dn |
| 78 | 204233_s_at | CHKA | EpiA_Dn |
| 79 | 201560_at | CLIC4 | EpiA_Dn |
| 80 | 201801_s_at | SLC29A1 | EpiA_Dn |
| 81 | 211913_s_at | MERTK | EpiA_Dn |
| 82 | 221881_s_at | CLIC4 | EpiA_Dn |
| 83 | 202779_s_at | LOC731049 /// UBE2S | EpiA_Dn |
| 84 | 200755_s_at | CALU | EpiA_Dn |
| 85 | 217946_s_at | SAE1 | EpiA_Dn |
| 86 | 208510_s_at | PPARG | EpiA_Dn |
| 87 | 209773_s_at | RRM2 | EpiA_Dn |
| 88 | 205700_at | HSD17B6 | EpiA_Dn |
| 89 | 220651_s_at | MCM10 | EpiA_Dn |
| 90 | 210087_s_at | MPZL1 | EpiA_Dn |
| 91 | 202647_s_at | NRAS | EpiA_Dn |
| 92 | 212282_at | TMEM97 | EpiA_Dn |
| 93 | 211714_x_at | TUBB | EpiA_Dn |
| 94 | 218516_s_at | IMPAD1 | EpiA_Dn |
| 95 | 204146_at | RAD51AP1 | EpiA_Dn |
| 96 | 204962_s_at | CENPA | EpiA_Dn |
| 97 | 204430_s_at | SLC2A5 | EpiA_Dn |
| 98 | 209026_x_at | TUBB | EpiA_Dn |
| 99 | 212281_s_at | TMEM97 | EpiA_Dn |
| 100 | 201291_s_at | TOP2A | EpiA_Dn |
| 101 | 209363_s_at | MED21 | EpiA_Dn |
| 102 | 203046_s_at | TIMELESS | EpiA_Dn |
| 103 | 219257_s_at | SPHK1 | EpiA_Dn |
| 104 | 202580_x_at | FOXM1 | EpiA_Dn |
| 105 | 202954_at | UBE2C | EpiA_Dn |
| 106 | 221591_s_at | FAM64A | EpiA_Dn |
| 107 | 221436_s_at | CDCA3 | EpiA_Dn |
| 108 | 210133_at | CCL11 | EpiA_Dn |
| 109 | 206102_at | GINS1 | EpiA_Dn |
| 110 | 219403_s_at | HPSE | EpiA_Dn |
| 111 | 219025_at | CD248 | EpiA_Dn |
| 112 | 218045_x_at | PTMS | EpiA_Dn |
| 113 | 214212_x_at | FERMT2 | EpiA_Dn |
| 114 | 217785_s_at | YKT6 | EpiA_Dn |
| 115 | 204318_s_at | GTSE1 | EpiA_Dn |
| 116 | 221194_s_at | RNFT1 | EpiA_Dn |
| 117 | 209642_at | BUB1 | EpiA_Dn |
| 118 | 221676_s_at | CORO1C | EpiA_Dn |
| 119 | 218374_s_at | C12orf4 | EpiA_Dn |
| 120 | 202108_at | PEPD | EpiA_Dn |
| 121 | 200727_s_at | ACTR2 | EpiA_Dn |
| 122 | 203418_at | CCNA2 | EpiA_Dn |
| 123 | 201710_at | MYBL2 | EpiA_Dn |
| 124 | 204730_at | RIMS3 | EpiA_Dn |
| 125 | 209408_at | KIF2C | EpiA_Dn |
| 126 | 207828_s_at | CENPF | EpiA_Dn |
| 127 | 219061_s_at | LAGE3 | EpiA_Dn |
| 128 | 213523_at | CCNE1 | EpiA_Dn |
| 129 | 218282_at | EDEM2 | EpiA_Dn |
| 130 | 209464_at | AURKB | EpiA_Dn |
| 131 | 218252_at | CKAP2 | EpiA_Dn |
| 132 | 218574_s_at | LMCD1 | EpiA_Dn |
| 133 | 218350_s_at | GMNN | EpiA_Dn |
| 134 | 200720_s_at | ACTR1A | EpiA_Dn |
| 135 | 201950_x_at | CAPZB | EpiA_Dn |
| 136 | 208074_s_at | AP2S1 | EpiA_Dn |
| 137 | 208627_s_at | YBX1 | EpiA_Dn |
| 138 | 208918_s_at | NADK | EpiA_Dn |
| 139 | 209427_at | SMTN | EpiA_Dn |
| 140 | 208079_s_at | AURKA | EpiA_Dn |
| 141 | 209891_at | SPC25 | EpiA_Dn |
| 142 | 209653_at | KPNA4 | EpiA_Dn |
| 143 | 211047_x_at | AP2S1 | EpiA_Dn |
| 144 | 219555_s_at | CENPN | EpiA_Dn |
| 145 | 208689_s_at | RPN2 | EpiA_Dn |
| 146 | 203588_s_at | TFDP2 | EpiA_Dn |
| 147 | 221677_s_at | DONSON | EpiA_Dn |
| 148 | 201252_at | PSMC4 | EpiA_Dn |
| 149 | 202064_s_at | SEL1L | EpiA_Dn |
| 150 | 203968_s_at | CDC6 | EpiA_Dn |
| 151 | 209707_at | PIGK | EpiA_Dn |
| 152 | 209714_s_at | CDKN3 | EpiA_Dn |
| 153 | 201802_at | SLC29A1 | EpiA_Dn |
| 154 | 218257_s_at | UGCGL1 | EpiA_Dn |

| | | | |
|---|---|---|---|
| 155 | 217094_s_at | ITCH | EpiA_Dn |
| 156 | 217770_at | PIGT | EpiA_Dn |
| 157 | 213696_s_at | MED8 | EpiA_Dn |
| 158 | 218781_at | SMC6 | EpiA_Dn |
| 159 | 205393_s_at | CHEK1 | EpiA_Dn |
| 160 | 202095_s_at | BIRC5 | EpiA_Dn |
| 161 | 211519_s_at | KIF2C | EpiA_Dn |
| 162 | 219551_at | EAF2 | EpiA_Dn |
| 163 | 218542_at | CEP55 | EpiA_Dn |
| 164 | 218088_s_at | RRAGC | EpiA_Dn |
| 165 | 210594_x_at | MPZL1 | EpiA_Dn |
| 166 | 200815_s_at | PAFAH1B1 | EpiA_Dn |
| 167 | 202613_at | CTPS | EpiA_Dn |
| 168 | 201663_s_at | SMC4 | EpiA_Dn |
| 169 | 214487_s_at | RAP2A /// RAP2B | EpiA_Dn |
| 170 | 202871_at | TRAF4 | EpiA_Dn |
| 171 | 220011_at | C1orf135 | EpiA_Dn |
| 172 | 208836_s_at | ATP1B3 | EpiA_Dn |
| 173 | 219544_at | C13orf34 | EpiA_Dn |
| 174 | 204092_s_at | AURKA | EpiA_Dn |
| 175 | 219918_s_at | ASPM | EpiA_Dn |
| 176 | 221522_at | ANKRD27 | EpiA_Dn |
| 177 | 215509_s_at | BUB1 | EpiA_Dn |
| 178 | 202487_s_at | H2AFV | EpiA_Dn |
| 179 | 202120_x_at | AP2S1 | EpiA_Dn |
| 180 | 203764_at | DLGAP5 | EpiA_Dn |
| 181 | 208628_s_at | YBX1 | EpiA_Dn |
| 182 | 222039_at | KIF18B | EpiA_Dn |
| 183 | 201475_x_at | MARS | EpiA_Dn |
| 184 | 219978_s_at | NUSAP1 | EpiA_Dn |
| 185 | 203516_at | SNTA1 | EpiA_Dn |
| 186 | 212020_s_at | MKI67 | EpiA_Dn |
| 187 | 205046_at | CENPE | EpiA_Dn |
| 188 | 212949_at | NCAPH | EpiA_Dn |
| 189 | 218497_s_at | RNASEH1 | EpiA_Dn |
| 190 | 204822_at | TTK | EpiA_Dn |
| 191 | 203109_at | UBE2M | EpiA_Dn |
| 192 | 217714_x_at | STMN1 | EpiA_Dn |
| 193 | 204026_s_at | ZWINT | EpiA_Dn |
| 194 | 201930_at | MCM6 | EpiA_Dn |
| 195 | 201897_s_at | CKS1B | EpiA_Dn |
| 196 | 211762_s_at | KPNA2 | EpiA_Dn |
| 197 | 213088_s_at | DNAJC9 | EpiA_Dn |
| 198 | 204460_s_at | RAD1 | EpiA_Dn |
| 199 | 220160_at | KPTN | EpiA_Dn |
| 200 | 201112_s_at | CSE1L | EpiA_Dn |
| 201 | 205704_s_at | ATP6V0A2 | EpiA_Dn |
| 202 | 206686_at | PDK1 | EpiA_Dn |
| 203 | 222158_s_at | PPPDE1 | EpiA_Dn |
| 204 | 218782_s_at | ATAD2 | EpiA_Dn |
| 205 | 221021_s_at | CTNNBL1 | EpiA_Dn |
| 206 | 218799_at | GPN2 | EpiA_Dn |
| 207 | 200868_s_at | RNF114 | EpiA_Dn |
| 208 | 203145_at | SPAG5 | EpiA_Dn |
| 209 | 218755_at | KIF20A | EpiA_Dn |
| 210 | 200975_at | PPT1 | EpiA_Dn |
| 211 | 209680_s_at | KIFC1 | EpiA_Dn |
| 212 | 220642_x_at | GPR89A /// GPR89B /// GPR89C | EpiA_Dn |
| 213 | 206296_x_at | MAP4K1 | EpiA_Dn |
| 214 | 211251_x_at | NFYC | EpiA_Dn |
| 215 | 210559_s_at | CDC2 | EpiA_Dn |
| 216 | 204240_s_at | SMC2 | EpiA_Dn |
| 217 | 219507_at | RSRC1 | EpiA_Dn |
| 218 | 202407_s_at | PRPF31 | EpiA_Dn |
| 219 | 207183_at | GPR19 | EpiA_Dn |
| 220 | 203422_at | POLD1 | EpiA_Dn |
| 221 | 204315_s_at | GTSE1 | EpiA_Dn |
| 222 | 213996_at | YPEL1 | EpiA_Dn |
| 223 | 204331_s_at | MRPS12 | EpiA_Dn |
| 224 | 214474_at | PRKAB2 | EpiA_Dn |
| 225 | 214442_s_at | PIAS2 | EpiA_Dn |
| 226 | 202820_at | AHR | EpiA_Dn |
| 227 | 214649_s_at | MTMR2 | EpiA_Dn |
| 228 | 220840_s_at | C1orf112 | EpiA_Dn |
| 229 | 213607_x_at | NADK | EpiA_Dn |
| 230 | 205240_at | GPSM2 | EpiA_Dn |
| 231 | 219512_at | DSN1 | EpiA_Dn |
| 232 | 202216_x_at | NFYC | EpiA_Dn |
| 233 | 201543_s_at | SAR1A | EpiA_Dn |
| 234 | 221528_s_at | ELMO2 | EpiA_Dn |
| 235 | 205930_at | GTF2E1 | EpiA_Dn |
| 236 | 212219_at | PSME4 | EpiA_Dn |
| 237 | 210334_x_at | BIRC5 | EpiA_Dn |
| 238 | 204825_at | MELK | EpiA_Dn |
| 239 | 221520_s_at | CDCA8 | EpiA_Dn |
| 240 | 202094_at | BIRC5 | EpiA_Dn |
| 241 | 38158_at | ESPL1 | EpiA_Dn |
| 242 | 201090_x_at | TUBA1B | EpiA_Dn |
| 243 | 212694_s_at | PCCB | EpiA_Dn |
| 244 | 210766_s_at | CSE1L | EpiA_Dn |
| 245 | 214880_x_at | CALD1 | EpiA_Dn |
| 246 | 218726_at | HJURP | EpiA_Dn |
| 247 | 204243_at | RLF | EpiA_Dn |
| 248 | 210178_x_at | FUSIP1 | EpiA_Dn |
| 249 | 218295_s_at | NUP50 | EpiA_Dn |
| 250 | 201777_s_at | KIAA0494 | EpiA_Dn |
| 251 | 201504_s_at | TSN | EpiA_Dn |
| 252 | 211058_x_at | TUBA1B | EpiA_Dn |
| 253 | 204126_s_at | CDC45L | EpiA_Dn |
| 254 | 203214_x_at | CDC2 | EpiA_Dn |
| 255 | 214173_x_at | C19orf2 | EpiA_Dn |
| 256 | 204128_s_at | RFC3 | EpiA_Dn |
| 257 | 210216_x_at | RAD1 | EpiA_Dn |
| 258 | 213646_x_at | TUBA1B | EpiA_Dn |
| 259 | 201177_s_at | UBA2 | EpiA_Dn |
| 260 | 220060_s_at | C12orf48 | EpiA_Dn |
| 261 | 219306_at | KIF15 | EpiA_Dn |
| 262 | 203755_at | BUB1B | EpiA_Dn |
| 263 | 212639_x_at | TUBA1B | EpiA_Dn |
| 264 | 209727_at | GM2A | EpiA_Dn |
| 265 | 210008_s_at | MRPS12 | EpiA_Dn |
| 266 | 203013_at | ECD | EpiA_Dn |
| 267 | 219219_at | TMEM160 | EpiA_Dn |
| 268 | 204558_at | RAD54L | EpiA_Dn |
| 269 | 222077_s_at | RACGAP1 | EpiA_Dn |
| 270 | 211072_x_at | TUBA1B | EpiA_Dn |
| 271 | 208973_at | ERI3 | EpiA_Dn |
| 272 | 211750_x_at | TUBA1C | EpiA_Dn |
| 273 | 221046_s_at | GTPBP8 | EpiA_Dn |
| 274 | 220295_x_at | DEPDC1 | EpiA_Dn |
| 275 | 214006_s_at | GGCX | EpiA_Dn |
| 276 | 209825_s_at | UCK2 | EpiA_Dn |
| 277 | 213827_at | SNX26 | EpiA_Dn |
| 278 | 209251_x_at | TUBA1C | EpiA_Dn |
| 279 | 202058_s_at | KPNA1 | EpiA_Dn |
| 280 | 211814_s_at | CCNE2 | EpiA_Dn |
| 281 | 219650_at | ERCC6L | EpiA_Dn |
| 282 | 204603_at | EXO1 | EpiA_Dn |
| 283 | 205909_at | POLE2 | EpiA_Dn |
| 284 | 210681_s_at | USP15 | EpiA_Dn |
| 285 | 214431_at | GMPS | EpiA_Dn |
| 286 | 218299_at | C11orf24 | EpiA_Dn |
| 287 | 203015_s_at | SSX2IP | EpiA_Dn |
| 288 | 210821_x_at | CENPA | EpiA_Dn |
| 289 | 204317_at | GTSE1 | EpiA_Dn |
| 290 | 206364_at | KIF14 | EpiA_Dn |
| 291 | 222250_s_at | INTS7 | EpiA_Dn |
| 292 | 203271_s_at | UNC119 | EpiA_Dn |
| 293 | 200625_s_at | CAP1 | EpiA_Dn |
| 294 | 204947_at | E2F1 | EpiA_Dn |
| 295 | 200021_at | CFL1 | EpiA_Dn |
| 296 | 200052_s_at | ILF2 | EpiA_Dn |
| 297 | 210527_x_at | TUBA3C | EpiA_Dn |
| 298 | 218479_s_at | XPO4 | EpiA_Dn |
| 299 | 202869_at | OAS1 | EpiA_Dn |
| 300 | 208644_at | PARP1 | EpiA_Dn |
| 301 | 212165_at | TMEM183A /// TMEM183B | EpiA_Dn |
| 302 | 214849_at | KCTD20 | EpiA_Dn |
| 303 | 203436_at | RPP30 | EpiA_Dn |
| 304 | 220721_at | ZNF614 | EpiA_Dn |
| 305 | 218447_at | C16orf61 | EpiA_Dn |
| 306 | 205085_at | ORC1L | EpiA_Dn |
| 307 | 204514_at | DPH2 | EpiA_Dn |
| 308 | 200039_s_at | PSMB2 | EpiA_Dn |
| 309 | 219510_at | POLQ | EpiA_Dn |
| 310 | 219502_at | NEIL3 | EpiA_Dn |
| 311 | 202338_at | TK1 | EpiA_Dn |

| | | | |
|---|---|---|---|
| 312 | 204441_s_at | POLA2 | EpiA_Dn |
| 313 | 218235_s_at | UTP11L | EpiA_Dn |
| 314 | 211114_x_at | SIP1 | EpiA_Dn |
| 315 | 203213_at | CDC2 | EpiA_Dn |
| 316 | 216940_x_at | YBX1 /// YBX1P2 | EpiA_Dn |
| 317 | 211786_at | TNFRSF9 | EpiA_Dn |
| 318 | 206621_s_at | EIF4H | EpiA_Up |
| 319 | 215462_at | PLK3 | EpiA_Up |
| 320 | 208078_s_at | SIK1 | EpiA_Up |
| 321 | 216595_at | FAM186A | EpiA_Up |
| 322 | 215637_at | TSGA14 | EpiA_Up |
| 323 | 211419_s_at | CHN2 | EpiA_Up |
| 324 | 214271_x_at | RPL12 | EpiA_Up |
| 325 | 215386_at | — | EpiA_Up |
| 326 | 214458_at | TRAF3IP1 | EpiA_Up |
| 327 | 215102_at | DPY19L1P1 | EpiA_Up |
| 328 | 209375_at | XPC | EpiA_Up |
| 329 | 211441_x_at | CYP3A43 | EpiA_Up |
| 330 | 207418_s_at | DDO | EpiA_Up |
| 331 | 216735_x_at | — | EpiA_Up |
| 332 | 216497_at | HNRNPA1 /// HNRNPA1L2 /// HNRPA1L-2 /// HNRPA1P5 /// LOC100128701 /// LOC100128836 /// LOC120364 /// LOC391670 /// LOC402112 /// LOC642817 /// LOC643033 /// LOC644037 /// LOC645001 /// LOC728170 /// LOC728643 /// LOC728732 /// LOC729102 /// LOC729366 /// LOC730246 /// RP11-569O4.6 | EpiA_Up |
| 333 | 202701_at | BMP1 | EpiA_Up |
| 334 | 219503_s_at | TMEM40 | EpiA_Up |
| 335 | 215284_at | — | EpiA_Up |
| 336 | 206222_at | TNFRSF10C | EpiA_Up |
| 337 | 200663_at | CD63 | EpiA_Up |
| 338 | 215892_at | ZNF440 | EpiA_Up |
| 339 | 214873_at | LRP5L | EpiA_Up |
| 340 | 219281_at | MSRA | EpiA_Up |
| 341 | 217873_at | CAB39 | EpiA_Up |
| 342 | 41220_at | SEPT9 | EpiA_Up |
| 343 | 222061_at | CD58 | EpiA_Up |
| 344 | 200847_s_at | TMEM66 | EpiA_Up |
| 345 | 211517_s_at | IL5RA | EpiA_Up |
| 346 | 213922_at | TTBK2 | EpiA_Up |
| 347 | 211698_at | EID1 | EpiA_Up |
| 348 | 215624_at | TSC2 | EpiA_Up |
| 349 | 212726_at | PHF2 | EpiA_Up |
| 350 | 220497_at | ZNF214 | EpiA_Up |
| 351 | 204227_s_at | TK2 | EpiA_Up |
| 352 | 216135_at | IQCK | EpiA_Up |
| 353 | 206910_x_at | CFHR2 | EpiA_Up |
| 354 | 210486_at | ANKMY1 | EpiA_Up |
| 355 | 214082_at | CA5B | EpiA_Up |
| 356 | 204874_x_at | BAIAP3 | EpiA_Up |
| 357 | 200677_at | PTTG1IP | EpiA_Up |
| 358 | 221617_at | TAF9B | EpiA_Up |
| 359 | 219834_at | ALS2CR8 | EpiA_Up |
| 360 | 206540_at | GLB1L | EpiA_Up |
| 361 | 219354_at | KLHL26 | EpiA_Up |
| 362 | 202561_at | TNKS | EpiA_Up |
| 363 | 217682_at | — | EpiA_Up |
| 364 | 217107_at | — | EpiA_Up |
| 365 | 206855_s_at | HYAL2 | EpiA_Up |
| 366 | 219135_s_at | LMF1 | EpiA_Up |
| 367 | 219136_s_at | LMF1 | EpiA_Up |
| 368 | 215626_at | — | EpiA_Up |
| 369 | 212736_at | C16orf45 | EpiA_Up |
| 370 | 219891_at | PGPEP1 | EpiA_Up |
| 371 | 213848_at | — | EpiA_Up |
| 372 | 220364_at | FLJ11235 | EpiA_Up |
| 373 | 221889_at | KCTD13 | EpiA_Up |
| 374 | 205271_s_at | CCRK | EpiA_Up |
| 375 | 214147_at | C1orf175 | EpiA_Up |
| 376 | 219106_s_at | KBTBD10 | EpiA_Up |
| 377 | 217574_at | CDH8 | EpiA_Up |
| 378 | 214192_at | NUP88 | EpiA_Up |
| 379 | 208646_at | RPS14 /// RPS14P3 | EpiA_Up |
| 380 | 206594_at | PASK | EpiA_Up |
| 381 | 214118_x_at | PCM1 | EpiA_Up |
| 382 | 202419_at | KDSR | EpiA_Up |
| 383 | 207785_s_at | RBPJ | EpiA_Up |
| 384 | 215146_s_at | TTC28 | EpiA_Up |
| 385 | 216342_x_at | RPS4P13 /// RPS4P17 /// RPS4P7 /// RPS4X | EpiA_Up |
| 386 | 221867_at | N4BP1 | EpiA_Up |
| 387 | 210129_s_at | TTLL3 | EpiA_Up |
| 388 | 220271_x_at | EFCAB6 | EpiA_Up |
| 389 | 219482_at | SETD4 | EpiA_Up |
| 390 | 208741_at | SAP18 | EpiA_Up |
| 391 | 209240_at | OGT | EpiA_Up |
| 392 | 217863_at | PIAS1 | EpiA_Up |
| 393 | 215972_at | — | EpiA_Up |
| 394 | 201132_at | HNRNPH2 | EpiA_Up |
| 395 | 217016_x_at | FLJ23172 | EpiA_Up |
| 396 | 203380_x_at | SFRS5 | EpiA_Up |
| 397 | 219252_s_at | GEMIN8 | EpiA_Up |
| 398 | 215030_at | GRSF1 | EpiA_Up |
| 399 | 221493_at | TSPYL1 | EpiA_Up |
| 400 | 220361_at | IQCH | EpiA_Up |
| 401 | 221905_at | CYLD | EpiA_Up |
| 402 | 204792_s_at | IFT140 | EpiA_Up |
| 403 | 215598_at | TTC12 | EpiA_Up |
| 404 | 221480_at | HNRNPD | EpiA_Up |
| 405 | 200928_s_at | RAB14 | EpiA_Up |
| 406 | 220218_at | C9orf68 | EpiA_Up |
| 407 | 210962_s_at | AKAP9 | EpiA_Up |
| 408 | 209838_at | COPS2 | EpiA_Up |
| 409 | 213364_s_at | SNX1 | EpiA_Up |
| 410 | 200074_s_at | RPL14 /// RPL14P1 | EpiA_Up |
| 411 | 212427_at | KIAA0368 | EpiA_Up |
| 412 | 214045_at | LIAS | EpiA_Up |
| 413 | 218517_at | PHF17 | EpiA_Up |
| 414 | 220614_at | C6orf103 | EpiA_Up |
| 415 | 212074_at | UNC84A | EpiA_Up |
| 416 | 204276_at | TK2 | EpiA_Up |
| 417 | 203563_at | AFAP1 | EpiA_Up |
| 418 | 213838_at | NOL7 | EpiA_Up |
| 419 | 212710_at | CAMSAP1 | EpiA_Up |
| 420 | 213215_at | AP3S2 | EpiA_Up |
| 421 | 46142_at | LMF1 | EpiA_Up |
| 422 | 212826_s_at | SLC25A6 | EpiA_Up |
| 423 | 208796_s_at | CCNG1 | EpiA_Up |
| 424 | 202615_at | GNAQ | EpiA_Up |
| 425 | 218396_at | VPS13C | EpiA_Up |
| 426 | 211938_at | EIF4B | EpiA_Up |
| 427 | 212425_at | SCAMP1 | EpiA_Up |
| 428 | 219973_at | ARSJ | EpiA_Up |
| 429 | 206315_at | CRLF1 | EpiA_Up |
| 430 | 220539_at | C10orf92 | EpiA_Up |
| 431 | 215266_at | DNAH3 | EpiA_Up |
| 432 | 204662_at | CP110 | EpiA_Up |
| 433 | 213185_at | KIAA0556 | EpiA_Up |
| 434 | 213058_at | TTC28 | EpiA_Up |
| 435 | 212343_at | YIPF6 | EpiA_Up |
| 436 | 218785_s_at | RABL5 | EpiA_Up |
| 437 | 204055_s_at | CTAGE5 | EpiA_Up |
| 438 | 45653_at | KCTD13 | EpiA_Up |
| 439 | 202962_at | KIF13B | EpiA_Up |
| 440 | 214800_x_at | BTF3 | EpiA_Up |
| 441 | 215185_at | — | EpiA_Up |
| 442 | 204625_s_at | ITGB3 | EpiA_Up |
| 443 | 212179_at | SFRS18 | EpiA_Up |
| 444 | 217828_at | SLTM | EpiA_Up |
| 445 | 205584_at | ALG13 | EpiA_Up |
| 446 | 209256_s_at | KLHDC10 | EpiA_Up |
| 447 | 218980_at | FHOD3 | EpiA_Up |
| 448 | 202174_s_at | PCM1 | EpiA_Up |
| 449 | 218147_s_at | GLT8D1 | EpiA_Up |
| 450 | 210111_s_at | KLHDC10 | EpiA_Up |
| 451 | 212293_at | HIPK1 | EpiA_Up |
| 452 | 213190_at | COG7 | EpiA_Up |
| 453 | 212416_at | SCAMP1 | EpiA_Up |
| 454 | 221476_s_at | RPL15 | EpiA_Up |
| 455 | 32029_at | PDPK1 | EpiA_Up |
| 456 | 210958_s_at | MAST4 | EpiA_Up |
| 457 | 214937_x_at | PCM1 | EpiA_Up |
| 458 | 209884_s_at | SLC4A7 | EpiA_Up |

| | | | |
|---|---|---|---|
| 459 | 212633_at | KIAA0776 | EpiA_Up |
| 460 | 221257_x_at | FBXO38 | EpiA_Up |
| 461 | 202163_s_at | CNOT8 | EpiA_Up |
| 462 | 220050_at | C9orf9 | EpiA_Up |
| 463 | 212221_x_at | IDS | EpiA_Up |
| 464 | 90265_at | ADAP1 | EpiA_Up |
| 465 | 203835_at | LRRC32 | EpiA_Up |
| 466 | 209486_at | UTP3 | EpiA_Up |
| 467 | 204008_at | DNAL4 | EpiA_Up |
| 468 | 218976_at | DNAJC12 | EpiA_Up |
| 469 | 202603_at | — | EpiA_Up |
| 470 | 205839_s_at | BZRAP1 | EpiA_Up |
| 471 | 217996_at | PHLDA1 | EpiA_Up |
| 472 | 219381_at | C5orf42 | EpiA_Up |
| 473 | 214848_at | — | EpiA_Up |
| 474 | 212109_at | HN1L | EpiA_Up |
| 475 | 208865_at | CSNK1A1 | EpiA_Up |
| 476 | 218265_at | SECISBP2 | EpiA_Up |
| 477 | 213024_at | TMF1 | EpiA_Up |
| 478 | 212936_at | FAM172A | EpiA_Up |
| 479 | 213974_at | ADAMTSL3 | EpiA_Up |
| 480 | 217047_s_at | FAM13A | EpiA_Up |
| 481 | 204703_at | IFT88 | EpiA_Up |
| 482 | 204958_at | PLK3 | EpiA_Up |
| 483 | 220344_at | C11orf16 | EpiA_Up |
| 484 | 208866_at | CSNK1A1 | EpiA_Up |
| 485 | 200066_at | IK | EpiA_Up |
| 486 | 207698_at | C6orf123 | EpiA_Up |
| 487 | 222134_at | DDO | EpiA_Up |
| 488 | 212140_at | PDS5A | EpiA_Up |
| 489 | 209963_s_at | EPOR | EpiA_Up |
| 490 | 200597_at | EIF3A | EpiA_Up |
| 491 | 222322_at | — | EpiA_Up |
| 492 | 219186_at | ZBTB7A | EpiA_Up |
| 493 | 219957_at | RUFY2 | EpiA_Up |
| 494 | 219680_at | NLRX1 | EpiA_Up |
| 495 | 213832_at | KCND3 | EpiA_Up |
| 496 | 222258_s_at | SH3BP4 | EpiA_Up |
| 497 | 201889_at | FAM3C | EpiA_Up |
| 498 | 215085_x_at | DLEC1 | EpiA_Up |
| 499 | 219251_s_at | WDR60 | EpiA_Up |
| 500 | 221103_s_at | WDR52 | EpiA_Up |
| 501 | 213275_x_at | CTSB | EpiA_Up |
| 502 | 218471_s_at | BBS1 | EpiA_Up |
| 503 | 202241_at | TRIB1 | EpiA_Up |
| 504 | 205364_at | ACOX2 | EpiA_Up |
| 505 | 57739_at | DND1 | EpiA_Up |
| 506 | 206815_at | SPAG8 | EpiA_Up |
| 507 | 212912_at | RPS6KA2 | EpiA_Up |
| 508 | 206153_at | CYP4F11 | EpiA_Up |
| 509 | 219396_s_at | NEIL1 | EpiA_Up |
| 510 | 219332_at | MICALL2 | EpiA_Up |
| 511 | 201861_s_at | LRRFIP1 | EpiA_Up |
| 512 | 203480_s_at | OTUD4 | EpiA_Up |
| 513 | 205583_s_at | ALG13 | EpiA_Up |
| 514 | 219122_s_at | THG1L | EpiA_Up |
| 515 | 211471_s_at | RAB36 | EpiA_Up |
| 516 | 202105_at | IGBP1 | EpiA_Up |
| 517 | 204577_s_at | CLUAP1 | EpiA_Up |
| 518 | 202973_x_at | FAM13A | EpiA_Up |
| 519 | 204491_at | PDE4D | EpiA_Up |
| 520 | 213626_at | CBR4 | EpiA_Up |
| 521 | 221773_at | ELK3 | EpiA_Up |
| 522 | 206798_x_at | DLEC1 | EpiA_Up |
| 523 | 222220_s_at | TSNAXIP1 | EpiA_Up |
| 524 | 209068_at | HNRPDL | EpiA_Up |
| 525 | 208600_s_at | GPR39 | EpiA_Up |
| 526 | 201581_at | TMX4 | EpiA_Up |
| 527 | 215472_at | PACRG | EpiA_Up |
| 528 | 201880_at | ARIH1 | EpiA_Up |
| 529 | 203348_s_at | ETV5 | EpiA_Up |
| 530 | 202081_at | IER2 | EpiA_Up |
| 531 | 205069_s_at | ARHGAP26 | EpiA_Up |
| 532 | 201473_at | JUNB | EpiA_Up |
| 533 | 200810_s_at | CIRBP | EpiA_Up |
| 534 | 220426_at | C20orf195 | EpiA_Up |
| 535 | 37986_at | EPOR | EpiA_Up |
| 536 | 206492_at | FHIT | EpiA_Up |
| 537 | 201260_s_at | SYPL1 | EpiA_Up |
| 538 | 221621_at | C17orf86 | EpiA_Up |
| 539 | 211004_s_at | ALDH3B1 | EpiA_Up |
| 540 | 219597_s_at | DUOX1 | EpiA_Up |
| 541 | 203513_at | SPG11 | EpiA_Up |
| 542 | 210103_s_at | FOXA2 | EpiA_Up |
| 543 | 206081_at | SLC24A1 | EpiA_Up |
| 544 | 206938_at | SRD5A2 | EpiA_Up |
| 545 | 220141_at | C11orf63 | EpiA_Up |
| 546 | 215498_s_at | MAP2K3 | EpiA_Up |
| 547 | 213385_at | CHN2 | EpiA_Up |
| 548 | 214252_s_at | CLN5 | EpiA_Up |
| 549 | 213792_s_at | INSR | EpiA_Up |
| 550 | 204545_at | PEX6 | EpiA_Up |
| 551 | 204788_s_at | PPOX | EpiA_Up |
| 552 | 212993_at | NACC2 | EpiA_Up |
| 553 | 221577_x_at | GDF15 | EpiA_Up |
| 554 | 213589_s_at | B3GNTL1 | EpiA_Up |
| 555 | 212616_at | CHD9 | EpiA_Up |
| 556 | 204084_s_at | CLN5 | EpiA_Up |
| 557 | 213895_at | EMP1 | EpiA_Up |
| 558 | 215130_s_at | IQCK | EpiA_Up |
| 559 | 208760_at | UBE2I | EpiA_Up |
| 560 | 201059_at | CTTN | EpiA_Up |
| 561 | 204497_at | ADCY9 | EpiA_Up |
| 562 | 201501_s_at | GRSF1 | EpiA_Up |
| 563 | 219351_at | TRAPPC2 | EpiA_Up |
| 564 | 209894_at | LEPR | EpiA_Up |
| 565 | 202084_s_at | SEC14L1 | EpiA_Up |
| 566 | 202181_at | KIAA0247 | EpiA_Up |
| 567 | 212927_at | SMC5 | EpiA_Up |
| 568 | 209640_at | PML | EpiA_Up |
| 569 | 203763_at | DYNC2LI1 | EpiA_Up |
| 570 | 204576_s_at | CLUAP1 | EpiA_Up |
| 571 | 219916_s_at | RNF39 | EpiA_Up |
| 572 | 218501_at | ARHGEF3 | EpiA_Up |
| 573 | 203144_s_at | KIAA0040 | EpiA_Up |
| 574 | 219644_at | CCDC41 | EpiA_Up |
| 575 | 218950_at | ARAP3 | EpiA_Up |
| 576 | 215341_at | DNAH6 | EpiA_Up |
| 577 | 219109_at | SPAG16 | EpiA_Up |
| 578 | 201862_s_at | LRRFIP1 | EpiA_Up |
| 579 | 207896_s_at | DLEC1 | EpiA_Up |
| 580 | 207170_s_at | LETMD1 | EpiA_Up |
| 581 | 220500_s_at | RABL2A /// RABL2B | EpiA_Up |
| 582 | 216119_s_at | SPEF1 | EpiA_Up |
| 583 | 201694_s_at | EGR1 | EpiA_Up |
| 584 | 219951_s_at | C20orf12 | EpiA_Up |
| 585 | 219271_at | GALNT14 | EpiA_Up |
| 586 | 220581_at | C6orf97 | EpiA_Up |
| 587 | 210345_s_at | DNAH9 | EpiA_Up |
| 588 | 209568_s_at | RGL1 | EpiA_Up |
| 589 | 201906_s_at | CTDSPL | EpiA_Up |
| 590 | 201018_at | EIF1AX | EpiA_Up |
| 591 | 215808_at | KLK10 | EpiA_Up |
| 592 | 221096_s_at | TMCO6 | EpiA_Up |
| 593 | 207375_s_at | IL15RA | EpiA_Up |
| 594 | 208407_s_at | CTNND1 | EpiA_Up |
| 595 | 201939_at | PLK2 | EpiA_Up |
| 596 | 222348_at | MAST4 | EpiA_Up |
| 597 | 210612_s_at | SYNJ2 | EpiA_Up |
| 598 | 220389_at | CCDC81 | EpiA_Up |
| 599 | 206874_s_at | — | EpiA_Up |
| 600 | 201693_s_at | EGR1 | EpiA_Up |
| 601 | 203349_s_at | ETV5 | EpiA_Up |
| 602 | 205011_at | VWA5A | EpiA_Up |
| 603 | 213704_at | RABGGTB | EpiA_Up |
| 604 | 202761_s_at | SYNE2 | EpiA_Up |
| 605 | 213106_at | ATP8A1 | EpiA_Up |
| 606 | 205856_at | SLC14A1 | EpiA_Up |
| 607 | 203573_s_at | RABGGTA | EpiA_Up |
| 608 | 220107_s_at | FAM164C | EpiA_Up |
| 609 | 204099_at | SMARCD3 | EpiA_Up |
| 610 | 222111_at | — | EpiA_Up |
| 611 | 201887_at | IL13RA1 | EpiA_Up |
| 612 | 219686_at | STK32B | EpiA_Up |
| 613 | 218328_at | COQ4 | EpiA_Up |
| 614 | 40016_g_at | MAST4 | EpiA_Up |
| 615 | 221934_s_at | DALRD3 /// LOC100133719 | EpiA_Up |
| 616 | 202552_s_at | CRIM1 | EpiA_Up |

| # | Probe | Gene | Direction |
|---|---|---|---|
| 617 | 218584_at | TCTN1 | EpiA_Up |
| 618 | 205834_s_at | PARTI | EpiA_Up |
| 619 | 207959_s_at | DNAH9 | EpiA_Up |
| 620 | 204085_s_at | CLN5 | EpiA_Up |
| 621 | 203897_at | LYRM1 | EpiA_Up |
| 622 | 215054_at | EPOR | EpiA_Up |
| 623 | 205193_at | MAFF | EpiA_Up |
| 624 | 201941_at | CPD | EpiA_Up |
| 625 | 214919_s_at | ANKHD1-EIF4EBP3 /// EIF4EBP3 | EpiA_Up |
| 626 | 217645_at | COX16 | EpiA_Up |
| 627 | 209962_at | EPOR | EpiA_Up |
| 628 | 211297_s_at | CDK7 | EpiA_Up |
| 629 | 219455_at | C7orf63 | EpiA_Up |
| 630 | 205459_s_at | NPAS2 | EpiA_Up |
| 631 | 204168_at | MGST2 | EpiA_Up |
| 632 | 203997_at | PTPN3 | EpiA_Up |
| 633 | 219157_at | KLHL2 | EpiA_Up |
| 634 | 202067_s_at | LDLR | EpiA_Up |
| 635 | 203408_s_at | SATB1 | EpiA_Up |
| 636 | 219587_at | TTC12 | EpiA_Up |
| 637 | 219222_at | RBKS | EpiA_Up |
| 638 | 209227_at | TUSC3 | EpiA_Up |
| 639 | 201408_at | PPP1CB | EpiA_Up |
| 640 | 209457_at | DUSP5 | EpiA_Up |
| 641 | 205580_s_at | HRH1 | EpiA_Up |
| 642 | 209184_s_at | IRS2 | EpiA_Up |
| 643 | 208873_s_at | REEP5 | EpiA_Up |
| 644 | 201341_at | ENC1 | EpiA_Up |
| 645 | 205251_at | PER2 | EpiA_Up |
| 646 | 218931_at | RAB17 | EpiA_Up |
| 647 | 212321_at | SGPL1 | EpiA_Up |
| 648 | 212828_at | SYNJ2 | EpiA_Up |
| 649 | 218826_at | SLC35F2 | EpiA_Up |
| 650 | 218769_s_at | ANKRA2 | EpiA_Up |
| 651 | 210367_s_at | PTGES | EpiA_Up |
| 652 | 214109_at | LRBA | EpiA_Up |
| 653 | 221973_at | — | EpiA_Up |
| 654 | 210106_at | RDH5 | EpiA_Up |
| 655 | 205074_at | SLC22A5 | EpiA_Up |
| 656 | 210674_s_at | PCDHA1 /// PCDHA10 /// PCDHA11 /// PCDHA12 /// PCDHA13 /// PCDHA2 /// PCDHA3 /// PCDHA4 /// PCDHA5 /// PCDHA6 /// PCDHA7 /// PCDHA8 /// PCDHA9 /// PCDHAC1 /// PCDHAC2 | EpiA_Up |
| 657 | 215304_at | — | EpiA_Up |
| 658 | 208920_at | SRI | EpiA_Up |
| 659 | 213375_s_at | N4BP2L1 | EpiA_Up |
| 660 | 213750_at | RSL1D1 | EpiA_Up |
| 661 | 214428_x_at | C4A /// C4B | EpiA_Up |
| 662 | 218086_at | NPDC1 | EpiA_Up |
| 663 | 209185_s_at | IRS2 | EpiA_Up |
| 664 | 220917_s_at | WDR19 | EpiA_Up |
| 665 | 201042_at | TGM2 | EpiA_Up |
| 666 | 221489_s_at | SPRY4 | EpiA_Up |
| 667 | 207797_s_at | LRP2BP | EpiA_Up |
| 668 | 220280_s_at | ANKMY1 | EpiA_Up |
| 669 | 205227_at | IL1RAP | EpiA_Up |
| 670 | 209164_s_at | CYB561 | EpiA_Up |
| 671 | 35666_at | SEMA3F | EpiA_Up |
| 672 | 211986_at | AHNAK | EpiA_Up |
| 673 | 219542_at | NEK11 | EpiA_Up |
| 674 | 218764_at | PRKCH | EpiA_Up |
| 675 | 209740_s_at | PNPLA4 | EpiA_Up |
| 676 | 214204_at | PACRG | EpiA_Up |
| 677 | 213304_at | FAM179B | EpiA_Up |
| 678 | 220520_s_at | NUP62CL | EpiA_Up |
| 679 | 207517_at | LAMC2 | EpiA_Up |
| 680 | 218795_at | ACP6 | EpiA_Up |
| 681 | 220540_at | KCNK15 | EpiA_Up |
| 682 | 213142_x_at | PION | EpiA_Up |
| 683 | 57540_at | RBKS | EpiA_Up |
| 684 | 209194_at | CETN2 | EpiA_Up |
| 685 | 209163_at | CYB561 | EpiA_Up |
| 686 | 200972_at | TSPAN3 | EpiA_Up |
| 687 | 219151_s_at | RABL2A /// RABL2B | EpiA_Up |
| 688 | 214235_at | CYP3A5 | EpiA_Up |
| 689 | 212586_at | CAST | EpiA_Up |
| 690 | 201998_at | ST6GAL1 | EpiA_Up |
| 691 | 203143_s_at | KIAA0040 | EpiA_Up |
| 692 | 210168_at | C6 | EpiA_Up |
| 693 | 215856_at | SIGLEC15 | EpiA_Up |
| 694 | 203739_at | ZNF217 | EpiA_Up |
| 695 | 206526_at | RIBC2 | EpiA_Up |
| 696 | 211200_s_at | EFCAB2 | EpiA_Up |
| 697 | 218437_s_at | LZTFL1 | EpiA_Up |
| 698 | 208683_at | CAPN2 | EpiA_Up |
| 699 | 215033_at | TM4SF1 | EpiA_Up |
| 700 | 39548_at | NPAS2 | EpiA_Up |
| 701 | 204973_at | GJB1 | EpiA_Up |
| 702 | 203767_s_at | STS | EpiA_Up |
| 703 | 208623_s_at | EZR | EpiA_Up |
| 704 | 212231_at | FBXO21 | EpiA_Up |
| 705 | 205593_s_at | PDE9A | EpiA_Up |
| 706 | 208451_s_at | C4A // C4B | EpiA_Up |
| 707 | 202478_at | TRIB2 | EpiA_Up |
| 708 | 222325_at | — | EpiA_Up |
| 709 | 208322_s_at | ST3GAL1 | EpiA_Up |
| 710 | 40284_at | FOXA2 | EpiA_Up |
| 711 | 212229_s_at | FBXO21 | EpiA_Up |
| 712 | 216012_at | — | EpiA_Up |
| 713 | 211998_at | H3F3B | EpiA_Up |
| 714 | 211603_s_at | ETV4 | EpiA_Up |
| 715 | 212558_at | SPRY1 | EpiA_Up |
| 716 | 203608_at | ALDH5A1 | EpiA_Up |
| 717 | 209794_at | SRGAP3 | EpiA_Up |
| 718 | 212188_at | KCTD12 | EpiA_Up |
| 719 | 206076_at | LRRC23 | EpiA_Up |
| 720 | 220302_at | MAK | EpiA_Up |
| 721 | 218541_s_at | C8orf4 | EpiA_Up |
| 722 | 220623_s_at | TSGA10 | EpiA_Up |
| 723 | 205014_at | FGFBP1 | EpiA_Up |
| 724 | 210026_s_at | CARD10 | EpiA_Up |
| 725 | 208153_s_at | FAT2 | EpiA_Up |
| 726 | 214222_at | DNAH7 | EpiA_Up |
| 727 | 207490_at | TUBA4B | EpiA_Up |
| 728 | 220636_at | DNAI2 | EpiA_Up |
| 729 | 219522_at | FJX1 | EpiA_Up |
| 730 | 213392_at | IQCK | EpiA_Up |
| 731 | 213386_at | C9orf125 | EpiA_Up |
| 732 | 220769_s_at | WDR78 | EpiA_Up |
| 733 | 208140_s_at | LRRC48 | EpiA_Up |
| 734 | 207981_s_at | ESRRG | EpiA_Up |
| 735 | 219833_s_at | EFHC1 | EpiA_Up |
| 736 | 211596_s_at | LRIG1 | EpiA_Up |
| 737 | 212538_at | DOCK9 | EpiA_Up |
| 738 | 214234_s_at | CYP3A5 | EpiA_Up |
| 739 | 205266_at | LIF | EpiA_Up |
| 740 | 220390_at | AGBL2 | EpiA_Up |
| 741 | 219416_at | SCARA3 | EpiA_Up |
| 742 | 218736_s_at | PALMD | EpiA_Up |
| 743 | 222125_s_at | P4HTM | EpiA_Up |
| 744 | 220591_s_at | EFHC2 | EpiA_Up |
| 745 | 205906_at | FOXJ1 | EpiA_Up |
| 746 | 205709_s_at | CDS1 | EpiA_Up |
| 747 | 214811_at | RIMBP2 | EpiA_Up |
| 748 | 205640_at | ALDH3B1 | EpiA_Up |
| 749 | 210861_s_at | WISP3 | EpiA_Up |
| 750 | 221946_at | C9orf116 | EpiA_Up |
| 751 | 201474_s_at | ITGA3 | EpiA_Up |
| 752 | 207624_s_at | RPGR | EpiA_Up |
| 753 | 208268_at | ADAM28 | EpiA_Up |
| 754 | 208893_s_at | DUSP6 | EpiA_Up |
| 755 | 210021_s_at | CCNO | EpiA_Up |
| 756 | 205579_at | HRH1 | EpiA_Up |
| 757 | 203074_at | ANXA8 /// ANXA8L1 /// ANXA8L2 | EpiA_Up |
| 758 | 219313_at | GRAMD1C | EpiA_Up |
| 759 | 220308_at | CCDC19 | EpiA_Up |
| 760 | 219274_at | TSPAN12 | EpiA_Up |
| 761 | 222068_s_at | LRRC50 | EpiA_Up |
| 762 | 202068_s_at | LDLR | EpiA_Up |
| 763 | 212192_at | KCTD12 | EpiA_Up |
| 764 | 222043_at | CLU | EpiA_Up |
| 765 | 213056_at | FRMD4B | EpiA_Up |

| # | ID | Gene | Type |
|---|---|---|---|
| 766 | 221215_s_at | RIPK4 | EpiA_Up |
| 767 | 209627_s_at | OSBPL3 | EpiA_Up |
| 768 | 210323_at | TEKT2 | EpiA_Up |
| 769 | 205997_at | ADAM28 | EpiA_Up |
| 770 | 220173_at | C14orf45 | EpiA_Up |
| 771 | 36711_at | MAFF | EpiA_Up |
| 772 | 202827_s_at | MMP14 | EpiA_Up |
| 773 | 203407_at | PPL | EpiA_Up |
| 774 | 219182_at | FLJ22167 | EpiA_Up |
| 775 | 205714_s_at | ZMYND10 | EpiA_Up |
| 776 | 204446_s_at | ALOX5 | EpiA_Up |
| 777 | 220125_at | DNAI1 | EpiA_Up |
| 778 | 204011_at | SPRY2 | EpiA_Up |
| 779 | 213572_s_at | SERPINB1 | EpiA_Up |
| 780 | 204989_s_at | ITGB4 | EpiA_Up |
| 781 | 208892_s_at | DUSP6 | EpiA_Up |
| 782 | 219580_s_at | TMC5 | EpiA_Up |
| 783 | 206483_at | LRRC6 | EpiA_Up |
| 784 | 208891_at | DUSP6 | EpiA_Up |
| 785 | 204015_s_at | DUSP4 | EpiA_Up |
| 786 | 59437_at | C9orf116 | EpiA_Up |
| 787 | 218035_s_at | RBM47 | EpiA_Up |
| 788 | 211026_s_at | MGLL | EpiA_Up |
| 789 | 220156_at | EFCAB1 | EpiA_Up |
| 790 | 216663_s_at | ZMYND10 | EpiA_Up |
| 791 | 219115_s_at | IL20RA | EpiA_Up |
| 792 | 201596_x_at | KRT18 | EpiA_Up |
| 793 | 203585_at | ZNF185 | EpiA_Up |
| 794 | 64900_at | FLJ22167 | EpiA_Up |
| 795 | 205334_at | S100A1 | EpiA_Up |
| 796 | 219866_at | CLIC5 | EpiA_Up |
| 797 | 205680_at | MMP10 | EpiA_Up |
| 798 | 204526_s_at | TBC1D8 | EpiA_Up |
| 799 | 205016_at | TGFA | EpiA_Up |
| 800 | 205668_at | LY75 | EpiA_Up |
| 801 | 218211_s_at | MLPH | EpiA_Up |
| 802 | 209386_at | TM4SF1 | EpiA_Up |
| 803 | 205765_at | CYP3A5 | EpiA_Up |
| 804 | 204124_at | SLC34A2 | EpiA_Up |
| 805 | 219857_at | C10orf81 | EpiA_Up |
| 806 | 203661_s_at | TMOD1 | EpiA_Up |
| 807 | 220168_at | CASC1 | EpiA_Up |
| 808 | 209114_at | TSPAN1 | EpiA_Up |
| 809 | 205896_at | SLC22A4 | EpiA_Up |
| 810 | 213285_at | TMEM30B | EpiA_Up |
| 811 | 202267_at | LAMC2 | EpiA_Up |
| 812 | 213462_at | NPAS2 | EpiA_Up |
| 813 | 206884_s_at | SCEL | EpiA_Up |
| 814 | 203662_s_at | TMOD1 | EpiA_Up |
| 815 | 211429_s_at | SERPINA1 | EpiA_Up |
| 816 | 204990_s_at | ITGB4 | EpiA_Up |
| 817 | 212560_at | SORL1 | EpiA_Up |
| 818 | 39549_at | NPAS2 | EpiA_Up |
| 819 | 218966_at | MYO5C | EpiA_Up |
| 820 | 203726_s_at | LAMA3 | EpiA_Up |
| 821 | 206859_s_at | PAEP | EpiA_Up |
| 822 | 202504_at | TRIM29 | EpiA_Up |
| 823 | 204014_at | DUSP4 | EpiA_Up |
| 824 | 205597_at | SLC44A4 | EpiA_Up |
| 825 | 204542_at | ST6GALNAC2 | EpiA_Up |
| 826 | 202834_at | AGT | EpiA_Up |
| 827 | 201012_at | ANXA1 | EpiA_Up |
| 828 | 209292_at | ID4 | EpiA_Up |
| 829 | 218876_at | TPPP3 | EpiA_Up |
| 830 | 221530_s_at | BHLHE41 | EpiA_Up |
| 831 | 208792_s_at | CLU | EpiA_Up |
| 832 | 206197_at | NME5 | EpiA_Up |
| 833 | 208791_at | CLU | EpiA_Up |
| 834 | 220269_at | ZBBX | EpiA_Up |
| 835 | 204591_at | CHL1 | EpiA_Up |
| 836 | 222271_at | — | EpiA_Up |
| 837 | 213432_at | MUC5B | EpiA_Up |
| 838 | 219230_at | TMEM100 | EpiA_Up |
| 839 | 213317_at | CLIC5 | EpiA_Up |
| 840 | 212909_at | LYPD1 | EpiA_Up |
| 841 | 219836_at | ZBED2 | EpiA_Up |
| 842 | 220979_s_at | ST6GALNAC5 | EpiA_Up |
| 843 | 209792_s_at | KLK10 | EpiA_Up |
| 844 | 213994_s_at | SPON1 | EpiA_Up |
| 845 | 204733_at | KLK6 | EpiA_Up |
| 846 | 212531_at | LCN2 | EpiA_Up |
| 847 | 218963_s_at | KRT23 | EpiA_Up |
| 848 | 213993_at | SPON1 | EpiA_Up |
| 849 | 205328_at | CLDN10 | EpiA_Up |
| 850 | 220196_at | MUC16 | EpiA_Up |
| Gene List 2 - EpiB | | | |
| 1 | 203417_at | MFAP2 | EpiB_Dn |
| 2 | 201505_at | LAMB1 | EpiB_Dn |
| 3 | 202976_s_at | RHOBTB3 | EpiB_Dn |
| 4 | 217996_at | PHLDA1 | EpiB_Dn |
| 5 | 202975_s_at | RHOBTB3 | EpiB_Dn |
| 6 | 211651_s_at | LAMB1 | EpiB_Dn |
| 7 | 217997_at | PHLDA1 | EpiB_Dn |
| 8 | 201939_at | PLK2 | EpiB_Dn |
| 9 | 204011_at | SPRY2 | EpiB_Dn |
| 10 | 212158_at | SDC2 | EpiB_Dn |
| 11 | 204955_at | SRPX | EpiB_Dn |
| 12 | 202149_at | NEDD9 | EpiB_Dn |
| 13 | 212386_at | TCF4 | EpiB_Dn |
| 14 | 205990_s_at | WNT5A | EpiB_Dn |
| 15 | 212651_at | RHOBTB1 | EpiB_Dn |
| 16 | 201310_s_at | C5orf13 | EpiB_Dn |
| 17 | 202336_s_at | PAM | EpiB_Dn |
| 18 | 217897_at | FXYD6 | EpiB_Dn |
| 19 | 208712_at | CCND1 | EpiB_Dn |
| 20 | 208782_at | FSTL1 | EpiB_Dn |
| 21 | 209118_s_at | TUBA1A | EpiB_Dn |
| 22 | 202007_at | NID1 | EpiB_Dn |
| 23 | 201426_s_at | VIM | EpiB_Dn |
| 24 | 212233_at | MAP1B | EpiB_Dn |
| 25 | 212958_x_at | PAM | EpiB_Dn |
| 26 | 213891_s_at | TCF4 | EpiB_Dn |
| 27 | 210220_at | FZD2 | EpiB_Dn |
| 28 | 203355_at | PSD3 | EpiB_Dn |
| 29 | 212382_at | TCF4 | EpiB_Dn |
| 30 | 200907_s_at | PALLD | EpiB_Dn |
| 31 | 222146_s_at | TCF4 | EpiB_Dn |
| 32 | 200897_s_at | PALLD | EpiB_Dn |
| 33 | 212558_at | SPRY1 | EpiB_Dn |
| 34 | 212364_at | MYO1B | EpiB_Dn |
| 35 | 212387_at | TCF4 | EpiB_Dn |
| 36 | 203753_at | TCF4 | EpiB_Dn |
| 37 | 219179_at | DACT1 | EpiB_Dn |
| 38 | 212372_at | MYH10 | EpiB_Dn |
| 39 | 218613_at | PSD3 | EpiB_Dn |
| 40 | 201417_at | SOX4 | EpiB_Dn |
| 41 | 222101_s_at | DCHS1 | EpiB_Dn |
| 42 | 214620_x_at | PAM | EpiB_Dn |
| 43 | 204451_at | FZD1 | EpiB_Dn |
| 44 | 213668_s_at | SOX4 | EpiB_Dn |
| 45 | 218181_s_at | MAP4K4 | EpiB_Dn |
| 46 | 208891_at | DUSP6 | EpiB_Dn |
| 47 | 208711_s_at | CCND1 | EpiB_Dn |
| 48 | 209082_s_at | COL18A1 | EpiB_Dn |
| 49 | 208892_s_at | DUSP6 | EpiB_Dn |
| 50 | 203627_at | IGF1R | EpiB_Dn |
| 51 | 209288_s_at | CDC42EP3 | EpiB_Dn |
| 52 | 212792_at | DPY19L1 | EpiB_Dn |
| 53 | 203477_at | COL15A1 | EpiB_Dn |
| 54 | 201416_at | SOX4 | EpiB_Dn |
| 55 | 203349_s_at | ETV5 | EpiB_Dn |
| 56 | 214953_s_at | APP | EpiB_Dn |
| 57 | 222258_s_at | SH3BP4 | EpiB_Dn |
| 58 | 221489_s_at | SPRY4 | EpiB_Dn |
| 59 | 200602_at | APP | EpiB_Dn |
| 60 | 209081_s_at | COL18A1 | EpiB_Dn |
| 61 | 200771_at | LAMC1 | EpiB_Dn |
| 62 | 211066_x_at | PCDHGA1 /// PCDHGA10 /// PCDHGA11 /// PCDHGA12 /// PCDHGA2 /// PCDHGA3 /// PCDHGA4 /// PCDHGA5 /// PCDHGA6 /// PCDHGA7 /// PCDHGA8 /// PCDHGA9 /// PCDHGB1 /// PCDHGB2 /// PCDHGB3 /// PCDHGB4 /// | EpiB_Dn |

-continued

| | | | |
|---|---|---|---|
| | | PCDHGB5 /// PCDHGB6 /// | |
| | | PCDHGB7 /// PCDHGC3 /// | |
| | | PCDHGB4 /// PCDHGC5 | |
| 63 | 203044_at | CHSY1 | EpiB_Dn |
| 64 | 206314_at | ZNF167 | EpiB_Dn |
| 65 | 204793_at | GPRASP1 | EpiB_Dn |
| 66 | 212812_at | — | EpiB_Dn |
| 67 | 215836_s_at | PCDHGA1 /// PCDHGA10 /// | EpiB_Dn |
| | | PCDHGA11 /// PCDHGA12 /// | |
| | | PCDHGA2 /// PCDHGA3 /// | |
| | | PCDHGA4 /// PCDHGA5 /// | |
| | | PCDHGA6 /// PCDHGA7 /// | |
| | | PCDHGA8 /// PCDHGA9 /// | |
| | | PCDHGB1 /// PCDHGB2 /// | |
| | | PCDHGB3 /// PCDHGB4 /// | |
| | | PCDHGB5 /// PCDHGB6 /// | |
| | | PCDHGB7 /// PCDHGC3 /// | |
| | | PCDHGC4 /// PCDHGC5 | |
| 68 | 209286_at | CDC42EP3 | EpiB_Dn |
| 69 | 202123_s_at | ABL1 | EpiB_Dn |
| 70 | 219747_at | C4orf31 | EpiB_Dn |
| 71 | 203394_s_at | HES1 | EpiB_Dn |
| 72 | 203688_at | PKD2 | EpiB_Dn |
| 73 | 209079_x_at | PCDHGA1 /// PCDHGA10 /// | EpiB_Dn |
| | | PCDHGA11 /// PCDHGA12 /// | |
| | | PCDHGA2 /// PCDHGA3 /// | |
| | | PCDHGA4 /// PCDHGA5 /// | |
| | | PCDHGA6 /// PCDHGA7 /// | |
| | | PCDHGA8 /// PCDHGA9 /// | |
| | | PCDHGB1 /// PCDHGB2 /// | |
| | | PCDHGB3 /// PCDHGB4 /// | |
| | | PCDHGB5 /// PCDHGB6 /// | |
| | | PCDHGB7 /// PCDHGC3 /// | |
| | | PCDHGC4 /// PCDHGC5 | |
| 74 | 212842_x_at | RGPD4 /// RGPD5 /// | EpiB_Dn |
| | | RGPD6 /// RGPD8 | |
| 75 | 212071_s_at | SPTBN1 | EpiB_Dn |
| 76 | 201307_at | SEPT11 | EpiB_Dn |
| 77 | 202457_s_at | PPP3CA | EpiB_Dn |
| 78 | 203763_at | DYNC2LI1 | EpiB_Dn |
| 79 | 219631_at | LRP12 | EpiB_Dn |
| 80 | 205717_x_at | PCDHGA1 /// PCDHGA10 /// | EpiB_Dn |
| | | PCDHGA11 /// PCDHGA12 /// | |
| | | PCDHGA2 /// PCDHGA3 /// | |
| | | PCDHGA4 /// PCDHGA5 /// | |
| | | PCDHGA6 /// PCDHGA7 /// | |
| | | PCDHGA8 /// PCDHGA9 /// | |
| | | PCDHGB1 /// PCDHGB2 /// | |
| | | PCDHGB3 /// PCDHGB4 /// | |
| | | PCDHGB5 /// PCDHGB6 /// | |
| | | PCDHGB7 /// PCDHGC3 /// | |
| | | PCDHGC4 /// PCDHGC5 | |
| 81 | 214629_x_at | RTN4 | EpiB_Dn |
| 82 | 211509_s_at | RTN4 | EpiB_Dn |
| 83 | 221542_s_at | ERLIN2 | EpiB_Dn |
| 84 | 202084_s_at | SEC14L1 | EpiB_Dn |
| 85 | 200603_at | PRKAR1A | EpiB_Dn |
| 86 | 201375_s_at | PPP2CB | EpiB_Dn |
| 87 | 213278_at | MTMR9 | EpiB_Dn |
| 88 | 213626_at | CBR4 | EpiB_Dn |
| 89 | 219432_at | EVC | EpiB_Dn |
| 90 | 200847_s_at | TMEM66 | EpiB_Dn |
| 91 | 203097_s_at | RAPGEF2 | EpiB_Dn |
| 92 | 208669_s_at | EID1 | EpiB_Dn |
| 93 | 211698_at | EID1 | EpiB_Dn |
| 94 | 208030_s_at | ADD1 | EpiB_Dn |
| 95 | 41220_at | SEPT9 | EpiB_Dn |
| 96 | 203343_at | UGDH | EpiB_Dn |
| 97 | 200595_s_at | EIF3A | EpiB_Dn |
| 98 | 216727_at | STK38 | EpiB_Up |
| 99 | 214634_at | HIST1H4B | EpiB_Up |
| 100 | 219893_at | CCDC71 | EpiB_Up |
| 101 | 210557_x_at | CSF1 | EpiB_Up |
| 102 | 215579_at | APOBEC3G | EpiB_Up |
| 103 | 209587_at | PITX1 | EpiB_Up |
| 104 | 220033_at | — | EpiB_Up |
| 105 | 204789_at | FMNL1 | EpiB_Up |
| 106 | 204514_at | DPH2 | EpiB_Up |
| 107 | 216583_x_at | NHP2 | EpiB_Up |
| 108 | 207727_s_at | MUTYH | EpiB_Up |
| 109 | 214084_x_at | LOC648998 | EpiB_Up |
| 110 | 213297_at | RMND5B | EpiB_Up |
| 111 | 209477_at | EMD | EpiB_Up |
| 112 | 211920_at | CFB | EpiB_Up |
| 113 | 219690_at | TMEM149 | EpiB_Up |
| 114 | 218539_at | FBXO34 | EpiB_Up |
| 115 | 221600_s_at | C11orf67 | EpiB_Up |
| 116 | 221680_s_at | ETV7 | EpiB_Up |
| 117 | 213127_s_at | MED8 | EpiB_Up |
| 118 | 218080_x_at | FAF1 | EpiB_Up |
| 119 | 202849_x_at | GRK6 | EpiB_Up |
| 120 | 201678_s_at | C3orf37 | EpiB_Up |
| 121 | 218488_at | EIF2B3 | EpiB_Up |
| 122 | 202883_s_at | PPP2R1B | EpiB_Up |
| 123 | 215633_x_at | LST1 | EpiB_Up |
| 124 | 213735_s_at | COX5B | EpiB_Up |
| 125 | 217329_x_at | — | EpiB_Up |
| 126 | 207485_x_at | BTN3A1 | EpiB_Up |
| 127 | 210212_x_at | MTCP1NB | EpiB_Up |
| 128 | 216862_s_at | MTCP1NB | EpiB_Up |
| 129 | 211025_x_at | COX5B | EpiB_Up |
| 130 | 203805_s_at | FANCA | EpiB_Up |
| 131 | 204922_at | C11orf80 | EpiB_Up |
| 132 | 202855_s_at | SLC16A3 | EpiB_Up |
| 133 | 209770_at | BTN3A1 | EpiB_Up |
| 134 | 211063_s_at | NCK1 | EpiB_Up |
| 135 | 219275_at | PDCD5 | EpiB_Up |
| 136 | 205671_s_at | HLA-DOB | EpiB_Up |
| 137 | 203960_s_at | HSPB11 | EpiB_Up |
| 138 | 213539_at | CD3D | EpiB_Up |
| 139 | 208502_s_at | PITX1 | EpiB_Up |
| 140 | 205317_s_at | SLC15A2 | EpiB_Up |
| 141 | 202110_at | COX7B | EpiB_Up |
| 142 | 209716_at | CSF1 | EpiB_Up |
| 143 | 57163_at | ELOVL1 | EpiB_Up |
| 144 | 208967_s_at | AK2 | EpiB_Up |
| 145 | 201625_s_at | INSIG1 | EpiB_Up |
| 146 | 1294_at | UBA7 | EpiB_Up |
| 147 | 208012_x_at | SP110 | EpiB_Up |
| 148 | 218028_at | ELOVL1 | EpiB_Up |
| 149 | 220094_s_at | CCDC90A | EpiB_Up |
| 150 | 200814_at | PSME1 | EpiB_Up |
| 151 | 202864_s_at | SP100 | EpiB_Up |
| 152 | 212174_at | AK2 | EpiB_Up |
| 153 | 203689_s_at | FMR1 | EpiB_Up |
| 154 | 202074_s_at | OPTN | EpiB_Up |
| 155 | 205101_at | CIITA | EpiB_Up |
| 156 | 219566_at | PLEKHF1 | EpiB_Up |
| 157 | 201587_s_at | IRAK1 | EpiB_Up |
| 158 | 204820_s_at | BTN3A2 /// BTN3A3 | EpiB_Up |
| 159 | 218746_at | TAPBPL | EpiB_Up |
| 160 | 219593_at | SLC15A3 | EpiB_Up |
| 161 | 201762_s_at | PSME2 | EpiB_Up |
| 162 | 208829_at | TAPBP | EpiB_Up |
| 163 | 211671_s_at | NR3C1 | EpiB_Up |
| 164 | 221978_at | HLA-F | EpiB_Up |
| 165 | 221087_s_at | APOL3 | EpiB_Up |
| 166 | 219132_at | PELI2 | EpiB_Up |
| 167 | 200629_at | WARS | EpiB_Up |
| 168 | 206011_at | CASP1 | EpiB_Up |
| 169 | 211367_s_at | CASP1 | EpiB_Up |
| 170 | 202481_at | DHRS3 | EpiB_Up |
| 171 | 204821_at | BTN3A3 | EpiB_Up |
| 172 | 205316_at | SLC15A2 | EpiB_Up |
| 173 | 205379_at | CBR3 | EpiB_Up |
| 174 | 214058_at | MYCL1 | EpiB_Up |
| 175 | 218747_s_at | TAPBPL | EpiB_Up |
| 176 | 204769_s_at | TAP2 | EpiB_Up |
| 177 | 218543_s_at | PARP12 | EpiB_Up |
| 178 | 209970_x_at | CASP1 | EpiB_Up |
| 179 | 211366_x_at | CASP1 | EpiB_Up |
| 180 | 202446_s_at | PLSCR1 | EpiB_Up |
| 181 | 202659_at | PSMB10 | EpiB_Up |
| 182 | 208296_x_at | TNFAIP8 | EpiB_Up |
| 183 | 206247_at | MICB | EpiB_Up |
| 184 | 201649_at | UBE2L6 | EpiB_Up |
| 185 | 213523_at | CCNE1 | EpiB_Up |
| 186 | 202531_at | IRF1 | EpiB_Up |

| Index | Probe | Gene Symbol | Category |
|---|---|---|---|
| 187 | 211368_s_at | CASP1 | EpiB_Up |
| 188 | 200862_at | DHCR24 | EpiB_Up |
| 189 | 209969_s_at | STAT1 | EpiB_Up |
| 190 | 209040_s_at | PSMB8 | EpiB_Up |
| 191 | 202307_s_at | TAP1 | EpiB_Up |
| 192 | 202270_at | GBP1 | EpiB_Up |
| 193 | 209644_x_at | CDKN2A | EpiB_Up |
| 194 | 219684_at | RTP4 | EpiB_Up |
| 195 | 202269_x_at | GBP1 | EpiB_Up |
| 196 | 202357_s_at | C2 /// CFB | EpiB_Up |
| 197 | 207039_at | CDKN2A | EpiB_Up |
| 198 | 204279_at | PSMB9 | EpiB_Up |
| 199 | 204070_at | RARRES3 | EpiB_Up |
| 200 | 204533_at | CXCL10 | EpiB_Up |

| Index | Probe | Gene Symbol | Category |
|---|---|---|---|
| | | Gene List 2 - Mes | |
| 1 | 203325_s_at | COL5A1 | Mes_Up |
| 2 | 213125_at | OLFML2B | Mes_Up |
| 3 | 212489_at | COL5A1 | Mes_Up |
| 4 | 212488_at | COL5A1 | Mes_Up |
| 5 | 209365_s_at | ECM1 | Mes_Up |
| 6 | 202952_s_at | ADAM12 | Mes_Up |
| 7 | 221541_at | CRISPLD2 | Mes_Up |
| 8 | 221729_at | COL5A2 | Mes_Up |
| 9 | 221019_s_at | COLEC12 | Mes_Up |
| 10 | 203876_s_at | MMP11 | Mes_Up |
| 11 | 221730_at | COL5A2 | Mes_Up |
| 12 | 205479_s_at | PLAU | Mes_Up |
| 13 | 203878_s_at | MMP11 | Mes_Up |
| 14 | 203083_at | THBS2 | Mes_Up |
| 15 | 210511_s_at | INHBA | Mes_Up |
| 16 | 209955_s_at | FAP | Mes_Up |
| 17 | 213909_at | LRRC15 | Mes_Up |
| 18 | 202450_s_at | CTSK | Mes_Up |
| 19 | 205941_s_at | COL10A1 | Mes_Up |
| 20 | 218468_s_at | GREM1 | Mes_Up |
| 21 | 217428_s_at | COL10A1 | Mes_Up |
| 22 | 218469_at | GREM1 | Mes_Up |
| 23 | 210809_s_at | POSTN | Mes_Up |
| 24 | 204320_at | COL11A1 | Mes_Up |
| 25 | 37892_at | COL11A1 | Mes_Up |
| | | Gene List 2 - StemA | |
| 1 | 202237_at | NNMT | StemA_Dn |
| 2 | 219630_at | PDZK1IP1 | StemA_Dn |
| 3 | 217478_s_at | HLA-DMA | StemA_Dn |
| 4 | 209619_at | CD74 | StemA_Dn |
| 5 | 202804_at | ABCC1 | StemA_Dn |
| 6 | 217995_at | SQRDL | StemA_Dn |
| 7 | 202748_at | GBP2 | StemA_Dn |
| 8 | 202659_at | PSMB10 | StemA_Dn |
| 9 | 214211_at | FTH1 | StemA_Dn |
| 10 | 202180_s_at | MVP | StemA_Dn |
| 11 | 200904_at | HLA-E | StemA_Dn |
| 12 | 203281_s_at | UBA7 | StemA_Dn |
| 13 | 219319_at | HIF3A | StemA_Up |
| 14 | 218457_s_at | DNMT3A | StemA_Up |
| 15 | 205741_s_at | DTNA | StemA_Up |
| 16 | 204612_at | PKIA | StemA_Up |
| 17 | 205123_s_at | TMEFF1 | StemA_Up |
| 18 | 213283_s_at | SALL2 | StemA_Up |
| 19 | 221016_s_at | TCF7L1 | StemA_Up |
| 20 | 209757_s_at | MYCN | StemA_Up |
| 21 | 204915_s_at | SOX11 | StemA_Up |
| 22 | 205122_at | TMEFF1 | StemA_Up |
| 23 | 205347_s_at | TMSB15A | StemA_Up |
| 24 | 204914_s_at | SOX11 | StemA_Up |
| 25 | 204913_s_at | SOX11 | StemA_Up |

| Index | Probe | Gene | Category |
|---|---|---|---|
| | | Gene List 2 - StemB | |
| 1 | 221950_at | EMX2 | StemB_Dn |
| 2 | 213317_at | CLIC5 | StemB_Dn |
| 3 | 202207_at | ARL4C | StemB_Dn |
| 4 | 212909_at | LYPD1 | StemB_Dn |
| 5 | 219836_at | ZBED2 | StemB_Dn |
| 6 | 202206_at | ARL4C | StemB_Dn |
| 7 | 204069_at | MEIS1 | StemB_Dn |
| 8 | 220979_s_at | ST6GALNAC5 | StemB_Dn |
| 9 | 204733_at | KLK6 | StemB_Dn |
| 10 | 219866_at | CLIC5 | StemB_Dn |
| 11 | 204885_s_at | MSLN | StemB_Dn |
| 12 | 202524_s_at | SPOCK2 | StemB_Dn |
| 13 | 202208_s_at | ARL4C | StemB_Dn |
| 14 | 40093_at | BCAM | StemB_Dn |
| 15 | 208978_at | CRIP2 | StemB_Dn |
| 16 | 204783_at | MLF1 | StemB_Dn |
| 17 | 213201_s_at | TNNT1 | StemB_Dn |
| 18 | 206067_s_at | WT1 | StemB_Dn |
| 19 | 201324_at | EMP1 | StemB_Dn |
| 20 | 212148_at | PBX1 | StemB_Dn |
| 21 | 203009_at | BCAM | StemB_Dn |
| 22 | 205334_at | S100A1 | StemB_Dn |
| 23 | 201325_s_at | EMP1 | StemB_Dn |
| 24 | 203632_s_at | GPRC5B | StemB_Dn |
| 25 | 204784_s_at | MLF1 | StemB_Dn |
| 26 | 219416_at | SCARA3 | StemB_Dn |
| 27 | 209437_s_at | SPON1 | StemB_Dn |
| 28 | 205227_at | IL1RAP | StemB_Dn |
| 29 | 201998_at | ST6GAL1 | StemB_Dn |
| 30 | 209436_at | SPON1 | StemB_Dn |
| 31 | 216953_s_at | WT1 | StemB_Dn |
| 32 | 213993_at | SPON1 | StemB_Dn |
| 33 | 218176_at | MAGEF1 | StemB_Dn |
| 34 | 203661_s_at | TMOD1 | StemB_Dn |
| 35 | 203662_s_at | TMOD1 | StemB_Dn |
| 36 | 213994_s_at | SPON1 | StemB_Dn |
| 37 | 209596_at | MXRA5 | StemB_Dn |
| 38 | 205778_at | KLK7 | StemB_Dn |
| 39 | 220274_at | IQCA1 | StemB_Dn |
| 40 | 213135_at | TIAM1 | StemB_Dn |
| 41 | 203518_at | PRKCI | StemB_Dn |
| 42 | 215716_s_at | ATP2B1 | StemB_Dn |
| 43 | 221530_s_at | BHLHE41 | StemB_Dn |
| 44 | 219229_at | SLCO3A1 | StemB_Dn |
| 45 | 204457_s_at | GAS1 | StemB_Dn |
| 46 | 210115_at | RPL39L | StemB_Dn |
| 47 | 204369_at | PIK3CA | StemB_Dn |
| 48 | 209899_s_at | PUF60 | StemB_Dn |
| 49 | 212430_at | RBM38 | StemB_Dn |
| 50 | 213669_at | FCHO1 | StemB_Dn |
| 51 | 203853_s_at | GAB2 | StemB_Dn |
| 52 | 205481_at | ADORA1 | StemB_Dn |
| 53 | 207076_s_at | ASS1 | StemB_Dn |
| 54 | 215108_x_at | TOX3 | StemB_Dn |
| 55 | 215813_s_at | PTGS1 | StemB_Dn |
| 56 | 212816_s_at | CBS | StemB_Dn |
| 57 | 206125_s_at | KLK8 | StemB_Dn |
| 58 | 216623_x_at | TOX3 | StemB_Dn |
| 59 | 205128_x_at | PTGS1 | StemB_Dn |
| 60 | 209195_s_at | ADCY6 | StemB_Dn |
| 61 | 213698_at | ZMYM6 | StemB_Up |
| 62 | 214771_x_at | MPRIP | StemB_Up |
| 63 | 213913_s_at | TBC1D30 | StemB_Up |
| 64 | 211885_x_at | FUT6 | StemB_Up |
| 65 | 212197_x_at | MPRIP | StemB_Up |
| 66 | 45526_g_at | NAT15 | StemB_Up |
| 67 | 204633_s_at | RPS6KA5 | StemB_Up |
| 68 | 206043_s_at | ATP2C2 | StemB_Up |
| 69 | 201128_s_at | ACLY | StemB_Up |
| 70 | 216518_at | — | StemB_Up |
| 71 | 221173_at | USH1C | StemB_Up |
| 72 | 213358_at | KIAA0802 | StemB_Up |
| 73 | 205042_at | GNE | StemB_Up |
| 74 | 212383_at | ATP6V0A1 | StemB_Up |
| 75 | 213143_at | C2orf72 | StemB_Up |
| 76 | 205137_x_at | USH1C | StemB_Up |
| 77 | 221636_s_at | MOSC2 | StemB_Up |
| 78 | 205848_at | GAS2 | StemB_Up |
| 79 | 219570_at | KIF16B | StemB_Up |
| 80 | 214307_at | HGD | StemB_Up |
| 81 | 212071_s_at | SPTBN1 | StemB_Up |
| 82 | 205857_at | SLC18A2 | StemB_Up |

| # | Probe | Gene Symbol | Category |
|---|---|---|---|
| 83 | 204394_at | SLC43A1 | StemB_Up |
| 84 | 202211_at | ARFGAP3 | StemB_Up |
| 85 | 211889_x_at | CEACAM1 | StemB_Up |
| 86 | 213744_at | ATRNL1 | StemB_Up |
| 87 | 214308_s_at | HGD | StemB_Up |
| 88 | 209426_s_at | AMACR /// C1QTNF3 | StemB_Up |
| 89 | 211184_s_at | USH1C | StemB_Up |
| 90 | 205776_at | FMO5 | StemB_Up |
| 91 | 209395_at | CHI3L1 | StemB_Up |
| 92 | 219405_at | TRIM68 | StemB_Up |
| 93 | 209396_s_at | CHI3L1 | StemB_Up |
| 94 | 213707_s_at | DLX5 | StemB_Up |
| 95 | 213324_at | SRC | StemB_Up |
| 96 | 208096_s_at | COL21A1 | StemB_Up |
| 97 | 206245_s_at | IVNS1ABP | StemB_Up |
| 98 | 203343_at | UGDH | StemB_Up |
| 99 | 214825_at | FAM155A | StemB_Up |
| 100 | 218763_at | STX18 | StemB_Up |
| 101 | 202851_at | FLJ11506 | StemB_Up |
| 102 | 206286_s_at | TDGF1 /// TDGF3 | StemB_Up |
| 103 | 204389_at | MAOA | StemB_Up |
| 104 | 205278_at | GAD1 | StemB_Up |
| 105 | 202699_s_at | TMEM63A | StemB_Up |
| 106 | 208209_s_at | C4BPB | StemB_Up |
| 107 | 211883_x_at | CEACAM1 | StemB_Up |
| 108 | 206576_s_at | CEACAM1 | StemB_Up |
| 109 | 204388_s_at | MAOA | StemB_Up |
| 110 | 205771_s_at | AKAP7 | StemB_Up |
| 111 | 207357_s_at | GALNT10 | StemB_Up |
| 112 | 219142_at | RASL11B | StemB_Up |
| 113 | 215447_at | TFPI | StemB_Up |
| 114 | 215983_s_at | UBXN8 | StemB_Up |
| 115 | 205513_at | TCN1 | StemB_Up |
| 116 | 206204_at | GRB14 | StemB_Up |
| 117 | 206756_at | CHST7 | StemB_Up |
| 118 | 213036_x_at | ATP2A3 | StemB_Up |
| 119 | 205221_at | HGD | StemB_Up |
| 120 | 202908_at | WFS1 | StemB_Up |
| 121 | 202786_at | STK39 | StemB_Up |
| 122 | 204687_at | DKFZP564O0823 | StemB_Up |
| 123 | 219478_at | WFDC1 | StemB_Up |
| 124 | 203467_at | PMM1 | StemB_Up |
| 125 | 204818_at | HSD17B2 | StemB_Up |
| 126 | 203059_s_at | PAPSS2 | StemB_Up |
| 127 | 204793_at | GPRASP1 | StemB_Up |
| 128 | 212096_s_at | MTUS1 | StemB_Up |
| 129 | 203303_at | DYNLT3 | StemB_Up |
| 130 | 219747_at | C4orf31 | StemB_Up |
| 131 | 209498_at | CEACAM1 | StemB_Up |
| 132 | 211657_at | CEACAM6 | StemB_Up |
| 133 | 213745_at | ATRNL1 | StemB_Up |
| 134 | 209847_at | CDH17 | StemB_Up |
| 135 | 203757_s_at | CEACAM6 | StemB_Up |
| 136 | 208596_s_at | UGT1A1 /// UGT1A10 /// UGT1A3 /// UGT1A4 /// UGT1A5 /// UGT1A6 /// UGT1A7 /// UGT1A8 /// UGT1A9 | StemB_Up |
| 137 | 204579_at | FGFR4 | StemB_Up |
| 138 | 205894_at | ARSE | StemB_Up |
| 139 | 209892_at | FUT4 | StemB_Up |
| 140 | 205141_at | ANG | StemB_Up |
| 141 | 207414_s_at | PCSK6 | StemB_Up |
| 142 | 201819_at | SCARB1 | StemB_Up |
| 143 | 202742_s_at | PRKACB | StemB_Up |
| 144 | 213059_at | CREB3L1 | StemB_Up |
| 145 | 204272_at | LGALS4 | StemB_Up |
| 146 | 209513_s_at | HSDL2 | StemB_Up |
| 147 | 205799_s_at | SLC3A1 | StemB_Up |
| 148 | 205158_at | RNASE4 | StemB_Up |
| 149 | 219263_at | RNF128 | StemB_Up |
| 150 | 205517_at | GATA4 | StemB_Up |
| 151 | 208510_s_at | PPARG | StemB_Up |
| 152 | 202741_at | PRKACB | StemB_Up |
| 153 | 212741_at | MAOA | StemB_Up |
| 154 | 209890_at | TSPAN5 | StemB_Up |
| 155 | 202975_s_at | RHOBTB3 | StemB_Up |
| 156 | 201809_s_at | ENG | StemB_Up |
| 157 | 213397_x_at | RNASE4 | StemB_Up |
| 158 | 220102_at | FOXL2 | StemB_Up |
| 159 | 211651_s_at | LAMB1 | StemB_Up |
| 160 | 219179_at | DACT1 | StemB_Up |
| 161 | 204304_s_at | PROM1 | StemB_Up |
| 162 | 210664_s_at | TFPI | StemB_Up |
| 163 | 206167_s_at | ARHGAP6 | StemB_Up |
| 164 | 201505_at | LAMB1 | StemB_Up |
| 165 | 203058_s_at | PAPSS2 | StemB_Up |
| 166 | 204548_at | STAR | StemB_Up |
| 167 | 204931_at | TCF21 | StemB_Up |
| 168 | 205466_s_at | HS3ST1 | StemB_Up |
| 169 | 212224_at | ALDH1A1 | StemB_Up |
| 170 | 204351_at | S100P | StemB_Up |
| 171 | 202609_at | EPS8 | StemB_Up |
| 172 | 209243_s_at | PEG3 /// ZIM2 | StemB_Up |
| 173 | 203060_s_at | PAPSS2 | StemB_Up |
| 174 | 204719_at | ABCA8 | StemB_Up |
| 175 | 203824_at | TSPAN8 | StemB_Up |

Gene List 3. EMT-signature genes in cultured cell lines

| Probe | Gene Symbol | Category |
|---|---|---|
| 201130_s_at | CDH1 | Epithelial |
| 201131_s_at | CDH1 | Epithelial |
| 201650_at | KRT19 | Epithelial |
| 202005_at | ST14 | Epithelial |
| 202890_at | MAP7 | Epithelial |
| 203256_at | CDH3 | Epithelial |
| 203287_at | LAD1 | Epithelial |
| 204503_at | EVPL | Epithelial |
| 205490_x_at | GJB3 | Epithelial |
| 205709_s_at | CDS1 | Epithelial |
| 209873_s_at | PKP3 | Epithelial |
| 210715_s_at | SPINT2 | Epithelial |
| 211778_s_at | OVOL2 | Epithelial |
| 215243_s_at | GJB3 | Epithelial |
| 216641_s_at | LAD1 | Epithelial |
| 216905_s_at | ST14 | Epithelial |
| 218792_s_at | BSPRY | Epithelial |
| 219121_s_at | ESRP1 | Epithelial |
| 219388_at | GRHL2 | Epithelial |
| 219395_at | ESRP2 | Epithelial |
| 201839_s_at | EPCAM | Epithelial |
| 202826_at | SPINT1 | Epithelial |
| 206043_s_at | ATP2C2 | Epithelial |
| 209872_s_at | PKP3 | Epithelial |
| 219850_s_at | EHF | Epithelial |
| 203726_s_at | LAMA3 | Epithelial |
| 90265_at | ADAP1 | Epithelial |
| 206884_s_at | SCEL | Epithelial |
| 202489_s_at | FXYD3 | Epithelial |
| 212543_at | AIM1 | Epithelial |
| 212925_at | C19orf21 | Epithelial |
| 201428_at | CLDN4 | Epithelial |
| 204740_at | CNKSR1 | Epithelial |
| 205016_at | TGFA | Epithelial |
| 220638_s_at | CBLC | Epithelial |
| 210827_s_at | ELF3 | Epithelial |
| 218966_at | MYO5C | Epithelial |
| 219150_s_at | ADAP1 | Epithelial |
| 208190_s_at | LSR | Epithelial |
| 203407_at | PPL | Epithelial |
| 209163_at | CYB561 | Epithelial |
| 203713_s_at | LLGL2 | Epithelial |
| 204989_s_at | ITGB4 | Epithelial |
| 200752_s_at | CAPN1 | Epithelial |
| 201778_s_at | KIAA0494 | Epithelial |
| 208083_s_at | ITGB6 | Epithelial |
| 31846_at | RHOD | Epithelial |
| 91826_at | EPS8L1 | Epithelial |
| 201015_s_at | JUP | Epithelial |
| 204733_at | KLK6 | Epithelial |
| 213307_at | SHANK2 | Epithelial |
| 219856_at | C1orf116 | Epithelial |
| 202525_at | PRSS8 | Epithelial |

Gene List 3. EMT-signature genes in cultured cell lines

| Probe | Gene Symbol | Category |
|---|---|---|
| 221215_s_at | RIPK4 | Epithelial |
| 202889_x_at | MAP7 | Epithelial |
| 207291_at | PRRG4 | Epithelial |
| 209114_at | TSPAN1 | Epithelial |
| 215471_at | MAP7 | Epithelial |
| 218779_x_at | EPS8L1 | Epithelial |
| 219476_at | C1orf116 | Epithelial |
| 219513_s_at | SH2D3A | Epithelial |
| 202790_at | CLDN7 | Epithelial |
| 204765_at | ARHGEF5 | Epithelial |
| 205014_at | FGFBP1 | Epithelial |
| 218960_at | TMPRSS4 | Epithelial |
| 203953_s_at | CLDN3 | Epithelial |
| 210761_s_at | GRB7 | Epithelial |
| 212531_at | LCN2 | Epithelial |
| 218186_at | RAB25 | Epithelial |
| 203954_x_at | CLDN3 | Epithelial |
| 214734_at | EXPH5 | Epithelial |
| 218677_at | S100A14 | Epithelial |
| 204990_s_at | ITGB4 | Epithelial |
| 206683_at | ZNF165 | Epithelial |
| 201510_at | ELF3 | Epithelial |
| 202454_s_at | ERBB3 | Epithelial |
| 205015_s_at | TGFA | Epithelial |
| 205466_s_at | HS3ST1 | Epithelial |
| 205780_at | BIK | Epithelial |
| 213308_at | SHANK2 | Epithelial |
| 221665_s_at | EPS8L1 | Epithelial |
| 209164_s_at | CYB561 | Epithelial |
| 219241_x_at | SSH3 | Epithelial |
| 33323_r_at | SFN | Epithelial |
| 51192_at | SSH3 | Epithelial |
| 205455_at | MST1R | Epithelial |
| 214493_s_at | INADL | Epithelial |
| 220144_s_at | ANKRD5 | Epithelial |
| 202286_s_at | TACSTD2 | Epithelial |
| 213929_at | EXPH5 | Epithelial |
| 209260_at | SFN | Epithelial |
| 214798_at | ATP2C2 | Epithelial |
| 217939_s_at | AFTPH | Epithelial |
| 209008_x_at | KRT8 | Epithelial |
| 209885_at | RHOD | Epithelial |
| 33322_i_at | SFN | Epithelial |
| 208084_at | ITGB6 | Epithelial |
| 209792_s_at | KLK10 | Epithelial |
| 207540_s_at | SYK | Epithelial |
| 217681_at | WNT7B | Epithelial |
| 219919_s_at | SSH3 | Epithelial |
| 202358_s_at | SNX19 | Epithelial |
| 211905_s_at | ITGB4 | Epithelial |
| 202546_at | VAMP8 | Epithelial |
| 208779_x_at | DDR1 | Epithelial |
| 210136_at | MBP | Epithelial |
| 1007_s_at | DDR1 | Epithelial |
| 203005_at | LTBR | Epithelial |
| 204014_at | DUSP4 | Epithelial |
| 207169_x_at | DDR1 | Epithelial |
| 211258_s_at | TGFA | Epithelial |
| 209173_at | AGR2 | Epithelial |
| 210749_x_at | DDR1 | Epithelial |
| 219936_s_at | GPR87 | Epithelial |
| 221655_x_at | EPS8L1 | Epithelial |
| 201596_x_at | KRT18 | Epithelial |
| 211661_x_at | PTAFR | Epithelial |
| 214705_at | INADL | Epithelial |
| 217200_x_at | CYB561 | Epithelial |
| 218309_at | CAMK2N1 | Epithelial |
| 203397_s_at | GALNT3 | Epithelial |
| 214355_x_at | CTAGE4 | Epithelial |
| 207986_x_at | CYB561 | Epithelial |
| 221081_s_at | DENND2D | Epithelial |
| 203453_at | SCNN1A | Epithelial |
| 209211_at | KLF5 | Epithelial |
| 215549_x_at | CTAGE4 | Epithelial |
| 205847_at | PRSS22 | Epithelial |
| 209369_at | ANXA3 | Epithelial |
| 213618_at | ARAP2 | Epithelial |
| 219648_at | MREG | Epithelial |
| 202295_s_at | CTSH | Epithelial |
| 212657_s_at | IL1RN | Epithelial |
| 202688_at | TNFSF10 | Epithelial |
| 205617_at | PRRG2 | Epithelial |
| 207717_s_at | PKP2 | Epithelial |
| 210058_at | MAPK13 | Epithelial |
| 203535_at | S100A9 | Epithelial |
| 218693_at | TSPAN15 | Epithelial |
| 201079_at | SYNGR2 | Epithelial |
| 202687_s_at | TNFSF10 | Epithelial |
| 203110_at | PTK2B | Epithelial |
| 209502_s_at | BAIAP2 | Epithelial |
| 201776_s_at | KIAA0494 | Epithelial |
| 209016_s_at | KRT7 | Epithelial |
| 203317_at | PSD4 | Epithelial |
| 204019_s_at | SH3YL1 | Epithelial |
| 205977_s_at | EPHA1 | Epithelial |
| 206200_s_at | ANXA11 | Epithelial |
| 208862_s_at | CTNND1 | Epithelial |
| 215729_s_at | VGLL1 | Epithelial |
| 218180_s_at | EPS8L2 | Epithelial |
| 204015_s_at | DUSP4 | Epithelial |
| 208407_s_at | CTNND1 | Epithelial |
| 219058_x_at | TINAGL1 | Epithelial |
| 35148_at | TJP3 | Epithelial |
| 202597_at | IRF6 | Epithelial |
| 203216_s_at | MYO6 | Epithelial |
| 205239_at | AREG | Epithelial |
| 221664_s_at | FUR | Epithelial |
| 203108_at | GPRC5A | Epithelial |
| 204856_at | B3GNT3 | Epithelial |
| 209269_s_at | SYK | Epithelial |
| 215923_s_at | PSD4 | Epithelial |
| 216568_x_at | — | Epithelial |
| 218035_s_at | RBM47 | Epithelial |
| 218928_s_at | SLC37A1 | Epithelial |
| 211599_x_at | MET | Epithelial |
| 212444_at | — | Epithelial |
| 220030_at | STYK1 | Epithelial |
| 201531_at | ZFP36 | Epithelial |
| 204505_s_at | EPB49 | Epithelial |
| 205032_at | ITGA2 | Epithelial |
| 209212_s_at | KLF5 | Epithelial |
| 216243_s_at | IL1RN | Epithelial |
| 201775_s_at | KIAA0494 | Epithelial |
| 213085_s_at | WWC1 | Epithelial |
| 204855_at | SERPINB5 | Epithelial |
| 205074_at | SLC22A5 | Epithelial |
| 206109_at | FUT1 | Epithelial |
| 209529_at | PPAP2C | Epithelial |
| 218849_s_at | PPP1R13L | Epithelial |
| 200660_at | S100A11 | Epithelial |
| 218780_at | HOOK2 | Epithelial |
| 211240_x_at | CTNND1 | Epithelial |
| 214329_x_at | TNFSF10 | Epithelial |
| 203510_at | MET | Epithelial |
| 204679_at | KCNK1 | Epithelial |
| 208650_s_at | CD24 | Epithelial |
| 213807_x_at | MET | Epithelial |
| 220945_x_at | MANSC1 | Epithelial |
| 204363_at | F3 | Epithelial |
| 204678_s_at | KCNK1 | Epithelial |
| 206595_at | CST6 | Epithelial |
| 209772_s_at | CD24 | Epithelial |
| 210059_s_at | MAPK13 | Epithelial |
| 200872_at | S100A10 | Epithelial |
| 205980_s_at | ARHGAP8 | Epithelial |
| 266_s_at | CD24 | Epithelial |
| 200804_at | TMBIM6 | Epithelial |
| 204341_at | TRIM16 | Epithelial |
| 206295_at | IL18 | Epithelial |
| 209126_x_at | KRT6B | Epithelial |

Gene List 3. EMT-signature genes in cultured cell lines

| Probe | Gene Symbol | Category |
|---|---|---|
| 221696_s_at | STYK1 | Epithelial |
| 202071_at | SDC4 | Epithelial |
| 208540_x_at | S100A11 | Epithelial |
| 208949_s_at | LGALS3 | Epithelial |
| 202267_at | LAMC2 | Epithelial |
| 203918_at | PCDH1 | Epithelial |
| 208651_x_at | CD24 | Epithelial |
| 209771_x_at | CD24 | Epithelial |
| 214783_s_at | ANXA11 | Epithelial |
| 202720_at | TES | Epithelial |
| 208009_s_at | ARHGEF16 | Epithelial |
| 214088_s_at | FUT3 | Epithelial |
| 216074_x_at | WWC1 | Epithelial |
| 216379_x_at | CD24 | Epithelial |
| 219976_at | HOOK1 | Epithelial |
| 220318_at | EPN3 | Epithelial |
| 219696_at | DENND1B | Epithelial |
| 203780_at | MPZL2 | Epithelial |
| 218931_at | RAB17 | Epithelial |
| 38766_at | SRCAP | Epithelial |
| 201005_at | CD9 | Epithelial |
| 206125_s_at | KLK8 | Epithelial |
| 209190_s_at | DIAPH1 | Epithelial |
| 209222_s_at | OSBPL2 | Epithelial |
| 213667_at | SRCAP | Epithelial |
| 219215_s_at | SLC39A4 | Epithelial |
| 37117_at | ARHGAP8 | Epithelial |
| 200606_at | DSP | Epithelial |
| 217109_at | MUC4 | Epithelial |
| 217149_x_at | TNK1 | Epithelial |
| 218019_s_at | PDXK | Epithelial |
| 221610_s_at | STAP2 | Epithelial |
| 210816_s_at | CYB561 | Epithelial |
| 212338_at | MYO1D | Epithelial |
| 217744_s_at | PERP | Epithelial |
| 202719_s_at | TES | Epithelial |
| 204927_at | RASSF7 | Epithelial |
| 207525_s_at | GIPC1 | Epithelial |
| 208890_s_at | PLXNB2 | Epithelial |
| 210314_x_at | TNFSF13 | Epithelial |
| 221927_s_at | ABHD11 | Epithelial |
| 219858_s_at | MFSD6 | Epithelial |
| 40359_at | RASSF7 | Epithelial |
| 201242_s_at | ATP1B1 | Epithelial |
| 207549_x_at | CD46 | Epithelial |
| 208783_s_at | CD46 | Epithelial |
| 219411_at | ELMO3 | Epithelial |
| 219450_at | C4orf9 | Epithelial |
| 204254_s_at | VDR | Epithelial |
| 213412_at | TJP3 | Epithelial |
| 204952_at | LYPD3 | Epithelial |
| 222333_at | ALS2CL | Epithelial |
| 212242_at | TUBA4A | Epithelial |
| 217730_at | TMBIM1 | Epithelial |
| 218942_at | PIP4K2C | Epithelial |
| 222354_at | FUR | Epithelial |
| 201188_s_at | ITPR3 | Epithelial |
| 202481_at | DHRS3 | Epithelial |
| 210085_s_at | ANXA9 | Epithelial |
| 219127_at | ATAD4 | Epithelial |
| 201189_s_at | ITPR3 | Epithelial |
| 217875_s_at | PMEPA1 | Epithelial |
| 217979_at | TSPAN13 | Epithelial |
| 204328_at | TMC6 | Epithelial |
| 206414_s_at | ASAP2 | Epithelial |
| 211574_s_at | CD46 | Epithelial |
| 217110_s_at | MUC4 | Epithelial |
| 219946_x_at | MYH14 | Epithelial |
| 221841_s_at | KLF4 | Epithelial |
| 203180_at | ALDH1A3 | Epithelial |
| 210480_s_at | MYO6 | Epithelial |
| 211712_s_at | ANXA9 | Epithelial |
| 202704_at | TOB1 | Epithelial |
| 203779_s_at | MPZL2 | Epithelial |
| 204734_at | KRT15 | Epithelial |
| 205258_at | INHBB | Epithelial |
| 211004_s_at | ALDH3B1 | Epithelial |
| 202820_at | AHR | Epithelial |
| 203028_s_at | CYBA | Epithelial |
| 209221_s_at | OSBPL2 | Epithelial |
| 209499_x_at | TNFSF12 | Epithelial |
| 202149_at | NEDD9 | Epithelial |
| 202510_s_at | TNFAIP2 | Epithelial |
| 205403_at | IL1R2 | Epithelial |
| 206831_s_at | ARSD | Epithelial |
| 200878_at | EPAS1 | Epithelial |
| 206687_s_at | PTPN6 | Epithelial |
| 210117_at | SPAG1 | Epithelial |
| 210150_s_at | LAMA5 | Epithelial |
| 213050_at | COBL | Epithelial |
| 214154_s_at | PKP2 | Epithelial |
| 219916_s_at | RNF39 | Epithelial |
| 202150_s_at | NEDD9 | Epithelial |
| 216918_s_at | DST | Epithelial |
| 221666_s_at | PYCARD | Epithelial |
| 202359_s_at | SNX19 | Epithelial |
| 204455_at | DST | Epithelial |
| 207935_s_at | KRT13 | Epithelial |
| 212255_s_at | ATP2C1 | Epithelial |
| 218261_at | AP1M2 | Epithelial |
| 205487_s_at | VGLL1 | Epithelial |
| 205640_at | ALDH3B1 | Epithelial |
| 212312_at | BCL2L1 | Epithelial |
| 206048_at | OVOL2 | Epithelial |
| 218066_at | SLC12A7 | Epithelial |
| 203143_s_at | KIAA0040 | Epithelial |
| 204446_s_at | ALOX5 | Epithelial |
| 208156_x_at | EPPK1 | Epithelial |
| 208510_s_at | PPARG | Epithelial |
| 219836_at | ZBED2 | Epithelial |
| 220196_at | MUC16 | Epithelial |
| 65517_at | AP1M2 | Epithelial |
| 207992_s_at | AMPD3 | Epithelial |
| 201243_s_at | ATP1B1 | Epithelial |
| 205469_s_at | IRF5 | Epithelial |
| 201328_at | ETS2 | Epithelial |
| 201329_s_at | ETS2 | Epithelial |
| 203215_s_at | MYO6 | Epithelial |
| 205293_x_at | BAIAP2 | Epithelial |
| 217901_at | DSG2 | Epithelial |
| 207178_s_at | FRK | Epithelial |
| 208078_s_at | SIK1 | Epithelial |
| 212339_at | EPB41L1 | Epithelial |
| 202699_s_at | TMEM63A | Epithelial |
| 209270_at | LAMB3 | Epithelial |
| 202023_at | EFNA1 | Epithelial |
| 202531_at | IRF1 | Epithelial |
| 203072_at | MYO1E | Epithelial |
| 204168_at | MGST2 | Epithelial |
| 219010_at | C1orf106 | Epithelial |
| 220056_at | IL22RA1 | Epithelial |
| 209500_x_at | TNFSF12 | Epithelial |
| 210237_at | ARTN | Epithelial |
| 211372_s_at | IL1R2 | Epithelial |
| 213816_s_at | MET | Epithelial |
| 201474_s_at | ITGA3 | Epithelial |
| 202085_at | TJP2 | Epithelial |
| 208161_s_at | ABCC3 | Epithelial |
| 219522_at | RAB20 | Epithelial |
| 205465_x_at | HS3ST1 | Epithelial |
| 205668_at | LY75 | Epithelial |
| 213076_at | ITPKC | Epithelial |
| 202504_at | TRIM29 | Epithelial |
| 220907_at | GPR110 | Epithelial |
| 203038_at | PTPRK | Epithelial |
| 203236_s_at | LGALS9 | Epithelial |
| 204255_s_at | VDR | Epithelial |
| 204542_at | ST6GALNAC2 | Epithelial |
| 220266_s_at | KLF4 | Epithelial |
| 204681_s_at | RAPGEF5 | Epithelial |

Gene List 3. EMT-signature genes in cultured cell lines

| Probe | Gene Symbol | Category |
|---|---|---|
| 206277_at | P2RY2 | Epithelial |
| 202430_s_at | PLSCR1 | Epithelial |
| 202833_s_at | SERPINA1 | Epithelial |
| 203021_at | SLPI | Epithelial |
| 206482_at | PTK6 | Epithelial |
| 216581_at | — | Epithelial |
| 220149_at | C2orf54 | Epithelial |
| 220998_s_at | UNC93B1 | Epithelial |
| 200666_s_at | DNAJB1 | Epithelial |
| 205093_at | PLEKHA6 | Epithelial |
| 206665_s_at | BCL2L1 | Epithelial |
| 202609_at | EPS8 | Epithelial |
| 202488_s_at | FXYD3 | Epithelial |
| 202869_at | OAS1 | Epithelial |
| 207180_s_at | HTATIP2 | Epithelial |
| 217534_at | FAM49B | Epithelial |
| 218342_s_at | ERMP1 | Epithelial |
| 200923_at | LGALS3BP | Epithelial |
| 201798_s_at | MYOF | Epithelial |
| 209448_at | HTATIP2 | Epithelial |
| 213393_at | MFSD9 | Epithelial |
| 218816_at | LRRC1 | Epithelial |
| 60474_at | FERMT1 | Epithelial |
| 203892_at | WFDC2 | Epithelial |
| 209373_at | MALL | Epithelial |
| 217995_at | SQRDL | Epithelial |
| 219229_at | SLCO3A1 | Epithelial |
| 201260_s_at | SYPL1 | Epithelial |
| 202506_at | SSFA2 | Epithelial |
| 206604_at | OVOL1 | Epithelial |
| 211488_s_at | ITGB8 | Epithelial |
| 203759_at | ST3GAL4 | Epithelial |
| 208690_s_at | PDLIM1 | Epithelial |
| 209360_s_at | RUNX1 | Epithelial |
| 203074_at | ANXA8 | Epithelial |
| 213279_at | DHRS1 | Epithelial |
| 218796_at | FERMT1 | Epithelial |
| 218840_s_at | NADSYN1 | Epithelial |
| 205769_at | SLC27A2 | Epithelial |
| 209468_at | LRP5 | Epithelial |
| 206747_at | GPRIN2 | Epithelial |
| 209040_s_at | PSMB8 | Epithelial |
| 211864_s_at | MYOF | Epithelial |
| 208817_at | COMT | Epithelial |
| 215037_s_at | BCL2L1 | Epithelial |
| 210248_at | WNT7A | Epithelial |
| 210367_s_at | PTGES | Epithelial |
| 201953_at | CIB1 | Epithelial |
| 212089_at | LMNA | Epithelial |
| 220603_s_at | MCTP2 | Epithelial |
| 205816_at | ITGB8 | Epithelial |
| 211429_s_at | SERPINA1 | Epithelial |
| 212717_at | PLEKHM1 | Epithelial |
| 212727_at | DLG3 | Epithelial |
| 218963_s_at | KRT23 | Epithelial |
| 219580_s_at | TMC5 | Epithelial |
| 203324_s_at | CAV2 | Epithelial |
| 207517_at | LAMC2 | Epithelial |
| 219332_at | MICALL2 | Epithelial |
| 219735_s_at | TFCP2L1 | Epithelial |
| 220468_at | ARL14 | Epithelial |
| 203066_at | GALNAC4S-6ST | Epithelial |
| 208623_s_at | EZR | Epithelial |
| 212660_at | PHF15 | Epithelial |
| 214786_at | MAP3K1 | Epithelial |
| 217728_at | S100A6 | Epithelial |
| 222362_at | AGFG2 | Epithelial |
| 200766_at | CTSD | Epithelial |
| 215189_at | KRT86 | Epithelial |
| 218706_s_at | GRAMD3 | Epithelial |
| 218810_at | ZC3H12A | Epithelial |
| 205968_at | KCNS3 | Epithelial |
| 212070_at | GPR56 | Epithelial |
| 214958_s_at | TMC6 | Epithelial |
| 222303_at | — | Epithelial |
| 201286_at | SDC1 | Epithelial |
| 204895_x_at | MUC4 | Epithelial |
| 205645_at | REPS2 | Epithelial |
| 205768_s_at | SLC27A2 | Epithelial |
| 205807_s_at | TUFT1 | Epithelial |
| 215808_at | KLK10 | Epithelial |
| 217947_at | CMTM6 | Epithelial |
| 218451_at | CDCP1 | Epithelial |
| 218856_at | TNFRSF21 | Epithelial |
| 219045_at | RHOF | Epithelial |
| 202838_at | FUCA1 | Epithelial |
| 205552_s_at | OAS1 | Epithelial |
| 209326_at | SLC35A2 | Epithelial |
| 217835_x_at | C20orf24 | Epithelial |
| 219844_at | C10orf118 | Epithelial |
| 39249_at | AQP3 | Epithelial |
| 204942_s_at | ALDH3B2 | Epithelial |
| 216052_x_at | ARTN | Epithelial |
| 203833_s_at | TGOLN2 | Epithelial |
| 218322_s_at | ACSL5 | Epithelial |
| 219115_s_at | IL20RA | Epithelial |
| 201368_at | ZFP36L2 | Epithelial |
| 217351_at | — | Epithelial |
| 219503_s_at | TMEM40 | Epithelial |
| 201032_at | BLCAP | Epithelial |
| 212560_at | SORL1 | Epithelial |
| 213317_at | CLIC5 | Epithelial |
| 213839_at | CLMN | Epithelial |
| 218543_s_at | PARP12 | Epithelial |
| 205190_at | PLS1 | Epithelial |
| 212285_s_at | AGRN | Epithelial |
| 216060_s_at | DAAM1 | Epithelial |
| 222157_s_at | TBC1D2 | Epithelial |
| 205793_s_at | TNK1 | Epithelial |
| 207675_x_at | ARTN | Epithelial |
| 213716_s_at | SECTM1 | Epithelial |
| 220073_s_at | PLEKHG6 | Epithelial |
| 220948_s_at | ATP1A1 | Epithelial |
| 200879_s_at | EPAS1 | Epithelial |
| 206542_s_at | SMARCA2 | Epithelial |
| 214581_x_at | TNFRSF21 | Epithelial |
| 220484_at | MCOLN3 | Epithelial |
| 201777_s_at | KIAA0494 | Epithelial |
| 203323_at | CAV2 | Epithelial |
| 208600_s_at | GPR39 | Epithelial |
| 217429_x_at | AGRN | Epithelial |
| 220289_s_at | AIM1L | Epithelial |
| 222154_s_at | LOC26010 | Epithelial |
| 31845_at | ELF4 | Epithelial |
| 218018_at | PDXK | Epithelial |
| 204068_at | STK3 | Epithelial |
| 212336_at | EPB41L1 | Epithelial |
| 202086_at | MX1 | Epithelial |
| 206522_s_at | LPAR2 | Epithelial |
| 217707_x_at | SMARCA2 | Epithelial |
| 219751_at | SETD6 | Epithelial |
| 200748_s_at | FTH1 | Epithelial |
| 201983_s_at | EGFR | Epithelial |
| 203509_at | SORL1 | Epithelial |
| 207196_s_at | TNIP1 | Epithelial |
| 212640_at | PTPLB | Epithelial |
| 65086_at | YIPF2 | Epithelial |
| 210365_at | RUNX1 | Epithelial |
| 202287_s_at | TACSTD2 | Epithelial |
| 207126_x_at | UGT1A1 | Epithelial |
| 211495_x_at | TNFSF12 | Epithelial |
| 215125_s_at | UGT1A1 | Epithelial |
| 219296_at | ZDHHC13 | Epithelial |
| 36936_at | TSTA3 | Epithelial |
| 200774_at | FAM120A | Epithelial |
| 209641_s_at | ABCC3 | Epithelial |
| 209800_at | KRT16 | Epithelial |
| 210582_s_at | LIMK2 | Epithelial |
| 211628_x_at | FTHP1 | Epithelial |

Gene List 3. EMT-signature genes in cultured cell lines

| Probe | Gene Symbol | Category |
|---|---|---|
| 202193_at | LIMK2 | Epithelial |
| 208622_s_at | EZR | Epithelial |
| 212975_at | DENND3 | Epithelial |
| 215732_s_at | DTX2 | Epithelial |
| 217551_at | LOC441453 | Epithelial |
| 218154_at | GSDMD | Epithelial |
| 219352_at | HERC6 | Epithelial |
| 220734_s_at | GLTPD1 | Epithelial |
| 201984_s_at | EGFR | Epithelial |
| 201125_s_at | ITGB5 | Epithelial |
| 213514_s_at | DIAPH1 | Epithelial |
| 202145_at | LY6E | Epithelial |
| 208908_s_at | CAST | Epithelial |
| 211320_s_at | PTPRU | Epithelial |
| 212823_s_at | PLEKHG3 | Epithelial |
| 214763_at | ACOT11 | Epithelial |
| 215411_s_at | TRAF3IP2 | Epithelial |
| 217837_s_at | VPS24 | Epithelial |
| 218776_s_at | TMEM62 | Epithelial |
| 202744_at | SLC20A2 | Epithelial |
| 206082_at | HCP5 | Epithelial |
| 208818_s_at | COMT | Epithelial |
| 202949_s_at | FHL2 | Epithelial |
| 203490_at | ELF4 | Epithelial |
| 204537_s_at | GABRE | Epithelial |
| 218631_at | AVPI1 | Epithelial |
| 218844_at | ACSF2 | Epithelial |
| 219474_at | C3orf52 | Epithelial |
| 221042_s_at | CLMN | Epithelial |
| 218804_at | ANO1 | Epithelial |
| 204908_s_at | BCL3 | Epithelial |
| 210740_s_at | ITPK1 | Epithelial |
| 214657_s_at | NCRNA00084 | Epithelial |
| 219716_at | APOL6 | Epithelial |
| 203942_s_at | MARK2 | Epithelial |
| 208829_at | TAPBP | Epithelial |
| 212297_at | ATP13A3 | Epithelial |
| 212807_s_at | SORT1 | Epithelial |
| 218065_s_at | TMEM9B | Epithelial |
| 200601_at | ACTN4 | Epithelial |
| 203747_at | AQP3 | Epithelial |
| 204070_at | RARRES3 | Epithelial |
| 207467_x_at | CAST | Epithelial |
| 208596_s_at | UGT1A1 | Epithelial |
| 210984_x_at | EGFR | Epithelial |
| 217853_at | TNS3 | Epithelial |
| 220174_at | LRRC8E | Epithelial |
| 218159_at | DDRGK1 | Epithelial |
| 204250_s_at | CEP164 | Mesenchymal |
| 206538_at | MRAS | Mesenchymal |
| 209825_s_at | UCK2 | Mesenchymal |
| 211787_s_at | EIF4A1 | Mesenchymal |
| 212371_at | PPPDE1 | Mesenchymal |
| 212422_at | PDCD11 | Mesenchymal |
| 216850_at | SNRPN | Mesenchymal |
| 220576_at | PGAP1 | Mesenchymal |
| 222344_at | — | Mesenchymal |
| 201342_at | SNRPC | Mesenchymal |
| 201763_s_at | DAXX | Mesenchymal |
| 202224_at | CRK | Mesenchymal |
| 202332_at | CSNK1E | Mesenchymal |
| 202578_s_at | DDX19A | Mesenchymal |
| 206583_at | ZNF673 | Mesenchymal |
| 206853_at | MAP3K7 | Mesenchymal |
| 207939_x_at | RNPS1 | Mesenchymal |
| 209049_s_at | ZMYND8 | Mesenchymal |
| 213631_x_at | DHODH | Mesenchymal |
| 214999_s_at | RAB11FIP3 | Mesenchymal |
| 220040_x_at | ZC4H2 | Mesenchymal |
| 217779_s_at | PNRC2 | Mesenchymal |
| 203373_at | SOCS2 | Mesenchymal |
| 203958_s_at | ZBTB40 | Mesenchymal |
| 203959_s_at | ZBTB40 | Mesenchymal |
| 204320_at | COL11A1 | Mesenchymal |
| 209776_s_at | SLC19A1 | Mesenchymal |
| 218889_at | NOC3L | Mesenchymal |
| 219098_at | MYBBP1A | Mesenchymal |
| 200593_s_at | HNRNPU | Mesenchymal |
| 202268_s_at | NAE1 | Mesenchymal |
| 202875_s_at | PBX2 | Mesenchymal |
| 208984_x_at | RBM10 | Mesenchymal |
| 213186_at | DZIP3 | Mesenchymal |
| 215470_at | GTF2H2B | Mesenchymal |
| 219968_at | ZNF589 | Mesenchymal |
| 203187_at | DOCK1 | Mesenchymal |
| 205331_s_at | REEP2 | Mesenchymal |
| 211536_x_at | MAP3K7 | Mesenchymal |
| 211714_x_at | TUBB | Mesenchymal |
| 212615_at | CHD9 | Mesenchymal |
| 221505_at | ANP32E | Mesenchymal |
| 204402_at | RHBDD3 | Mesenchymal |
| 200775_s_at | HNRNPK | Mesenchymal |
| 202405_at | TIAL1 | Mesenchymal |
| 205412_at | ACAT1 | Mesenchymal |
| 212910_at | THAP11 | Mesenchymal |
| 215285_s_at | PHTF1 | Mesenchymal |
| 217949_s_at | VKORC1 | Mesenchymal |
| 219002_at | FASTKD1 | Mesenchymal |
| 204788_s_at | PPOX | Mesenchymal |
| 208939_at | SEPHS1 | Mesenchymal |
| 214862_x_at | — | Mesenchymal |
| 218045_x_at | PTMS | Mesenchymal |
| 217221_x_at | RBM10 | Mesenchymal |
| 221910_at | ETV1 | Mesenchymal |
| 201530_x_at | EIF4A1 | Mesenchymal |
| 202725_at | POLR2A | Mesenchymal |
| 204208_at | RNGTT | Mesenchymal |
| 220650_s_at | SLC9A5 | Mesenchymal |
| 221699_s_at | DDX50 | Mesenchymal |
| 202806_at | DBN1 | Mesenchymal |
| 204436_at | PLEKHO2 | Mesenchymal |
| 206852_at | EPHA7 | Mesenchymal |
| 207268_x_at | ABI2 | Mesenchymal |
| 207754_at | RASSF8 | Mesenchymal |
| 211071_s_at | MLLT11 | Mesenchymal |
| 213176_s_at | LTBP4 | Mesenchymal |
| 214951_at | SLC26A10 | Mesenchymal |
| 200746_s_at | GNB1 | Mesenchymal |
| 200959_at | FUS | Mesenchymal |
| 200982_s_at | ANXA6 | Mesenchymal |
| 209883_at | GLT25D2 | Mesenchymal |
| 219578_s_at | CPEB1 | Mesenchymal |
| 34764_at | LARS2 | Mesenchymal |
| 201396_s_at | SGTA | Mesenchymal |
| 202754_at | R3HDM1 | Mesenchymal |
| 209200_at | MEF2C | Mesenchymal |
| 209856_x_at | ABI2 | Mesenchymal |
| 210672_s_at | C16orf35 | Mesenchymal |
| 212348_s_at | KDM1 | Mesenchymal |
| 212490_at | DNAJC8 | Mesenchymal |
| 206241_at | KPNA5 | Mesenchymal |
| 203322_at | ADNP2 | Mesenchymal |
| 204560_at | FKBP5 | Mesenchymal |
| 212104_s_at | RBM9 | Mesenchymal |
| 212618_at | ZNF609 | Mesenchymal |
| 219782_s_at | ZNF771 | Mesenchymal |
| 220797_at | METT10D | Mesenchymal |
| 200626_s_at | MATR3 | Mesenchymal |
| 201072_s_at | SMARCC1 | Mesenchymal |
| 201718_s_at | EPB41L2 | Mesenchymal |
| 203079_s_at | CUL2 | Mesenchymal |
| 205652_s_at | TTLL1 | Mesenchymal |
| 209483_s_at | NSL1 | Mesenchymal |
| 212984_at | ATF2 | Mesenchymal |
| 217631_at | GTPBP4 | Mesenchymal |
| 219006_at | NDUFAF4 | Mesenchymal |
| 220298_s_at | SPATA6 | Mesenchymal |
| 214363_s_at | MATR3 | Mesenchymal |
| 215718_s_at | PHF3 | Mesenchymal |
| 220992_s_at | C1orf25 | Mesenchymal |

Gene List 3. EMT-signature genes in cultured cell lines

| Probe | Gene Symbol | Category |
|---|---|---|
| 208591_s_at | PDE3B | Mesenchymal |
| 200995_at | IPO7 | Mesenchymal |
| 203782_s_at | POLRMT | Mesenchymal |
| 205817_at | SIX1 | Mesenchymal |
| 207232_s_at | DZIP3 | Mesenchymal |
| 44563_at | WRAP53 | Mesenchymal |
| 203537_at | PRPSAP2 | Mesenchymal |
| 204230_s_at | SLC17A7 | Mesenchymal |
| 209208_at | MPDU1 | Mesenchymal |
| 209375_at | XPC | Mesenchymal |
| 209556_at | NCDN | Mesenchymal |
| 212309_at | CLASP2 | Mesenchymal |
| 213218_at | ZNF187 | Mesenchymal |
| 210171_s_at | CREM | Mesenchymal |
| 218909_at | RPS6KC1 | Mesenchymal |
| 201138_s_at | SSB | Mesenchymal |
| 209265_s_at | METTL3 | Mesenchymal |
| 209484_s_at | NSL1 | Mesenchymal |
| 216098_s_at | HTR7 | Mesenchymal |
| 216305_s_at | C2orf3 | Mesenchymal |
| 217987_at | ASNSD1 | Mesenchymal |
| 219575_s_at | COG8 | Mesenchymal |
| 219688_at | BBS7 | Mesenchymal |
| 91682_at | — | Mesenchymal |
| 203151_at | MAP1A | Mesenchymal |
| 208765_s_at | HNRNPR | Mesenchymal |
| 208802_at | SRP72 | Mesenchymal |
| 208910_s_at | C1QBP | Mesenchymal |
| 219260_s_at | C17orf81 | Mesenchymal |
| 200873_s_at | CCT8 | Mesenchymal |
| 201802_at | SLC29A1 | Mesenchymal |
| 212852_s_at | TROVE2 | Mesenchymal |
| 214214_s_at | C1QBP | Mesenchymal |
| 217061_s_at | ETV1 | Mesenchymal |
| 219306_at | KIF15 | Mesenchymal |
| 37433_at | PIAS2 | Mesenchymal |
| 201667_at | GJA1 | Mesenchymal |
| 203871_at | SENP3 | Mesenchymal |
| 208786_s_at | MAP1LC3B | Mesenchymal |
| 213220_at | NCRNA00081 | Mesenchymal |
| 219295_s_at | PCOLCE2 | Mesenchymal |
| 221540_x_at | GTF2H2 | Mesenchymal |
| 336_at | TBXA2R | Mesenchymal |
| 201706_s_at | PEX19 | Mesenchymal |
| 203861_s_at | ACTN2 | Mesenchymal |
| 207127_s_at | HNRNPH3 | Mesenchymal |
| 207153_s_at | GLMN | Mesenchymal |
| 209048_s_at | ZMYND8 | Mesenchymal |
| 213604_at | TCEB3 | Mesenchymal |
| 48580_at | CXXC1 | Mesenchymal |
| 201801_s_at | SLC29A1 | Mesenchymal |
| 201935_s_at | EIF4G3 | Mesenchymal |
| 212303_x_at | KHSRP | Mesenchymal |
| 221912_s_at | CCDC28B | Mesenchymal |
| 204442_x_at | LTBP4 | Mesenchymal |
| 204796_at | EML1 | Mesenchymal |
| 210588_x_at | HNRNPH3 | Mesenchymal |
| 212880_at | WDR7 | Mesenchymal |
| 214881_s_at | UBTF | Mesenchymal |
| 218058_at | CXXC1 | Mesenchymal |
| 218587_s_at | KTELC1 | Mesenchymal |
| 219170_at | FSD1 | Mesenchymal |
| 202432_at | PPP3CB | Mesenchymal |
| 203264_s_at | ARHGEF9 | Mesenchymal |
| 203441_s_at | CDH2 | Mesenchymal |
| 204042_at | WASF3 | Mesenchymal |
| 206233_at | B4GALT6 | Mesenchymal |
| 213632_at | DHODH | Mesenchymal |
| 201528_at | RPA1 | Mesenchymal |
| 206854_s_at | MAP3K7 | Mesenchymal |
| 210438_x_at | TROVE2 | Mesenchymal |
| 217025_s_at | DBN1 | Mesenchymal |
| 218222_x_at | ARNT | Mesenchymal |
| 202401_s_at | SRF | Mesenchymal |
| 202557_at | HSPA13 | Mesenchymal |
| 208673_s_at | SFRS3 | Mesenchymal |
| 41397_at | ZNF821 | Mesenchymal |
| 201516_at | SRM | Mesenchymal |
| 202502_at | ACADM | Mesenchymal |
| 203092_at | TIMM44 | Mesenchymal |
| 204300_at | PET112L | Mesenchymal |
| 204992_s_at | PFN2 | Mesenchymal |
| 206147_x_at | SCML2 | Mesenchymal |
| 207559_s_at | ZMYM3 | Mesenchymal |
| 208447_s_at | PRPS1 | Mesenchymal |
| 213306_at | MPDZ | Mesenchymal |
| 213474_at | KCTD7 | Mesenchymal |
| 216693_x_at | HDGFRP3 | Mesenchymal |
| 221825_at | ANGEL2 | Mesenchymal |
| 200744_s_at | GNB1 | Mesenchymal |
| 200815_s_at | PAFAH1B1 | Mesenchymal |
| 212674_s_at | DHX30 | Mesenchymal |
| 212817_at | DNAJB5 | Mesenchymal |
| 215991_s_at | KIAA0090 | Mesenchymal |
| 217951_s_at | PHF3 | Mesenchymal |
| 221606_s_at | NSBP1 | Mesenchymal |
| 35776_at | ITSN1 | Mesenchymal |
| 203520_s_at | ZNF318 | Mesenchymal |
| 203940_s_at | VASH1 | Mesenchymal |
| 208682_s_at | MAGED2 | Mesenchymal |
| 212739_s_at | NME4 | Mesenchymal |
| 204819_at | FGD1 | Mesenchymal |
| 200041_s_at | BAT1 | Mesenchymal |
| 202397_at | NUTF2 | Mesenchymal |
| 206663_at | SP4 | Mesenchymal |
| 209440_at | PRPS1 | Mesenchymal |
| 209693_at | ASTN2 | Mesenchymal |
| 213627_at | MAGED2 | Mesenchymal |
| 212855_at | DCUN1D4 | Mesenchymal |
| 219708_at | NT5M | Mesenchymal |
| 44654_at | G6PC3 | Mesenchymal |
| 200813_s_at | PAFAH1B1 | Mesenchymal |
| 208799_at | PSMB5 | Mesenchymal |
| 209490_s_at | PPT2 | Mesenchymal |
| 219820_at | SLC6A16 | Mesenchymal |
| 202465_at | PCOLCE | Mesenchymal |
| 200083_at | USP22 | Mesenchymal |
| 205830_at | CLGN | Mesenchymal |
| 58780_s_at | FLJ10357 | Mesenchymal |
| 205493_s_at | DPYSL4 | Mesenchymal |
| 207006_s_at | CCDC106 | Mesenchymal |
| 210875_s_at | ZEB1 | Mesenchymal |
| 221554_at | STRADA | Mesenchymal |
| 201936_s_at | EIF4G3 | Mesenchymal |
| 203223_at | RABEP1 | Mesenchymal |
| 204797_s_at | EML1 | Mesenchymal |
| 213312_at | C6orf62 | Mesenchymal |
| 201309_x_at | C5orf13 | Mesenchymal |
| 204355_at | DHX30 | Mesenchymal |
| 208986_at | TCF12 | Mesenchymal |
| 217952_x_at | PHF3 | Mesenchymal |
| 218607_s_at | SDAD1 | Mesenchymal |
| 220143_x_at | LUC7L | Mesenchymal |
| 208670_s_at | EID1 | Mesenchymal |
| 209947_at | UBAP2L | Mesenchymal |
| 218336_at | PFDN2 | Mesenchymal |
| 219781_s_at | ZNF771 | Mesenchymal |
| 216271_x_at | SYDE1 | Mesenchymal |
| 200053_at | SPAG7 | Mesenchymal |
| 201081_s_at | PIP4K2B | Mesenchymal |
| 202564_x_at | ARL2 | Mesenchymal |
| 204483_at | ENO3 | Mesenchymal |
| 204735_at | PDE4A | Mesenchymal |
| 213469_at | PGAP1 | Mesenchymal |
| 201310_s_at | C5orf13 | Mesenchymal |
| 203146_s_at | GABBR1 | Mesenchymal |
| 205079_s_at | MPDZ | Mesenchymal |
| 209526_s_at | HDGFRP3 | Mesenchymal |
| 212635_at | TNPO1 | Mesenchymal |
| 204372_s_at | KHSRP | Mesenchymal |

Gene List 3. EMT-signature genes in cultured cell lines

| Probe | Gene Symbol | Category |
|---|---|---|
| 209657_s_at | HSF2 | Mesenchymal |
| 218529_at | CD320 | Mesenchymal |
| 205021_s_at | FOXN3 | Mesenchymal |
| 205347_s_at | TMSB15A | Mesenchymal |
| 205407_at | RECK | Mesenchymal |
| 207808_s_at | PROS1 | Mesenchymal |
| 212738_at | ARHGAP19 | Mesenchymal |
| 213677_s_at | PMS1 | Mesenchymal |
| 214297_at | CSPG4 | Mesenchymal |
| 202179_at | BLMH | Mesenchymal |
| 204557_s_at | DZIP1 | Mesenchymal |
| 212887_at | SEC23A | Mesenchymal |
| 200000_s_at | PRPF8 | Mesenchymal |
| 202123_s_at | ABL1 | Mesenchymal |
| 203884_s_at | RAB11FIP2 | Mesenchymal |
| 207822_at | FGFR1 | Mesenchymal |
| 220326_s_at | FLJ10357 | Mesenchymal |
| 203093_s_at | TIMM44 | Mesenchymal |
| 204592_at | DLG4 | Mesenchymal |
| 200060_s_at | RNPS1 | Mesenchymal |
| 209524_at | HDGFRP3 | Mesenchymal |
| 213278_at | MTMR9 | Mesenchymal |
| 213314_at | C6orf162 | Mesenchymal |
| 221786_at | C6orf120 | Mesenchymal |
| 204344_s_at | SEC23A | Mesenchymal |
| 210250_x_at | ADSL | Mesenchymal |
| 214878_at | ZNF37A | Mesenchymal |
| 201529_s_at | RPA1 | Mesenchymal |
| 213262_at | SACS | Mesenchymal |
| 215113_s_at | SENP3 | Mesenchymal |
| 218641_at | LOC65998 | Mesenchymal |
| 220565_at | CCR10 | Mesenchymal |
| 206506_s_at | SUPT3H | Mesenchymal |
| 211537_x_at | MAP3K7 | Mesenchymal |
| 37577_at | ARHGAP19 | Mesenchymal |
| 205408_at | MLLT10 | Mesenchymal |
| 207541_s_at | EXOSC10 | Mesenchymal |
| 213234_at | KIAA1467 | Mesenchymal |
| 213489_at | MAPRE2 | Mesenchymal |
| 217812_at | YTHDF2 | Mesenchymal |
| 220258_s_at | WRAP53 | Mesenchymal |
| 220993_s_at | GPR63 | Mesenchymal |
| 202967_at | GSTA4 | Mesenchymal |
| 203263_s_at | ARHGEF9 | Mesenchymal |
| 204900_x_at | SAP30 | Mesenchymal |
| 218759_at | DVL2 | Mesenchymal |
| 201725_at | CDC123 | Mesenchymal |
| 215407_s_at | ASTN2 | Mesenchymal |
| 216551_x_at | PLCG1 | Mesenchymal |
| 218148_at | CENPT | Mesenchymal |
| 35201_at | HNRNPL | Mesenchymal |
| 206902_s_at | EXOG | Mesenchymal |
| 209525_at | HDGFRP3 | Mesenchymal |
| 210232_at | CDC42 | Mesenchymal |
| 221911_at | ETV1 | Mesenchymal |
| 202072_at | HNRNPL | Mesenchymal |
| 203874_s_at | SMARCA1 | Mesenchymal |
| 204104_at | SNAPC2 | Mesenchymal |
| 203883_s_at | RAB11FIP2 | Mesenchymal |
| 215058_at | DENND5B | Mesenchymal |
| 219240_s_at | C10orf88 | Mesenchymal |
| 220938_s_at | GMEB1 | Mesenchymal |
| 219205_at | SRR | Mesenchymal |
| 209118_s_at | TUBA1A | Mesenchymal |
| 218380_at | NLRP1 | Mesenchymal |
| 52169_at | STRADA | Mesenchymal |
| 209092_s_at | GLOD4 | Mesenchymal |
| 209967_s_at | CREM | Mesenchymal |
| 212736_at | C16orf45 | Mesenchymal |
| 217053_x_at | ETV1 | Mesenchymal |
| 217815_at | SUPT16H | Mesenchymal |
| 201312_s_at | SH3BGRL | Mesenchymal |
| 202144_s_at | ADSL | Mesenchymal |
| 216506_x_at | MLLT10 | Mesenchymal |
| 203875_at | SMARCA1 | Mesenchymal |
| 209174_s_at | QRICH1 | Mesenchymal |
| 214230_at | CDC42 | Mesenchymal |
| 202576_s_at | DDX19A | Mesenchymal |
| 202577_s_at | DDX19A | Mesenchymal |
| 200097_s_at | HNRNPK | Mesenchymal |
| 207219_at | ZNF643 | Mesenchymal |
| 210288_at | KLRG1 | Mesenchymal |
| 212551_at | CAP2 | Mesenchymal |
| 219204_s_at | SRR | Mesenchymal |
| 201311_s_at | SH3BGRL | Mesenchymal |
| 207937_x_at | FGFR1 | Mesenchymal |
| 218152_at | HMG20A | Mesenchymal |
| 218993_at | RNMTL1 | Mesenchymal |
| 212554_at | CAP2 | Mesenchymal |
| 215294_s_at | SMARCA1 | Mesenchymal |
| 218196_at | OSTM1 | Mesenchymal |
| 35617_at | MAPK7 | Mesenchymal |
| 203172_at | FXR2 | Mesenchymal |
| 214582_at | PDE3B | Mesenchymal |
| 206501_x_at | ETV1 | Mesenchymal |
| 220278_at | KDM4D | Mesenchymal |
| 214508_x_at | CREM | Mesenchymal |
| 207630_s_at | CREM | Mesenchymal |
| 219446_at | RIC8B | Mesenchymal |
| 202260_s_at | STXBP1 | Mesenchymal |
| 213194_at | ROBO1 | Mesenchymal |
| 211089_s_at | NEK3 | Mesenchymal |
| 212813_at | JAM3 | Mesenchymal |
| 213118_at | UHRF1BP1L | Mesenchymal |
| 218025_s_at | PECI | Mesenchymal |
| 205521_at | EXOG | Mesenchymal |
| 207830_s_at | PPP1R8 | Mesenchymal |
| 212265_at | QKI | Mesenchymal |
| 212962_at | SYDE1 | Mesenchymal |
| 57532_at | DVL2 | Mesenchymal |
| 213434_at | STX2 | Mesenchymal |
| 201426_s_at | VIM | Mesenchymal |
| 214552_s_at | RABEP1 | Mesenchymal |
| 218223_s_at | PLEKHO1 | Mesenchymal |
| 219479_at | KDELC1 | Mesenchymal |
| 222317_at | PDE3B | Mesenchymal |
| 213116_at | NEK3 | Mesenchymal |
| 207292_s_at | MAPK7 | Mesenchymal |
| 209406_at | BAG2 | Mesenchymal |
| 221759_at | G6PC3 | Mesenchymal |
| 205215_at | RNF2 | Mesenchymal |
| 211038_s_at | CROCCL1 | Mesenchymal |
| 211602_s_at | TRPC1 | Mesenchymal |
| 35265_at | FXR2 | Mesenchymal |
| 203388_at | ARRB2 | Mesenchymal |
| 212262_at | QKI | Mesenchymal |
| 214724_at | DIXDC1 | Mesenchymal |
| 218517_at | PHF17 | Mesenchymal |
| 202789_at | PLCG1 | Mesenchymal |
| 205803_s_at | TRPC1 | Mesenchymal |
| 212263_at | QKI | Mesenchymal |
| 212624_s_at | CHN1 | Mesenchymal |
| 203011_at | IMPA1 | Mesenchymal |
| 204065_at | CHST10 | Mesenchymal |
| 201980_s_at | RSU1 | Mesenchymal |
| 203278_s_at | PHF21A | Mesenchymal |
| 211535_s_at | FGFR1 | Mesenchymal |
| 219317_at | POLI | Mesenchymal |
| 214543_x_at | QKI | Mesenchymal |
| 217650_x_at | ST3GAL2 | Mesenchymal |
| 212512_s_at | CARM1 | Mesenchymal |
| 218974_at | SOBP | Mesenchymal |
| 204899_s_at | SAP30 | Mesenchymal |
| 204795_at | PRR3 | Mesenchymal |
| 204432_at | SOX12 | Mesenchymal |
| 204854_at | LEPREL2 | Mesenchymal |
| 212764_at | ZEB1 | Mesenchymal |
| 205545_x_at | DNAJC8 | Mesenchymal |
| 207346_at | STX2 | Mesenchymal |
| 220977_x_at | EPB41L5 | Mesenchymal |

Gene List 3. EMT-signature genes in cultured cell lines

| Probe | Gene Symbol | Category |
|---|---|---|
| 210151_s_at | DYRK3 | Mesenchymal |
| 219731_at | — | Mesenchymal |
| 204392_at | CAMK1 | Mesenchymal |
| 209537_at | EXTL2 | Mesenchymal |
| 212758_s_at | ZEB1 | Mesenchymal |
| 205802_at | TRPC1 | Mesenchymal |
| 210973_s_at | FGFR1 | Mesenchymal |
| 216503_s_at | MLLT10 | Mesenchymal |
| 212491_s_at | DNAJC8 | Mesenchymal |
| 205346_at | ST3GAL2 | Mesenchymal |
| 204521_at | C12orf24 | Mesenchymal |
| 65493_at | HEATR6 | Mesenchymal |
| 209407_s_at | DEAF1 | Mesenchymal |
| 219400_at | CNTNAP1 | Mesenchymal |
| 219469_at | DYNC2H1 | Mesenchymal |
| 216272_x_at | SYDE1 | Mesenchymal |
| 218991_at | HEATR6 | Mesenchymal |
| 216873_at | ATP8B2 | Mesenchymal |
| 221078_s_at | CCDC88A | Mesenchymal |
| 213302_at | PFAS | Mesenchymal |
| 44702_at | SYDE1 | Mesenchymal |
| 212413_at | Sep6 | Mesenchymal |
| 212414_s_at | N-PAC | Mesenchymal |
| 204165_at | WASF1 | Mesenchymal |
| 214298_x_at | Sep6 | Mesenchymal |
| 202921_at | ANK2 | Mesenchymal |
| 215146_s_at | TTC28 | Mesenchymal |
| 209210_s_at | FERMT2 | Mesenchymal |
| 213058_at | TTC28 | Mesenchymal |
| 209209_s_at | FERMT2 | Mesenchymal |
| 219387_at | CCDC88A | Mesenchymal |
| 220750_s_at | LEPRE1 | Mesenchymal |
| 207719_x_at | CEP170 | Mesenchymal |
| 212746_s_at | CEP170 | Mesenchymal |
| 214212_x_at | FERMT2 | Mesenchymal |
| 202920_at | ANK2 | Mesenchymal |
| 212561_at | DENND5A | Mesenchymal |

Gene List 4. EMT-signature genes in clinical samples

| Probe | Gene | Category |
|---|---|---|
| 1007_s_at | DDR1 | Epithelial |
| 1487_at | ESRRA | Epithelial |
| 200601_at | ACTN4 | Epithelial |
| 200632_s_at | NDRG1 | Epithelial |
| 200639_s_at | YWHAZ | Epithelial |
| 200660_at | S100A11 | Epithelial |
| 200752_s_at | CAPN1 | Epithelial |
| 200767_s_at | FAM120A | Epithelial |
| 200774_at | FAM120A | Epithelial |
| 200824_at | GSTP1 | Epithelial |
| 200916_at | TAGLN2 | Epithelial |
| 201015_s_at | JUP | Epithelial |
| 201059_at | CTTN | Epithelial |
| 201079_at | SYNGR2 | Epithelial |
| 201131_s_at | CDH1 | Epithelial |
| 201188_s_at | ITPR3 | Epithelial |
| 201189_s_at | ITPR3 | Epithelial |
| 201201_at | CSTB | Epithelial |
| 201331_s_at | STAT6 | Epithelial |
| 201349_at | SLC9A3R1 | Epithelial |
| 201373_at | PLEC1 | Epithelial |
| 201412_at | LRP10 | Epithelial |
| 201428_at | CLDN4 | Epithelial |
| 201467_s_at | NQO1 | Epithelial |
| 201468_s_at | NQO1 | Epithelial |
| 201510_at | ELF3 | Epithelial |
| 201596_x_at | KRT18 | Epithelial |
| 201644_at | TSTA3 | Epithelial |
| 201650_at | KRT19 | Epithelial |
| 201674_s_at | AKAP1 | Epithelial |
| 201690_s_at | TPD52 | Epithelial |
| 201704_at | ENTPD6 | Epithelial |
| 201769_at | CLINT1 | Epithelial |
| 201827_at | SMARCD2 | Epithelial |
| 201839_s_at | EPCAM | Epithelial |
| 201925_s_at | CD55 | Epithelial |
| 201926_s_at | CD55 | Epithelial |
| 201941_at | CPD | Epithelial |
| 201953_at | CIB1 | Epithelial |
| 202005_at | ST14 | Epithelial |
| 202023_at | EFNA1 | Epithelial |
| 202067_s_at | LDLR | Epithelial |
| 202068_s_at | LDLR | Epithelial |
| 202071_at | SDC4 | Epithelial |
| 202085_at | TJP2 | Epithelial |
| 202096_s_at | TSPO | Epithelial |
| 202180_s_at | MVP | Epithelial |
| 202187_s_at | PPP2R5A | Epithelial |
| 202267_at | LAMC2 | Epithelial |
| 202286_s_at | TACSTD2 | Epithelial |
| 202387_at | BAG1 | Epithelial |
| 202454_s_at | ERBB3 | Epithelial |
| 202481_at | DHRS3 | Epithelial |
| 202488_s_at | FXYD3 | Epithelial |
| 202489_s_at | FXYD3 | Epithelial |
| 202504_at | TRIM29 | Epithelial |
| 202506_at | SSFA2 | Epithelial |
| 202525_at | PRSS8 | Epithelial |
| 202528_at | GALE | Epithelial |
| 202545_at | PRKCD | Epithelial |
| 202546_at | VAMP8 | Epithelial |
| 202597_at | IRF6 | Epithelial |
| 202659_at | PSMB10 | Epithelial |
| 202699_s_at | TMEM63A | Epithelial |
| 202700_s_at | TMEM63A | Epithelial |
| 202702_at | TRIM26 | Epithelial |
| 202712_s_at | CKMT1A | Epithelial |
| 202740_at | ACY1 | Epithelial |
| 202790_at | CLDN7 | Epithelial |
| 202826_at | SPINT1 | Epithelial |
| 202833_s_at | SERPINA1 | Epithelial |
| 202889_x_at | MAP7 | Epithelial |
| 202890_at | MAP7 | Epithelial |
| 202962_at | KIF13B | Epithelial |
| 202996_at | POLD4 | Epithelial |
| 203014_x_at | SGSM3 | Epithelial |
| 203021_at | SLPI | Epithelial |
| 203028_s_at | CYBA | Epithelial |
| 203108_at | GPRC5A | Epithelial |
| 203215_s_at | MYO6 | Epithelial |
| 203216_s_at | MYO6 | Epithelial |
| 203287_at | LAD1 | Epithelial |
| 203397_s_at | GALNT3 | Epithelial |
| 203407_at | PPL | Epithelial |
| 203411_s_at | LMNA | Epithelial |
| 203430_at | HEBP2 | Epithelial |
| 203431_s_at | RICS | Epithelial |
| 203453_at | SCNN1A | Epithelial |
| 203458_at | SPR | Epithelial |
| 203509_at | SORL1 | Epithelial |
| 203593_at | CD2AP | Epithelial |
| 203652_at | MAP3K11 | Epithelial |
| 203669_s_at | DGAT1 | Epithelial |
| 203713_s_at | LLGL2 | Epithelial |
| 203726_s_at | LAMA3 | Epithelial |
| 203757_s_at | CEACAM6 | Epithelial |
| 203779_s_at | MPZL2 | Epithelial |
| 203780_at | MPZL2 | Epithelial |
| 203904_x_at | CD82 | Epithelial |
| 203918_at | PCDH1 | Epithelial |
| 203942_s_at | MARK2 | Epithelial |
| 203953_s_at | CLDN3 | Epithelial |
| 203954_x_at | CLDN3 | Epithelial |
| 203974_at | HDHD1A | Epithelial |
| 203997_at | PTPN3 | Epithelial |

Gene List 4. EMT-signature genes in clinical samples

| Probe | Gene | Category |
|---|---|---|
| 204034_at | ETHE1 | Epithelial |
| 204124_at | SLC34A2 | Epithelial |
| 204166_at | SBNO2 | Epithelial |
| 204168_at | MGST2 | Epithelial |
| 204231_s_at | FAAH | Epithelial |
| 204351_at | S100P | Epithelial |
| 204398_s_at | EML2 | Epithelial |
| 204401_at | KCNN4 | Epithelial |
| 204480_s_at | C9orf16 | Epithelial |
| 204494_s_at | C15orf39 | Epithelial |
| 204503_at | EVPL | Epithelial |
| 204519_s_at | PLLP | Epithelial |
| 204526_s_at | TBC1D8 | Epithelial |
| 204547_at | RAB40B | Epithelial |
| 204578_at | HISPPD2A | Epithelial |
| 204608_at | ASL | Epithelial |
| 204632_at | RPS6KA4 | Epithelial |
| 204656_at | SHB | Epithelial |
| 204734_at | KRT15 | Epithelial |
| 204757_s_at | C2CD2L | Epithelial |
| 204856_at | B3GNT3 | Epithelial |
| 204875_s_at | GMDS | Epithelial |
| 204922_at | C11orf80 | Epithelial |
| 204927_at | RASSF7 | Epithelial |
| 204942_s_at | ALDH3B2 | Epithelial |
| 204973_at | GJB1 | Epithelial |
| 204975_at | EMP2 | Epithelial |
| 204981_at | SLC22A18 | Epithelial |
| 204989_s_at | ITGB4 | Epithelial |
| 204990_s_at | ITGB4 | Epithelial |
| 205011_at | VWA5A | Epithelial |
| 205014_at | FGFBP1 | Epithelial |
| 205016_at | TGFA | Epithelial |
| 205019_s_at | VIPR1 | Epithelial |
| 205068_s_at | ARHGAP26 | Epithelial |
| 205093_at | PLEKHA6 | Epithelial |
| 205172_x_at | CLTB | Epithelial |
| 205190_at | PLS1 | Epithelial |
| 205193_at | MAFF | Epithelial |
| 205263_at | BCL10 | Epithelial |
| 205266_at | LIF | Epithelial |
| 205328_at | CLDN10 | Epithelial |
| 205349_at | GNA15 | Epithelial |
| 205455_at | MST1R | Epithelial |
| 205459_s_at | NPAS2 | Epithelial |
| 205460_at | NPAS2 | Epithelial |
| 205487_s_at | VGLL1 | Epithelial |
| 205490_x_at | GJB3 | Epithelial |
| 205538_at | CORO2A | Epithelial |
| 205597_at | SLC44A4 | Epithelial |
| 205617_at | PRRG2 | Epithelial |
| 205622_at | SMPD2 | Epithelial |
| 205634_x_at | ZDHHC24 | Epithelial |
| 205640_at | ALDH3B1 | Epithelial |
| 205668_at | LY75 | Epithelial |
| 205709_s_at | CDS1 | Epithelial |
| 205759_s_at | SULT2B1 | Epithelial |
| 205765_at | CYP3A5 | Epithelial |
| 205780_at | BIK | Epithelial |
| 205807_s_at | TUFT1 | Epithelial |
| 205847_at | PRSS22 | Epithelial |
| 205977_s_at | EPHA1 | Epithelial |
| 205980_s_at | ARHGAP8 | Epithelial |
| 206043_s_at | ATP2C2 | Epithelial |
| 206048_at | OVOL2 | Epithelial |
| 206153_at | CYP4F11 | Epithelial |
| 206200_s_at | ANXA11 | Epithelial |
| 206277_at | P2RY2 | Epithelial |
| 206284_x_at | CLTB | Epithelial |
| 206482_at | PTK6 | Epithelial |
| 206576_s_at | CEACAM1 | Epithelial |
| 206599_at | LOC100133772 | Epithelial |
| 206600_s_at | LOC100133772 | Epithelial |
| 206628_at | SLC5A1 | Epithelial |
| 206698_at | XK | Epithelial |
| 206770_s_at | SLC35A3 | Epithelial |
| 207109_at | POU2F3 | Epithelial |
| 207169_x_at | DDR1 | Epithelial |
| 207180_s_at | HTATIP2 | Epithelial |
| 207291_at | PRRG4 | Epithelial |
| 207517_at | LAMC2 | Epithelial |
| 207525_s_at | GIPC1 | Epithelial |
| 207667_s_at | MAP2K3 | Epithelial |
| 207847_s_at | MUC1 | Epithelial |
| 207949_s_at | ICA1 | Epithelial |
| 207986_x_at | CYB561 | Epithelial |
| 208009_s_at | ARHGEF16 | Epithelial |
| 208083_s_at | ITGB6 | Epithelial |
| 208084_at | ITGB6 | Epithelial |
| 208161_s_at | ABCC3 | Epithelial |
| 208165_s_at | PRSS16 | Epithelial |
| 208190_s_at | LSR | Epithelial |
| 208505_s_at | FUT2 | Epithelial |
| 208540_x_at | S100A11 | Epithelial |
| 208613_s_at | FLNB | Epithelial |
| 208622_s_at | EZR | Epithelial |
| 208623_s_at | EZR | Epithelial |
| 208650_s_at | CD24 | Epithelial |
| 208651_x_at | CD24 | Epithelial |
| 208779_x_at | DDR1 | Epithelial |
| 208817_at | COMT | Epithelial |
| 208818_s_at | COMT | Epithelial |
| 208862_s_at | CTNND1 | Epithelial |
| 208890_s_at | PLXNB2 | Epithelial |
| 208928_at | POR | Epithelial |
| 208949_s_at | LGALS3 | Epithelial |
| 209008_x_at | KRT8 | Epithelial |
| 209016_s_at | KRT7 | Epithelial |
| 209114_at | TSPAN1 | Epithelial |
| 209126_x_at | KRT6B | Epithelial |
| 209163_at | CYB561 | Epithelial |
| 209164_s_at | CYB561 | Epithelial |
| 209173_at | AGR2 | Epithelial |
| 209190_s_at | DIAPH1 | Epithelial |
| 209211_at | KLF5 | Epithelial |
| 209212_s_at | KLF5 | Epithelial |
| 209260_at | SFN | Epithelial |
| 209270_at | LAMB3 | Epithelial |
| 209275_s_at | CLN3 | Epithelial |
| 209354_at | TNFRSF14 | Epithelial |
| 209367_at | STXBP2 | Epithelial |
| 209373_at | MALL | Epithelial |
| 209386_at | TM4SF1 | Epithelial |
| 209387_s_at | TM4SF1 | Epithelial |
| 209448_at | HTATIP2 | Epithelial |
| 209498_at | CEACAM1 | Epithelial |
| 209499_x_at | TNFSF12-TNFSF13 | Epithelial |
| 209500_x_at | TNFSF12-TNFSF13 | Epithelial |
| 209502_s_at | BAIAP2 | Epithelial |
| 209529_at | PPAP2C | Epithelial |
| 209587_at | PITX1 | Epithelial |
| 209605_at | TST | Epithelial |
| 209626_s_at | OSBPL3 | Epithelial |
| 209627_s_at | OSBPL3 | Epithelial |
| 209641_s_at | ABCC3 | Epithelial |
| 209771_x_at | CD24 | Epithelial |
| 209772_s_at | CD24 | Epithelial |
| 209803_s_at | PHLDA2 | Epithelial |
| 209872_s_at | PKP3 | Epithelial |
| 209873_s_at | PKP3 | Epithelial |
| 210010_s_at | SLC25A1 | Epithelial |
| 210058_at | MAPK13 | Epithelial |
| 210059_s_at | MAPK13 | Epithelial |
| 210117_at | SPAG1 | Epithelial |
| 210205_at | B3GALT4 | Epithelial |
| 210301_at | XDH | Epithelial |
| 210314_x_at | TNFSF13 | Epithelial |
| 210397_at | DEFB1 | Epithelial |
| 210480_s_at | MYO6 | Epithelial |
| 210519_s_at | NQO1 | Epithelial |

Gene List 4. EMT-signature genes in clinical samples

| Probe | Gene | Category |
|---|---|---|
| 210547_x_at | ICA1 | Epithelial |
| 210592_s_at | SAT1 | Epithelial |
| 210608_s_at | FUT2 | Epithelial |
| 210652_s_at | TTC39A | Epithelial |
| 210678_s_at | AGPAT2 | Epithelial |
| 210740_s_at | ITPK1 | Epithelial |
| 210749_x_at | DDR1 | Epithelial |
| 210761_s_at | GRB7 | Epithelial |
| 210791_s_at | RICS | Epithelial |
| 210827_s_at | ELF3 | Epithelial |
| 210859_x_at | CLN3 | Epithelial |
| 211002_s_at | TRIM29 | Epithelial |
| 211043_s_at | CLTB | Epithelial |
| 211240_x_at | CTNND1 | Epithelial |
| 211429_s_at | SERPINA1 | Epithelial |
| 211628_x_at | FTHP1 | Epithelial |
| 211657_at | CEACAM6 | Epithelial |
| 211695_x_at | MUC1 | Epithelial |
| 211778_s_at | OVOL2 | Epithelial |
| 211883_x_at | CEACAM1 | Epithelial |
| 211889_x_at | CEACAM1 | Epithelial |
| 212053_at | PDXDC1 | Epithelial |
| 212070_at | GPR56 | Epithelial |
| 212089_at | LMNA | Epithelial |
| 212127_at | RANGAP1 | Epithelial |
| 212268_at | SERPINB1 | Epithelial |
| 212339_at | EPB41L1 | Epithelial |
| 212443_at | NBEAL2 | Epithelial |
| 212444_at | — | Epithelial |
| 212456_at | KIAA0664 | Epithelial |
| 212527_at | PPPDE2 | Epithelial |
| 212531_at | LCN2 | Epithelial |
| 212543_at | AIM1 | Epithelial |
| 212560_at | SORL1 | Epithelial |
| 212659_s_at | IL1RN | Epithelial |
| 212727_at | DLG3 | Epithelial |
| 212841_s_at | PPFIBP2 | Epithelial |
| 212925_at | C19orf21 | Epithelial |
| 213050_at | COBL | Epithelial |
| 213076_at | ITPKC | Epithelial |
| 213078_x_at | LPCAT4 | Epithelial |
| 213085_s_at | WWC1 | Epithelial |
| 213172_at | TTC9 | Epithelial |
| 213174_at | TTC9 | Epithelial |
| 213191_at | TICAM1 | Epithelial |
| 213230_at | CDR2L | Epithelial |
| 213242_x_at | KIAA0284 | Epithelial |
| 213285_at | TMEM30B | Epithelial |
| 213308_at | SHANK2 | Epithelial |
| 213412_at | TJP3 | Epithelial |
| 213432_at | MUC5B | Epithelial |
| 213441_x_at | SPDEF | Epithelial |
| 213462_at | NPAS2 | Epithelial |
| 213506_at | F2RL1 | Epithelial |
| 213542_at | ZNF710 | Epithelial |
| 213572_s_at | SERPINB1 | Epithelial |
| 213590_at | LOC100133772 | Epithelial |
| 213667_at | SRCAP | Epithelial |
| 213693_s_at | MUC1 | Epithelial |
| 213929_at | EXPH5 | Epithelial |
| 214070_s_at | ATP10B | Epithelial |
| 214088_s_at | FUT3 | Epithelial |
| 214106_s_at | GMDS | Epithelial |
| 214234_s_at | CYP3A5 | Epithelial |
| 214235_at | CYP3A5 | Epithelial |
| 214404_x_at | SPDEF | Epithelial |
| 214665_s_at | CHP | Epithelial |
| 214734_at | EXPH5 | Epithelial |
| 214779_s_at | SGSM3 | Epithelial |
| 214783_s_at | ANXA11 | Epithelial |
| 214924_s_at | TRAK1 | Epithelial |
| 215034_s_at | TM4SF1 | Epithelial |
| 215243_s_at | GJB3 | Epithelial |
| 215471_s_at | MAP7 | Epithelial |
| 215498_s_at | MAP2K3 | Epithelial |
| 215499_at | MAP2K3 | Epithelial |
| 215729_s_at | VGLL1 | Epithelial |
| 215732_s_at | DTX2 | Epithelial |
| 216010_x_at | FUT3 | Epithelial |
| 216074_x_at | WWC1 | Epithelial |
| 216251_s_at | TTLL12 | Epithelial |
| 216379_x_at | CD24 | Epithelial |
| 216568_x_at | — | Epithelial |
| 216641_s_at | LAD1 | Epithelial |
| 216836_s_at | ERBB2 | Epithelial |
| 216905_s_at | ST14 | Epithelial |
| 217109_at | MUC4 | Epithelial |
| 217110_s_at | MUC4 | Epithelial |
| 217149_x_at | TNK1 | Epithelial |
| 217200_x_at | CYB561 | Epithelial |
| 217551_at | LOC441453 | Epithelial |
| 217728_at | S100A6 | Epithelial |
| 217730_at | TMBIM1 | Epithelial |
| 217744_s_at | PERP | Epithelial |
| 217751_at | GSTK1 | Epithelial |
| 217794_at | PRR13 | Epithelial |
| 217867_x_at | BACE2 | Epithelial |
| 217939_s_at | AFTPH | Epithelial |
| 217995_at | SQRDL | Epithelial |
| 218028_at | ELOVL1 | Epithelial |
| 218035_s_at | RBM47 | Epithelial |
| 218144_s_at | INF2 | Epithelial |
| 218161_s_at | CLN6 | Epithelial |
| 218180_s_at | EPS8L2 | Epithelial |
| 218186_s_at | RAB25 | Epithelial |
| 218211_s_at | MLPH | Epithelial |
| 218261_at | AP1M2 | Epithelial |
| 218301_at | RNPEPL1 | Epithelial |
| 218451_at | CDCP1 | Epithelial |
| 218498_s_at | ERO1L | Epithelial |
| 218500_at | C8orf55 | Epithelial |
| 218644_at | PLEK2 | Epithelial |
| 218677_at | S100A14 | Epithelial |
| 218693_at | TSPAN15 | Epithelial |
| 218776_s_at | TMEM62 | Epithelial |
| 218779_x_at | EPS8L1 | Epithelial |
| 218792_s_at | BSPRY | Epithelial |
| 218806_s_at | VAV3 | Epithelial |
| 218807_at | VAV3 | Epithelial |
| 218810_at | ZC3H12A | Epithelial |
| 218840_s_at | NADSYN1 | Epithelial |
| 218856_at | TNFRSF21 | Epithelial |
| 218858_at | DEPDC6 | Epithelial |
| 218885_s_at | GALNT12 | Epithelial |
| 218900_at | CNNM4 | Epithelial |
| 218921_at | SIGIRR | Epithelial |
| 218928_s_at | SLC37A1 | Epithelial |
| 218931_at | RAB17 | Epithelial |
| 218960_at | TMPRSS4 | Epithelial |
| 218963_s_at | KRT23 | Epithelial |
| 218966_at | MYO5C | Epithelial |
| 219010_at | C1orf106 | Epithelial |
| 219121_s_at | ESRP1 | Epithelial |
| 219127_at | ATAD4 | Epithelial |
| 219150_s_at | ADAP1 | Epithelial |
| 219188_s_at | MACROD1 | Epithelial |
| 219215_s_at | SLC39A4 | Epithelial |
| 219241_x_at | SSH3 | Epithelial |
| 219274_at | TSPAN12 | Epithelial |
| 219313_at | GRAMD1C | Epithelial |
| 219327_s_at | GPRC5C | Epithelial |
| 219332_at | MICALL2 | Epithelial |
| 219360_s_at | TRPM4 | Epithelial |
| 219388_at | GRHL2 | Epithelial |
| 219395_at | ESRP2 | Epithelial |
| 219411_at | ELMO3 | Epithelial |
| 219429_at | FA2H | Epithelial |
| 219461_at | PAK6 | Epithelial |
| 219476_at | C1orf116 | Epithelial |
| 219508_at | GCNT3 | Epithelial |

Gene List 4. EMT-signature genes in clinical samples

| Probe | Gene | Category |
|---|---|---|
| 219513_s_at | SH2D3A | Epithelial |
| 219517_at | ELL3 | Epithelial |
| 219518_s_at | ELL3 | Epithelial |
| 219580_s_at | TMC5 | Epithelial |
| 219622_at | RAB20 | Epithelial |
| 219630_at | PDZK1IP1 | Epithelial |
| 219681_s_at | RAB11FIP1 | Epithelial |
| 219716_at | APOL6 | Epithelial |
| 219749_at | SH2D4A | Epithelial |
| 219756_s_at | POF1B | Epithelial |
| 219768_at | VTCN1 | Epithelial |
| 219850_s_at | EHF | Epithelial |
| 219856_at | C1orf116 | Epithelial |
| 219857_at | C10orf81 | Epithelial |
| 219916_s_at | RNF39 | Epithelial |
| 219919_s_at | SSH3 | Epithelial |
| 219946_x_at | MYH14 | Epithelial |
| 220030_at | STYK1 | Epithelial |
| 220161_s_at | EPB41L4B | Epithelial |
| 220174_at | LRRC8E | Epithelial |
| 220192_x_at | SPDEF | Epithelial |
| 220196_at | MUC16 | Epithelial |
| 220312_at | FAM83E | Epithelial |
| 220475_at | SLC28A3 | Epithelial |
| 220638_s_at | CBLC | Epithelial |
| 220945_x_at | MANSC1 | Epithelial |
| 220948_s_at | ATP1A1 | Epithelial |
| 220964_s_at | RAB1B | Epithelial |
| 220998_s_at | UNC93B1 | Epithelial |
| 221042_at | CLMN | Epithelial |
| 221081_s_at | DENND2D | Epithelial |
| 221122_at | HRASLS2 | Epithelial |
| 221215_s_at | RIPK4 | Epithelial |
| 221256_s_at | HDHD3 | Epithelial |
| 221610_s_at | STAP2 | Epithelial |
| 221655_x_at | EPS8L1 | Epithelial |
| 221656_s_at | ARHGEF10L | Epithelial |
| 221664_s_at | F11R | Epithelial |
| 221665_s_at | EPS8L1 | Epithelial |
| 221696_s_at | STYK1 | Epithelial |
| 221764_at | C19orf22 | Epithelial |
| 221880_s_at | FAM174B | Epithelial |
| 221927_s_at | ABHD11 | Epithelial |
| 222126_at | AGFG2 | Epithelial |
| 222165_x_at | C9orf16 | Epithelial |
| 222333_at | ALS2CL | Epithelial |
| 222362_at | AGFG2 | Epithelial |
| 266_s_at | CD24 | Epithelial |
| 32837_at | AGPAT2 | Epithelial |
| 33322_i_at | SFN | Epithelial |
| 33323_r_at | SFN | Epithelial |
| 35148_at | TJP3 | Epithelial |
| 36711_at | MAFF | Epithelial |
| 36936_at | TSTA3 | Epithelial |
| 37117_at | ARHGAP8 | Epithelial |
| 38766_at | SRCAP | Epithelial |
| 39548_at | NPAS2 | Epithelial |
| 39549_at | NPAS2 | Epithelial |
| 39891_at | ZNF710 | Epithelial |
| 40359_at | RASSF7 | Epithelial |
| 40472_at | LPCAT4 | Epithelial |
| 41047_at | C9orf16 | Epithelial |
| 51158_at | FAM174B | Epithelial |
| 51192_at | SSH3 | Epithelial |
| 52940_at | SIGIRR | Epithelial |
| 57163_at | ELOVL1 | Epithelial |
| 64486_at | CORO1B | Epithelial |
| 65517_at | AP1M2 | Epithelial |
| 90265_at | ADAP1 | Epithelial |
| 91826_at | EPS8L1 | Epithelial |
| 200783_s_at | STMN1 | Mesenchymal |
| 200953_s_at | CCND2 | Mesenchymal |
| 200975_at | PPT1 | Mesenchymal |
| 200982_s_at | ANXA6 | Mesenchymal |
| 201054_at | HNRNPAO | Mesenchymal |
| 201116_s_at | CPE | Mesenchymal |
| 201117_s_at | CPE | Mesenchymal |
| 201147_s_at | TIMP3 | Mesenchymal |
| 201148_s_at | TIMP3 | Mesenchymal |
| 201149_s_at | TIMP3 | Mesenchymal |
| 201150_s_at | TIMP3 | Mesenchymal |
| 201272_at | AKR1B1 | Mesenchymal |
| 201309_x_at | C5orf13 | Mesenchymal |
| 201310_s_at | C5orf13 | Mesenchymal |
| 201387_s_at | UCHL1 | Mesenchymal |
| 201426_s_at | VIM | Mesenchymal |
| 201518_at | CBX1 | Mesenchymal |
| 201539_s_at | FHL1 | Mesenchymal |
| 201540_at | FHL1 | Mesenchymal |
| 201560_at | CLIC4 | Mesenchymal |
| 201564_s_at | FSCN1 | Mesenchymal |
| 201669_s_at | MARCKS | Mesenchymal |
| 202141_s_at | COPS8 | Mesenchymal |
| 202142_at | COPS8 | Mesenchymal |
| 202143_s_at | COPS8 | Mesenchymal |
| 202179_at | BLMH | Mesenchymal |
| 202302_s_at | RSRC2 | Mesenchymal |
| 202557_at | HSPA13 | Mesenchymal |
| 202558_s_at | HSPA13 | Mesenchymal |
| 202732_at | PKIG | Mesenchymal |
| 202789_at | PLCG1 | Mesenchymal |
| 202976_s_at | RHOBTB3 | Mesenchymal |
| 203044_at | CHSY1 | Mesenchymal |
| 203184_at | FBN2 | Mesenchymal |
| 203188_at | B3GNT1 | Mesenchymal |
| 203217_s_at | ST3GAL5 | Mesenchymal |
| 203296_s_at | ATP1A2 | Mesenchymal |
| 203417_at | MFAP2 | Mesenchymal |
| 203440_at | CDH2 | Mesenchymal |
| 203441_s_at | CDH2 | Mesenchymal |
| 203688_at | PKD2 | Mesenchymal |
| 203706_s_at | FZD7 | Mesenchymal |
| 203753_at | TCF4 | Mesenchymal |
| 203813_s_at | SLIT3 | Mesenchymal |
| 203874_s_at | SMARCA1 | Mesenchymal |
| 203919_at | TCEA2 | Mesenchymal |
| 204065_at | CHST10 | Mesenchymal |
| 204140_at | TPST1 | Mesenchymal |
| 204165_at | WASF1 | Mesenchymal |
| 204173_at | MYL6B | Mesenchymal |
| 204400_at | EFS | Mesenchymal |
| 204466_s_at | SNCA | Mesenchymal |
| 204521_at | C12orf24 | Mesenchymal |
| 204528_s_at | NAP1L1 | Mesenchymal |
| 204556_s_at | DZIP1 | Mesenchymal |
| 204557_s_at | DZIP1 | Mesenchymal |
| 204589_at | NUAK1 | Mesenchymal |
| 204612_at | PKIA | Mesenchymal |
| 204749_at | NAP1L3 | Mesenchymal |
| 204759_at | RCBTB2 | Mesenchymal |
| 204773_at | IL11RA | Mesenchymal |
| 204795_at | PRR3 | Mesenchymal |
| 204915_s_at | SOX11 | Mesenchymal |
| 205031_at | EFNB3 | Mesenchymal |
| 205079_s_at | MPDZ | Mesenchymal |
| 205122_at | TMEFF1 | Mesenchymal |
| 205123_s_at | TMEFF1 | Mesenchymal |
| 205303_at | KCNJ8 | Mesenchymal |
| 205304_s_at | KCNJ8 | Mesenchymal |
| 205347_s_at | TMSB15A | Mesenchymal |
| 205407_at | RECK | Mesenchymal |
| 205525_at | CALD1 | Mesenchymal |
| 205545_x_at | DNAJC8 | Mesenchymal |
| 205741_s_at | DTNA | Mesenchymal |
| 205794_s_at | NOVA1 | Mesenchymal |
| 205802_at | TRPC1 | Mesenchymal |
| 205803_s_at | TRPC1 | Mesenchymal |
| 205933_at | SETBP1 | Mesenchymal |
| 205961_s_at | PSIP1 | Mesenchymal |
| 206314_at | ZNF167 | Mesenchymal |

Gene List 4. EMT-signature genes in clinical samples

| Probe | Gene | Category |
|---|---|---|
| 206580_s_at | EFEMP2 | Mesenchymal |
| 207030_s_at | CSRP2 | Mesenchymal |
| 207068_at | ZFP37 | Mesenchymal |
| 207719_x_at | CEP170 | Mesenchymal |
| 207781_s_at | ZNF711 | Mesenchymal |
| 207876_s_at | FLNC | Mesenchymal |
| 208752_x_at | NAP1L1 | Mesenchymal |
| 208753_s_at | NAP1L1 | Mesenchymal |
| 208782_at | FSTL1 | Mesenchymal |
| 208848_at | ADH5 | Mesenchymal |
| 208962_s_at | FADS1 | Mesenchymal |
| 208963_x_at | FADS1 | Mesenchymal |
| 208964_s_at | FADS1 | Mesenchymal |
| 209087_x_at | MCAM | Mesenchymal |
| 209118_s_at | TUBA1A | Mesenchymal |
| 209197_at | SYT11 | Mesenchymal |
| 209198_s_at | SYT11 | Mesenchymal |
| 209209_s_at | FERMT2 | Mesenchymal |
| 209210_s_at | FERMT2 | Mesenchymal |
| 209285_s_at | C3orf63 | Mesenchymal |
| 209337_at | PSIP1 | Mesenchymal |
| 209440_at | PRPS1 | Mesenchymal |
| 209674_at | CRY1 | Mesenchymal |
| 209866_s_at | LPHN3 | Mesenchymal |
| 209867_s_at | LPHN3 | Mesenchymal |
| 210105_at | FYN | Mesenchymal |
| 210220_at | FZD2 | Mesenchymal |
| 210298_x_at | FHL1 | Mesenchymal |
| 210299_s_at | FHL1 | Mesenchymal |
| 210852_s_at | AASS | Mesenchymal |
| 210875_s_at | ZEB1 | Mesenchymal |
| 210882_s_at | TRO | Mesenchymal |
| 210933_s_at | FSCN1 | Mesenchymal |
| 210973_s_at | FGFR1 | Mesenchymal |
| 211071_s_at | MLLT11 | Mesenchymal |
| 211126_s_at | CSRP2 | Mesenchymal |
| 211276_at | TCEAL2 | Mesenchymal |
| 211535_s_at | FGFR1 | Mesenchymal |
| 211602_s_at | TRPC1 | Mesenchymal |
| 211700_s_at | TRO | Mesenchymal |
| 211701_s_at | TRO | Mesenchymal |
| 211958_at | IGFBP5 | Mesenchymal |
| 211959_at | IGFBP5 | Mesenchymal |
| 212233_at | MAP1B | Mesenchymal |
| 212262_at | QKI | Mesenchymal |
| 212263_at | QKI | Mesenchymal |
| 212265_at | QKI | Mesenchymal |
| 212358_at | CLIP3 | Mesenchymal |
| 212382_at | TCF4 | Mesenchymal |
| 212385_at | TCF4 | Mesenchymal |
| 212386_at | TCF4 | Mesenchymal |
| 212387_at | TCF4 | Mesenchymal |
| 212413_at | SEP6 | Mesenchymal |
| 212414_s_at | N-PAC | Mesenchymal |
| 212486_s_at | FYN | Mesenchymal |
| 212491_s_at | DNAJC8 | Mesenchymal |
| 212561_at | DENND5A | Mesenchymal |
| 212624_s_at | CHN1 | Mesenchymal |
| 212651_at | RHOBTB1 | Mesenchymal |
| 212713_at | MFAP4 | Mesenchymal |
| 212746_s_at | CEP170 | Mesenchymal |
| 212758_s_at | ZEB1 | Mesenchymal |
| 212764_at | ZEB1 | Mesenchymal |
| 212854_x_at | NBPF10 | Mesenchymal |
| 212915_at | PDZRN3 | Mesenchymal |
| 212967_x_at | NAP1L1 | Mesenchymal |
| 212977_at | CXCR7 | Mesenchymal |
| 212982_at | ZDHHC17 | Mesenchymal |
| 213110_s_at | COL4A5 | Mesenchymal |
| 213170_at | GPX7 | Mesenchymal |
| 213218_at | ZNF187 | Mesenchymal |
| 213262_at | SACS | Mesenchymal |
| 213283_s_at | SALL2 | Mesenchymal |
| 213306_at | MPDZ | Mesenchymal |
| 213316_at | KIAA1462 | Mesenchymal |
| 213329_at | SRGAP2 | Mesenchymal |
| 213340_s_at | KIAA0495 | Mesenchymal |
| 213348_at | CDKN1C | Mesenchymal |
| 213411_at | — | Mesenchymal |
| 213434_at | STX2 | Mesenchymal |
| 213666_at | SEP6 | Mesenchymal |
| 213864_s_at | NAP1L1 | Mesenchymal |
| 213891_s_at | TCF4 | Mesenchymal |
| 213992_at | COL4A6 | Mesenchymal |
| 214023_x_at | TUBB2B | Mesenchymal |
| 214043_at | PTPRD | Mesenchymal |
| 214051_at | TMSB15B | Mesenchymal |
| 214212_x_at | FERMT2 | Mesenchymal |
| 214505_s_at | FHL1 | Mesenchymal |
| 214761_at | ZNF423 | Mesenchymal |
| 214913_at | ADAMTS3 | Mesenchymal |
| 214954_at | SUSD5 | Mesenchymal |
| 215143_at | DPY19L2P2 | Mesenchymal |
| 216033_s_at | FYN | Mesenchymal |
| 216048_s_at | RHOBTB3 | Mesenchymal |
| 216873_s_at | ATP8B2 | Mesenchymal |
| 217714_x_at | STMN1 | Mesenchymal |
| 217820_s_at | ENAH | Mesenchymal |
| 217897_at | FXYD6 | Mesenchymal |
| 218025_s_at | PECI | Mesenchymal |
| 218032_at | SNN | Mesenchymal |
| 218127_at | NFYB | Mesenchymal |
| 218181_s_at | MAP4K4 | Mesenchymal |
| 218223_s_at | PLEKHO1 | Mesenchymal |
| 218236_s_at | PRKD3 | Mesenchymal |
| 218263_s_at | ZBED5 | Mesenchymal |
| 218332_at | BEX1 | Mesenchymal |
| 218338_at | PHC1 | Mesenchymal |
| 218370_s_at | S100PBP | Mesenchymal |
| 218380_at | NLRP1 | Mesenchymal |
| 218573_at | MAGEH1 | Mesenchymal |
| 218646_at | C4orf27 | Mesenchymal |
| 218675_at | SLC22A17 | Mesenchymal |
| 218694_at | ARMCX1 | Mesenchymal |
| 218824_at | PNMAL1 | Mesenchymal |
| 219213_at | JAM2 | Mesenchymal |
| 219304_s_at | PDGFD | Mesenchymal |
| 219372_at | IFT81 | Mesenchymal |
| 219387_at | CCDC88A | Mesenchymal |
| 219410_at | TMEM45A | Mesenchymal |
| 219479_at | KDELC1 | Mesenchymal |
| 219532_at | ELOVL4 | Mesenchymal |
| 219534_x_at | CDKN1C | Mesenchymal |
| 219670_at | BEND5 | Mesenchymal |
| 219740_at | VASH2 | Mesenchymal |
| 219825_at | CYP26B1 | Mesenchymal |
| 219855_at | NUDT11 | Mesenchymal |
| 219972_s_at | C14orf135 | Mesenchymal |
| 220040_x_at | ZC4H2 | Mesenchymal |
| 220750_at | LEPRE1 | Mesenchymal |
| 221016_s_at | TCF7L1 | Mesenchymal |
| 221078_s_at | CCDC88A | Mesenchymal |
| 221234_s_at | BACH2 | Mesenchymal |
| 221261_x_at | MAGED4 | Mesenchymal |
| 221959_at | FAM110B | Mesenchymal |
| 222101_s_at | DCHS1 | Mesenchymal |
| 222146_s_at | TCF4 | Mesenchymal |
| 222164_at | FGFR1 | Mesenchymal |

The invention claimed is:

1. A method of increasing susceptibility to an anti-cancer treatment in a patient suffering from epithelial ovarian cancer (EOC) wherein the method comprises:
   a) providing a set of expression data in a patient sample obtained from a patient suffering from epithelial ovarian cancer (EOC);
   b) assigning the set of expression data derived from said patient sample to one of two subtype clusters for epithelial ovarian cancer (EOC), wherein the first of the two subtype clusters of epithelial ovarian cancer (EOC) is characterized by the genes referred to in Gene List 2-Mes;

wherein the second of the two subtype clusters of epithelial ovarian cancer (EOC) is characterized by the genes referred to in Gene List 2-StemA;

c) determining an epithelial-mesenchymal transition (EMT) score for the patient sample; and d) administering an EMT reversal agent to increase patient susceptibility to an anti-cancer treatment, if the set of expression data derived from said patient sample is assigned to one of two subtype clusters for epithelial ovarian cancer (EOC) in b), and if the EMT score in c) indicates that said patient sample is of the mesenchymal phenotype.

2. The method of claim 1, wherein assigning the set of expression data derived from said patient sample to one of two subtype clusters for epithelial ovarian cancer (EOC) is carried out either a') by clustering the expression data derived from the patient sample together with the expression data which make up said two different subtype clusters of epithelial ovarian cancer (EOC) to determine to which group the expression data of the patient sample belongs; or b') by subjecting the expression data obtained from the patient sample together with the expression data which make up said two different subtype clusters of epithelial ovarian cancer (EOC) to a regression analysis.

3. The method of claim 1, wherein the EMT score referred to under c) is determined by:

e) computing an enrichment score by integration of the difference between the empirical cumulative distribution functions of genes from Gene List 3 and genes not in Gene List 3 for each set of expression data from the individual patient samples to determine the epithelial rank or mesenchymal rank of a sample;

f) determining the EMT score by substracting the value for the epithelial rank from the value for the mesenchymal rank.

4. The method of claim 1, wherein the EMT score referred to under c) for a patient cancer sample is determined by:

g) computing an enrichment score by integration of the difference between the empirical cumulative distribution functions of genes from Gene List 4 and genes not in Gene List 4 for each set of expression data from the individual patient cancer sample to determine the epithelial rank or mesenchymal rank of a sample;

h) determining an EMT score by subtracting the value for the epithelial rank from the value for the mesenchymal rank.

5. The method of claim 3, wherein integration of the difference between the empirical cumulative distribution functions of genes from Gene List 3 or Gene List 4 and genes not in Gene List 3 or Gene List 4, respectively, for each set of expression data from the individual patient cancer sample to determine the epithelial rank or mesenchymal rank of a sample is carried out using single sample enrichment analysis.

6. The method of claim 1, wherein the EMT score in c) in greater than about zero.

* * * * *